(12) United States Patent
Simpson et al.

(10) Patent No.: US 11,992,312 B2
(45) Date of Patent: *May 28, 2024

(54) TRANSCUTANEOUS ANALYTE SENSOR SYSTEMS AND METHODS

(71) Applicant: DexCom, Inc., San Diego, CA (US)

(72) Inventors: Peter C. Simpson, Cardiff, CA (US); Minglian Shi, San Diego, CA (US); Sebastian Bohm, San Diego, CA (US); Maria Noel Brown Wells, San Diego, CA (US); John Patrick Majewski, Solana Beach, CA (US); Leah Morta Edra, San Diego, CA (US); Disha B. Sheth, Oceanside, CA (US); John Michael Gray, San Diego, CA (US); Shanger Wang, San Diego, CA (US); Ted Tang Lee, San Diego, CA (US); Michael L. Moore, Poway, CA (US); Jason Mitchell, San Diego, CA (US); Jennifer Blackwell, San Diego, CA (US); Neel Narayan Shah, Carlsbad, CA (US); Todd Andrew Newhouse, San Diego, CA (US); Jason Halac, San Diego, CA (US); Ryan Everett Schoonmaker, Oceanside, CA (US); Paul V. Neale, San Diego, CA (US); Jiong Zou, San Diego, CA (US); Sean T. Saint, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 220 days.

This patent is subject to a terminal disclaimer.

(21) Appl. No.: 17/342,071

(22) Filed: Jun. 8, 2021

(65) Prior Publication Data

US 2021/0361200 A1 Nov. 25, 2021

Related U.S. Application Data

(63) Continuation of application No. 15/798,249, filed on Oct. 30, 2017, now Pat. No. 11,058,329, which is a
(Continued)

(51) Int. Cl.
*A61B 5/145* (2006.01)
*A61B 5/00* (2006.01)
(Continued)

(52) U.S. Cl.
CPC ...... *A61B 5/14532* (2013.01); *A61B 5/14503* (2013.01); *A61B 5/683* (2013.01);
(Continued)

(58) Field of Classification Search
CPC . A61B 5/14532; A61B 5/14503; A61B 5/683; A61B 5/6833; A61B 5/0004;
(Continued)

(56) References Cited

U.S. PATENT DOCUMENTS

| 6,248,067 B1 | 6/2001 | Causey, III et al. |
| 9,775,543 B2 | 10/2017 | Brister et al. |

(Continued)

FOREIGN PATENT DOCUMENTS

| CN | 102724913 A | 10/2012 |
| CN | 102791197 A | 11/2012 |

(Continued)

OTHER PUBLICATIONS

Extended European Search Report for Application No. 17866098.1 dated Apr. 9, 2020, 09 pages.
(Continued)

*Primary Examiner* — Eric F Winakur
*Assistant Examiner* — Abid A Mustansir
(74) *Attorney, Agent, or Firm* — Snell & Wilmer LLP

(57) ABSTRACT

Sensor systems can be used to measure an analyte concentration. Sensor systems can include a base having a distal
(Continued)

side configured to face towards a person's skin. An adhesive can couple the base to the skin. A transcutaneous analyte measurement sensor can be coupled to the base and can be located at least partially in the host. A transmitter can be coupled to the base and can transmit analyte measurement data to a remote device.

15 Claims, 47 Drawing Sheets

Related U.S. Application Data continuation of application No. 15/798,064, filed on Oct. 30, 2017, now Pat. No. 10,827,955.

(60) Provisional application No. 62/415,419, filed on Oct. 31, 2016.

(51) Int. Cl.
*A61B 5/1473* (2006.01)
*A61B 5/1486* (2006.01)

(52) U.S. Cl.
CPC .......... *A61B 5/6833* (2013.01); *A61B 5/0004* (2013.01); *A61B 5/0015* (2013.01); *A61B 5/1473* (2013.01); *A61B 5/14865* (2013.01); *A61B 5/6849* (2013.01); *A61B 2560/045* (2013.01)

(58) Field of Classification Search
CPC . A61B 5/0015; A61B 5/1473; A61B 5/14865; A61B 5/6849; A61B 2560/045
See application file for complete search history.

(56) References Cited

U.S. PATENT DOCUMENTS

| | | |
|---|---|---|
| 2007/0073129 A1 | 3/2007 | Shah et al. |
| 2008/0194938 A1* | 8/2008 | Brister .............. A61B 5/6833 600/373 |
| 2011/0021889 A1 | 1/2011 | Hoss et al. |
| 2011/0077490 A1 | 3/2011 | Simpson et al. |
| 2011/0172508 A1 | 7/2011 | Chickering, III et al. |
| 2011/0190603 A1 | 8/2011 | Stafford |
| 2014/0114158 A1 | 4/2014 | Brister et al. |
| 2014/0187876 A1 | 7/2014 | Ohkoshi |
| 2014/0275897 A1 | 9/2014 | Pushpala et al. |
| 2015/0080690 A1 | 3/2015 | Frey et al. |
| 2015/0289788 A1 | 10/2015 | Simpson et al. |
| 2016/0022179 A1* | 1/2016 | Di Resta ............ A61B 5/68335 600/316 |
| 2016/0157766 A1 | 6/2016 | Simpson et al. |
| 2017/0176372 A1 | 6/2017 | Hanko et al. |
| 2017/0188911 A1 | 7/2017 | Halac et al. |
| 2018/0116570 A1 | 5/2018 | Simpson et al. |
| 2018/0116572 A1 | 5/2018 | Simpson et al. |

FOREIGN PATENT DOCUMENTS

| | | |
|---|---|---|
| CN | 103781422 A | 5/2014 |
| CN | 104507388 A | 4/2015 |
| WO | WO-2006038044 A2 | 4/2006 |
| WO | WO-2011011643 A1 | 1/2011 |
| WO | WO-2015138688 A1 | 9/2015 |

OTHER PUBLICATIONS

International Preliminary Report on Patentability for Application No. PCT/US2017/059112 dated May 9, 2019, 11 pages.
International Search Report and Written opinion for Application No. PCT/US2017/059112 dated Apr. 17, 2018, 13 pages.

* cited by examiner

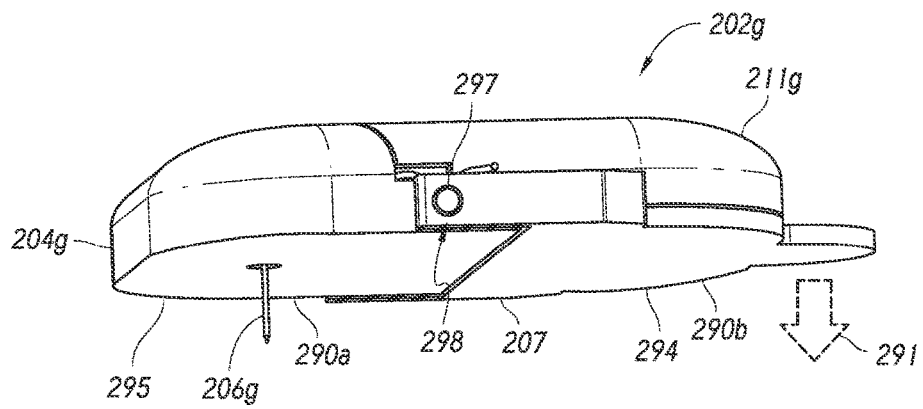
FIG. 20
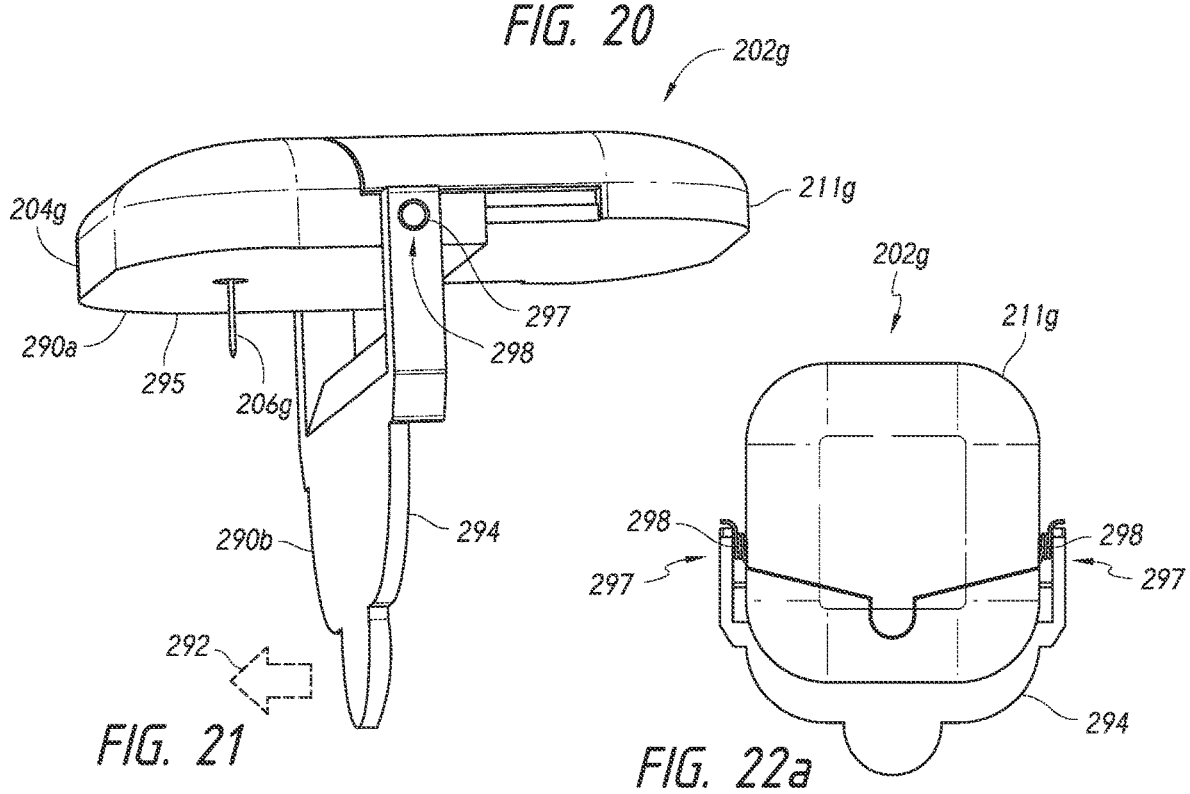
FIG. 21
FIG. 22a
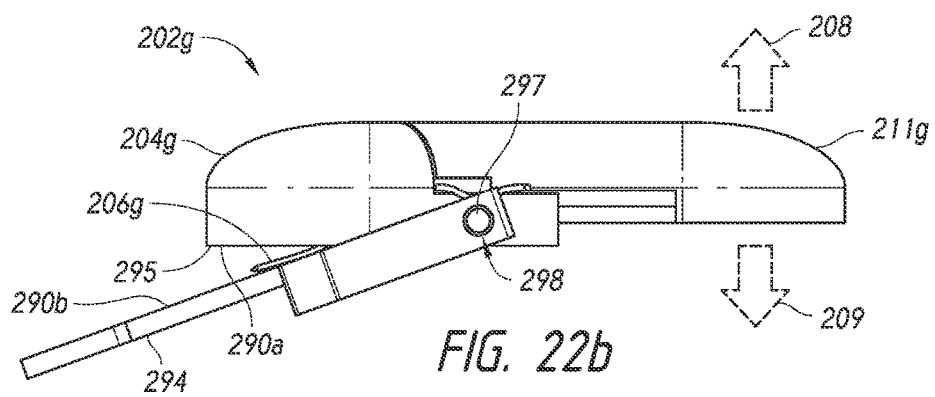
FIG. 22b

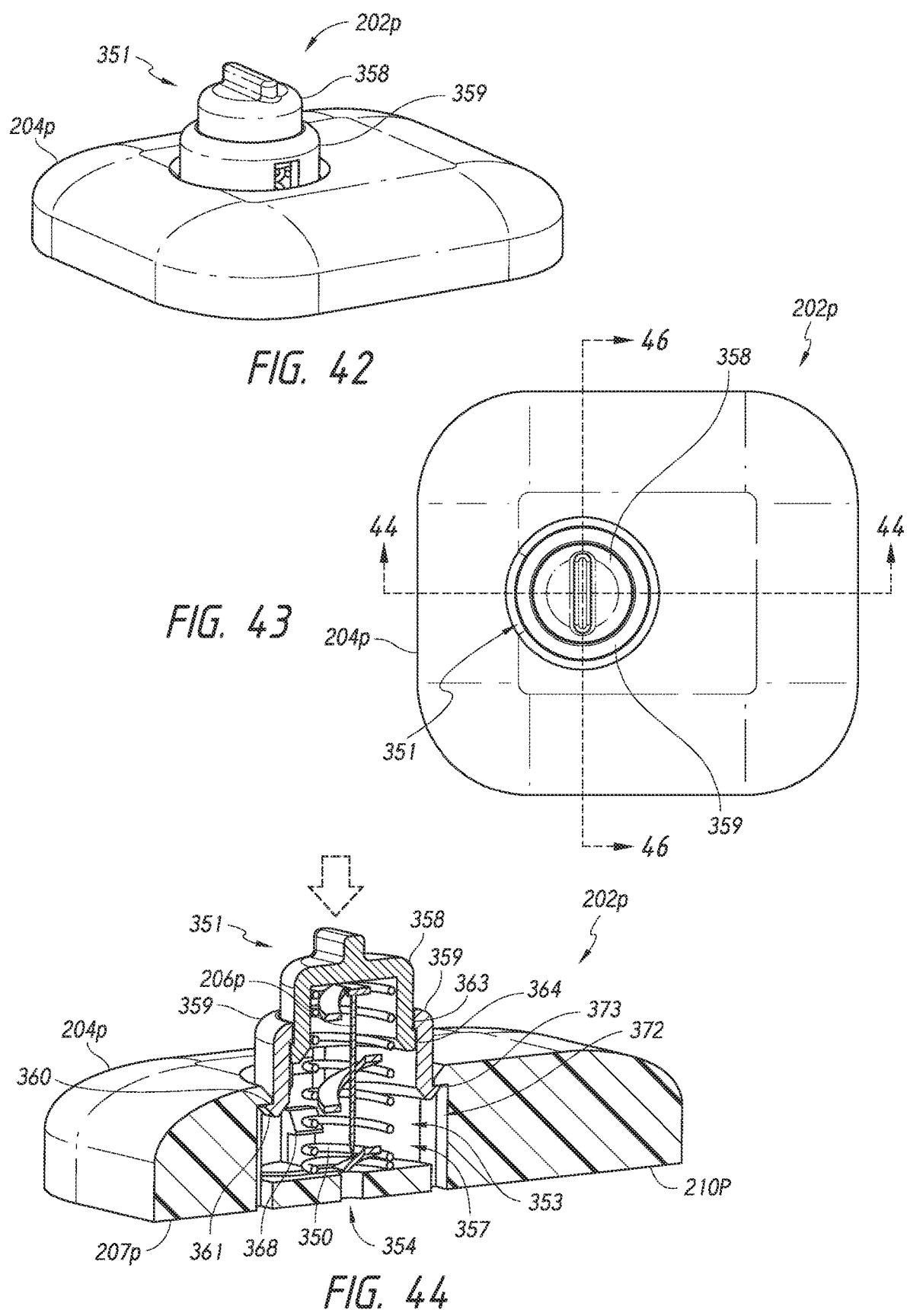

$$F = \frac{\pi^2 EI}{(KL)^2} \qquad I_y = \frac{\pi}{4} r^4 \qquad I_x = \frac{\pi}{4} r^4$$
FIG. 54   FIG. 55   FIG. 56
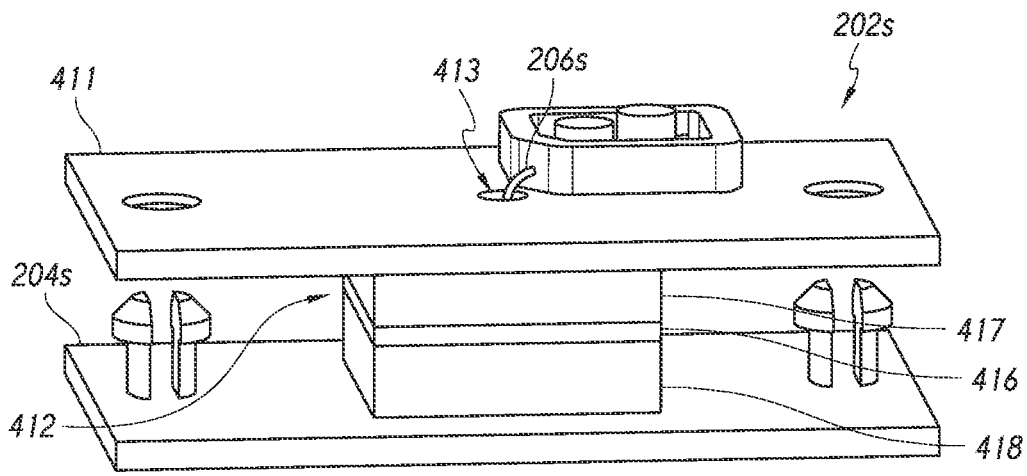
FIG. 57
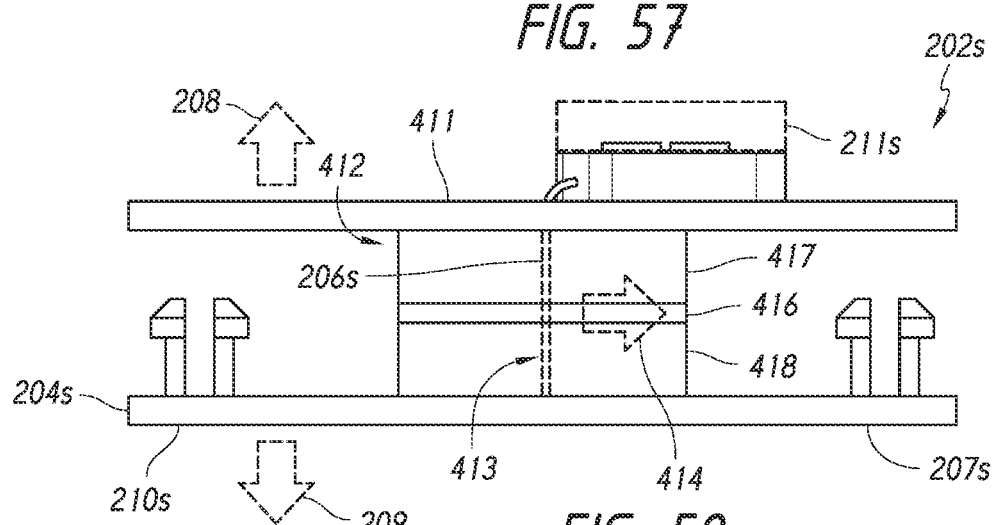
FIG. 58
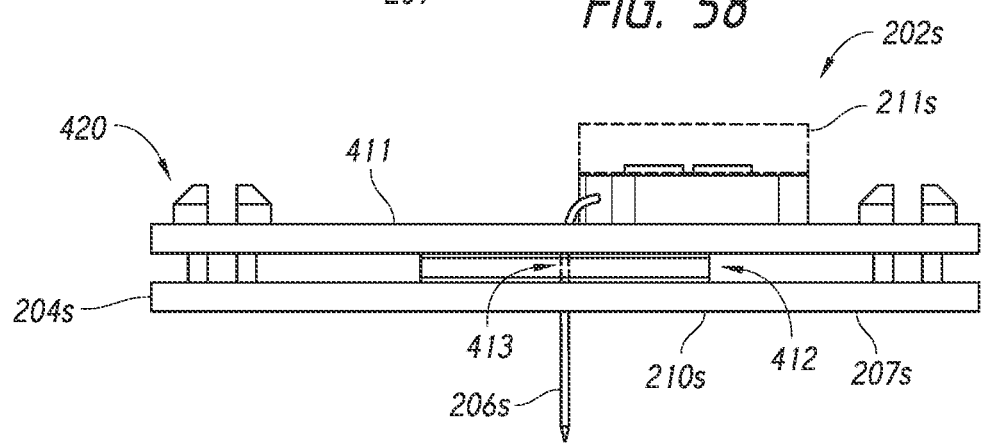
FIG. 59

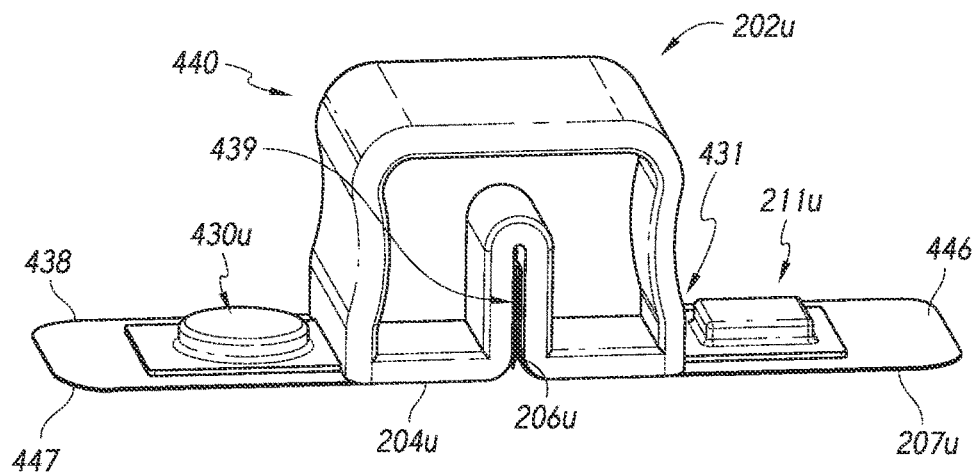
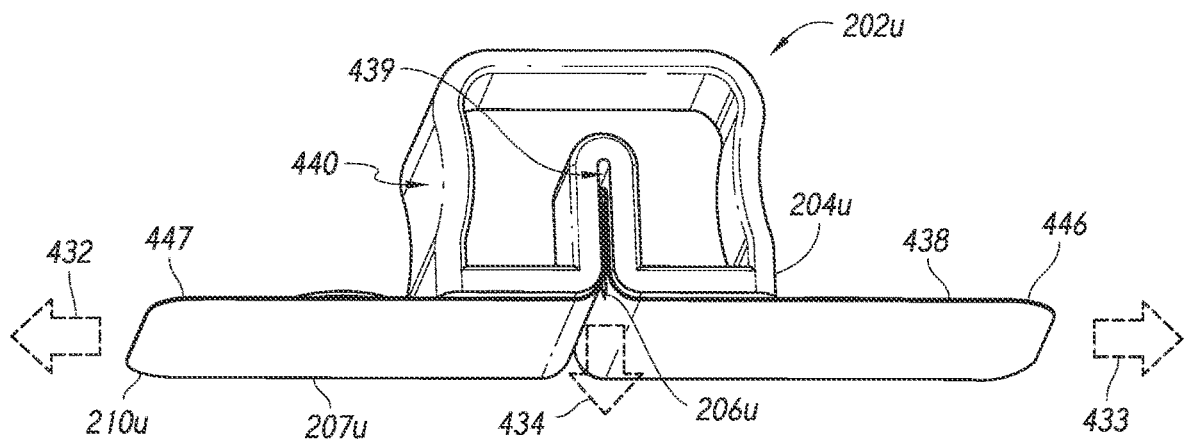
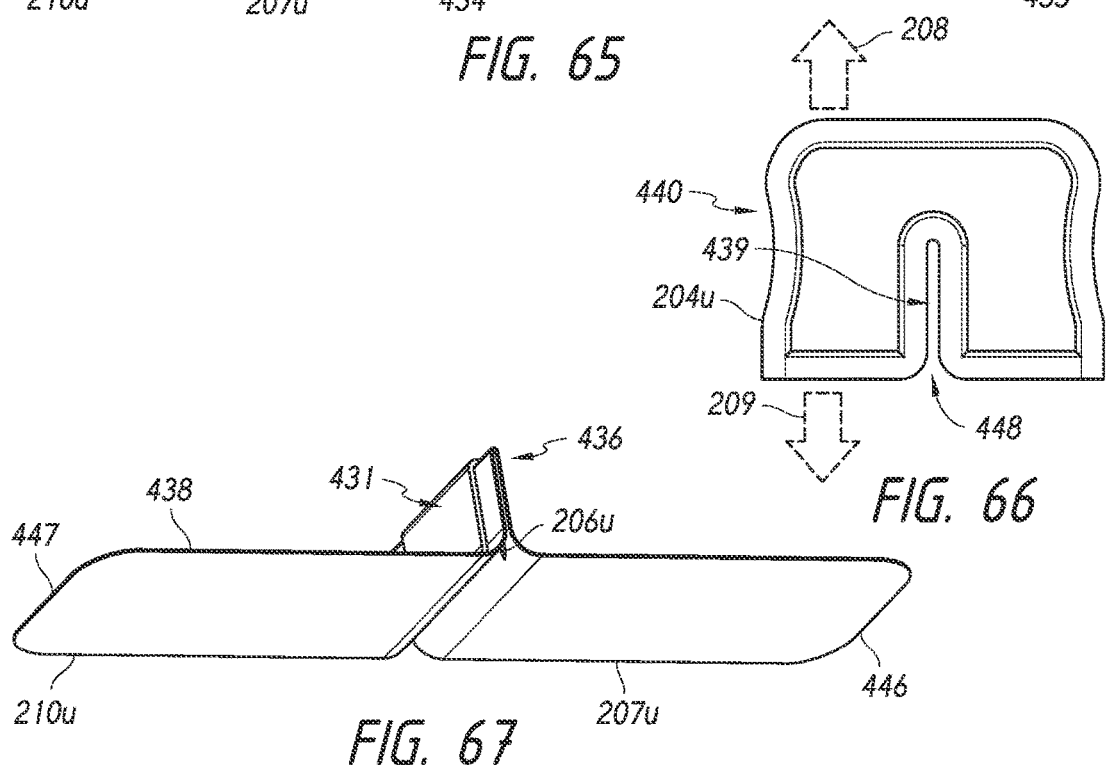

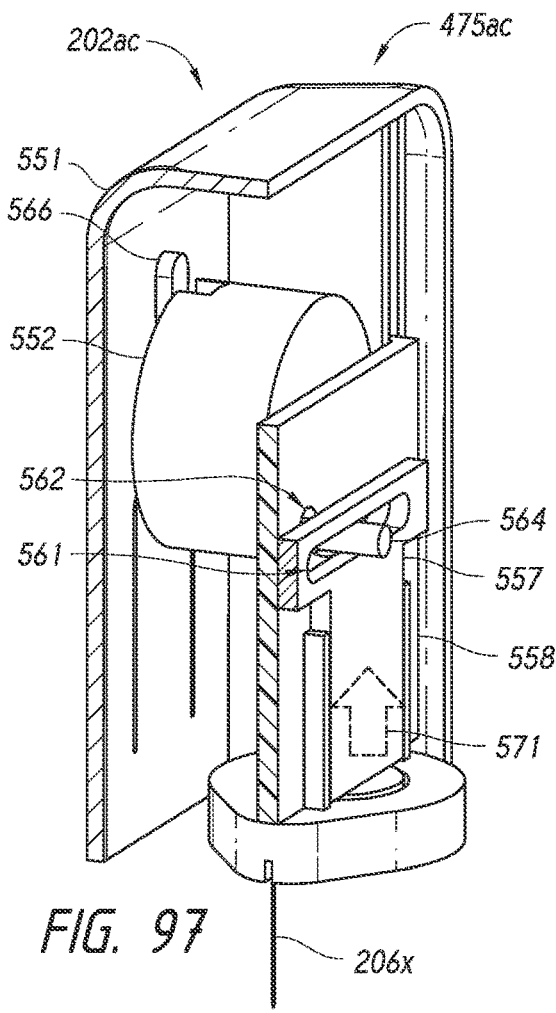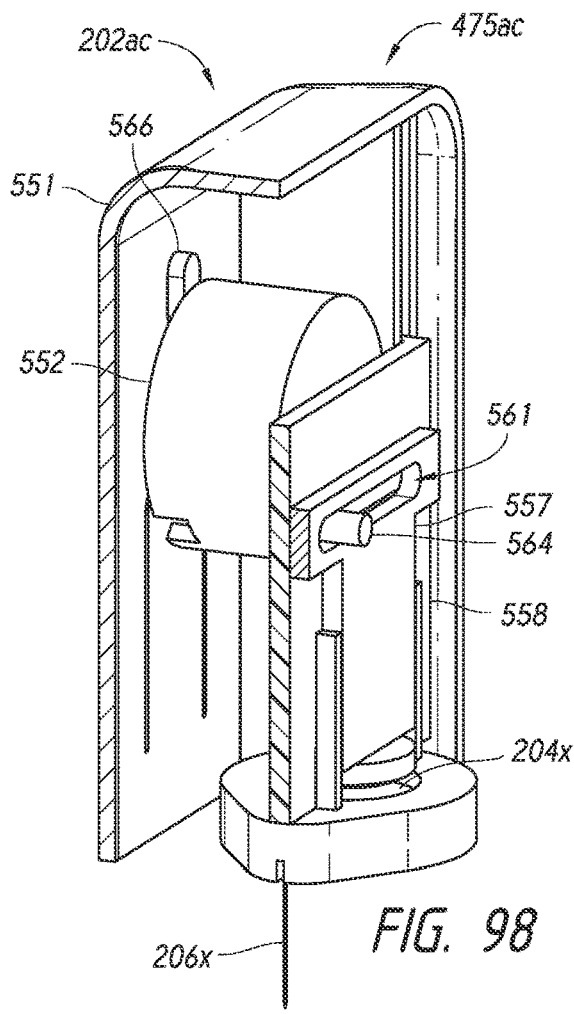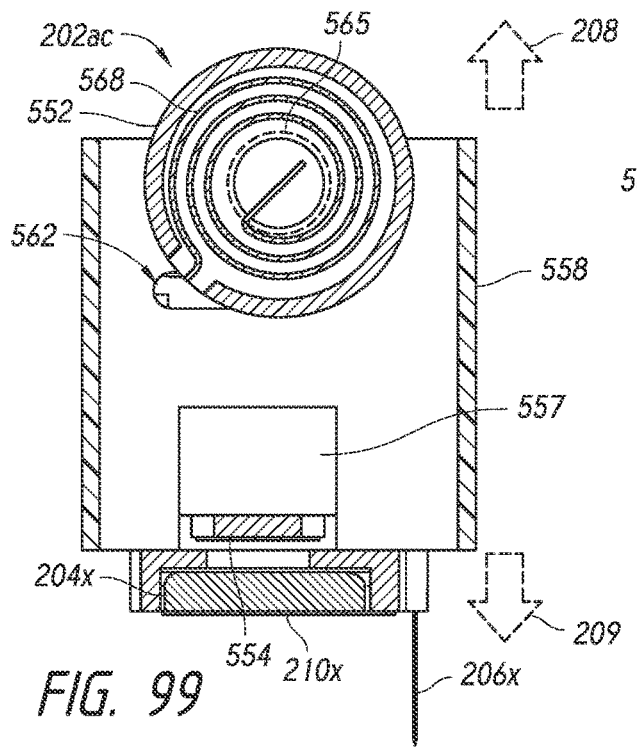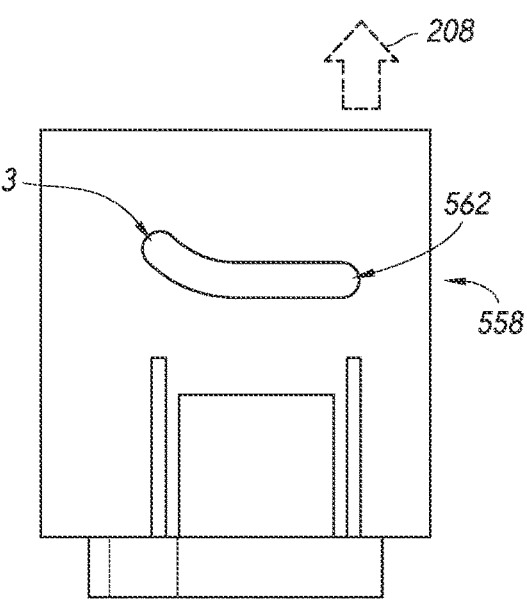

TRANSCUTANEOUS ANALYTE SENSOR SYSTEMS AND METHODS

INCORPORATION BY REFERENCE TO RELATED APPLICATION

Any and all priority claims identified in the Application Data Sheet, or any correction thereto, are hereby incorporated by reference under 37 CFR 1.57. This application is a continuation of U.S. application Ser. No. 15/798,249, filed Oct. 30, 2017, which is a continuation of U.S. application Ser. No. 15/798,064, filed Oct. 30, 2017, which claims the benefit of U.S. Provisional Application No. 62/415,419, filed Oct. 31, 2016. Each of the aforementioned applications is incorporated by reference herein in its entirety, and each is hereby expressly made a part of this specification.

BACKGROUND

Field

Various embodiments disclosed herein relate to measuring an analyte in a person. Certain embodiments relate to systems and methods for applying a transcutaneous analyte measurement system to a person.

Background

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which can cause an array of physiological derangements associated with the deterioration of small blood vessels, for example, kidney failure, skin ulcers, or bleeding into the vitreous of the eye. A hypoglycemic reaction (low blood sugar) can be induced by an inadvertent overdose of insulin, or after a normal dose of insulin or glucose-lowering agent accompanied by extraordinary exercise or insufficient food intake.

Conventionally, a person with diabetes carries a self-monitoring blood glucose monitor, which typically requires uncomfortable finger pricking methods. Due to the lack of comfort and convenience, a person with diabetes normally only measures his or her glucose levels two to four times per day. Unfortunately, such time intervals are so far spread apart that the person with diabetes likely finds out too late of a hyperglycemic or hypoglycemic condition, sometimes incurring dangerous side effects. Glucose levels may be alternatively monitored continuously by a sensor system including an on-skin sensor assembly. The sensor system may have a wireless transmitter which transmits measurement data to a receiver which can process and display information based on the measurements.

The process of applying the sensor to the person is important for such a system to be effective and user friendly. The application process can result in the sensor assembly being attached to the person in a state where it is capable of sensing glucose-level information, communicating the glucose-level information to the transmitter, and transmitting the glucose-level information to the receiver.

The analyte sensor can be placed at least partially into subcutaneous tissue. A user can actuate an applicator to insert the analyte sensor into its functional location. This transcutaneous insertion can lead to incomplete sensor insertion, improper sensor insertion, exposed needles, and/or unnecessary pain. Thus, in some cases it can be advantageous for systems that more reliably enable transcutaneous sensor insertion and removal while being easy to use and relatively pain-free.

SUMMARY

Various systems and methods described herein enable reliable, simple, and pain-minimizing transcutaneous insertion of analyte sensors. Some embodiments comprise an on-skin sensor assembly. Some embodiments comprise a system for applying an on-skin sensor assembly to a person's skin. The sensor can be an analyte sensor, a glucose sensor, any sensor described herein and/or incorporated by reference, and/or any other suitable sensor.

In some embodiments (i.e., optional and independently combinable with any of the aspects and embodiments identified herein), a sensor system for measuring an analyte concentration comprises a base having a distal side configured to face towards a skin of a host; a first adhesive coupled to the base and configured to couple the base to the skin; a transmitter coupled to the base and configured to transmit analyte measurement data; a transcutaneous analyte measurement sensor coupled to the base; and a collapsible support member configured to resist non-axial forces of the sensor, the collapsible support member comprises a channel, and a portion of the sensor passes through the channel, wherein the channel is configured to resist a buckling force of the sensor as the sensor moves from the proximal position to the distal position.

In some embodiments (i.e., optional and independently combinable with any of the aspects and embodiments identified herein), a sensor system for measuring an analyte concentration comprises a base having a distal side configured to face towards a skin of a host; a first adhesive coupled to the base and configured to couple the base to the skin; a transmitter coupled to the base and configured to transmit analyte measurement data; a transcutaneous analyte measurement sensor coupled to the base; and wherein the sensor is configured to be bent against the first adhesive or the base after removal of the base from the skin.

In some embodiments (i.e., optional and independently combinable with any of the aspects and embodiments identified herein), a sensor system for measuring an analyte concentration comprises a base having a distal side configured to face towards a skin of a host; a first adhesive coupled to the base and configured to couple the base to the skin; a transmitter coupled to the base and configured to transmit analyte measurement data; and/or a transcutaneous analyte measurement sensor coupled to the base.

In several embodiments (i.e., optional and independently combinable with any of the aspects and embodiments identified herein), the base is configured to retract a distal tip of the sensor into an interior area of the base. The system can comprise a spring (e.g., a helical spring, a conical spring, a compression spring, a tension spring, a leaf spring, a torsion spring) configured to retract the distal tip of the sensor into the interior area of the base.

In some embodiments, the system is configured to cover the distal tip of the sensor (e.g., after the sensor has been removed from the tissue).

In several embodiments, the system comprises a latch. The latch can comprise a locked state in which the latch couples the transmitter to the base. The latch can also comprise an unlocked state configured to enable removing the transmitter from the base.

In some embodiments, the sensor system is configured to retract at least a portion of the sensor into a receptacle in response to removing the sensor system from the skin. The sensor can comprise a retractable distal tip. The base can comprise an interior area configured to receive the distal tip in response to a retraction of the distal tip. The system can comprise a spring configured to retract the distal tip. The spring can be coupled to the base.

In several embodiments, the system comprises a first adhesive configured to couple the base to the skin. The system can comprise a second adhesive configured to bend and/or deflect a portion of the sensor against the base.

In some embodiments, the sensor comprises a section located distally relative to the base. The section can comprise a first portion and a second portion. The first portion of the sensor can be configured to facilitate maintaining the second portion in a straight configuration during insertion of the section into the skin. The first portion of the sensor can be configured to soften in response to being located in vivo.

In several embodiments, the first portion comprises a first buckling resistance prior to the insertion and a second buckling resistance after 12 hours to 48 hours of being located in vivo. The second buckling resistance can be less than the first buckling resistance. The second buckling resistance can be at least 30 percent less and/or at least 70 percent less than the first buckling resistance.

In some embodiments, the system comprises a pull tab system that includes a pull tab. The pull tab system can be configured to retract the sensor in response to moving the pull tab relative to the base.

In several embodiments, the pull tab system comprises a channel and an intermediate portion that couples the channel to the pull tab. The pull tab can protrude away from the base. A first portion of the sensor can pass through the channel. The pull tab system can be configured such that pulling the pull tab moves the channel to retract the sensor.

In some embodiments, the channel is formed by a hole, a slot, a hoop, a hook, a valley, and/or any suitable structure. The channel can be formed by a wall configured to push and/or pull the sensor. The channel can be open on one side to facilitate assembling the system (by enabling the sensor to be inserted into the channel through the open side).

In several embodiments, the base can comprise a second hole. A second portion of the sensor can pass through the second hole. The pull tab system can be configured such that pulling the pull tab retracts the sensor by pulling the second portion of the sensor out of the second hole and into an interior area of the sensor system.

In some embodiments, the pull tab system is slidably coupled to the base such that the pull tab system is configured to slide in a first direction that is within 20 degrees (e.g., within plus or minus 20 degrees) and/or within 45 degrees (e.g., within plus or minus 45 degrees) of being perpendicular to a proximal direction oriented away from the skin. (The pull tab system can be configured to slide in a direction that is within plus or minus 20 degrees and/or within plus or minus 45 degrees of being perpendicular to a distal direction oriented towards the skin.)

In several embodiments, the transmitter is slidably coupled to the base such that the transmitter is configured to slide in a second direction that is within plus or minus 20 degrees and/or within plus or minus 45 degrees of being perpendicular to the proximal direction. The second direction can be within plus or minus 20 degrees and/or within plus or minus 45 degrees of being parallel to the first direction.

In some embodiments, the system comprises a push button system having a push button. The push button system can be configured to retract the sensor in response to pushing the button. At least a portion of the push button system can protrude away from the base. The push button system can be configured such that pressing the portion of the push button system into the base engages a sensor retraction hoop or hook that pulls and/or pushes the sensor into an interior area of the sensor system.

In several embodiments, the push button system comprises a channel and an intermediate portion that couples the channel to the push button. The push button can protrude away from the base. A first portion of the sensor can pass through the channel. The push button system can be configured such that pushing the button moves the channel to retract the sensor.

In some embodiments, the channel is formed by a hole, a slot, and/or a hook. The channel can be formed by a wall configured to push and/or pull the sensor. The channel can be open on one side to facilitate assembling the system (by enabling the sensor to be inserted into the channel through the open side).

In several embodiments, the base comprises a second hole. A second portion of the sensor can pass through the second hole. The push button system can be configured such that pushing the button retracts the sensor by pulling the second portion of the sensor out of the second hole and into an interior area of the sensor system by making a third portion of the sensor form a U-shape.

In some embodiments, the push button system is slidably coupled to the base such that the push button system is configured to slide in a first direction that is within plus or minus 20 degrees and/or within plus or minus 45 degrees of being perpendicular to a proximal direction oriented away from the distal side of the base.

In several embodiments, the transmitter is slidably coupled to the base such that the transmitter is configured to slide in a second direction that is within plus or minus 20 degrees and/or within plus or minus 45 degrees of being perpendicular to the proximal direction. The second direction can be within plus or minus 20 degrees and/or within plus or minus 45 degrees of being parallel to the first direction.

In some embodiments, the system comprises a spring-loaded arm slidably coupled to the base such that removing the sensor system from the skin causes the sensor to automatically retract in response to the arm sliding relative to the base. The base can be configured to face towards the skin in a first direction. The arm can be configured to slide in a second direction that is within plus or minus 20 degrees and/or within plus or minus 45 degrees of perpendicular to the first direction. At least a portion of the sensor can pass through a portion of the arm such that moving the arm in the second direction causes the portion of the arm to retract the sensor into an interior area (e.g., a cavity) of the sensor system.

In several embodiments, the system comprises an independent or integrally molded spring and a releasable interlocking feature (such as a pin). The spring can be in at least one of a compressed state and an extended state (e.g., a stretched state) such that moving the interlocking feature (e.g., removing the release pin) causes the spring to move at least a first portion of the sensor into the base.

In some embodiments, the system comprises an arm slidably coupled to the base. The arm can comprise a first channel (e.g., formed by a hole, a slot, hoop, and/or a hook). The first channel can be aligned with a second hole of the base such that a second portion of the sensor passes through the first channel and the second hole. The spring can be at least one of compressed and extended (e.g., stretched)

between a first wall of the base and a second wall of the arm. The interlocking feature (e.g., the release pin) can pass through a third hole of the base and can interfere with a portion of the arm to prevent the spring from moving the arm to retract the sensor.

In several embodiments, the interlocking feature (e.g., the release pin) comprises a distal face having a second adhesive configured to be applied to the skin such that removing the base from the skin uncouples the first adhesive from the skin but does not uncouple the second adhesive from the skin, which causes the interlocking feature (e.g., the release pin) to be removed from the third hole, and thereby enables the spring to move the arm to retract the sensor. The first adhesive and the second adhesive can be two independent adhesive members or can be parts of one adhesive. The first and second adhesives can be coupled by a compliant adhesive backing member.

In some embodiments, the system comprises a spring-loaded arm slidably coupled to the base and configured such that removing the sensor system from the skin causes the arm to contact a first portion of the sensor and bend the sensor such that a second portion of the sensor is located between the arm and the base.

In several embodiments, the base is configured to face towards the skin in a first direction. The sensor system can comprise a spring oriented within plus or minus 20 degrees and/or within plus or minus 45 degrees of perpendicular to the first direction. The spring can be located in an interior area of the sensor system and can be configured to cause the arm to collide with the first portion of the sensor.

In some embodiments, the base is configured to face towards the skin in a first direction. The arm can be configured to slide in a second direction that is within plus or minus 20 degrees of perpendicular to the first direction such that the second portion of the sensor is oriented within plus or minus 20 degrees of perpendicular to the first direction.

In several embodiments, the sensor passes through a hole of the base. The first portion of the sensor can be located distally relative to the hole of the base. The arm can be spring-loaded towards the first portion of the sensor. The arm can comprise a protrusion that protrudes towards the first portion of the sensor such that sliding the arm causes the protrusion to collide with the first portion of the sensor and positions the protrusion directly distally relative to the hole of the base.

In some embodiments, the protrusion of the arm comprises a second adhesive configured to couple the arm to the skin such that the second adhesive holds the arm in a first position in which the arm does not bend the sensor. Uncoupling the second adhesive from the skin can cause the arm to the bend the sensor such that the second portion of the sensor is located between the arm and the base.

In several embodiments, the system comprises an arm rotatably coupled to the base by a hinge. The hinge can be configured such that uncoupling the base from the skin causes the hinge to rotate such that the arm bends at least a first portion of the sensor and covers at least a second portion of the sensor. The system can comprise a spring (e.g., a torsional spring) coupled to the arm such that the spring biases the arm in a rotational direction towards the second portion of the sensor.

In some embodiments, the hinge is located in an interior area of the sensor system. The arm can comprise a portion configured to cover the second portion of the sensor. The sensor system can comprise a first state in which the portion of the arm is located in the interior area and a second state in which the portion of the arm is located distally relative to the base.

In several embodiments, the sensor system comprises a first portion and a second portion. The second portion can be coupled to the first portion by a hinge configured such that increasing or decreasing a pivot angle between the first portion and the second portion retracts the sensor.

In some embodiments, the system comprises a spring (e.g., a helical spring, a compression spring, a tension spring, a leaf spring, a torsional spring). The spring can be configured to increase or decrease the pivot angle (e.g., once released by a triggering mechanism and/or any suitable mechanism).

In several embodiments, the hinge comprises a pin rotatably coupled to a sleeve configured to retain the pin as the second portion rotates relative to the first portion.

In some embodiments, the base comprises the first portion and the second portion. The first portion can couple the first adhesive to the second portion.

In several embodiments, the base comprises the first portion. The second portion can comprise the transmitter.

In some embodiments, a distal portion of the sensor passes through a hole of the base. A proximal portion of the sensor can be coupled to the second portion such that increasing or decreasing the pivot angle retracts the distal portion of the sensor through the hole of the base and into an area between the first and second portions of the sensor system.

In several embodiments, the base comprises a left half and a right half. The left half can comprise the hole of the base. The right half can comprise at least a portion of the hinge.

In some embodiments, the second portion comprises a lift tab configured to enable a user to grip a distally facing surface to rotate the second portion relative to the first portion. The lift tab can comprise a protrusion that protrudes away from the hinge.

In several embodiments, the base comprises a first portion and a second portion. The second portion of the base can be coupled to the first portion of the base by a hinge configured such that decreasing a pivot angle between the first and second portions of the base places a portion of the sensor between the first and second portions of the base. The hinge can comprise a first pin rotatably coupled to a first hole configured to retain the first pin as the first portion of the base rotates relative to the second portion of the base. The hinge can comprise a second pin rotatably coupled to a second hole configured to retain the second pin as the first portion of the base rotates relative to the second portion of the base. The first pin can protrude in a first direction. The second pin can protrude in a second direction that is opposite relative to the first direction.

In some embodiments, the first adhesive comprises a first section and a second section. The first section can be coupled to the first portion of the base such that the first section is configured to adhere the first portion of the base to the skin. The second section can be coupled to the second portion of the base such that the second section is configured to adhere the second portion of the base to the skin. The hinge can be configured to enable the first section of the first adhesive to face towards the second section of the first adhesive while the portion of the sensor is at least partially confined between the first and second portions of the base.

In several embodiments, the system is configured to bend and/or deflect the portion of the sensor in response to rotating the hinge. The portion of the sensor can be bent between the first and second portions of the base to guard against a distal tip of the sensor penetrating tissue after the sensor system is removed from the skin.

In some embodiments, the first portion of the base is rotationally spring-loaded relative to the second portion of the base such that the system is configured to decrease the pivot angle in response to a rotational spring bias. The system can comprise a torsional spring coupled to the hinge such that the torsional spring is configured to decrease the pivot angle to place the portion of the sensor between the first and second portions of the base.

In some embodiments, the system comprises an adhesive portion configured to bend at least a portion of the sensor towards the base. A distal tip of the sensor can be located between the base and the adhesive portion. The system can comprise an adhesive portion configured to collapse at least a portion of the sensor against the base.

In several embodiments, the system comprises a pliable sheet that covers a distal tip of the sensor and adheres to the first adhesive such that the pliable sheet guards against the distal tip of the sensor penetrating tissue after the sensor system is removed from the skin.

In some embodiments, the first adhesive couples the pliable sheet to the base. The pliable sheet can comprise a first state in which the pliable sheet is folded, is located proximally relative to the distal tip, does not cover the distal tip, and forms a tab configured to enable a user to unfold the pliable sheet.

In several embodiments, the pliable sheet comprises a second state in which the pliable sheet is at least partially unfolded relative to the first state, is at least partially located distally relative to the distal tip, and the distal tip of the sensor is at least partially confined between the pliable sheet and the first adhesive.

In some embodiments, the system comprises a second sheet having a second puncture resistance that is greater than a first puncture resistance of the pliable sheet. The second sheet can be located between the distal tip and the pliable sheet to protect the pliable sheet from being punctured by the distal tip. The second sheet can be coupled to the pliable sheet such that the second sheet deforms the distal tip as the pliable sheet is folded over the distal tip.

In some embodiments, a distal tip of the sensor is at least partially confined between a pliable sheet and the base such that the pliable sheet holds at least a portion of the sensor in a bent position and the pliable sheet is adhered to the first adhesive.

In some embodiments, the pliable sheet comprises a first state and a second state. In the first state, the pliable sheet can be located proximally relative to the first adhesive when the sensor system is coupled to the skin. In the second state, the pliable sheet can be located distally relative to the first adhesive when the distal tip of the sensor is at least partially confined between the pliable sheet and the base.

In several embodiments, a distal side of the base comprises a slot configured to receive a distal end of the sensor after the sensor is removed from the host. A first portion of the sensor can be bent and/or deflected such that the distal end of the sensor is located in the slot. Once the sensor is bent, the distal end of the sensor can be located proximally relative to the first adhesive.

In several embodiments, the base comprises a channel (e.g., a hole). A second portion of the sensor can pass through the hole. The slot can be directly coupled to the hole (e.g., such that the hole and the slot are in fluid communication). The slot can be oriented within plus or minus twenty degrees of perpendicular a central axis of the hole.

In some embodiments, the sensor system comprises a first portion and a second portion. The first portion can couple the first adhesive to the second portion. The second portion can be rotatably coupled to the first portion about an axis of rotation that is within plus or minus twenty degrees of being parallel to a proximal direction such that the sensor system is configured to retract the sensor in response to rotating the second portion relative to the first portion. The base can comprise the first portion. The second portion can comprise the transmitter.

In several embodiments, the system comprises an interior area between the first portion and the second portion. The interior area can be configured such that spinning the second portion relative to the first portion moves the interior area relative to at least one of the first portion and the second portion. The interior area can be configured such that spinning the second portion relative to the first portion retracts at least a portion of the sensor through a hole in the base and into the interior area.

In some embodiments, the base comprises a distally facing hole. The sensor can comprise a proximal portion coupled to the second portion and a distal portion that passes through the hole in the base.

In several embodiments, the system comprises a proximally facing indentation configured to provide traction for a user to rotate the second portion relative to the first portion. The system can comprise a proximal protrusion configured to provide traction for a user to rotate the second portion relative to the first portion.

In some embodiments, the system comprises an extendable cover having a first state configured to enable a distal end of the sensor to enter the host and having a second state configured to cover the distal end of the sensor after the sensor is removed from the host. The first state can be a contracted state. The second state can be an extended state.

In several embodiments, the cover is a pliable sheath having a channel in which a portion of the sensor is located. The cover can be rolled up along the channel.

In some embodiments, the extended state is a relaxed state such that the cover is configured to unroll from the retracted state in response to the sensor system being removed from the host.

In several embodiments, the retracted state has a higher stored mechanical energy than the extended state such that the cover is configured to unroll from the retracted state in response to the sensor system being removed from the host.

In some embodiments, the cover comprises bellows (e.g., a pleated expandable portion) configured to at least partially unfold to enable the cover to move from the retracted state to the extended state. The pleated expandable portion can comprise a channel in which a first portion of the sensor is located. The expandable portion can comprise a pleated collapsible portion. The cover can comprise a distal hole through which a second portion of the sensor passes in the retracted state.

In several embodiments, the retracted state has a higher stored mechanical energy than the extended state such that the pleated expandable portion is configured to expand from the retracted state in response to the sensor system being removed from the host.

In some embodiments, the system comprises a cap that covers a distal end of the sensor such that the cap is configured to prevent the distal end from penetrating a person after the sensor system is removed from the host and the cap is coupled to the distal side of the base.

In several embodiments, the cap comprises a channel and/or a cavity having a first central axis. The base can comprise a hole having a second central axis. A portion of the sensor can pass through the hole and into a channel. The first central axis can be within twenty degrees of parallel to the second central axis. The first central axis of the channel can pass through the hole of the base (e.g., as the first central axis extends beyond a proximal end of the channel).

In some embodiments, the system comprises a cap coupled to the base. The cap can cover at least a majority of the first adhesive. The cap can cover a distal end of the sensor such that the cap is configured to prevent the distal end from penetrating a person after the sensor system is removed from the host and the cap is coupled to the base. The cap can comprise sidewalls that protrude proximally past at least a portion of an outer perimeter of the sensor system (and/or past at least a portion of an outer perimeter of the base).

In several embodiments, the system comprises a sensor cover having an interior area and a protrusion. At least a portion of the base can be located in the interior area of the sensor cover such that a distal end of the sensor is located between the base and the sensor cover. The protrusion can be located in a hole of the base such that the protrusion unlatches the transmitter from the base.

In some embodiments, the system comprises a sensor cover configured to unlock the transmitter from the base in response to coupling the base to the sensor cover. The sensor cover can be configured to enable uncoupling the transmitter from the base in response to coupling the base to the sensor cover (e.g., by unlatching the transmitter from the base). The transmitter can be configured to be uncoupled from the base once the transmitter is unlocked from the base.

In several embodiments, the system comprises a first flex arm and a wall. The first flex arm can comprise a first state in which the first flex arm interferes with the wall to lock the transmitter to the base.

In some embodiments, the sensor cover comprises a protrusion configured such that coupling the base to the sensor cover causes the protrusion to move the first flex arm to a second state in which the first flex arm does not interfere with the wall such that the first flex arm does not lock the transmitter to the base.

In several embodiments, the base comprises a hole through which at least a portion of the protrusion passes to deflect the first flex arm to the second state.

In several embodiments, the sensor cover comprises a housing and a second flex arm. The housing can comprise an interior area. At least a portion of the base can be located inside the interior area of the housing. The second flex arm can couple the protrusion to the housing such that the second flex arm is configured to bend to move the protrusion to facilitate inserting the portion of the base into the interior area of the housing.

In some embodiments, the second flex arm is configured to move in a distal direction in response to coupling the base to the sensor cover. The first flex arm can be configured to move in a proximal direction in response to coupling the base to the sensor cover. A portion of the sensor can be bent in response to coupling the base to the sensor cover such that a distal end of the sensor is located between the base and the sensor cover.

In several embodiments, the sensor cover comprises a first side and a second side. The first side can be oriented within plus or minus thirty degrees of perpendicular to the second side. The first side can comprise a first hole through which the portion of the base is inserted. The second side can comprise a second hole configured to provide access to a proximal surface of the transmitter to facilitate removing the transmitter from the base.

In some embodiments, the system comprises a rail. The rail can slidably couple the base to the transmitter.

In several embodiments, the system comprises a sensor cover configured to unlatch the transmitter from the base in response to coupling the base to the sensor cover. The system can comprise a first flex arm configured to latch the base to the transmitter. The sensor cover can comprise a second flex arm configured to deflect the first flex arm to unlatch the transmitter from the base.

In some embodiments, the sensor cover comprises a distally facing wall. At least a portion coupled to the base (e.g., a proximal side of the base) can be pressed against the distally facing wall such that a protrusion of the second flex arm is pressed into a hole of the base to deflect the first flex arm.

In several embodiments, the system comprises a telescoping assembly coupled to the base. At least a first portion of the sensor can be located between a portion of the telescoping assembly and a distal side of the base such that the telescoping assembly is configured to move from a distal position to a proximal position to retract a second portion of the sensor into a protective cavity of the system.

In some embodiments, the base comprises an interior channel having a proximally facing opening. The telescoping assembly can be located at least partially in the interior channel such that the telescoping assembly is configured to move proximally at least partially in the interior channel from the distal position to the proximal position.

In several embodiments, when the telescoping assembly is in the distal position, the first portion of the sensor can be located in the interior channel of the base, and the second portion of the sensor can be located distally relative to the base. When the telescoping assembly is in the proximal position, the first and second portions of the sensor can be located in the interior channel of the base.

In some embodiments, the telescoping assembly comprises a first section and a second section. The first section can be slidably coupled to the second section. The second section can be slidably coupled to an interior channel of the base such that the telescoping assembly is configured to telescope relative to the base to retract the sensor.

In several embodiments, the interior channel comprises a first overhang (which can be oriented radially inward). The first overhang can be configured to interfere with a second overhang (which can be oriented radially outward) of the second section to retain at least a portion of the second section within the interior channel.

In some embodiments, the second section comprises a third overhang (which can be oriented radially inward). The third overhang can be configured to interfere with a fourth overhang (which can be oriented radially outward) of the first section to limit a distance the first section can move proximally relative to the second section.

In several embodiments, the system comprises a spring and a locking mechanism. The locking mechanism can be configured to lock the telescoping assembly in the distal position. The locking mechanism can comprise a first overhang of the base and a second overhang of the first section. The first and second overhangs can be configured such that in a first angular position of the first section relative to the base, the first overhang interferes with the second overhang to limit proximal travel of the first section relative to the base. In some embodiments, in a second angular position of the first section relative to the base, the first overhang does not limit the proximal travel of the first section relative to the base such that the spring pushes the telescoping assembly to the proximal position.

In some embodiments, the base comprises a first overhang configured to limit a first proximal travel of the second section relative to the base. The base can comprise a second overhang configured to impede proximal movement of the first section such that the telescoping assembly is held in the distal position.

In several embodiments, the base comprises a first channel. The second section can comprise a radially outward protrusion located in the first channel such that the first channel limits a first angular movement of the second section relative to the base, while the second section permits a second angular movement of the first section relative to the second section and relative to the base.

In some embodiments, the sensor comprises a deformable connection that communicatively couples (and/or electrically couples) a subcutaneous portion of the sensor to a connection portion of the sensor. The connection portion of the sensor can be located inside the base and can communicatively couple the subcutaneous portion of the sensor to a communication module of the sensor system.

In several embodiments, in the proximal position, the subcutaneous portion of the sensor can be located within a center region of a coil (e.g., a deformable connection) of the sensor. In many embodiments, the deformable connection is configured such that the subcutaneous portion of the sensor is not located in a center region of the deformable connection.

In some embodiments, the deformable connection of the sensor does not apply a biasing force. In several embodiments, the coil of the sensor can apply a biasing force to push the telescoping assembly to the proximal position. In many embodiments, a spring applies a biasing force.

In several embodiments, the system comprises a housing slidably coupled to the base. The housing can move proximally relative to the base to retract the sensor.

In some embodiments, at least a first portion of the sensor is located between a portion of the housing and a distal side of the base such that the housing is configured to move from a distal position to a proximal position to retract a second portion of the sensor.

In several embodiments, the base comprises an interior channel having a proximally facing opening. The housing can be located at least partially in the interior channel such that the housing is configured to move proximally at least partially in the interior channel from the distal position to the proximal position to retract the second portion of the sensor into the interior channel.

In some embodiments, the system comprises a cap coupled to the base and located proximally relative to the base. A first portion of the sensor can be coupled to the cap. The system can be configured such that moving the cap proximally relative to the base retracts the sensor.

In several embodiments, the cap is movable between a distal position and a proximal position. In the distal position, a second portion of the sensor can be located distally relative to the base. In the proximal position, the second portion of the sensor can be located proximally relative to the base. An interlock can removably secure the cap in the distal position.

In some embodiments, at least a portion of an outer perimeter of the cap protrudes farther radially outward (relative to a central axis of the second portion) than the base such that the outer portion of the outer perimeter provides a distally facing wall to enable a user to grip the cap as the user moves the cap from the distal position to the proximal position.

In several embodiments, the system comprises a linkage between the cap and the base. The linkage can be configured to limit a distance that the cap can move proximally relative to the base.

In some embodiments, the linkage comprises a pleated expandable portion that is collapsible and is configured to at least partially unfold to enable the cap to move from the distal position to the proximal position to retract the second portion of the sensor into the pleated expandable portion. The cap can be rigidly coupled to the transmitter such that moving the transmitter retracts the sensor proximally.

In several embodiments, a sensor system is configured to measure an analyte indication. A sensor system can comprise a base having a distal side configured to face towards a skin of a host; a first adhesive coupled to the base and configured to couple the base to the skin; a transmitter coupled to the base and configured to transmit analyte measurement data; and/or a transcutaneous analyte measurement sensor coupled to the base.

In some embodiments, the system comprises a collapsible support member configured to resist non-axial forces of the sensor. The collapsible support member can comprise a proximal end, a distal end, and a length measured from the proximal end to the distal end. The system can be configured to reduce the length in response to moving the sensor from a proximal position to a distal position.

In several embodiments, a collapsible support member comprises a channel. At least a portion of the sensor can pass through the channel. The channel can be configured to resist a buckling force of the sensor as the sensor moves from the proximal position to the distal position.

In some embodiments, the collapsible support member comprises a foam block having a channel. At least a portion of the sensor can pass through the channel.

In several embodiments, the collapsible support member comprises bellows having a channel. A portion of the sensor passes through the channel.

In some embodiments, the system comprises a tab coupled to the collapsible support member. The system can be configured such that actuating (e.g., pulling, pushing, moving, pressing) the tab causes the collapsible support member to collapse and causes at least a portion of the sensor to move distally relative to the base.

In several embodiments, the system comprises a foam portion (e.g., a foam block) coupled to the base and a channel mechanically supported by the foam portion. At least a portion of the sensor can be located in the channel. The portion of the sensor can comprise a central axis. The channel can be configured to resist lateral displacement of the portion of the sensor relative to the central axis. The foam portion can be configured to compress in response to the system moving the sensor from a proximal position (e.g., a proximal starting position) to a distal position (e.g., a distal ending position).

In some embodiments, the base comprises a distal portion and a proximal portion. The system can comprise a channel having walls configured to compress in response to the system moving the sensor from a proximal position to a distal position. The channel can be located at least partially between the distal portion and the proximal portion of the base such that a portion of the sensor is located in the channel. The walls of the channel can be configured to resist lateral displacement of the portion of the sensor.

In several embodiments, the walls comprise foam configured to compress in response to moving the proximal portion distally towards the distal portion of the base. The walls can be made from collapsible structures and/or compressible materials other than foam.

In some embodiments, the walls comprise a proximal section having a first material, an intermediate section having a second material, and a distal section having a third material. The second material can be more rigid than the first and third materials such that the intermediate section is configured to resist the lateral displacement. The second material can be stiffer than the first and third materials such that the intermediate section is configured to resist the lateral displacement. The second material can be less compressible than the first and third materials.

In several embodiments, the system comprises an interlock (e.g., a mechanical interlock) configured to secure the proximal portion of the base to the distal portion of the base in response to the system moving the sensor from the proximal position to the distal position.

In some embodiments, the system comprises bellows coupled to the base. At least a portion of the sensor can be located in an interior area of the bellows. The portion of the sensor can comprise a central axis. The bellows can be configured to resist lateral displacement of the portion relative to the central axis. The bellows can be configured to compress in response to the system moving the sensor from a proximal position to a distal position.

In several embodiments, the system comprises an interlock coupled to the base and configured to secure the bellows in a compressed state. The interlock can be a snap fit formed by an undercut.

In some embodiments, the system comprises a distal portion of the base and a proximal portion. The bellows can couple the distal portion to the proximal portion. The system can comprise a removable interference member (e.g., a safety member) located between the distal portion and the proximal portion such that the removable interference member is configured to block the system from moving the sensor from the proximal position (e.g., a proximal starting position) to the distal position (e.g., a distal ending position).

In several embodiments, the system comprises a pull tab and a slot configured such that at least a portion of the sensor is located in the slot. The system can be configured such that pulling the pull tab causes the system to move the sensor from a proximal position to a distal position In some embodiments, the system comprises a compliant sheet located in the slot and coupled to the pull tab such that the compliant sheet is configured to move (e.g., push, pull) the portion of the sensor distally in response to actuating (e.g., pulling) the pull tab.

In several embodiments, the system comprises a housing coupled to the base. The housing can comprise the slot and can be configured to cause the compliant sheet to push the portion of the sensor distally in response to pulling the pull tab. The slot can comprise a distally facing opening configured to allow the portion of the sensor to exit the slot distally and enter subcutaneous tissue of the host.

In some embodiments, a system comprises a guide member configured to resist non-axial forces of the sensor. The guide member can comprise an engagement feature releasably coupled to the sensor. The engagement feature can be configured to uncouple from the sensor in response to moving the sensor from a proximal position to a distal position.

In several embodiments, a guide member comprises a first portion and a second portion. At least a portion of the sensor can be located between the first and second portions of the guide member such that the first and second portions of the guide member are configured to resist a buckling force of the sensor.

In some embodiments, the first portion can be configured to move relative to the second portion of the guide member in response to the system moving the sensor from a proximal position to a distal position. The guide member can be configured such that displacement of the first portion relative to the second portion permits moving the sensor from the proximal position to the distal position.

In several embodiments, the portion of the sensor (that is located between the first and second portions of the guide member) comprises a central axis. The first and second portions of the guide member can form a channel. The portion of the sensor can be located in the channel. The channel can be configured to resist displacement of the portion of the sensor in a direction perpendicular to the central axis.

In some embodiments, the system comprises a channel having a first side and a second side configured to at least partially separate in response to the system moving the sensor from a proximal position to a distal position. A portion of the sensor can be located in the channel such that the channel is configured to at least partially separate to permit the sensor to move from the proximal position to the distal position. The portion of the sensor can comprise a central axis. The channel can be configured to resist displacement of the portion of the sensor in a direction perpendicular to the central axis.

In several embodiments, a sensor is coupled to a housing that is slidably coupled to the base. The system can be configured to move a portion of the sensor away from the distal side of the base in response to moving the housing in a first direction within plus or minus 20 degrees and/or within plus or minus 45 degrees of perpendicular to a distal direction.

In some embodiments, the system comprises a housing slidably coupled to the base. The base can comprise a curved channel and/or a channel oriented at an angle within plus or minus 45 degrees of parallel to a distal direction. A portion of the sensor can be located in the channel. The channel can be configured to deflect the portion of the sensor to redirect the portion distally in response to moving the housing relative to the base.

In several embodiments, a sensor path has a first section and a second section. The first section can be oriented within plus or minus 20 degrees of perpendicular to a distal direction and/or within plus or minus 45 degrees of perpendicular to a distal direction. The second section can be oriented within plus or minus 45 degrees of parallel to the distal direction. The system can be configured to deflect the sensor to cause the sensor to follow the sensor path such that the channel redirects the sensor towards the skin of the host.

In some embodiments, the base comprises a first portion and a second portion. The first portion can be configured to couple the second portion to the skin. The second portion can be slidably coupled to the first portion. The base can be configured such that moving the second portion in a first direction within plus or minus 20 degrees of perpendicular to a distal direction (and/or within plus or minus 45 degrees of perpendicular to a distal direction) causes a distal tip of the sensor to move in a second direction within plus or minus 45 degrees of parallel to the distal direction.

In several embodiments, the sensor comprises a distal section and a proximal section. The proximal section can be rigidly coupled to the second portion of the base. The distal section can pass through a channel of the first portion of the base. The channel can comprise a radius configured to deflect at least a portion of the sensor such that the portion of the sensor is redirected distally towards the skin of the host.

In some embodiments, the sensor is a glucose sensor and/or any type of sensor described herein and/or incorporated by reference. The transmitter can be coupled to the second portion of the base such that the second portion slidably couples the transmitter to the first portion of the base. The system can comprise at least one rail that slidably couples the second portion to the first portion of the base.

In several embodiments, the system comprises a removable applicator coupled to the base. The applicator can be any type of applicator described herein and/or incorporated by reference.

In some embodiments, the applicator comprises a curved channel configured to guide a portion of the sensor along a curved path as the portion of the sensor moves from a proximal position to a distal position. The applicator can comprise a leaf spring configured to drive the portion of the sensor along the curved path through the curved channel.

In several embodiments, a curved channel is coupled to the base. A curved portion of the sensor can be located in the curved channel. The curved channel can be configured to resist buckling forces of the curved portion as the system moves the curved portion from a proximal position to a distal position. The applicator can be configured to facilitate moving the curved portion from the proximal position to the distal position.

In some embodiments, the system comprises a spring configured to move the curved portion from the proximal position to the distal position. The spring can be any type of spring described herein and/or incorporated by reference. The spring can be a leaf spring in a flexed state.

In several embodiments, the system comprises an interlock (e.g., a mechanical interlock) configured to releasably hold the spring (e.g., a leaf spring) in a flexed state. The system can be configured to move the curved portion from the proximal position to the distal position in response to releasing the interlock. The system can comprise a tab (e.g., a pull tab) coupled to the interlock such the system is configured to disengage the interlock to enable the spring to move the curved portion from the proximal position to the distal position in response to actuating (e.g., pulling) the tab.

In some embodiments, the system comprises a first arm and a wall coupled to the base. A portion of the sensor can be secured between the first arm and the wall such that the first arm is configured to resist buckling forces of the sensor as the system moves the portion of the sensor from a proximal position to a distal position.

In several embodiments, the first arm is movably coupled to the base such that at least a portion of the first arm is configured to move (e.g., relative to the base, relative to an applicator housing) to enable the system to move the portion of the sensor from the proximal position to the distal position.

In some embodiments, at least one of the first arm and the wall form a channel. The portion of the sensor can be at least partially located in the channel such that the channel is configured to resist the buckling forces. The system can comprise a distal protrusion configured to move the first arm away from the wall to enable the system to move the portion of the sensor from the proximal position to the distal position. The portion of the sensor can comprise a central axis. The first arm can protrude in a direction within plus or minus 45 degrees of perpendicular to the central axis.

In several embodiments, the system comprises a removable applicator having a telescoping assembly that is removably coupled to the base. The telescoping assembly can comprise a first set of tongs configured to resist a first buckling force of a first section of the sensor.

In some embodiments, the telescoping assembly comprises a second set of tongs configured to resist a second buckling force of a second section of the sensor. The telescoping assembly can comprise a distal protrusion configured to move distally into a first area between the first set of tongs and into a second area between the second set of tongs to expand the first and second sets of tongs.

In several embodiments, the system comprises a removable applicator coupled to the base. The applicator can have a pair of biasing members (e.g., a set of tongs). A portion of the sensor can be located in an area between the pair of biasing members such that the pair of biasing members is configured to resist buckling forces of the sensor.

In some embodiments, the pair of biasing members is held in a compressed state by a channel configured to enable the pair of biasing members to expand in response to moving the pair of biasing members far enough distally that a distal end of the sensor is located distally relative to the distal side of the applicator. The pair of biasing members can be a set of tongs.

In several embodiments, the system comprises a first arm and a second arm that extend distally. A portion of the sensor can be located between the first and second arms such that the first and second arms are configured to resist buckling forces of the sensor. The first and second arms can be located in a channel of the system. The channel can hold the first and second arms in a compressed state. The channel can be configured such that moving the first and second arms distally causes the first and second arms to spread apart from each other to facilitate the system moving the portion of the sensor from a proximal position to a distal position.

In some embodiments, the system comprises a first arm and a second arm that extend distally. The first and second arms can be configured to have a closed state in which the first and second arms resist buckling forces of a portion of the sensor located between the first and second arms. The first and second arms can be configured to have an open state to enable the system to move the portion of the sensor from a proximal position to a distal position.

In several embodiments, the system comprises a tube coupled to the base. The tube can comprise a slot from a proximal portion of the tube to a distal portion of the tube. The tube can be configured to resist buckling forces of the sensor. The slot can be configured to enable moving a first portion of the sensor distally outside of the tube while moving a second portion of the sensor distally inside the tube.

In some embodiments, the system comprises a removable applicator coupled to the base. The applicator can couple the tube to the base such that the system is configured to move the base distally relative to the tube to pierce the skin with a distal end of the sensor. The tube can comprise a first side of the slot and a second side of the slot. The first and second sides of the slot can be coupled together by a linkage configured to break open in response to moving the first portion of the sensor distally. The tube can be at least 4 millimeters long as measured along a central axis of the tube.

In several embodiments, the system comprises an applicator having a channel configured to resist buckling forces of the sensor. A distal portion of the sensor can be located inside the channel. A proximal portion of the sensor can be located outside the channel. An intermediate portion of the sensor can couple the distal and proximal portions of the sensor. The intermediate portion of the sensor can be located in a slot of the channel.

In some embodiments, the slot is configured to enable the intermediate portion of the sensor to move distally through the slot as the sensor moves from a proximal position to a distal position. The channel can comprise a central axis oriented distally such that the channel is configured to guide the distal portion of the sensor towards the skin. The slot can be oriented radially outward from the central axis.

In several embodiments, the slot comprises at least one linkage that couples a first side of the slot to a second side of the slot. The at least one linkage can be configured to break in response to moving the intermediate portion of the sensor distally through the slot.

In some embodiments, the slot is configured to expand (e.g., widen) in response to moving the intermediate portion of the sensor distally through the slot.

In some embodiments, a telescoping assembly is coupled to the base. The telescoping assembly can comprise a distal portion, a proximal portion slidably coupled to the distal portion, and a spring compressed between the proximal portion and the base. The proximal portion can releasably secure the sensor in a first proximal starting position such that the spring is configured to push the base and the sensor distally in response to the system unlatching the base from the proximal portion.

In several embodiments, the proximal portion of the telescoping assembly comprises a latch configured to releasably secure the base in a second proximal starting position. The latch can be configured to release the base in response to moving the proximal portion distally relative to the distal portion to enable the spring to push the base and the sensor distally.

In some embodiments, the sensor is configured to move along a first path from the first proximal starting position to a first distal ending position. The proximal portion can be configured to move along a second path from a third proximal starting position to a third distal ending position. The first path of the sensor can be at least 40 percent longer than the second path of the proximal portion.

In several embodiments, the system is configured to cause the sensor to move a first distance in response to the proximal portion moving a second distance that is at least 50 percent shorter than the first distance.

In some embodiments, the proximal portion comprises a distally protruding arm having an inward protrusion that passes through a hole of the distal portion. The inward protrusion can be coupled to the base to secure the sensor in the first proximal starting position.

In several embodiments, the system is configured such that moving the proximal portion distally relative to the distal portion causes the distally protruding arm to flex outward to release the inward protrusion from the base to enable the spring to push at least a portion of the sensor into the skin.

In some embodiments, the system is configured to move the sensor a first distance in response to moving the proximal portion a second distance to unlatch the base. The first distance can be at least twice as long as the second distance such that the system is configured to magnify a first movement of the proximal portion into a larger second movement of the sensor and/or the base. The distal portion can comprise a channel configured to orient the base as the spring pushes the base distally.

In several embodiments, a first housing is rotatably coupled to the base. A spring can be compressed between a portion of the first housing and the sensor. The system can be configured to unlatch the sensor from the first housing to enable the spring to move the sensor distally in response to rotating the first housing relative to the base.

In some embodiments, the first housing comprises a first central axis (e.g., a rotational axis of the first housing). The sensor can comprise a portion configured to pierce the skin. The portion can comprise a second central axis. The first central axis can be oriented within plus or minus twenty degrees of parallel to the second central axis.

In several embodiments, the spring is a helical spring and/or a conical spring configured to expand distally to move the sensor distally. A first housing can be rotatably coupled to the base. A second housing can be coupled to the sensor. A spring can be compressed between a proximal end of the first housing and the sensor such that the spring is configured to push the second housing and the sensor distally relative to the base and the first housing in response to rotating the first housing relative to the base.

In some embodiments, the second housing is located in an interior area of the first housing. The first adhesive can be configured to secure the base to the skin to enable the first housing to rotate relative to the base and relative to the second housing.

In several embodiments, the first housing comprises a first central axis (e.g., a rotational axis). The sensor can comprise a portion configured to pierce the skin. The portion can comprise a second central axis. The first central axis can be oriented within plus or minus ten degrees of parallel to the second central axis.

In some embodiments, the spring is a conical spring configured to expand in response to rotating the first housing relative to the base. The system can comprise a mechanical interlock between the first housing and the second housing. The mechanical interlock can be configured to releasably hold the spring in a compressed state such that the sensor is in a proximal starting position. The mechanical interlock can comprise a first protrusion of the first housing that interferes with distal movement of a second protrusion of the second housing.

In several embodiments, the mechanical interlock is configured such that rotating the first protrusion relative to the second protrusion causes the second protrusion to fall distally off the first protrusion and thereby enables the second housing to move distally relative to the first housing. The first protrusion can be oriented radially outward, and the second protrusion can be oriented radially inward. The first protrusion can be oriented radially inward, and the second protrusion can be oriented radially outward. The mechanical interlock can comprise a ridge and a groove configured such that rotating the first housing relative to the base requires overcoming a torque threshold to move the ridge out of the groove.

In some embodiments, the system comprises an interface between the second housing and the base. The interface can comprise a ridge located in a groove configured to limit rotation of the second housing relative to the base during rotation of the first housing relative to the base. The interface can be oriented from a proximal portion of the second housing to a distal portion of the second housing.

In several embodiments, a removable applicator is coupled to the base. The applicator can comprise a rotating housing configured to push first and second arms distally. A second adhesive can couple the base to the first arm. The second arm can be configured to hold the base in a distal position while the first arm moves proximally to uncouple the first arm from the base.

In some embodiments, the applicator comprises a locking mechanism configured to prevent the first arm and/or the second arm from moving distally until the locking mechanism is disengaged. The applicator can comprise a locking mechanism configured to block rotational movement of the rotating housing. The system can be configured to disengage the locking mechanism in response to linear movement of the rotational housing.

In several embodiments, the system comprises a removable applicator coupled to the base. The applicator can comprise a first housing, a second housing rotatably coupled to the first housing, and a torsion spring. The torsion spring can have a first portion coupled to the first housing and a second portion coupled to the second housing such that the torsion spring is configured to rotate the second housing relative to the first housing.

In some embodiments, the applicator has a first arm slidably coupled to the first housing and coupled to the second housing such that the first arm is configured to linearly push the sensor from a proximal starting position to a distal ending position in response to the second housing rotating relative to the first housing.

In several embodiments, the applicator has a second arm slidably coupled to the first housing and coupled to the second housing such that the second arm is configured to block proximal movement of the sensor after the sensor has reached the distal ending position as the system uncouples the first arm from the base.

In some embodiments, a second adhesive couples the first arm to the base. The first and second arms can be configured to move linearly and distally in response to rotating the second housing relative to the first housing.

In several embodiments, a second arm is configured to block the proximal movement of the sensor as rotation of the second housing relative to the first housing uncouples the second adhesive from the base to enable the first arm to move proximally relative to the base and relative to the second arm.

In some embodiments, the first arm is coupled to a first linear channel. A first protrusion can couple the first linear channel to the second housing. The first linear channel can be configured such that a first rotational movement of the second housing relative to the first housing causes a first distal linear movement of the first arm relative to the first housing.

In several embodiments, the second arm is coupled to a second channel having a curved portion. The first protrusion can couple the second channel to the second housing. The second channel can be configured such that the first rotational movement of the second housing relative to the first housing causes a second distal linear movement of the second arm relative to the first housing.

In some embodiments, the curved portion of the second channel is configured such that continued rotational movement of the second housing relative to the first housing after the sensor has reached the distal ending position does not cause proximal movement of the second arm as the continued rotational movement uncouples the second adhesive from the base by moving the first arm proximally.

In several embodiments, the second housing is coupled to the first housing by a second protrusion about which the second housing is configured to rotate relative to the first housing. The second housing can be slidably coupled to the second protrusion such that the second housing is configured to move from a first position to a second position along the second protrusion. In the first position, a third protrusion can block rotational movement of the second housing relative to the first housing to impede distal movement of the sensor.

In some embodiments, the system comprises a release mechanism configured to enable the second housing to rotate relative to the first housing. The release mechanism can comprise a button and/or any suitable trigger. The first housing can comprise a button configured to move the second housing from the first position to the second position in which the second housing is configured to rotate relative to the first housing to move the sensor distally.

In several embodiments, a base comprises a proximal portion coupled to a distal portion by flex arms configured to cause the proximal portion to rotate relative to the distal portion in response to moving the proximal portion distally (relative to the distal portion) to insert at least a portion of the sensor into the skin. The proximal portion can couple the transmitter to the distal portion.

In some embodiments, the flex arms comprise at least one living hinge configured to rotate the proximal portion relative to the distal portion in response to moving the sensor distally. The flex arms can be spaced around a distal end of the sensor such that the flex arms are configured to rotate the distal end as the distal end moves from a proximal starting position to a distal ending position.

In several embodiments, a removable interference member is located between the distal portion and the proximal portion such that the removable interference member is configured to block the system from moving the sensor from a proximal starting position to a distal ending position. Removing the interference member can enable the system to move the sensor to the distal ending position.

In some embodiments, the base comprises a proximal portion coupled to a distal portion by a first arm and a second arm. A distal end portion of the sensor comprises a central axis. The first arm can be oriented at a first angle of plus or minus 45 degrees of perpendicular to the central axis. The second arm can be oriented at a second angle of plus or minus 45 degrees of perpendicular to the central axis.

In several embodiments, the first and second arms are configured to guide the proximal portion linearly relative to the distal portion as the proximal portion moves towards the distal portion. The first and second arms can be configured to cause the proximal portion to rotate relative to the distal portion in response to moving the distal end portion of the sensor from a proximal starting position to a distal ending position. The second arm can slant away from the first arm such that the first and second arms are configured to rotate the distal end portion of the sensor as the system moves the sensor from the proximal starting position to the distal ending position.

In some embodiments, a base comprises a first portion and a second portion coupled by a hinge configured such that pivoting the second portion towards the first portion causes the sensor to move from a proximal starting position to a distal ending position. The second portion can couple the transmitter to the first portion. The first portion can couple the first adhesive to the second portion.

In several embodiments, the base can be configured such that decreasing a pivot angle between the first portion and the second portion moves a distal end of the sensor out of a hole of the distal side of the base to facilitate the distal end piercing the skin. A proximal segment of the sensor can be coupled to the second portion such that the system can be configured to move a portion of the sensor out of an area between the first and second portions and distally through the hole of the base in response to decreasing the pivot angle.

In some embodiments, the base comprises a left half and a right half. The left half can comprise the hole of the base. The right half can comprise the hinge (such that the hole and the hinge are located on different halves of the base). The hinge can comprise a pin rotatably coupled to a sleeve configured to retain the pin as the second portion rotates relative to the first portion.

In several embodiments, the base comprises a first portion and a second portion coupled by a hinge configured such that pivoting the second portion towards the first portion causes the sensor to move from a proximal starting position to a distal ending position. A spring can be coupled to the base. The spring can be configured to facilitate pivoting the second portion relative to the first portion. The spring can be a torsional spring, a leaf spring, and/or any other type of spring described herein and/or incorporated by reference. The spring can be configured to apply a torque about the hinge.

In some embodiments, the system comprises a removable applicator. The applicator can comprise a housing; a first arm rotatably coupled to the housing by a hinge having a hinge axis; a second arm rotatably coupled to the housing about the hinge axis; a first spring configured to rotate the first arm in a first rotational direction to move the sensor from a proximal starting position to a distal ending position; and a second spring configured to rotate the second arm in a second rotational direction that is opposite to the first rotational direction.

In several embodiments, the second arm is configured to couple the base to the housing as the first arm rotates in the first rotational direction. The first arm can be configured to hold the sensor in the distal ending position while the second arm uncouples the base from the applicator by rotating in the second rotational direction.

In some embodiments, the applicator comprises a first mechanical interlock that releasably couples the second arm to the base such that the first arm is configured to move the second arm and the base in the first rotational direction. The first arm can be located at least partially between the base and the second arm. The first mechanical interlock can comprise a third flex arm that secures the first arm at least partially between the base and the second arm. The first mechanical interlock can be configured to uncouple from the base to enable the second arm to rotate in the second rotational direction in response to the first arm moving the second arm in the first rotational direction.

In several embodiments, the housing (or another portion of the applicator) comprises a second mechanical interlock configured to hold the first arm in a distal position while the second arm rotates in the second rotational direction. The second mechanical interlock can comprise a fourth flex arm configured to couple to least a portion of the first arm.

In some embodiments, the applicator comprises a fifth flex arm that couples the first arm (and/or the second arm) to the housing such that the sensor is in the proximal starting position. The fifth flex arm can be configured to resist a rotational force of the first spring. A portion of the fifth flex arm can protrude from an exterior of the housing such that the portion comprises an actuation tab and/or an actuation lever. The fifth flex arm can be configured to uncouple from the housing to enable the first arm to rotate in response to moving the actuation tab and/or the actuation lever.

In some embodiments, a sensor system is configured for measuring an analyte concentration. The sensor system can comprise a base having a distal side configured to face towards a skin of a host; a first adhesive coupled to the base and configured to couple the base to the skin; a transmitter coupled to the base and configured to transmit analyte measurement data; and/or a transcutaneous analyte measurement sensor coupled to the base.

In several embodiments, the sensor comprises a distal end portion having a central axis and a planar profile coincident with the central axis. The planar profile of the distal end portion can be parabolic.

In some embodiments, the distal end portion of the sensor is coated with a membrane. A distal tip of the sensor can be configured to pierce the skin and can be rounded to resist delamination of the membrane.

In several embodiments, the distal end portion of the sensor is coated with a membrane. The parabolic distal end portion can be configured to provide a gradual diameter increase to reduce tissue trauma and to provide a curved distal tip configured to resist delamination of the membrane. A slope of the parabolic distal end portion can comprise a linear derivative.

In some embodiments, a segment of the sensor is configured to be inserted into the skin. The segment can comprise a first maximum width. The parabolic distal end portion can comprise a second maximum width that is at least 50 percent of the first maximum width.

In several embodiments, the distal end portion is coated by a membrane configured to enable the sensor system to measure a glucose indication. The membrane can comprise a thickness that varies by less than plus or minus 30 percent relative to an average thickness of the membrane.

In some embodiments, the parabolic distal end portion comprises a distal section and a proximal section. The distal section can comprise a first angle relative to the central axis. The proximal section can comprise a second angle relative to the central axis. The first angle can be at least twice as large as the second angle such that the first angle is configured to resist delamination of the membrane and the second angle is configured to gradually increase a width of the profile.

In several embodiments, the sensor comprises a distal end portion having a central axis and a planar profile coincident with the central axis. A distal tip of the sensor can be curved such that the planar profile comprises a curved distal end that couples a first curved side to a second curved side.

In some embodiments, the distal end portion of the sensor is coated with a membrane. The curved distal end can be configured to resist delamination of the membrane. The first curved side and the second curved side can be configured to provide a smooth transition from the distal tip to resist delamination and to provide a gradual transition from a first diameter of the distal tip to a maximum diameter of the distal end portion.

In several embodiments, the sensor is a glucose sensor having a conductive core and a conductive layer configured to enable the system to apply a voltage between the conductive core and the conductive layer to measure a glucose indication.

In some embodiments, the sensor comprises a first electrical insulation layer located around a first section of the conductive core. The sensor can comprise a second electrical insulation layer located around a second section of the conductive core. The conductive layer can be located radially outward from the first insulation layer. The first insulation layer can be spaced apart from the second insulation layer to form a gap configured to enable the system to apply the voltage between the conductive core and the conductive layer. The sensor can comprise an electrical insulation cap that covers a distal end of the conductive core.

In several embodiments, the sensor comprises a distal end portion that is conical with a rounded distal tip. The rounded distal tip can be configured to resist delamination of a membrane that coats the distal end portion. The distal end portion can be conical to facilitate piercing the skin.

In some embodiments, the sensor comprises a distal end portion that is conical with a blunted tip. The blunted tip can be configured to resist delamination of a membrane that coats the distal end portion.

In several embodiments, the sensor comprises a distal end portion having a central axis and a planar profile coincident with the central axis. A distal tip of the sensor can be curved such that the planar profile comprises a curved distal end that couples a first straight side to a second straight side.

In some embodiments, the distal end portion can be coated by a membrane. The distal tip can be curved such that the distal tip is configured to resist delamination of the membrane. The first and second sides can be straight such that the sides are configured to linearly increase a diameter of the distal end portion to reduce tissue trauma caused by inserting the distal end portion into the skin.

In several embodiments, the curved distal end comprises a radius that is greater than 10 micrometers and less than 35 micrometers such that the curved distal end is configured to be large enough to resist delamination of a membrane that coats the curved distal end and small enough to reduce patient discomfort associated with piercing of the skin.

In some embodiments, the curved distal end comprises a maximum width that is greater than 10 micrometers and less than 35 micrometers such that the curved distal end is configured to be large enough to resist delamination of a membrane that coats the curved distal end and small enough to reduce patient discomfort associated with piercing of the skin. An angle between the first and second straight sides can be greater than 15 degrees and less than 25 degrees such that the angle is configured to reduce patient discomfort associated with piercing of the skin.

In several embodiments, the sensor comprises a distal end portion having a central axis and a planar profile coincident with the central axis. The planar profile can comprise a left portion having a first side coupled to a second side. The planar profile can comprise a right portion having a third side coupled to a fourth side. A first angle between the first side and the third side can be smaller than a second angle between the second side and the fourth side such that a proximal section of the end portion provides a more gradual width increase than a distal section of the end portion. The first, second, third, and fourth sides can be straight. The first, second, third, and fourth sides can be curved.

In some embodiments, a curved distal end couples the second side to the fourth side. The curved distal end can be configured to resist delamination of a membrane that coats the distal end portion of the sensor.

In several embodiments, the sensor is a glucose sensor comprising a membrane that coats the distal end portion of the sensor. The distal end portion can be configured to resist delamination of the membrane, reduce tissue trauma, and/or reduce patient discomfort caused by piercing the skin.

In some embodiments, the sensor comprises a distal end portion having a central axis and a first facet oriented at a first angle of less than 25 degrees relative to the central axis such that the first facet is configured to facilitate piercing the skin. The distal end portion of the sensor can comprise a second facet oriented at a second angle of less than 25 degrees relative to the central axis. The first facet can be oriented at a third angle relative to the second facet. The third angle can be greater than 10 degrees and less than 25 degrees.

In several embodiments, the first and second facets form a wedge configured to facilitate piercing the skin. The distal end portion of the sensor can be coated by a membrane. A rounded ridge can couple the first facet to the second facet such that the rounded ridge is configured to resist delamination of the membrane.

In some embodiments, the distal end portion of the sensor comprises a third facet oriented at a fourth angle of less than 25 degrees relative to the central axis. The first, second, and third facets can form a triangular pyramid configured to facilitate piercing the skin. The distal end portion of the sensor can be coated by a membrane. The triangular pyramid can comprise a rounded distal tip configured to resist delamination of the membrane.

In several embodiments, a first rounded ridge couples the first facet to the second facet. A second rounded ridge can couple the second facet to the third facet. The first rounded ridge and the second rounded ridge can be configured to reduce tissue trauma caused by inserting the distal end portion of the sensor into the host.

In some embodiments, the distal end portion of the sensor comprises a fourth facet oriented at a fifth angle of less than 25 degrees relative to the central axis. The first, second, third, and fourth facets can form a rectangular pyramid configured to facilitate piercing the skin.

In some embodiments, the sensor comprises a conductive distal end portion coated by a membrane. The conductive distal end portion can comprise a first step configured to resist proximal movement of the membrane relative to the first step.

In several embodiments, the sensor comprises a tapered end section coated by a membrane and having a distal tip. The tapered end section can comprise a first step configured to resist proximal movement of the membrane relative to the first step.

In some embodiments, the sensor comprises a tapered end section coated by a membrane. The tapered end section comprises the distal tip of the sensor. The sensor comprises a first step located within plus or minus 1 millimeter and/or within plus or minus 2.1 millimeters of the tapered end section. The first step can be configured to resist proximal movement of the membrane relative to the first step.

In several embodiments, the sensor is coated by a membrane. A portion of the sensor can comprise a first step. The sensor can comprise a groove configured to be inserted into tissue of the host. The first step can be located distally relative to the groove. The first step can be configured to resist proximal movement of the membrane relative to the first step.

In several embodiments, the sensor comprises a portion coated by a membrane. The portion of the sensor can comprise a first conductive layer electrically insulated from a second conductive layer by an insulation layer. The first conductive layer can be configured to be electrically coupled to the second conductive layer via tissue of the host. The first conductive layer can extend farther distally than the second conductive layer. The first conductive layer can comprise a first step configured to resist proximal movement of the membrane relative to the first step. The first step can be located farther distally than the second conductive layer.

In some embodiments, a distal portion of the sensor comprises a first step and a second step. The second step can be spaced proximally relative to the first step. The distal portion of the sensor can be coated by a membrane. The first step and the second step can face distally. The first step can be configured to resist proximal movement of the membrane relative to the first step.

In several embodiments, the first step comprises a surface oriented within plus or minus 25 degrees of perpendicular to a central axis of the portion of the sensor. The first step can comprise a surface oriented within plus or minus 15 degrees of perpendicular to a central axis of the portion of the sensor. The surface can form an interference feature configured to impede proximal movement of the membrane relative to the surface by causing a compressive force within the membrane in response to the proximal movement of the membrane.

In some embodiments, the sensor can comprise a first conductive layer electrically insulated from a second conductive layer by an insulation layer. The first conductive layer can be conductively coupled to the conductive distal end portion such that the conductive distal end portion is configured to be conductively coupled to the second conductive layer via tissue of the host.

In several embodiments, a sensor comprises a distal end portion coated by a membrane. The distal end portion can comprise a gap between a conductive core and a conductive layer of the sensor. The gap can be configured to enable a subcutaneous current between the conductive core and the conductive layer. The distal end portion can comprise a step located distally relative to the gap and configured to resist proximal movement of the membrane relative to the step.

In some embodiments, the step can comprise a surface oriented within plus or minus 25 degrees of perpendicular to a central axis of the distal end portion. The surface can form an interference feature configured to impede proximal movement of the membrane relative to the surface by causing a compressive force within the membrane in response to the proximal movement of the membrane. The conductive core can comprise the step. An insulation layer located around the conductive core can form the step.

In several embodiments, the distal end portion comprises at least one of a rounded distal tip, a parabolic shape, a conical shape, a wedge shape, a triangular pyramid shape, and a rectangular pyramid shape such that the distal end portion is configured to facilitate piercing the skin.

In some embodiments, the sensor comprises a distal end portion coated by a membrane. The distal end portion of the sensor can comprise a central axis, a distal tip, and a distally facing surface spaced proximally apart from the distal tip. The distally facing surface can form a mechanical interlock with the membrane such that the mechanical interlock is configured to impede proximal movement of the membrane relative to the distally facing surface.

In several embodiments, the sensor can comprise a conductive core, a conductive layer, and an insulation layer configured to electrically insulate the conductive core from the conductive layer. The conductive core can extend farther distally than the insulation layer to form a shortest conduction path between the conductive core and the conductive layer. The distally facing surface can be located distally relative to the shortest conduction path.

In some embodiments, the sensor comprises a conductive core and a conductive layer configured to enable the system to apply a voltage between the conductive core and the conductive layer to measure an analyte indication. The sensor can comprise a first electrical insulation layer located around a first section of the conductive core and a second electrical insulation layer located around a second section of the conductive core. The conductive layer can be located radially outward from the first insulation layer. The first insulation layer can be spaced apart from the second insulation layer to form a gap configured to enable the system to apply the voltage between the conductive core and the conductive layer. The distally facing surface can be located distally relative to the gap. The distally facing surface can be oriented within a range of plus or minus 20 degrees relative to perpendicular to the central axis.

Any of the features of each embodiment is applicable to all aspects and embodiments identified herein. Moreover, any of the features of an embodiment is independently combinable, partly or wholly with other embodiments described herein in any way (e.g., one, two, three, or more embodiments may be combinable in whole or in part). Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

BRIEF DESCRIPTION OF THE DRAWINGS

These and other features, aspects, and advantages are described below with reference to the drawings, which are intended to illustrate, but not to limit, the invention. In the drawings, like reference characters denote corresponding features consistently throughout similar embodiments.

FIG. 20 illustrates a perspective view of a base that comprises a first portion and a second portion, according to some embodiments.

FIG. 21 illustrates a perspective view of the base after the first portion illustrated in FIG. 20 has rotated, according to some embodiments.

FIG. 22a illustrates a top view of the system illustrated in FIG. 20, according to some embodiments.

FIG. 22b illustrates a side view of the system illustrated in FIG. 20, according to some embodiments.

FIG. 42 illustrates a perspective view of the system, according to some embodiments.

FIG. 43 illustrates a top view of the system, according to some embodiments.

FIG. 44 illustrates a perspective, cross-sectional view along line 44-44 from FIG. 43, according to some embodiments.

FIGS. 54-56 illustrate equations, according to some embodiments.

FIG. 57 illustrates a perspective view of a system with a collapsible support, according to some embodiments.

FIGS. 58 and 59 illustrate side views of the system, according to some embodiments.

FIGS. 64 and 65 illustrate perspective views of a system, according to some embodiments.

FIG. 66 illustrates a side view of a housing, according to some embodiments.

FIG. 67 illustrates a perspective view of the system without the housing, according to some embodiments.

FIGS. 95-98 illustrate perspective, cross-sectional views of a system, according to some embodiments.

FIGS. 99 and 100 illustrate side views of portions of the system, according to some embodiments.

DETAILED DESCRIPTION

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

System Introduction

Figure 1:
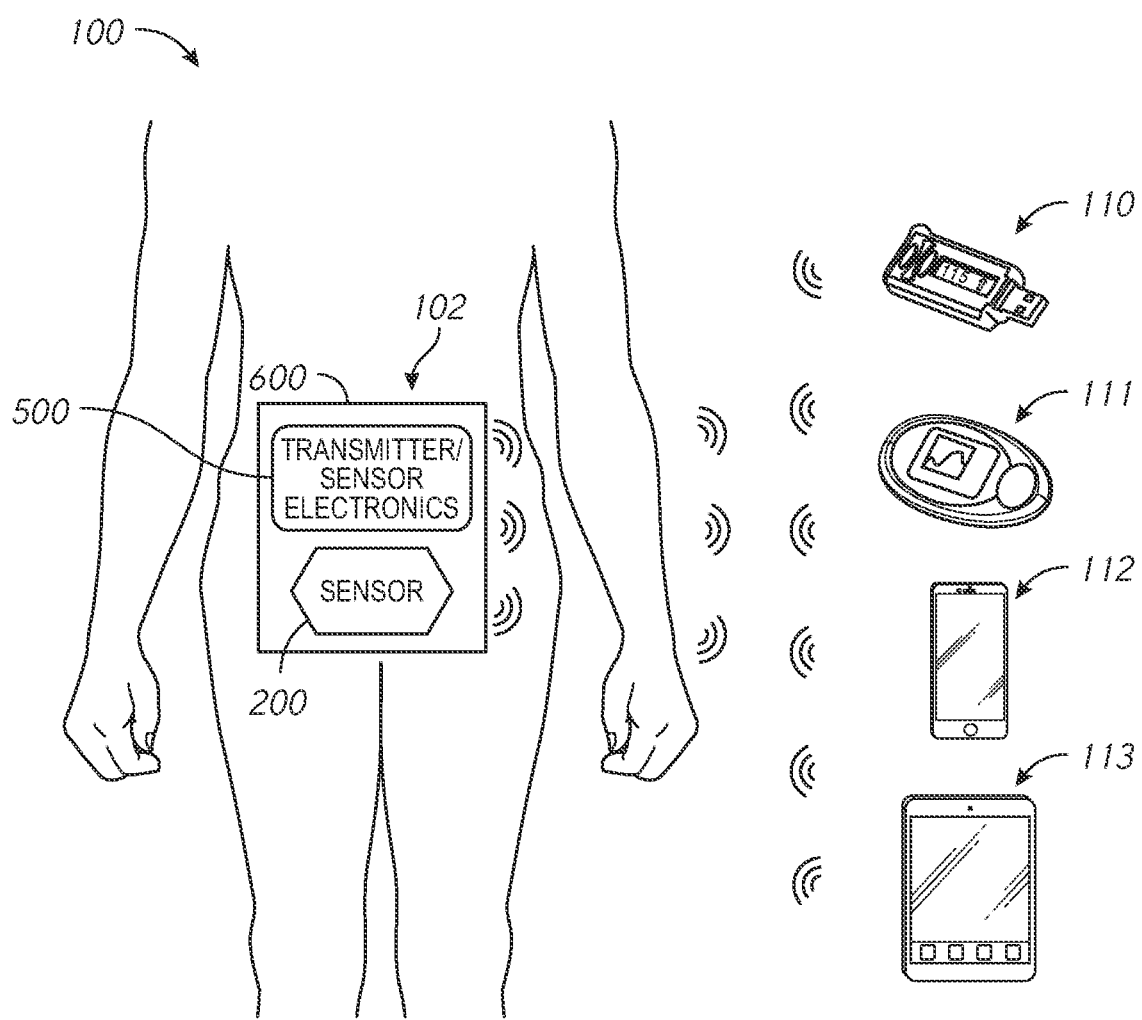
FIG. 1 illustrates a schematic view of an analyte sensor system, according to some embodiments.

U.S. Patent Publication No. US-2013-0267811-A1, the entire contents of which are incorporated by reference herein, explains how FIG. 1 is a schematic of a continuous analyte sensor system 100 attached to a host (e.g., a person). The analyte sensor system 100 communicates with other devices 110-113 (which can be located remotely from the host). A transcutaneous analyte sensor system 102 comprising an on-skin sensor assembly 600 is coupled to the skin of a host by a base (not shown), which can be a disposable housing having several parts that can move relative to each other.

Any of the features described in the context of FIG. 1 can be applicable to all aspects and embodiments identified herein. For example, the embodiments described in the context of FIG. 1 can be combined with the embodiments described in the context of FIGS. 2-126. Moreover, any of the features of an embodiment is independently combinable, partly or wholly with other embodiments described herein in any way (e.g., one, two, three, or more embodiments may be combinable in whole or in part). Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Referring now to FIG. 1, the system 102 includes a transcutaneous analyte sensor 200 and an electronics unit (referred to interchangeably as "sensor electronics" or "transmitter") 500 for wirelessly transmitting analyte information to a receiver. Transmitters can be removably coupled to a base (e.g., by the user). In some embodiments, the transmitter is not removable (e.g., by the user). Transmitters can be integrated into a base (e.g., at the factory).

The receiver can be located remotely relative to the system 102. In some embodiments, the receiver includes a display screen, which can display information to a person such as the host. Example receivers include computers such as smartphones, smartwatches, tablet computers, laptop computers, and desktop computers. In some embodiments, receivers can be Apple Watches, iPhones, and iPads made by Apple Inc. In still further embodiments, the system 102 can be configured for use in applying a drug delivery device, such an infusion device, to the skin of a patient. In such embodiments, the system can include a catheter instead of, or in addition to, a sensor, the catheter being connected to an infusion pump configured to deliver liquid medicines or other fluids into the patient's body. In embodiments, the catheter can be deployed into the skin in much the same manner as a sensor would be, for example as described herein.

In some embodiments, the receiver is mechanically coupled to the electronics unit 500 to enable the receiver to receive data (e.g., analyte data) from the electronics unit 500. To increase the convenience to users, in several embodiments, the receiver does not need to be mechanically coupled to the electronics unit 500 and can even receive data from the electronics unit 500 over great distances (e.g., when the receiver is many feet or even many miles from the electronics unit 500).

During use, a sensing portion of the sensor 200 can be under the host's skin and a contact portion of the sensor 200 can be electrically connected to the electronics unit 500. The electronics unit 500 can be engaged with a housing (e.g., a base) which is attached to an adhesive patch fastened to the skin of the host.

The on-skin sensor assembly 600 may be attached to the host with use of an applicator adapted to provide convenient and secure application. Such an applicator may also be used for attaching the electronics unit 500 to a base, inserting the sensor 200 through the host's skin, and/or connecting the sensor 200 to the electronics unit 500. Once the electronics unit 500 is engaged with the base and the sensor 200 has been inserted into the skin (and is connected to the electronics unit 500), the sensor assembly can detach from the applicator.

The continuous analyte sensor system 100 can include a sensor configuration that provides an output signal indicative of a concentration of an analyte. The output signal including (e.g., sensor data, such as a raw data stream, filtered data, smoothed data, and/or otherwise transformed sensor data) is sent to the receiver.

In some embodiments, the analyte sensor system 100 includes a transcutaneous glucose sensor, such as is described in U.S. Patent Publication No. US-2011-0027127-A1, the entire contents of which are hereby incorporated by reference. In some embodiments, the sensor system 100 includes a continuous glucose sensor and comprises a transcutaneous sensor (e.g., as described in U.S. Pat. No. 6,565,509, as described in U.S. Pat. No. 6,579,690, as described in U.S. Pat. No. 6,484,046). The contents of U.S. Pat. Nos. 6,565,509, 6,579,690, and 6,484,046 are hereby incorporated by reference in their entirety.

In several embodiments, the sensor system 100 includes a continuous glucose sensor and comprises a refillable subcutaneous sensor (e.g., as described in U.S. Pat. No. 6,512,939). In some embodiments, the sensor system 100 includes a continuous glucose sensor and comprises an intravascular sensor (e.g., as described in U.S. Pat. No. 6,477,395, as described in U.S. Pat. No. 6,424,847). The contents of U.S. Pat. Nos. 6,512,939, 6,477,395, and 6,424,847 are hereby incorporated by reference in their entirety.

Various signal processing techniques and glucose monitoring system embodiments suitable for use with embodiments described herein are described in U.S. Patent Publication No. US-2005-0203360-A1 and U.S. Patent Publication No. US-2009-0192745-A1, the contents of which are hereby incorporated by reference in their entirety. The sensor can extend through a housing, which can maintain the sensor on the skin and can provide for electrical connection of the sensor to sensor electronics, which can be provided in the electronics unit 500.

In several embodiments, the sensor is formed from a wire or is in a form of a wire. A distal end of the wire can be sharpened to form a conical shape (to facilitate inserting the wire into the tissue of the host). The sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments, the smallest dimension (e.g., a diameter) of the elongated conductive body is less than 0.1 inches, less than 0.075 inches, less than 0.05 inches, less than 0.025 inches, less than 0.01 inches, less than 0.004 inches, and/or less than 0.002 inches.

The sensor may have a circular cross section. In some embodiments, the cross section of the sensor and/or the elongated conductive body can be ovoid, rectangular, triangular, polyhedral, star-shaped, C-shaped, T-shaped, X-shaped, Y-shaped, irregular, or the like. In some embodiments, a conductive wire electrode is employed as a core. To such an electrode, one or two additional conducting layers may be added (e.g., with intervening insulating layers provided for electrical isolation). The conductive layers can be comprised of any suitable material. In certain embodiments, it may be desirable to employ a conductive layer comprising conductive particles (i.e., particles of a conductive material) in a polymer or other binder.

In some embodiments, the materials used to form the elongated conductive body (e.g., stainless steel, titanium, tantalum, platinum, platinum-iridium, iridium, certain polymers, and/or the like) can be strong and hard, and therefore can be resistant to breakage. For example, in several embodiments, the ultimate tensile strength of the elongated conductive body is greater than 80 kPsi and less than 500 kPsi, and/or the Young's modulus of the elongated conductive body is greater than 160 GPa and less than 220 GPa. In some embodiments, the yield strength of the elongated conductive body can be greater than 60 kPsi and less than 2200 kPsi.

The electronics unit 500 can be releasably coupled to the sensor 200. The electronics unit 500 can include electronic circuitry associated with measuring and processing the continuous analyte sensor data. The electronics unit 500 can be configured to perform algorithms associated with processing and calibration of the sensor data. For example, the electronics unit 500 can provide various aspects of the functionality of a sensor electronics module as described in U.S. Patent Publication No. US-2009-0240120-A1 and U.S. Patent Publication No. US-2012-0078071-A1, the entire contents of which are incorporated by reference herein. The electronics unit 500 may include hardware, firmware, and/or software that enable measurement of levels of the analyte via a glucose sensor, such as an analyte sensor 200.

For example, the electronics unit 500 can include a potentiostat, a power source for providing power to the sensor 200, signal processing components, data storage components, and a communication module (e.g., a telemetry module) for one-way or two-way data communication between the electronics unit 500 and one or more receivers, repeaters, and/or display devices, such as devices 110-113. Electronics can be affixed to a printed circuit board (PCB), or the like, and can take a variety of forms. The electronics can take the form of an integrated circuit (IC), such as an Application-Specific Integrated Circuit (ASIC), a microcontroller, and/or a processor. The electronics unit 500 may include sensor electronics that are configured to process sensor information, such as storing data, analyzing data streams, calibrating analyte sensor data, estimating analyte values, comparing estimated analyte values with time-corresponding measured analyte values, analyzing a variation of estimated analyte values, and the like. Examples of systems and methods for processing sensor analyte data are described in more detail in U.S. Pat. Nos. 7,310,544, 6,931,327, U.S. Patent Publication No. 2005-0043598-A1, U.S. Patent Publication No. 2007-0032706-A1, U.S. Patent Publication No. 2007-0016381-A1, U.S. Patent Publication No. 2008-0033254-A1, U.S. Patent Publication No. 2005-0203360-A1, U.S. Patent Publication No. 2005-0154271-

A1, U.S. Patent Publication No. 2005-0192557-A1, U.S. Patent Publication No. 2006-0222566-A1, U.S. Patent Publication No. 2007-0203966-A1 and U.S. Patent Publication No. 2007-0208245-A1, the contents of which are hereby incorporated by reference in their entirety.

One or more repeaters, receivers and/or display devices, such as a key fob repeater 110, a medical device receiver 111 (e.g., an insulin delivery device and/or a dedicated glucose sensor receiver), a smartphone 112, a portable computer 113, and the like can be communicatively coupled to the electronics unit 500 (e.g., to receive data from the electronics unit 500). The electronics unit 500 can also be referred to as a transmitter. In some embodiments, the devices 110-113 transmit data to the electronics unit 500. The sensor data can be transmitted from the sensor electronics unit 500 to one or more of the key fob repeater 110, the medical device receiver 111, the smartphone 112, the portable computer 113, and the like. In some embodiments, analyte values are displayed on a display device.

The electronics unit 500 may communicate with the devices 110-113, and/or any number of additional devices, via any suitable communication protocol. Example communication protocols include radio frequency; Bluetooth; universal serial bus; any of the wireless local area network (WLAN) communication standards, including the IEEE 802.11, 802.15, 802.20, 802.22 and other 802 communication protocols; ZigBee; wireless (e.g., cellular) telecommunication; paging network communication; magnetic induction; satellite data communication; and/or a proprietary communication protocol.

Additional sensor information is described in U.S. Pat. Nos. 7,497,827 and 8,828,201. The entire contents of U.S. Pat. Nos. 7,497,827 and 8,828,201 are incorporated by reference herein.

Any sensor shown and/or described herein can be an analyte sensor, a glucose sensor, and/or any other suitable sensor. A sensor described in the context of any embodiment can be any sensor described herein and/or incorporated by reference. Sensors shown or described herein can be configured to sense, measure, detect, and/or interact with any analyte.

As used herein, the term "analyte" is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products.

In some embodiments, the analyte for measurement by the sensing regions, devices, systems, and methods is glucose. However, other analytes are contemplated as well, including, but not limited to ketone bodies; Acetyl Co A; acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; cortisol; testosterone; choline; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; glycerol; free B-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione peroxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, ß); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, Dracunculus medinensis, Echinococcus granulosus, Entamoeba histolytica, enterovirus, Giardia duodenalisa, Helicobacter pylori, hepatitis B virus, herpes virus, HIV-1, IgE (atopic disease), influenza virus, Leishmania donovani, leptospira, measles/mumps/rubella, Mycobacterium leprae, Mycoplasma pneumoniae, Myoglobin, Onchocerca volvulus, parainfluenza virus, Plasmodium falciparum, poliovirus, Pseudomonas aeruginosa, respiratory syncytial virus, rickettsia (scrub typhus), Schistosoma mansoni, Toxoplasma gondii, Trepenoma pallidium, Trypanosoma cruzi/rangeli, vesicular stomatis virus, Wuchereria bancrofti, yellow fever virus); specific antigens (hepatitis B virus, HIV-1); acetone (e.g., succinylacetone); acetoacetic acid; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin; glucagon; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and intermediaries in the Citric Acid Cycle.

Embodiments can use a needle to facilitate inserting a sensor into tissue of a host. Some embodiments are illustrated without a needle, but can be combined with other needle embodiments to include a needle. Some embodiments do not use a needle, but include a sensor and/or another portion configured to facilitate piercing the skin of the host. Each embodiment can be configured to use a needle and can be configured to not use a needle.

Many embodiments described herein use an adhesive. One purpose of the adhesive can be to couple a base, a sensor module, and/or a sensor to a host (e.g., to skin of the host). The adhesive can be configured for adhering to skin. The adhesive can include a pad (e.g., that is located between the adhesive and the base). Additional adhesive information, including adhesive pad information, is described in U.S. patent application Ser. No. 14/835,603, which was filed on Aug. 25, 2015. The entire contents of U.S. patent application Ser. No. 14/835,603 are incorporated by reference herein.

U.S. Patent Publication No. US-2013-0267811-A1; U.S. Patent Application No. 62/165,837, which was filed on May 15, 2015; and U.S. Patent Application No. 62/244,520, which was filed on Oct. 21, 2015, include details regarding applicator system embodiments. The entire contents of U.S. Patent Publication No. US-2013-0267811-A1; U.S. Patent Application No. 62/165,837; and U.S. Patent Application No. 62/244,520 are incorporated by reference herein. The entire contents of U.S. Patent Publication No. US-2009-0076360-A1 are incorporated by reference herein.

U.S. Patent Publication No. US-2011-0077490-A1, U.S. Patent Publication No. US-2014-0107450-A1, and U.S. Patent Publication No. US-2014-0213866-A1 describe several needle-free embodiments. The entire contents of U.S. Patent Publication No. US-2011-0077490-A1, U.S. Patent Publication No. US-2014-0107450-A1, and U.S. Patent Publication No. US-2014-0213866-A1 are incorporated by reference herein.

The entire contents of the following application are incorporated by reference herein: U.S. patent application Ser. No. 12/893,850; filed Sep. 29, 2010; and titled Transcutaneous Analyte Sensor. The entire contents of the following application are incorporated by reference herein: U.S. patent application Ser. No. 14/250,320; filed Apr. 10, 2014; and titled Sensors for Continuous Analyte Monitoring, and Related Methods. The entire contents of the following application are incorporated by reference herein: U.S. patent application Ser. No. 13/780,808; filed Feb. 28, 2013; and titled Sensors for Continuous Analyte Monitoring, and Related Methods.

As used herein, the term "base" is used very broadly, is not limited to a single component and can include many components. The base can include components that move relative to each other. The base can include distal and proximal portions. A transmitter can be coupled to a proximal portion of the base, a distal portion of the base, and/or any portion of the base. A transmitter can be integrated into the base. A transmitter can be removably coupled to the base. The transmitter can be configured to transmit analyte measurement data (e.g., analyte indications) to a receiver.

As used herein, "passes" is used in a manner that does not require movement. For example a sensor can pass through a channel without moving (e.g., by being located in the channel).

As used herein, a transcutaneous analyte measurement sensor (e.g., a sensor) can include subcutaneous portions and portions that are not configured to enter tissue. A first segment of the sensor can be outside the host and a second segment of the sensor can be inside the host. The sensor can be a transcutaneous sensor because at least a portion of the sensor can be configured to enter the host. A sensor can be a sensor assembly with many layers, conductors, insulators, membranes, and components.

Some embodiments comprise one or more springs. These springs can be a torsion spring, a leaf spring, a helical spring, a conical spring, a compression spring, a tension spring, an integrally molded deforming body, a flex arm, any suitable type of spring or combination of springs, any spring described herein, and/or any spring incorporated by reference. Some embodiments are shown with a certain type of spring, however, embodiments can be created by substituting one type of spring for another type of spring.

Figure 126:
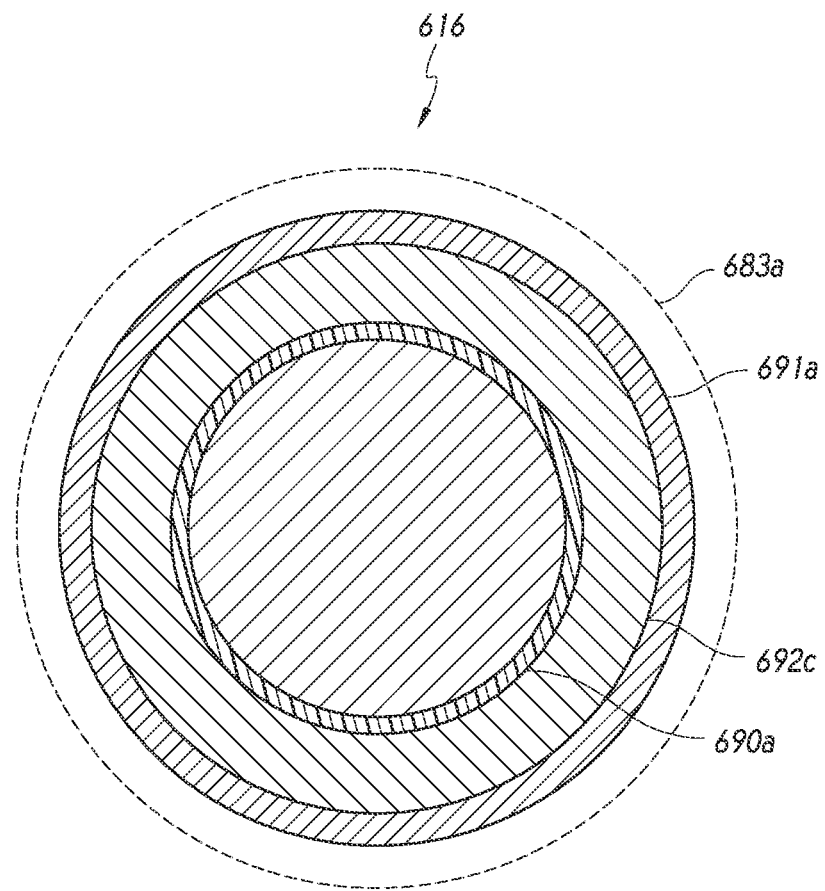
FIG. 126 illustrates a cross-sectional view along line 126-126 from FIG. 116, according to some embodiments.

FIGS. 1-126 illustrate sensor systems or at least portions of sensor systems that can be configured to measure an analyte indication. A sensor system can comprise a base having a distal side configured to face towards a skin of a host; a first adhesive coupled to the base and configured to couple the base to the skin; a transmitter coupled to the base and configured to transmit analyte measurement data; and/or a transcutaneous analyte measurement sensor coupled to the base. Many figures focus on particular features (rather than on all features described herein) to reduce unnecessary redundancy and to increase the clarity of descriptions related to particular features. Each feature, however, can be combined with all the other features described in the context of the figures included herein and/or incorporated by reference.

Sharp Protection

Measuring analyte data often involves inserting an analyte sensor into subcutaneous tissue. Some embodiments use a needle to facilitate inserting the sensor into subcutaneous tissue. Some embodiments have a sensor configured to be inserted into subcutaneous tissue without the aid of a needle. Each embodiment can be configured with or without a needle.

Once the sensor is removed from the tissue, the sensor becomes a biohazard that has the potential to transfer viruses, bacteria, and other pathogens from the tissue to another person who is inadvertently pierced by the sensor. Another unwanted side effect is that users can accidently pierce themselves. Thus, in some cases it is advantageous for systems and methods that protect people from "used" sensors (and/or needles).

Chemical Solutions

In some embodiments, at least a portion of the sensor is configured to soften in vivo such that the sensor is sufficiently prone to buckling at the time the sensor is removed from the tissue that the sensor does not pose a substantial risk of accidental, unintentional piercing (because the sensor's column lacks sufficient strength to easily pierce skin).

A coating can be applied to the sensor. The coating can be configured to stiffen the sensor to increase a maximum buckling load of the sensor. The coating can be configured to soften and/or dissolve in response to being located in tissue. As a result, the coating can become so soft and/or dissolve after of period of in vivo exposure that the sensor is no longer configured to pierce tissue.

In some embodiments, the wire of the sensor (and/or another portion of the sensor) remains sharp enough to pierce tissue after the coating has softened and/or dissolved, but the softening and/or dissolving of the coating renders the sensor sufficiently prone to buckling that the sensor is no longer configured to pierce tissue. In other words, rather than piercing the tissue, the sensor buckles.

In some embodiments, the sharp distal end of the sensor is made of the material that softens and/or dissolves in vivo. As a result, the sensor is initially sharp enough to pierce the skin, but once the sharp distal end has softened and/or dissolved, the sensor is no longer configured to pierce the skin. In other words, the distal end of the sensor becomes dull (e.g., less sharp) in response to in vivo exposure. The cross-sectional surface area of the distal tip grows such that the force required to pierce skin is greater than the buckling strength of the wire.

Some embodiments comprise a structure configured to support the sensor against buckling forces. The supporting structure can be located alongside the sensor. The sensor can pass through a channel of the supporting structure. The sensor can be at least partially contained within a channel of the supporting structure.

The supporting structure can be tubular, C-shaped, cylindrical, and/or have any other shape suitable to help prevent the sensor from buckling. The support structure can be made from a material that softens and/or dissolves in vivo such that the support structure becomes less rigid in vivo. This change may be a result of fluid exposure to interstitial fluid (e.g., hydration) or elevated temperature.

As used herein, the term "C-shaped" is used broadly and means that a structure has an open side such that C-shapes can include U-shapes, V-shapes, and other similar shapes.

A coupling between the sensor and the support structure can be made from a material that softens and/or dissolves in vivo. As a result, the support structure can be configured to resist buckling when the sensor is initially inserted into tissue, but then can have lower buckling-resistance capabilities.

The support structure and/or the sensor can comprise a sharp tip. The sharp tip can be configured to pierce the skin of the host.

The softening and/or dissolving material's purpose can be to add column strength and/or buckling resistance to the sensor to facilitate insertion. The material can be coupled mechanically (e.g., such as constrained in a tube) or chemically (e.g., adhesion) to the sensor.

The material can reduce accidental piercing risk via one or more of the following mechanisms. The material can degrade to a state where it is unable to hold the sensor rigid enough to pierce the skin. In vivo exposure can make the secondary material no longer sharp enough (e.g., at the distal tip) to pierce the skin. The material can soften and/or dissolve such that the sensor and the support structure uncouple and/or the support structure is no longer configured to hold the sensor in a rigid and/or approximately straight state.

The following application, the entire contents of which are incorporated by reference herein, includes information regarding softening and dissolving materials: U.S. patent application Ser. No. 14/250,320; filed Apr. 10, 2014; and titled Sensors for Continuous Analyte Monitoring, and Related Methods.

The coating material and/or the support structure material can be a biodegradable material and/or a material that dissolves upon insertion into the host. Example materials include at least one of a salt, a metallic salt, a sugar, a synthetic polymer, a glue or adhesive (such as cyanoacrylate), polylactic acid (PLA), polyglycolic acid, poly lactic-co-glycolic acid (PLGA), a polyanhydride, a polyphosphazene, or any material with a glass transition temperature of 37 plus or minus 10 degrees Celsius.

Figure 2:
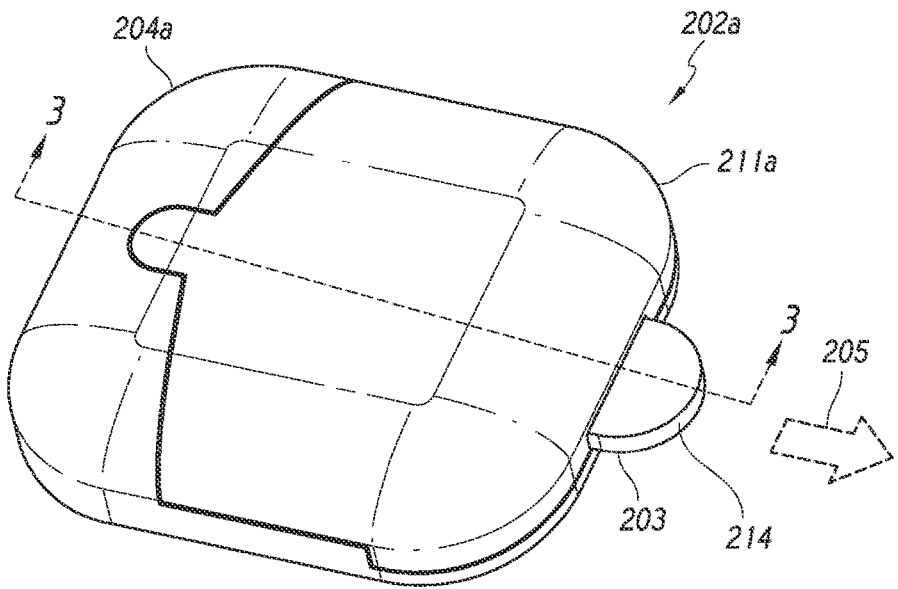
FIG. 2 illustrates a perspective view of a sensor system, according to some embodiments.
Figure 3:
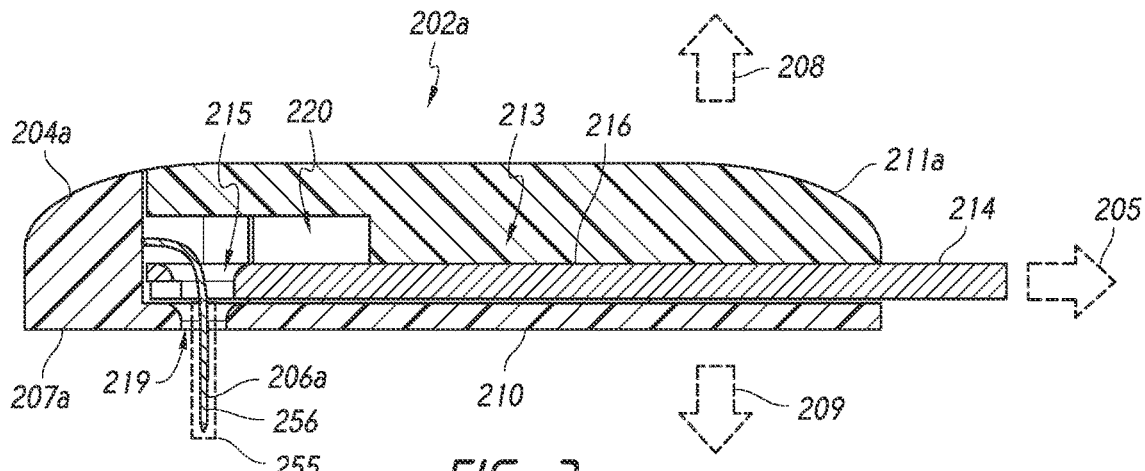
FIG. 3 illustrates a cross-sectional view along line 3-3 from FIG. 2, according to some embodiments.

FIG. 2 illustrates a perspective view of a sensor system 202a. FIG. 3 illustrates a cross-sectional view along line 3-3 from FIG. 2. Referring now to FIG. 3, the sensor 206a can comprise a section located distally relative to the base 204a. The section of the sensor 206a can comprise a first portion 255 and a second portion 256. The first portion 255 of the sensor 206a can be configured to facilitate maintaining the second portion 256 in a straight configuration during insertion of the section into the skin. The first portion 255 of the sensor 206a can be configured to soften in response to being located in vivo.

The first portion 255 can comprise a first buckling resistance prior to the insertion and a second buckling resistance after one hour, 12 hours, and/or 48 hours of being located in vivo. The second buckling resistance can be less than the first buckling resistance. The second buckling resistance can be at least 30 percent less and/or at least 70 percent less than the first buckling resistance.

Figure 116:
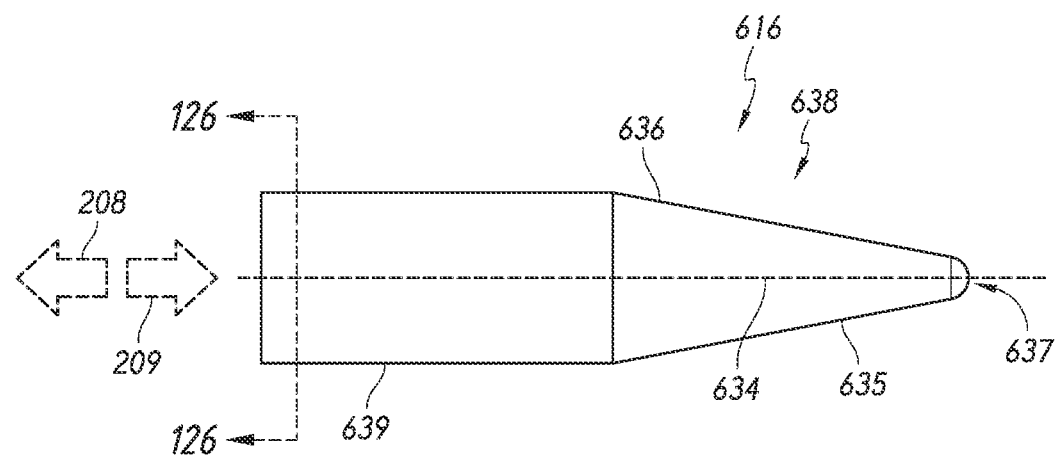

FIG. 126 illustrates a cross-sectional view along line 126-126 from FIG. 116. Any of the sensors described herein and/or incorporated by reference can include the features described in the context of FIG. 126. The features described in the context of FIG. 126 are not described in the context of each sensor embodiment to avoid unnecessary redundancy.

FIG. 126 illustrates an embodiment in which a portion (e.g., 692c, 683a, 691a, 690a, a sensor core, a sensor layer, a sensor support structure) of the sensor 616 is configured to soften in vivo. This portion can soften sufficiently in vivo that at the time the sensor 616 is removed from the tissue of the host, the sensor 616 is sufficiently prone to buckling that the sensor 616 does not pose a substantial risk of piercing another person.

The sensor 616 can comprise a first conductive layer 690a (e.g., platinum), a first insulation layer 692c (e.g., a polyurethane coating), and a second conductive layer 691a (e.g., a silver/silver chloride coating). The first insulation layer 692c can block direct electrical conductibility between the first conductive layer 690a and the second conductive layer 691a (e.g., such that the first conductive layer 690a and the second conductive layer 691a are electrically coupled only by tissue and/or fluid of the host as explained in the context of FIG. 125). The sensor 616 can comprise an outer membrane 683a.

The insulation layer 692a can be formulated to soften in response to being located in vivo. The softening of the insulation layer 692a (and/or any other portion of the sensor 616) makes the sensor 616 more prone to buckling, and thus, less prone to mistakenly piercing the skin (e.g., of the wrong person).

Sliding Arms

Once the sensor is removed from the tissue, the sensor can inadvertently pierce the skin of another person. Some embodiments overcome this potential hazard by retracting at least a portion of the sensor (e.g., as the sensor is removed from the skin and/or after the sensor is removed from the skin). Some embodiments cover the distal portion of the sensor to shield the sensor from piercing a person after the sensor is removed.

Several embodiments comprise an arm that is slidably coupled to the base. The arm can be configured to retract a distal portion of the sensor and/or cover the distal portion of the sensor.

Horizontal Pull Tab

One way to preclude a "used" sensor from inadvertently piercing the skin of a person is to retract the sensor (e.g., into an interior cavity of the system). The system (e.g., the wearable and/or the applicator) can include a portion configured to slide approximately parallel to the skin. Sliding the portion can retract the sensor. The portion that slides can be a pull tab and/or the transmitter. For example, pulling the pull tab and/or removing the transmitter can cause the system to retract the sensor.

Figure 4:
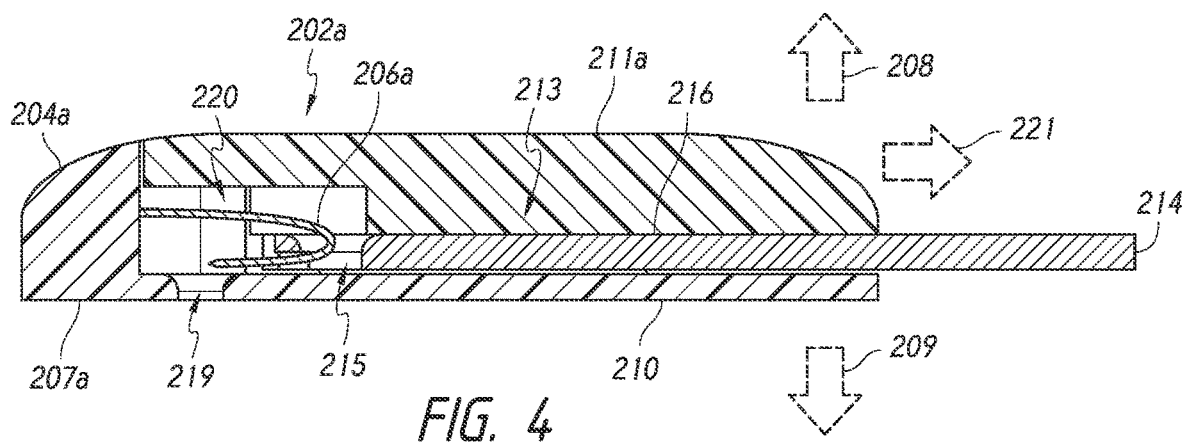
FIG. 4 illustrates a cross-sectional view like FIG. 3 except that the arm has been moved, according to some embodiments.

FIGS. 2-4 illustrate a sensor system 202a that includes an arm 203 slidably coupled to a base 204a. Sliding the arm 203 in the direction shown by arrow 205 can retract the sensor 206a to prevent the sensor 206a from piercing a person.

FIG. 2 illustrates a perspective view of the sensor system 202a. FIG. 3 illustrates a cross-sectional view along line 3-3 from FIG. 2. FIG. 4 also illustrates a cross-sectional view like FIG. 3 except that the arm 203 has been moved in the direction shown by arrow 205 in FIG. 2 to retract the sensor 206a.

Referring now to FIGS. 2-4, some embodiments comprise a sensor system 202a for measuring an analyte concentration. The sensor system 202a can comprise a base 204a having a distal side 207a configured to face towards a skin of a host. FIGS. 3 and 4 illustrate a proximal direction 208 (e.g., away from the skin) and a distal direction 209 (e.g., towards the skin).

The sensor system 202a can comprise a first adhesive 210 coupled to the base 204a and configured to couple the base 204a to the skin; a transmitter 211a coupled to the base 204a and configured to transmit analyte measurement data; and/or a transcutaneous analyte measurement sensor 206a coupled to the base 204a.

The system can comprise a pull tab system 213 that includes a pull tab 214. The pull tab system 213 can be configured to retract the sensor 206a in response to moving the pull tab 214 relative to the base 204a.

The pull tab system 213 can comprise a channel 215 and an intermediate portion 216 that couples the channel 215 to the pull tab 214. The pull tab 214 can protrude away from the base 204a. A first portion of the sensor 206a can pass through the channel 215. The pull tab system 213 can be configured such that pulling the pull tab 214 moves the channel 215 to retract the sensor 206a.

The channel 215 can be formed by a hole, a slot, and/or a hook. The channel 215 can be formed by a wall configured to push and/or pull the sensor 206a. The channel 215 can be open on one side to facilitate assembling the system (by enabling the sensor 206a to be inserted into the channel 215 through the open side).

The base 204a can comprise a channel (e.g., a second hole 219). A second portion of the sensor 206a can pass through the second hole 219. The pull tab system 213 can be configured such that pulling the pull tab retracts the sensor 206a by pulling the second portion of the sensor 206a out of the second hole 219 and into an interior area 220 of the sensor system 202a.

The pull tab system 213 can be slidably coupled to the base 204a such that the pull tab system 213 is configured to slide in a first direction 205 that is within 20 degrees (e.g., within plus or minus 20 degrees) and/or within 45 degrees (e.g., within plus or minus 45 degrees) of being perpendicular to a proximal direction 208 oriented away from the skin.

(The pull tab system 213 can be configured to slide in a direction 205 that is within plus or minus 20 degrees and/or within plus or minus 45 degrees of being perpendicular to a distal direction 209 oriented towards the skin.)

The transmitter 211a can be slidably coupled to the base 204a such that the transmitter 211a is configured to slide in a second direction 221 that is within plus or minus 20 degrees and/or within plus or minus 45 degrees of being perpendicular to the proximal direction 208. The second direction 221 can be within plus or minus 20 degrees and/or within plus or minus 45 degrees of being parallel to the first direction 205. (In some embodiments, the transmitter is coupled to the base by the user or permanent attachment to the base in the factory.)

Horizontal Push Tab Or Button

Figure 5:
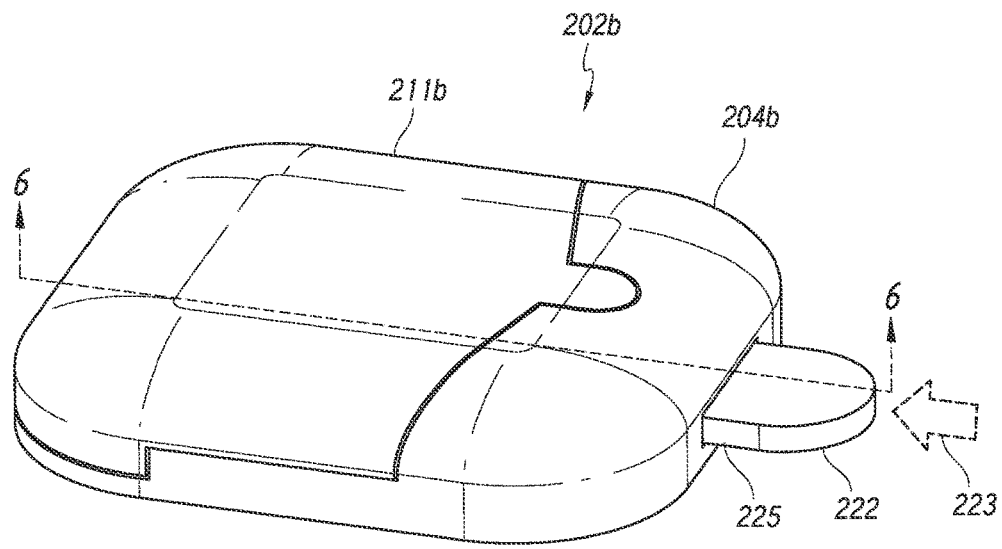
FIG. 5 illustrates a perspective view of a system, according to some embodiments.
Figure 6:
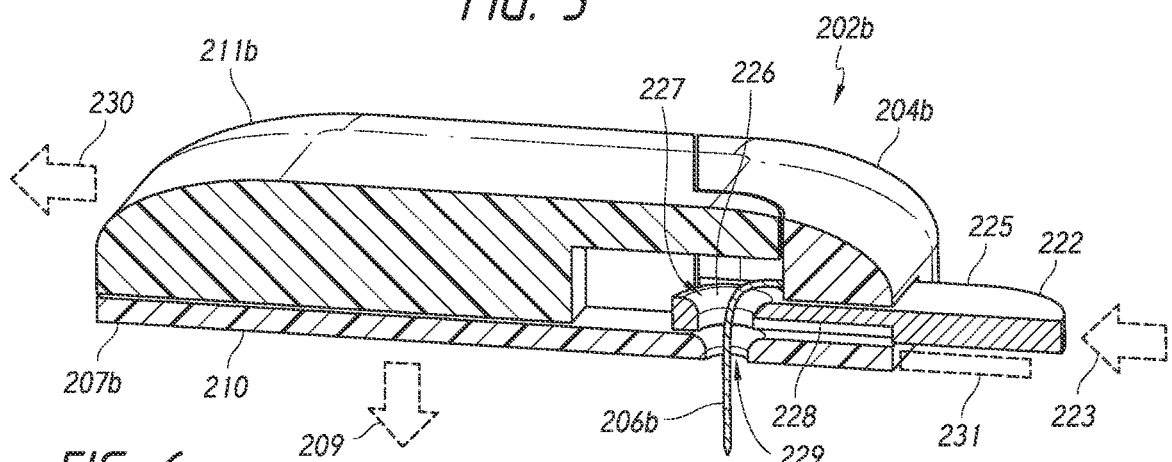
FIG. 6 illustrates a cross-sectional view along line 6-6 from FIG. 5, according to some embodiments.
Figure 7:
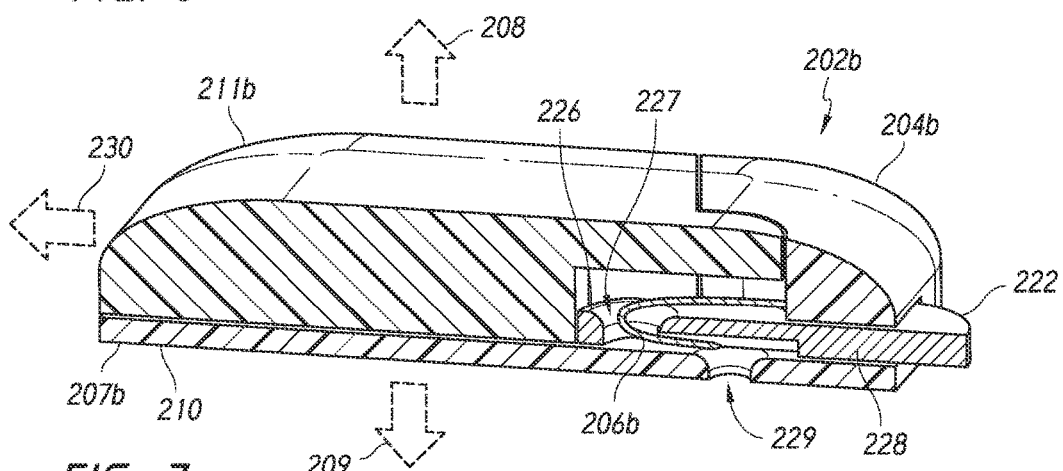
FIG. 7 illustrates the same cross-sectional view as shown in FIG. 6 except that the sensor has been retracted, according to some embodiments.

The embodiment illustrated in FIGS. 5-7 is also configured to retract the sensor 206b to prevent the sensor 206b from piercing the skin (e.g., after the sensor 206b has been removed from the host).

Rather than use a pull tab, the embodiment illustrated in FIGS. 5-7 includes a button 222, which can be a push tab or an electronic button. The system 202b can be configured such that pressing a button 222 (e.g., a push tab) into an outer housing causes the sensor 206b to retract into the outer housing. Thus, the system 202b precludes a "used" sensor 206b from inadvertently piercing the skin of a person by retracting the sensor 206b (e.g., into an interior cavity of the system 202b).

FIG. 5 illustrates a perspective view of the system 202b. FIG. 6 illustrates a cross-sectional view along line 6-6 from FIG. 5. FIG. 6 illustrates the sensor 206b prior to being retracted into an interior area of the sensor system 202b. FIG. 7 illustrates the same cross-sectional view as shown in FIG. 6 except that the sensor 206b has been retracted into the system 202b.

Referring now to FIGS. 5-7, the system 202b can comprise a push button system having a push button 222. The push button system can be configured to retract the sensor 206b in response to pushing the button 222 (e.g., in the direction shown by the arrow 223 in FIG. 5). In some embodiments, the button 222 is electrically activated rather than mechanically activated.

At least a portion 225 of the push button system can protrude away from the base 204b. The push button system can be configured such that pressing the portion 225 of the push button system into the base 204b engages a sensor retraction hoop or hook 226 that pulls and/or pushes the sensor 206b into an interior area of the sensor system 202b.

The push button system can further comprise a channel 227 and an intermediate portion 228 that couples the channel 227 to the push button 222. The push button 222 can protrude away from the base 204b. A first portion of the sensor 206b can pass through the channel 227. The push button system can be configured such that pushing the button 222 moves the channel 227 to retract the sensor 206b.

The channel 227 can be formed by a hole, a slot, and/or a hook 226. The channel 227 can be formed by a wall configured to push and/or pull the sensor 206b. The channel 227 can be open on one side to facilitate assembling the system 202b (by enabling the sensor 206b to be inserted into the channel 227 through the open side).

The base 204b can comprise a second channel formed by a second hole 229. A second portion of the sensor 206b can pass through the second hole 229. The push button system can be configured such that pushing the button 222 retracts the sensor 206b by pulling the second portion of the sensor 206b out of the second hole 229 and into an interior area of the sensor system 202b by making a third portion of the sensor 206b form a U-shape and/or a torturous shape.

The push button system can be slidably coupled to the base 204b such that the push button system is configured to slide in a first direction 223 that is within plus or minus 20 degrees and/or within plus or minus 45 degrees of being perpendicular to a proximal direction oriented away from the distal side of the base 204b. (The proximal direction is opposite relative to the distal direction 209.)

The push button system can comprise a first arm (e.g., a portion that includes the channel 227) and an intermediate portion 228 that couples the first arm to the push button 222. The push button 222 can protrude away from the base 204b. A first portion of the sensor 206b can pass through a channel 227 of the first arm (e.g., as illustrated in FIG. 6). The push button system can be configured such that pushing the button moves the first arm to retract the sensor 206b (e.g., as illustrated in FIG. 7).

The transmitter 211b can be slidably coupled to the base 204b such that the transmitter 211b is configured to slide in a second direction 230 that is within plus or minus 20 degrees and/or within plus or minus 45 degrees of being perpendicular to the proximal direction. The second direction 230 can be within plus or minus 20 degrees and/or within plus or minus 45 degrees of being parallel to the first direction 223.

In some embodiments, a first adhesive 210 that couples the system 202b to the skin can have a tab 231 configured to help a person peel the first adhesive 210 off the skin. This adhesive removal tab 231 can be at least partially covered by the push tab 222 to encourage the user to press the push tab 222 into the outer housing before using the adhesive removal tab 231 to peel the first adhesive 210 off the skin.

Trigger—Sliding Arm

Several embodiments automatically retract the sensor into an interior area of the system. For example, uncoupling the system from the skin can cause the sensor to retract automatically. Automatic retraction is advantageous because it does not rely on a person remembering to perform extra steps. For example, the system can retract the sensor in response to a person uncoupling at least a portion of a system from the skin.

Embodiments can comprise a trigger. Activating the trigger can cause the sensor to retract (e.g., into an interior cavity of the system).

The trigger can be spring-loaded such that uncoupling the base from the skin moves and/or removes a pin to release a compressed spring and/or an extended spring (e.g., a stretched spring). The spring can be in a high-energy state such that the system is configured to release a force of the spring in response to moving the pin. The spring can be any type of spring described herein and/or incorporated by reference. The spring can be a leaf spring, a flex arm (e.g., an integrally molded flex arm), a conical spring, and/or any suitable type of spring and/or combination of multiple springs.

Releasing the spring can cause the spring force to retract the sensor into an interior area of the system. The movement caused by releasing the spring can cause a pushing action and/or a pulling action to retract the sensor.

The system can have a first adhesive to couple the base to the skin. The system can also have a second adhesive that couples the release pin to the skin. As a result, uncoupling the base from the skin can pull the release pin out of the base and/or at least partially away from the base (as the release pin continues to be adhered to the skin). In some embodiments, the first and second adhesives may be on the same body.

In some embodiments, the pin can be configured to remain coupled to the base even after the base is uncoupled from the skin. For example, the pin can be configured to telescope a limited distance and be retained by an undercut feature. Thus, the post can remain attached to the base while moving to a position that releases the spring.

Figure 8:
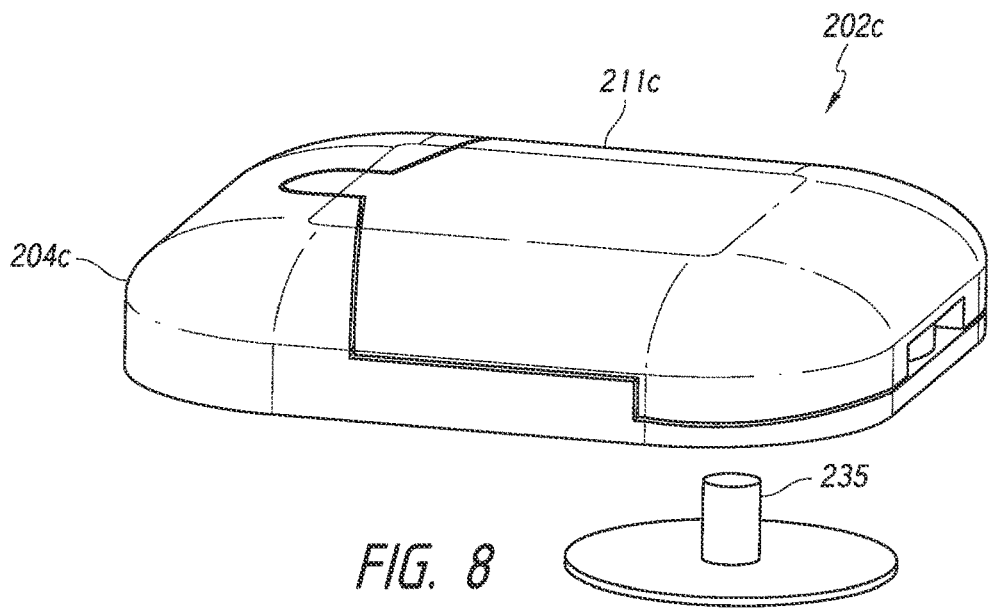
FIG. 8 illustrates a perspective view of a system with a spring-loaded arm, according to some embodiments.
Figure 9:
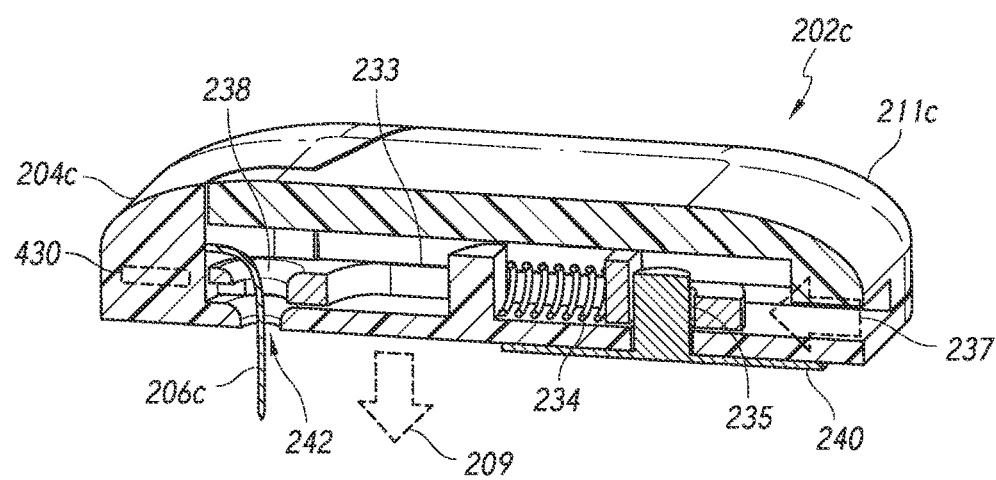
FIG. 9 illustrates a cross-sectional view from the perspective shown in FIG. 8, according to some embodiments.

FIG. 8 illustrates a perspective view of an embodiment with a spring-loaded arm 233 that is configured to retract the sensor 206c in response to releasing the arm 233. A release mechanism (e.g., a pin 235) can be used to hold the arm 233 in a starting position prior to the arm 233 retracting the sensor 206c. FIG. 9 illustrates a cross-sectional view from the perspective shown in FIG. 8. In FIG. 9, the arm 233 is in a high-energy state (due to the energy stored in the spring 234). Moving the pin 235 releases the spring 234 to drive the arm 233 to retract the sensor 206c (as shown in FIG. 10).

Figure 10:
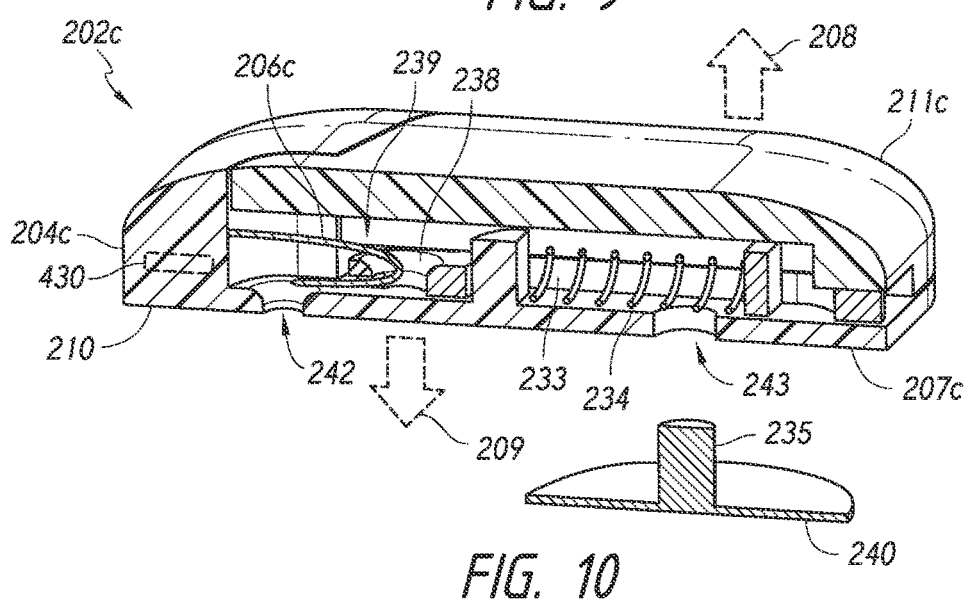
FIG. 10 illustrates the same cross-sectional view as illustrated in FIG. 9 except that the sensor has been retracted, according to some embodiments.

Referring now to FIGS. 8-10, some embodiments comprise a spring-loaded arm 233 slidably coupled to the base 204c such that removing the sensor system 202c from the skin causes the sensor 206c to automatically retract in response to the arm 233 sliding relative to the base 204c.

The base 204c can be configured to face towards the skin in a first direction 209 (e.g., a distal direction). The arm 233 can be configured to slide in a second direction 237 that is within plus or minus 20 degrees and/or within plus or minus 45 degrees of perpendicular to the first direction 209. At least a portion of the sensor 206c can pass through a portion 238 of the arm 233 such that moving the arm 233 in the second direction 237 causes the portion 238 of the arm 233 to retract the sensor 206c into an interior area 239 (e.g., a cavity) of the sensor system 202c.

Several embodiments comprise a spring 234 and a release pin 235. The spring 234 can be in at least one of a compressed state and an extended state (e.g., a stretched state) such that removing the release pin 235 causes the spring 234 to move at least a first portion of the sensor 206c into the base 204c.

Some embodiments comprise an arm 233 slidably coupled to the base 204c. The arm 233 can comprise a first channel 238 (e.g., formed by a hole, a slot, and/or a hook). The first channel 238 can be aligned with a second channel 242 (e.g., a second hole) of the base 204c such that a second portion of the sensor 206c passes through the first channel 238 and the second hole. The spring 234 can be at least one of compressed and extended (e.g., stretched) between a first wall of the base 204c and a second wall of the arm 233. The release pin 235 can pass through a third channel 243 (e.g., a third hole) of the base 204c and can interfere with a portion of the arm 233 to prevent the spring 234 from moving the arm 233 to retract the sensor 206c.

The release pin 235 can comprise a distal face having a second adhesive 240 configured to be applied to the skin such that removing the base 204c from the skin uncouples the first adhesive from the skin but does not uncouple the second adhesive 240 from the skin, which causes the release pin 235 to be removed from the third hole, and thereby enables the spring 234 to move the arm 233 to retract the sensor 206c. In some embodiments, the pin 235 moves relative to the base 204c, but remains coupled to the base 204c after the pin 235 releases the arm 233 to retract the sensor 206c into the system 202c.

The spring 234 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

A transmitter 211c can be removably coupled to the base 204c and/or integrated into the base 204c. The base 204c can comprise a battery 430 configured to provide electrical power to the sensor 206c and/or the transmitter 211c.

Trigger—External Arm

Several embodiments include a spring-loaded arm that is configured to bend and deflect a distal portion of the sensor. As a result, the spring-loaded arm can prevent the sensor from piercing the skin of a person.

The arm can slide approximately perpendicularly to a distal direction (rather than approximately parallel to a distal direction as used in some embodiments). The sliding arm can be located at least partially outside of the housing of the system.

Activating a trigger can cause the system to bend and deflect a distal portion of the sensor such that the distal portion can no longer pierce the skin. The distal portion of the sensor can be held between a sliding arm (that is activated by a triggering mechanism) and the base. Adhesive can secure the trigger in a starting position such that uncoupling the adhesive from the skin activates the trigger to bend the distal portion of the sensor.

Figure 11:
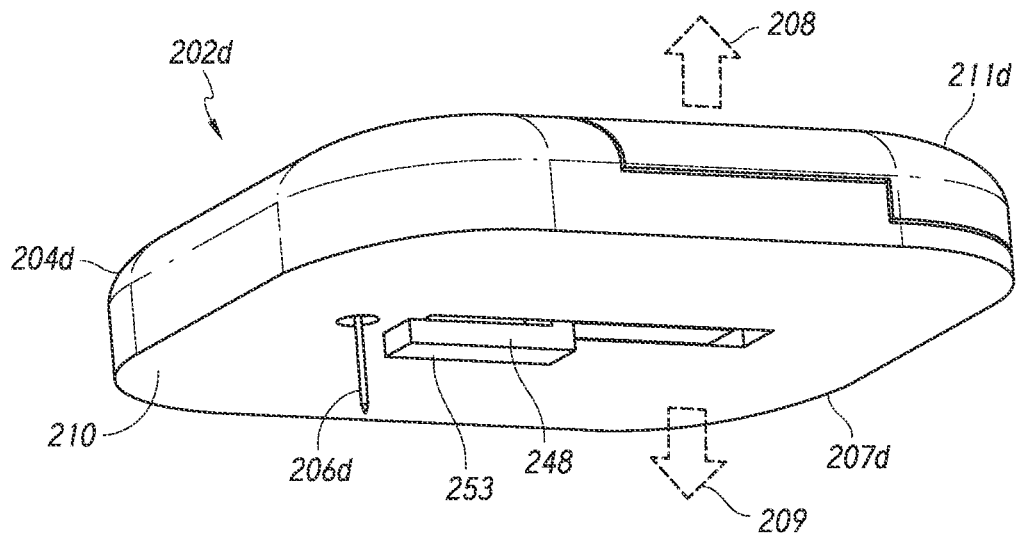
FIG. 11 illustrates a perspective view of an embodiment with a spring-loaded arm, according to some embodiments.
Figure 12:
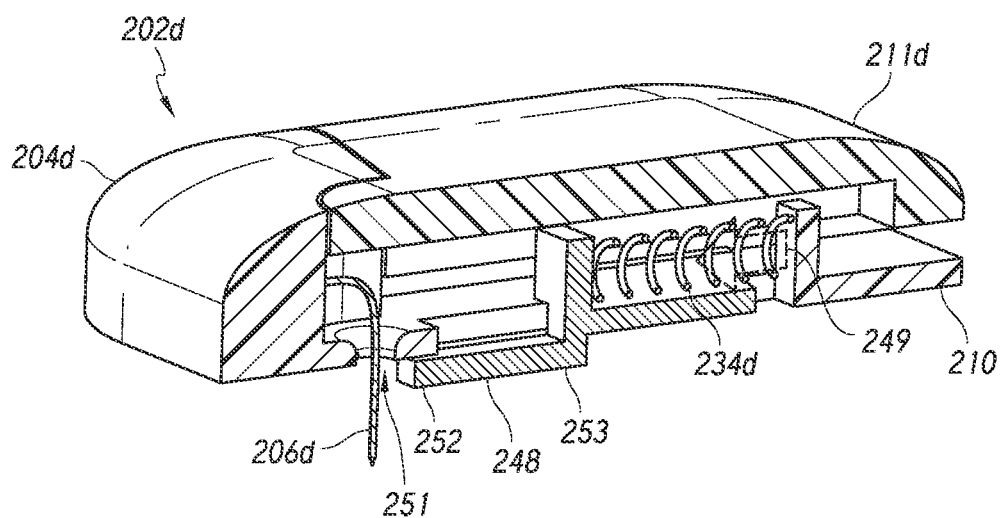
FIG. 12 illustrates a cross-sectional, perspective view of the embodiment shown in FIG. 11, according to some embodiments.
Figure 13:
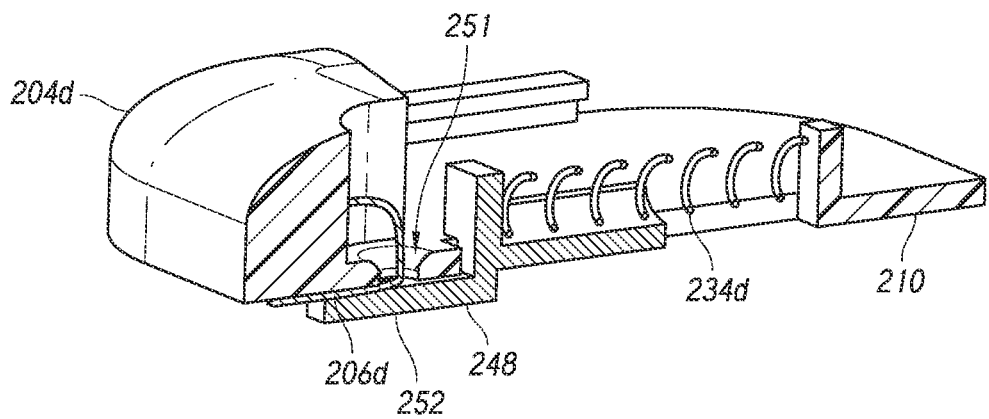
FIG. 13 illustrates a cross-sectional, perspective view of the embodiment shown in FIG. 12 except that the arm has moved relative to the base, according to some embodiments.

FIG. 11 illustrates a perspective view of an embodiment with a spring-loaded arm 248 that is configured to bend a portion of the sensor 206d against the distal side 207d of the base 204d to prevent the sensor 206d from inadvertently piercing a person after the sensor 206d is removed from the tissue of a host. FIG. 12 illustrates a cross-sectional, perspective view of the embodiment shown in FIG. 11. In FIG. 12, the arm 248 has not yet bent the sensor 206d. For example, the sensor configuration illustrated in FIG. 12 can be when the sensor 206d is at least partially located in tissue of the host. FIG. 13 illustrates a cross-sectional, perspective view of the embodiment shown in FIG. 11 except that the arm 248 has moved relative to the base 204d to bend the sensor 206d. In FIG. 13, the transmitter 211d has been uncoupled from the base 204d.

Referring now to FIGS. 11-13, some embodiments comprise a spring-loaded arm 248 slidably coupled to the base 204d and configured such that removing the sensor system 202d from the skin causes the arm 248 to collide with a first portion of the sensor 206d and bend the sensor 206d such that a second portion of the sensor 206d is located between the arm 248 and the base 204d (e.g., as shown in FIG. 13).

The base 204d can be configured to face towards the skin in a first direction 209 (e.g., a distal direction). The sensor system 202d can comprise a spring 234d oriented within plus or minus 20 degrees and/or within plus or minus 45 degrees of perpendicular to the first direction 209. The spring 234d can be located in an interior area of the sensor system 202d and can be configured to cause the arm 248 to collide with the first portion of the sensor 206d.

The spring 234d can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

The base 204d can be configured to face towards the skin in a first direction 209. The arm 248 can be configured to slide in a second direction 249 that is within plus or minus 20 degrees of perpendicular to the first direction 209 such that the second portion of the sensor 206d is oriented within plus or minus 20 degrees of perpendicular to the first direction 209.

The sensor 206d can pass through a channel 251 (e.g., a hole) of the base 204d. The first portion of the sensor 206d can be located distally relative to the hole of the base 204d. The arm 248 can be spring-loaded towards the first portion of the sensor 206d. The arm 248 can comprise a protrusion 252 that protrudes towards the first portion of the sensor 206d such that sliding the arm 248 causes the protrusion 252 to collide with the first portion of the sensor 206d and positions the protrusion 252 directly distally relative to the channel 251 (e.g., the hole) of the base 204d.

The protrusion of the arm 248 can comprise a second adhesive 253 configured to couple the arm 248 to the skin such that the second adhesive 253 holds the arm 248 in a first position in which the arm 248 does not bend the sensor 206d. Uncoupling the second adhesive 253 from the skin can cause the arm 248 to the bend the sensor 206d such that the second portion of the sensor 206d is located between the arm 248 and the base 204d.

Rotating Arms

Several embodiments comprise an arm that is rotatably coupled to the base. The rotating arm can prevent a sensor (and/or a needle) from posing a risk of piercing the skin.

The rotating arm can be configured to retract a distal portion of the sensor and/or cover the distal portion of the sensor to shield the sensor from inadvertently piercing a person. The rotating arm can be manually triggered or automatically triggered. In some embodiments, the arm automatically rotates in response to uncoupling the base from the skin.

Spring Flap

Some embodiments include an arm that is rotatably coupled to the base such that uncoupling the system from the skin releases the arm such that the arm rotates towards a distal portion of the sensor. The arm can bend the sensor and/or trap a distal portion of the sensor between the arm and the base to preclude the sensor from piercing skin unintentionally.

The arm can be driven (e.g., pushed directly or indirectly, pulled directly or indirectly) by a spring configured to rotate the arm towards a distal portion of the sensor. The spring can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

The system can have a first state in which the skin interferes with rotation of the arm. Once the system is uncoupled from the skin, the arm can be free to rotate to bend the sensor. For example, once the skin and/or a locking mechanism no longer constrains the spring, the spring force can cause the arm to rotate.

Figure 14:
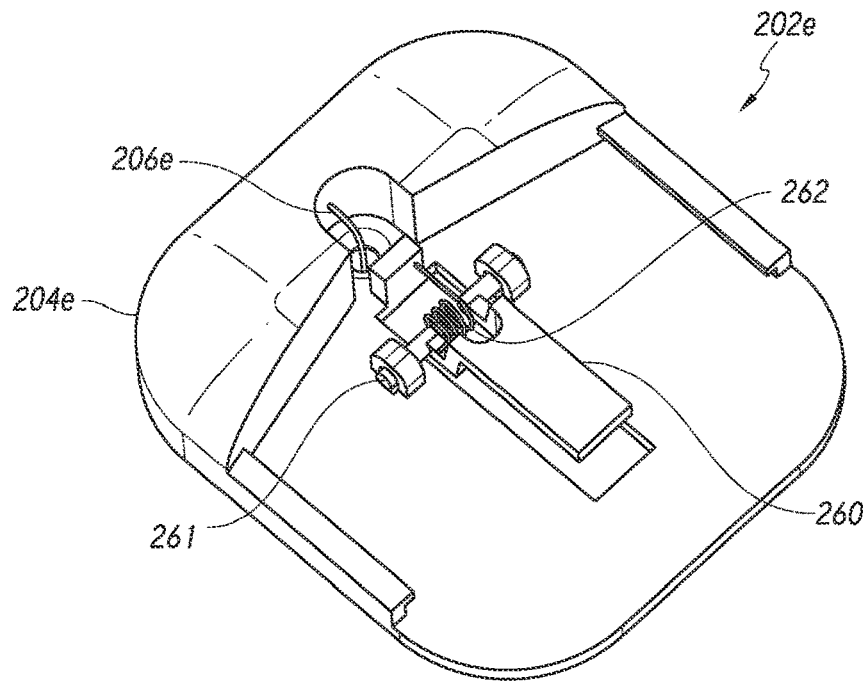
FIG. 14 illustrates a perspective view of a system with an arm rotatably coupled to a base, according to some embodiments.
Figure 15:
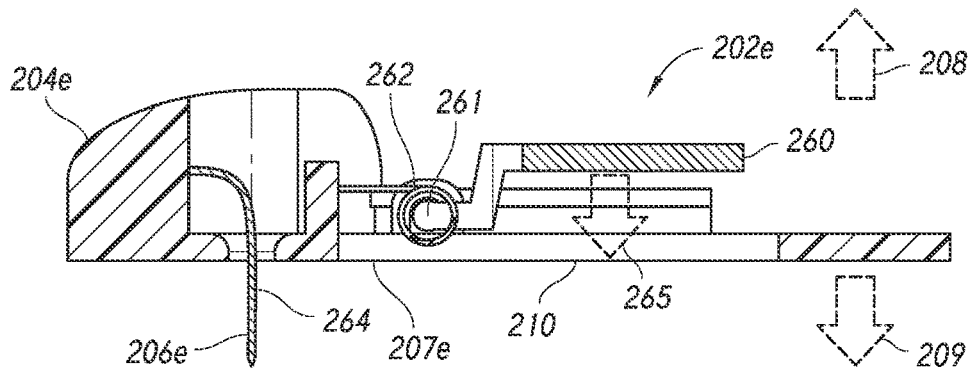
FIG. 15 illustrates a side, cross-sectional view of the system shown in FIG. 14, according to some embodiments.
Figure 16:
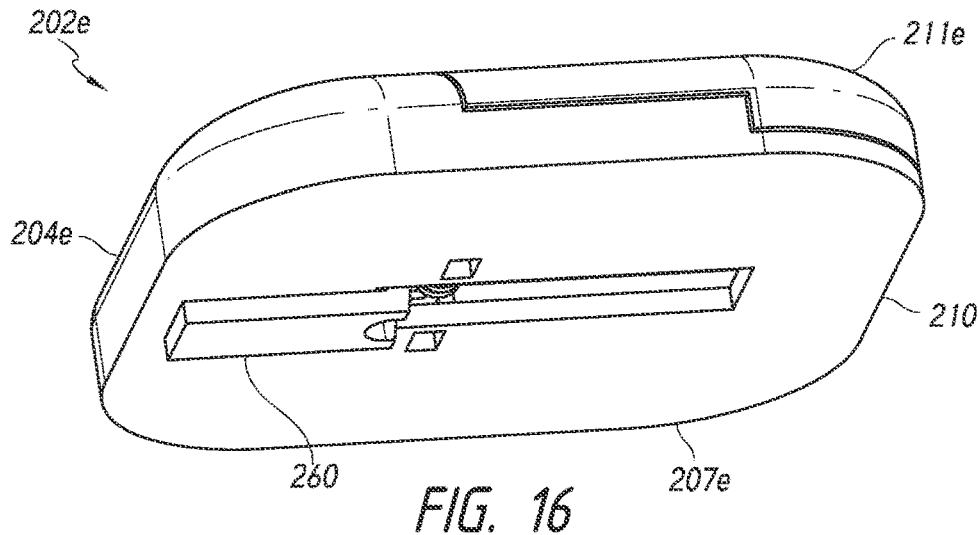
FIG. 16 illustrates a perspective view of the system shown in FIG. 14, according to some embodiments.

FIG. 14 illustrates a perspective view of a system 202e with an arm 260 rotatably coupled to a base 204e by a hinge 261. FIG. 15 illustrates a side, cross-sectional view of the system 202e shown in FIG. 14. The transmitter 211e is hidden in FIGS. 14 and 15 to facilitate clearly viewing the rotating arm 260. The optionally removable transmitter 211e is shown in FIG. 16. FIG. 16 illustrates a perspective view of the system 202e.

Referring now to FIGS. 14-16, the arm 260 can be spring loaded such that the arm 260 is configured to rotate in the direction shown by arrow 265 about the hinge 261. FIG. 15 illustrates a portion 264 of the sensor 206e. The portion 264 is located distally relative to the distal side 207e. At least a section of this portion 264 can be bent and/or deflected by the rotation of the arm 260 such that the section is located between the arm 260 and the distal side 207e (e.g., as shown in FIG. 16).

The arm 260 can have a starting position in which the arm 260 is located in a recession of the base 204e (e.g., as shown in FIGS. 14 and 15). The arm 260 can have an ending position in which the arm 260 shields the sensor 206e from penetrating skin (e.g., as shown in FIG. 16).

The hinge 261 can be configured such that uncoupling the base 204e from the skin causes the hinge 261 to rotate such that the arm 260 bends at least a first portion of the sensor 206e and covers at least a second portion of the sensor 206e.

The system 202e can comprise a torsional spring 262 coupled to the arm 260 such that the torsional spring 262 biases the arm 260 in a rotational direction 265 towards the second portion of the sensor 206e.

The hinge 261 can be located in an interior area of the sensor system 202e (as shown in FIGS. 14 and 15). The arm 260 can comprise a portion configured to cover the second portion of the sensor 206e. The sensor system 202e can comprise a first state in which the portion of the arm 260 is located in the interior area (as shown in FIGS. 14 and 15). The transmitter 211e is hidden in FIGS. 14 and 15, but the portion of the arm 260 is located in the interior area in FIGS. 14 and 15. The sensor system 202e can comprise a second state in which the portion of the arm 260 is located distally relative to the base 204e (as shown in FIG. 16).

Pivoting System

In some embodiments, a hinge is used to retract the sensor to shield the sensor from piercing skin. The movement of the hinge can pull the sensor out of the tissue of the host and into an area between a first part of the system and a second part of the system.

The system can comprise a lift tab configured to enable a user to easily move a proximal portion of the system to cause the hinge to rotate. This rotation can pivot the proximal portion relative to the distal portion of the system to retract the sensor.

Figure 17:
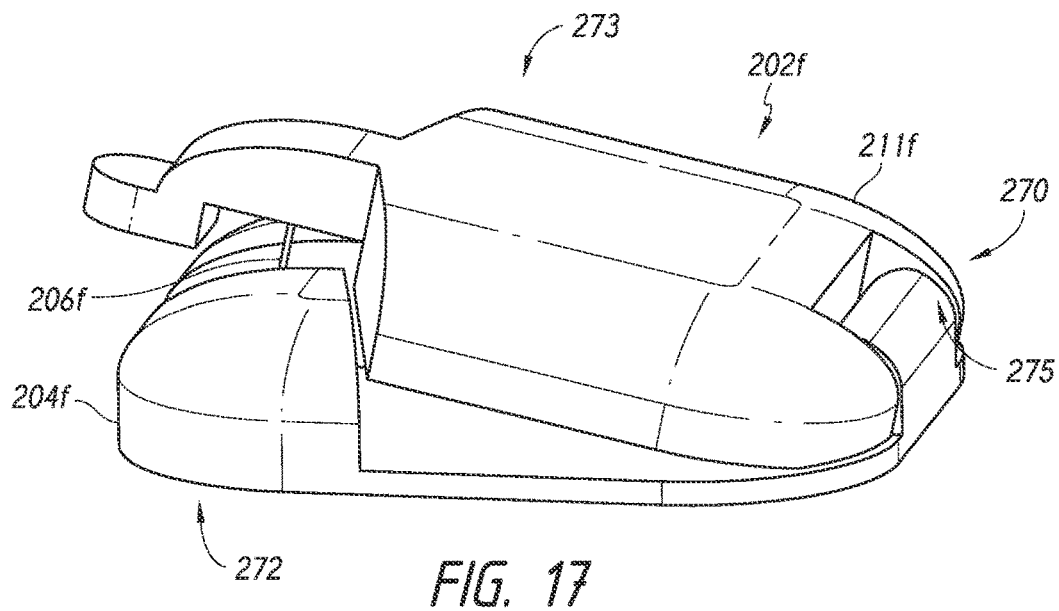
FIG. 17 illustrates a perspective view of a system that includes a hinge configured to retract a sensor, according to some embodiments.
Figure 18:
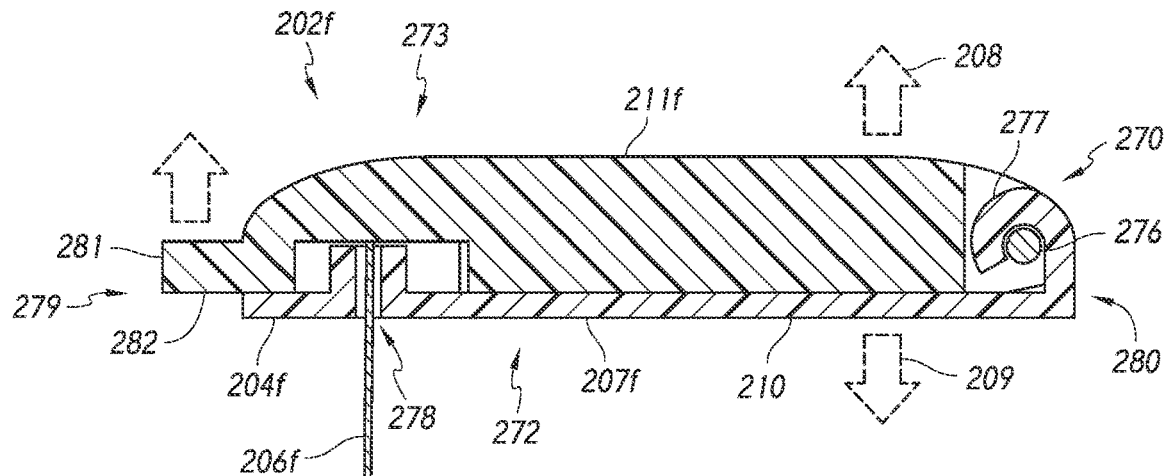
FIG. 18 illustrates a side, cross-sectional view of the system in a state prior to sensor retraction, according to some embodiments.
Figure 19:
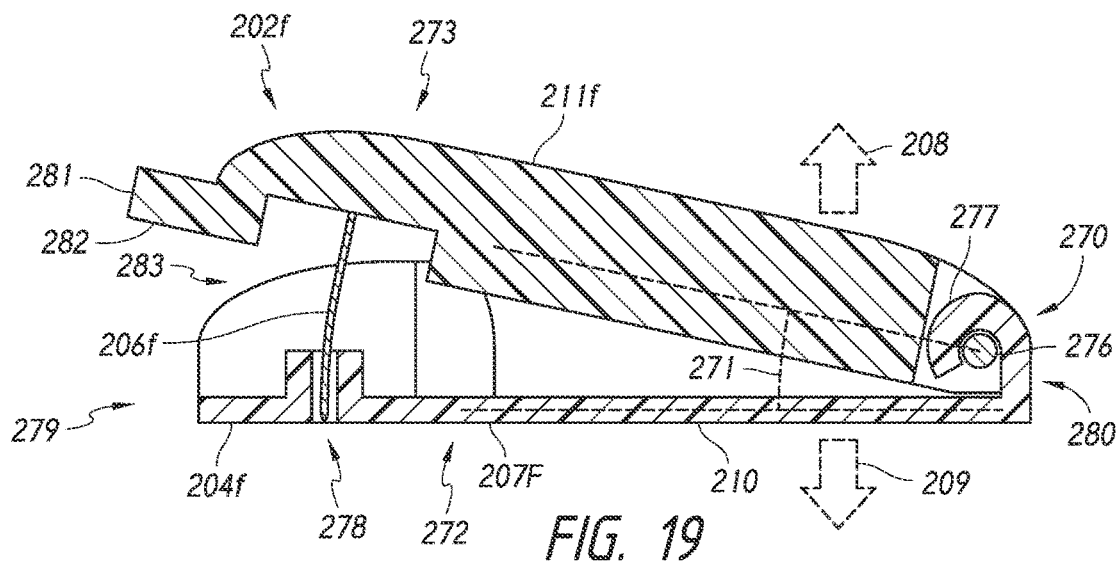
FIG. 19 illustrates a side, cross-sectional view of the system in a state after sensor retraction, according to some embodiments.

FIG. 17 illustrates a perspective view of a system 202f that includes a hinge 270 configured to retract the sensor 206f. FIG. 18 illustrates a side, cross-sectional view of the system 202f in a state prior to sensor retraction. FIG. 19 illustrates a side, cross-sectional view of the system 202f in a state after sensor retraction.

Referring now to FIGS. 17-19, some systems 202f comprise a first portion 272 coupled to a second portion 273 by a hinge 270. Pivoting the first portion 272 relative to the second portion 273 can retract the sensor 206f to preclude the sensor 206f from piercing the skin of another person. The second portion 273 can be coupled to the first portion 272 by a hinge 270 configured such that increasing a pivot angle 271 between the first portion 272 and the second portion 273 retracts the sensor 206f.

The sensor system 202f can comprise a base 204f, a transmitter 211f, and a distal side 207f. A spring 275 (e.g., a helical spring, a compression spring, a tension spring, a leaf spring, a torsional spring) can be configured to increase the pivot angle 271 (e.g., once released by a triggering mechanism and/or any suitable mechanism).

The spring 275 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

The hinge 270 can comprise a pin 276 rotatably coupled to a sleeve 277 configured to retain the pin 276 as the second portion 273 rotates relative to the first portion 272. As used herein, the term "sleeve" is used broadly and can mean a tubular part, a hollow axle, and/or a bushing designed to fit over another part to retain the other part during pivoting. Sleeve can be an open-ended flat or tubular packaging or cover. Some sleeves are not cylindrical or full cylinders (e.g., sleeves can have a slot).

The base 204f can comprise the first portion 272 and the second portion 273. The first portion 272 can couple the first adhesive 210 to the second portion 273.

The base 204f can comprise the first portion 272. The second portion 273 can comprise the transmitter 211f.

A distal portion of the sensor 206f can pass through a channel 278 (e.g., a hole) of the base 204f. A proximal portion of the sensor 206f can be coupled to the second portion 273 such that increasing the pivot angle 271 retracts the distal portion of the sensor 206f through the channel 278 of the base 204f and into an area between the first portion 272 and the second portion 273 of the sensor system 202f.

The base 204f can comprise a left half 279 and a right half 280. The left half 279 can comprise the channel 278 of the base 204f. The right half 280 can comprise at least a portion of the hinge 270.

The second portion 273 can comprise a lift tab 281 configured to enable a user to grip a distally facing surface 282 to rotate the second portion 273 relative to the first portion 272. The lift tab 281 can comprise a protrusion that protrudes away from the hinge 270. The lift tab may be coupled to a flex arm that releasably couples the first and second portions. Applying force to the lift tab may activate the decoupling.

Hinged Baseplate

In some embodiments, the system comprises a hinged base configured to fold over the sensor to preclude the sensor from piercing another person. The user can fold one side of the base over the sensor. A spring can move one side of the base over the sensor.

FIG. 20 illustrates a perspective view of a base 204g that comprises a first portion 294 and a second portion 295. The first portion 294 of the base 204g is configured to rotate relative to the second portion of the base 204g to shield a distal portion of the sensor 206g to prevent the sensor 206g from piercing a person. The first portion 294 can rotate about a hinge 297 in a direction indicated by arrow 291 in FIG. 20.

FIG. 21 illustrates a perspective view of the base 204g after the first portion 294 has rotated approximately 90 degrees relative to the second portion 295. The first portion 294 can continue rotating in the direction indicated by arrow 292 to arrive at the state illustrated in FIGS. 22a and 22b.

FIG. 22a illustrates a top view of the system 202g. FIG. 22b illustrates a side view of the system 202g. In FIGS. 22a and 22b, the sensor 206g is shielded from piercing skin by the first portion 294 of the base 204g.

Referring now to FIGS. 20-22b, the base 204g can comprise a first portion 294 and a second portion 295. The second portion 295 of the base 204g can be coupled to the first portion 294 of the base 204g by a hinge 297 configured such that decreasing a pivot angle between the first portion 294 and the second portion 295 of the base 204g places a portion of the sensor 206g between the first portion 294 and the second portion 294 of the base 204g. A transmitter 211g can be coupled to the base 204g.

The hinge 297 can comprise a first pin rotatably coupled to a first hole configured to retain the first pin as the first portion 294 of the base 204g rotates relative to the second portion 295 of the base 204g.

The hinge 297 can comprise a second pin rotatably coupled to a second hole configured to retain the second pin as the first portion 294 of the base 204g rotates relative to the second portion 295 of the base 204g. The first pin can protrude in a first direction. The second pin can protrude in a second direction that is opposite relative to the first direction.

The first adhesive can comprise a first section 290b and a second section 290a coupled to a distal side 207g of the base 204g. The first section 290b can be coupled to the first portion 294 of the base 204g such that the first section 290b is configured to adhere the first portion 294 of the base 204g to the skin. The second section 290a can be coupled to the second portion 295 of the base 204g such that the second section 290a is configured to adhere the second portion 295 of the base 204g to the skin. The hinge 297 can be configured to enable the first section 290b of the first adhesive to face towards the second section 290a of the first adhesive while the portion of the sensor 206g is at least partially confined between the first portion 294 and the second portion 295 of the base 204g.

The system 202g can be configured to bend the portion of the sensor 206g in response to rotating the hinge 297. The portion of the sensor 206g can be bent between the first portion 294 and the second portion 295 of the base 204g to guard against a distal tip of the sensor 206g penetrating tissue after the sensor system 202g is removed from the skin.

The first portion 294 of the base 204g can be rotationally spring-loaded relative to the second portion 295 of the base 204g such that the system 202g is configured to decrease the pivot angle in response to a rotational spring bias.

The system 202g can comprise a torsion spring 298 coupled to the hinge 297 such that the torsion spring 298 is configured to decrease the pivot angle to place the portion of the sensor 206g between the first portion 294 and the second portion 295 of the base 204g.

The spring 298 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

Patch Folds Over Sensor

One way to prevent the sensor from being a hazard is to fold a portion of the adhesive over the sensor. For example, the adhesive can have a larger footprint that is typically used to couple the base to the skin. A portion of the larger footprint can be folded over the sensor.

In some embodiments, the system can comprise a compliant, pliable sheet configured to fold over the sensor after the sensor is removed from the tissue. Prior to being used to shield the sensor, the sheet can be folded in a compact manner. Deploying the sheet over the sensor can include unfolding the sheet.

The sheet can include a puncture-resistant material such as a foil. This way, the sheet can be very easy to fold while the puncture-resistant material can be optimized to prevent the sensor's distal tip from piercing the puncture-resistant material.

In some embodiments, the sheet has a puncture resistance that blocks the sensor from puncturing the sheet during normal operating conditions. As a result, an additional puncture-resistant material is not necessary.

Figure 23:
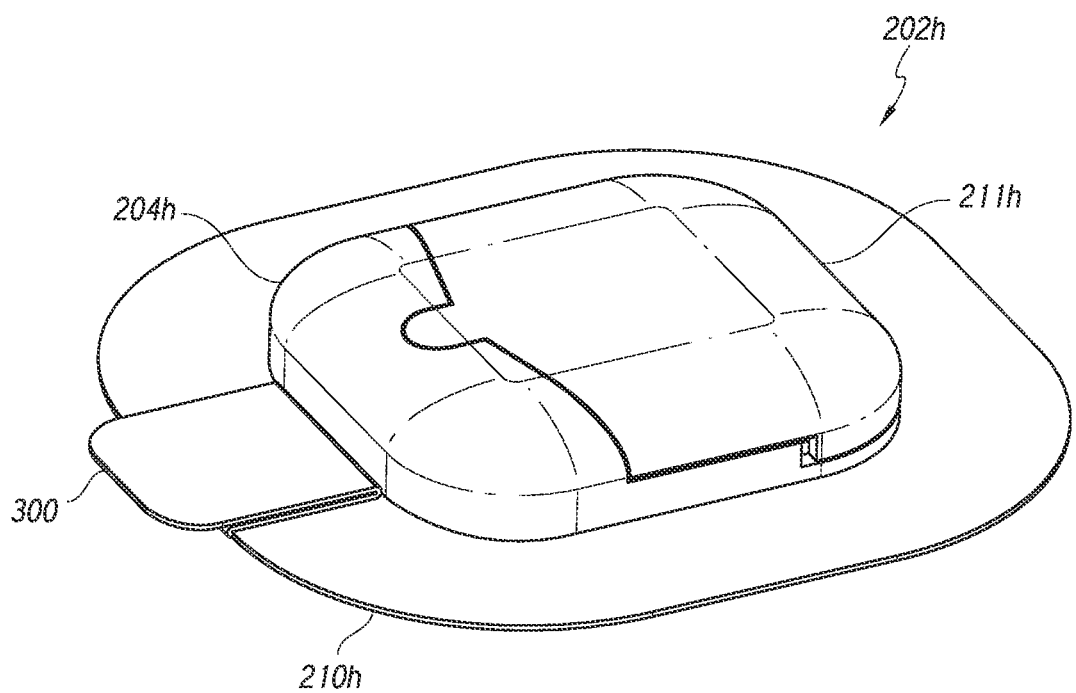
FIGS. 23 and 24 illustrate perspective views of a sensor system that includes a pliable sheet, according to some embodiments.
Figure 24:
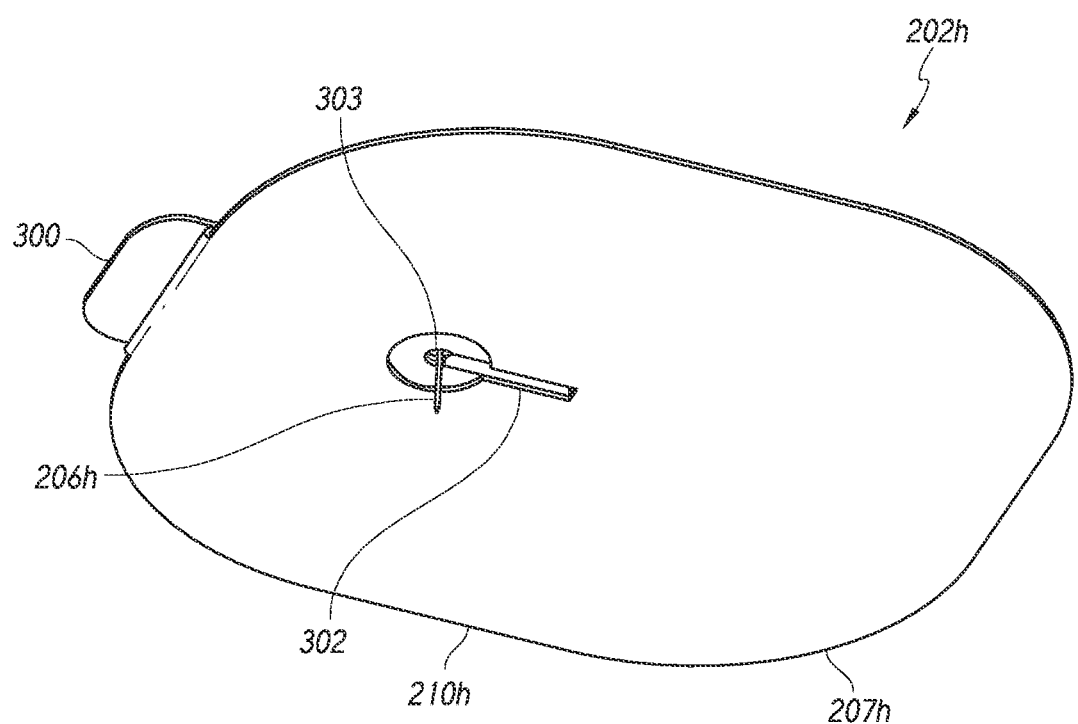
Figure 25:
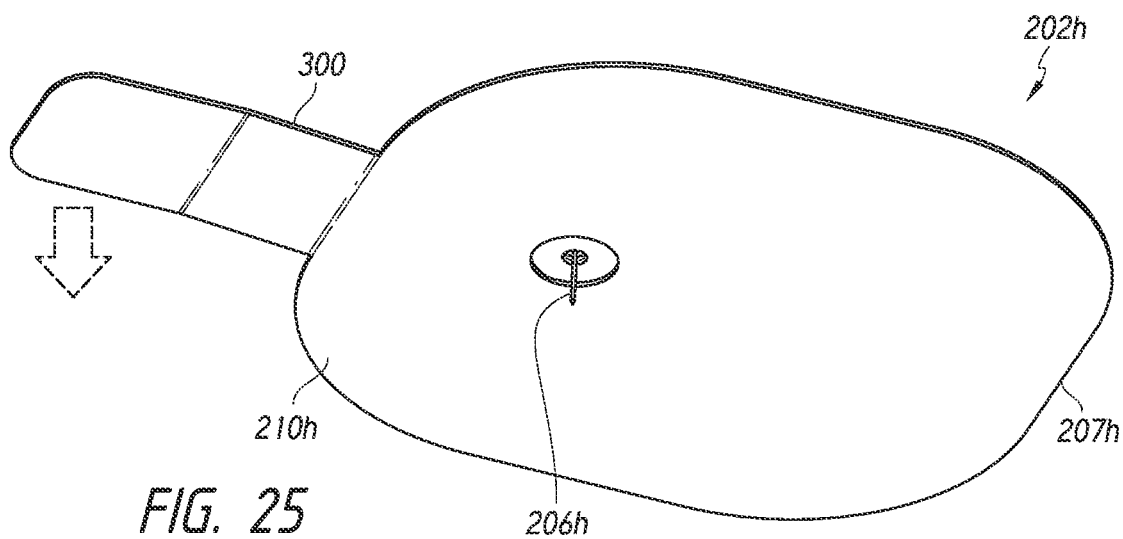
FIG. 25 illustrates a perspective view of the pliable sheet as the pliable sheet is unfolded, according to some embodiments.
Figure 26:
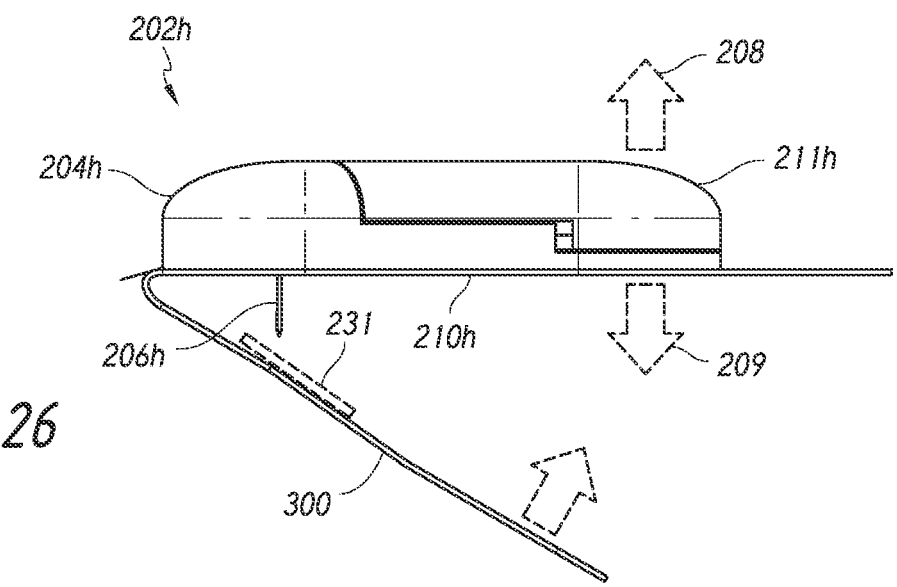
FIG. 26 illustrates a side view of the pliable sheet, according to some embodiments.

FIG. 23 illustrates a perspective view of a sensor system 202h that includes a pliable sheet 300 configured to cover a distal tip of the sensor 206h. FIG. 24 illustrates another perspective view of the system 202h in a state when the pliable sheet 300 is folded in a storage position. FIG. 25 illustrates a perspective view of the pliable sheet 300 as the pliable sheet 300 is unfolded. The pliable sheet 300 continues to move towards the distal tip of the sensor 206h until the pliable sheet 300 arrives at the state shown in the side view illustrated in FIG. 26. Then, the pliable sheet 300 can continue moving towards the distal tip of the sensor 206h until the pliable sheet 300 covers the distal tip of the sensor 206h (as illustrated in the perspective view shown in FIG. 27).

Referring now to FIGS. 23-27, the system 202h can comprise an adhesive portion of the sheet 300 configured to bend at least a portion of the sensor 206h towards the base 204h. A distal tip of the sensor 206h can be located between the base 204h and the adhesive portion. A transmitter 211h can be coupled to the base 204h.

The system 202h can comprise a pliable sheet 300 that covers a distal tip of the sensor 206h and adheres to the first adhesive 210h such that the pliable sheet 300 guards against the distal tip of the sensor 206h penetrating tissue after the sensor system 202h is removed from the skin. The pliable sheet 300 can be coupled to the distal side 207h of the base 204h (e.g., as shown in FIG. 27).

The first adhesive 210h can couple the pliable sheet 300 to the base 204h. The pliable sheet 300 can comprise a first state in which the pliable sheet 300 is folded, is located proximally relative to the distal tip, does not cover the distal tip, and forms a tab configured to enable a user to unfold the pliable sheet 300 (e.g., as shown in FIGS. 23 and 24).

Figure 27:
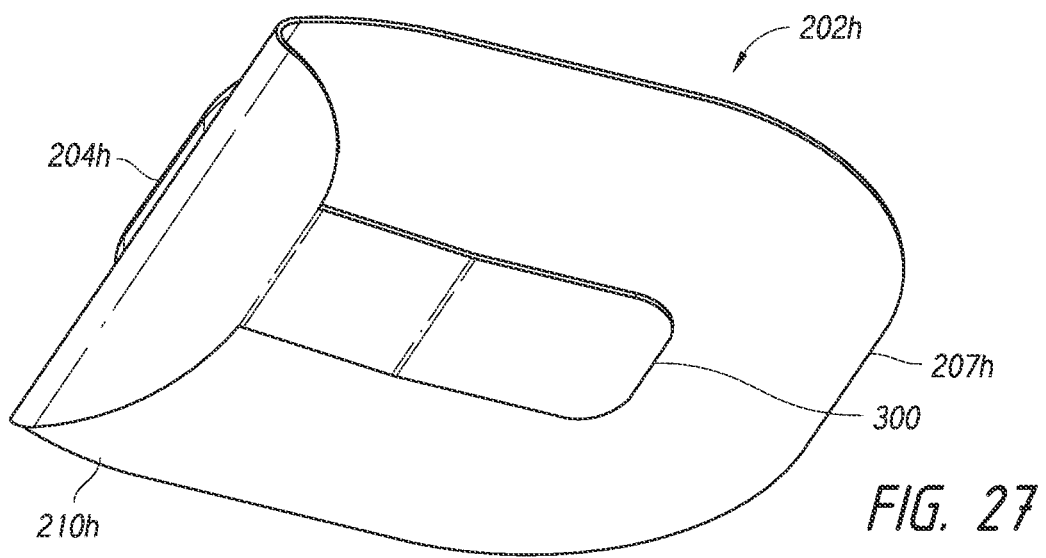
FIG. 27 illustrates a perspective view of the pliable sheet as the pliable sheet covers a sensor tip, according to some embodiments.

The pliable sheet 300 can comprise a second state in which the pliable sheet 300 is at least partially unfolded relative to the first state, is at least partially located distally relative to the distal tip, and the distal tip of the sensor 206h is at least partially confined between the pliable sheet 300 and the first adhesive 210h (e.g., as shown in FIG. 27).

The system 202h can comprise a second sheet 301 having a second puncture resistance that is greater than a first puncture resistance of the pliable sheet 300. The second sheet 301 can be located between the distal tip and the pliable sheet 300 to protect the pliable sheet 300 from being punctured by the distal tip. The second sheet 301 can be coupled to the pliable sheet 300 such that the second sheet 301 deforms the distal tip as the pliable sheet 300 is folded over the distal tip.

A distal tip of the sensor 206h can be at least partially confined between a pliable sheet 300 and the base 204h such that the pliable sheet 300 holds at least a portion of the sensor 206h in a bent position and the pliable sheet 300 is adhered to the first adhesive 210h.

The pliable sheet 300 can comprise a first state and a second state. In the first state, the pliable sheet 300 can be located proximally relative to the first adhesive 210h when the sensor system 202h is coupled to the skin. In the second state, the pliable sheet 300 can be located distally relative to the first adhesive 210h when the distal tip of the sensor 206h is at least partially confined between the pliable sheet 300 and the base 204h. As used herein, the term "pliable" means able to at least one of be bent and be folded. The sheet can also be compliant.

Protective Slot to Hold Sensor

A distal side of the base can include a slot configured to hold a distal end of the sensor after the sensor is removed from the tissue. The distal end of the sensor can be manually pressed into the slot.

The sensor can permanently deform to hold the distal end of the sensor in the slot. Once the distal end of the sensor is located in the slot, the sensor is precluded from piercing another person. In some embodiments, the sensor elastically deforms to at least partially enter the slot.

Referring now to FIG. 24, a distal side 207h of the base 204h can comprise a slot 302 configured to receive a distal end of the sensor 206h after the sensor 206h is removed from the host. A first portion of the sensor 206h can be bent and/or deflected such that the distal end of the sensor 206h is located in the slot 302. Once the sensor 206h is bent, the distal end of the sensor 206h can be located proximally relative to the first adhesive 210h.

The base 204h (labeled in FIG. 23) can comprise a channel 303 (e.g., a hole). A second portion of the sensor 206h can pass through the channel 303. The slot 302 can be directly coupled to the channel 303 (e.g., such that the channel 303 and the slot 302 are in fluid communication). The slot 302 can be oriented within plus or minus twenty degrees of perpendicular a central axis of the channel 303.

Spinning Retraction

There are many ways to retract a sensor to prevent the sensor from piercing the skin. In some embodiments, a portion of the system can rotate (relative to the base) to retract (e.g., "wind in") the sensor into an interior cavity of the system.

The portion that rotates can comprise the transmitter. The portion that rotates can be a spinning dial, which can be located radially inward or outward relative to a portion of the base that couples the rotating portion to the first adhesive. The rotating portion can include traction features (e.g., a divot, a protrusion, a rough surface finish) to enable users to grip the rotating portion.

Figure 28:
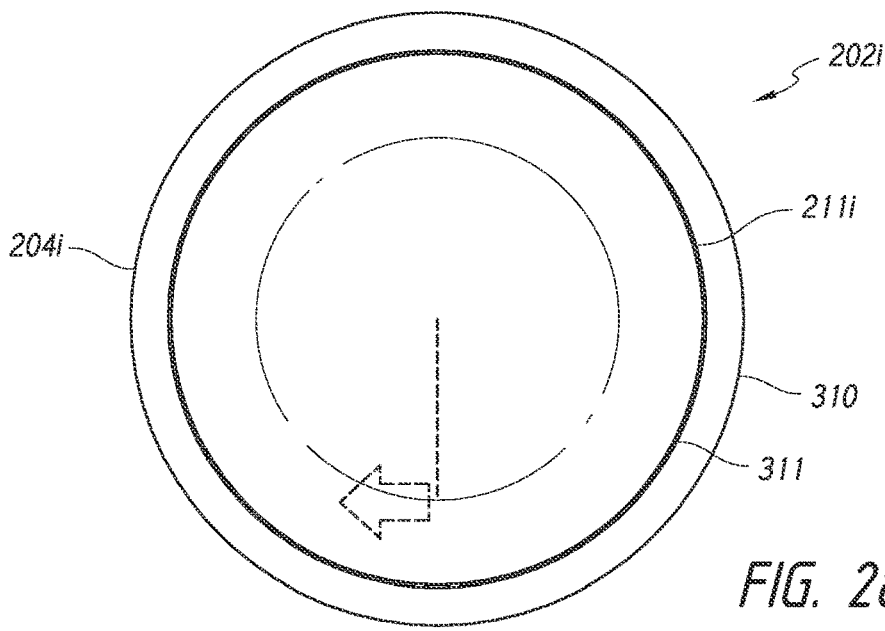
FIG. 28 illustrates a top view of a system configured to retract a sensor, according to some embodiments.
Figure 29:
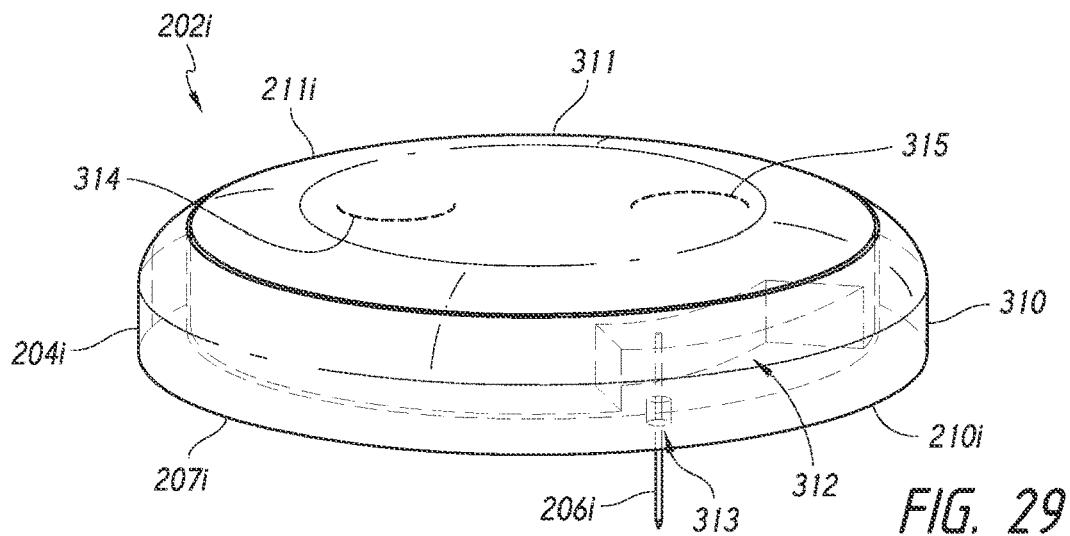
FIG. 29 illustrates a perspective view of the system illustrated in FIG. 28, according to some embodiments.
Figure 30:
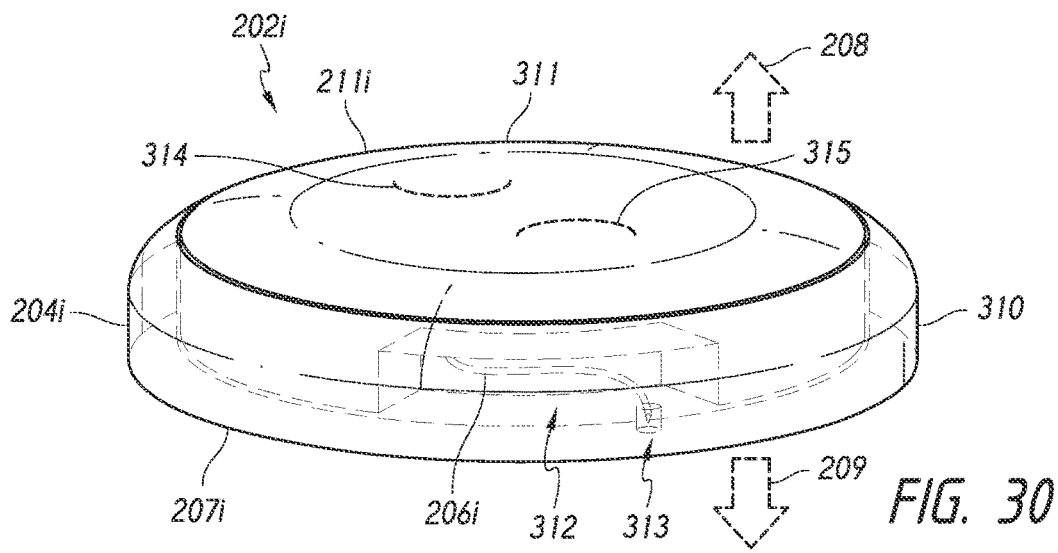
FIG. 30 illustrates a perspective view of the system after the sensor has been retracted into a housing, according to some embodiments.

FIG. 28 illustrates a top view of a system 202i configured to "wind up" a sensor 206i. FIG. 29 illustrates a perspective view of the system 206i. In FIG. 29, the sensor is deployed (e.g., extends distally from the distal side 207i, located in tissue of the host). FIG. 30 illustrates a perspective view of the system 206i after the sensor 206i has been retracted into the housing.

Referring now to FIGS. 28-30, the sensor system 202i can comprise a first portion 310 and a second portion 311. The first portion 310 can couple the first adhesive 210i to the second portion 311. The second portion 311 can be rotatably coupled to the first portion 310 about an axis of rotation that is within plus or minus twenty degrees of being parallel to a proximal direction such that the sensor system 202i is configured to retract the sensor 206i in response to rotating the second portion 311 relative to the first portion 310. The base 204i can comprise the first portion 310. The second portion 311 can comprise the transmitter 211i. The sensor 206i can exit a distal side 207i of the base 204i.

The system 202i can comprise an interior area 312 between the first portion 310 and the second portion 311. The interior area 312 can be configured such that spinning the second portion 311 relative to the first portion 310 moves the interior area 312 relative to at least one of the first portion 310 and the second portion 311. The interior area 312 can be configured such that spinning the second portion 311 relative to the first portion 310 retracts at least a portion of the sensor 206i through a channel 313 (e.g., a hole) in the base 204i and into the interior area 312.

The base 204i can comprise a distally facing hole 313. The sensor 206i can comprise a proximal portion coupled to the second portion 311 and a distal portion that passes through the hole 313 in the base 204i (e.g., as shown in FIG. 29).

The system 202i can comprise a proximally facing indentation 314 configured to provide traction for a user to rotate the second portion 311 relative to the first portion 310. The system 202i can comprise a proximal protrusion 315 configured to provide traction for a user to rotate the second portion 311 relative to the first portion 310.

Sensor Covers

One way to preclude the sensor from inadvertently piercing tissue is to cover the sensor (e.g., before or after use). The system can comprise a cover coupled to the base such that a distal tip of the sensor is located between the cover and the distal side of the base. Sensor covers can have many different shapes. A cover can be coupled to the base such that a distal tip of the sensor is located in an interior area of the cover.

A cover (e.g., a shroud) can be coupled to the distal side of the base. Once the sensor is removed from the tissue, the cover can be manually unrolled over the sensor. In some embodiments, the relaxed state of the cover is the unrolled state such that the cover automatically unrolls once the tissue (or a part of the system) is no longer blocking the cover from unrolling. The cover can be a shroud configured to cover a portion of the sensor.

Figure 31:
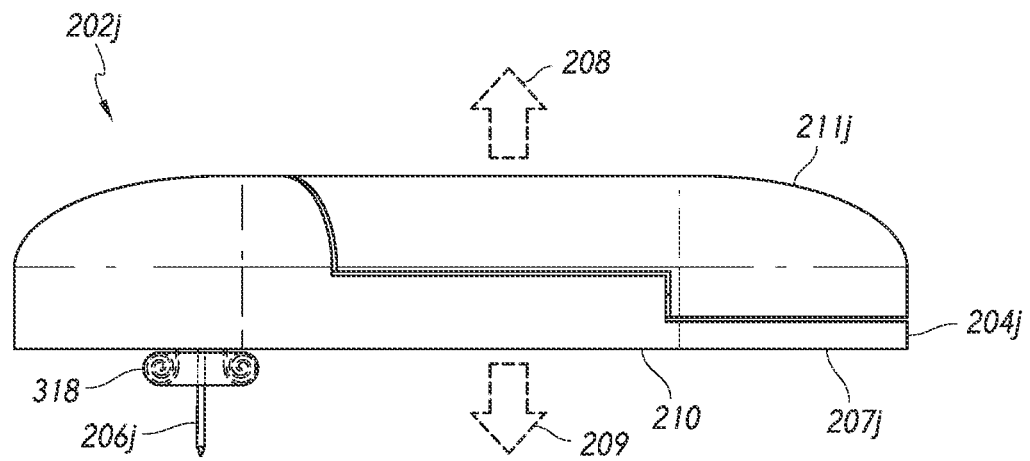
FIGS. 31 and 32 illustrate a side view of a system that comprises an extendable sensor cover, according to some embodiments.
Figure 32:
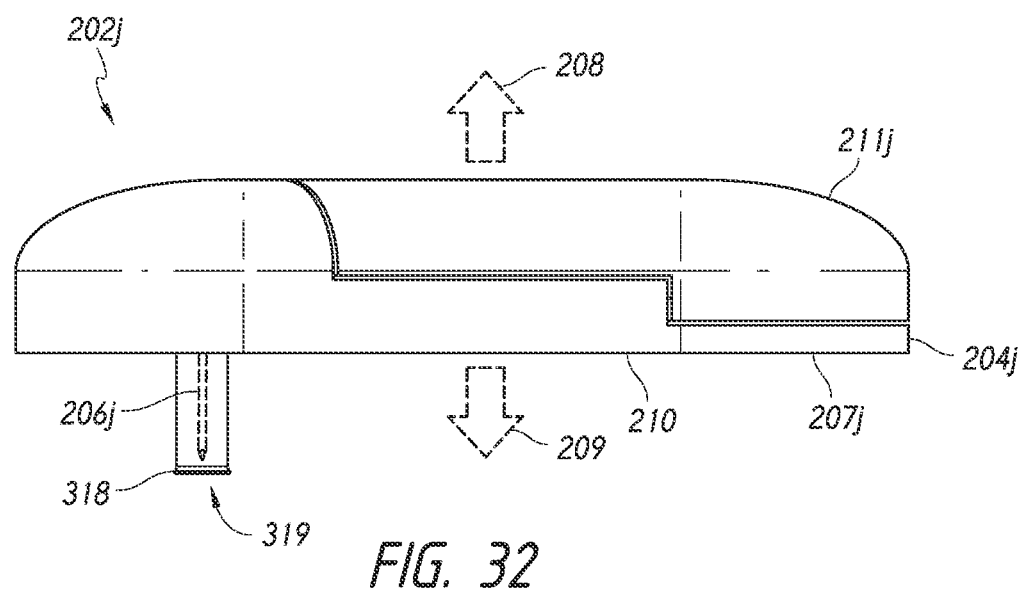

FIGS. 31 and 32 illustrate a side view of a system 202j that comprises an extendable sensor cover 318. The system 202j can comprise a transmitter 211j and a base 204j. The base 204j can comprise a distal side 207j that has adhesive 210 configured to couple the base 204j to the skin of a host.

The extendable cover 318 has a contracted state (e.g., a retracted state as shown in FIG. 31) configured to enable a distal end of the sensor 206j to enter the host. The extendable cover 318 has an extended state (e.g., as shown in FIG. 32) configured to cover 318 the distal end of the sensor 206j after the sensor 206j is removed from the host.

As used herein, the term "retracted" is used broadly and can mean moved, pulled, and/or drawn back. The covers can also be contracted (e.g., made smaller or shorter).

The cover 318 can be a pliable sheath having a channel 319 in which a portion of the sensor 206j is located. The cover 318 can be rolled up along the channel 319.

In some embodiments, the extended state is a relaxed state such that the cover 318 is configured to unroll from the retracted state in response to the sensor system 202j being removed from the host.

The retracted state can have higher stored mechanical energy than the extended state such that the cover 318 is configured to unroll from the retracted state in response to the sensor system 202j being removed from the host.

In some embodiments, bellows are configured to expand from a contracted state to cover a distal end of the sensor. The bellows can help shield the distal end of the sensor from piercing skin.

Figure 33:
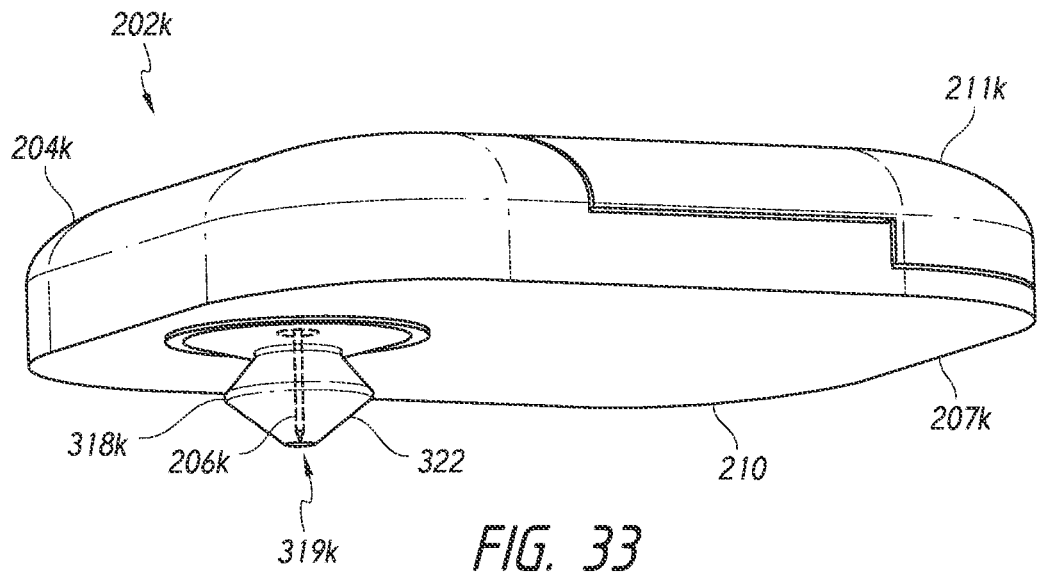
FIGS. 33 and 34 illustrate perspective views of a system 202k, according to some embodiments.
Figure 34:
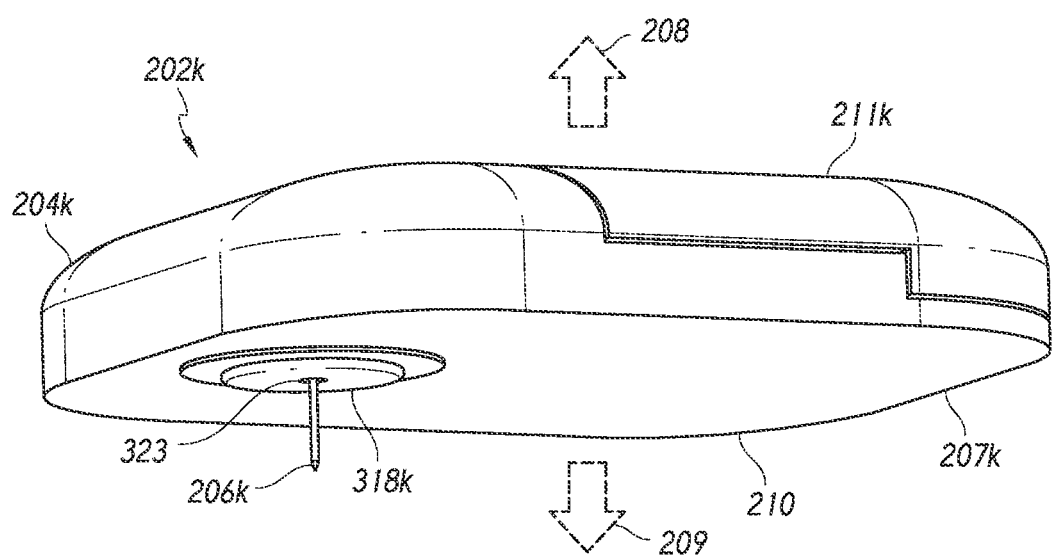

FIGS. 33 and 34 illustrate another type of sensor cover 318k that can be part of a system 202k that comprises a base 204k, a transmitter 211k, a sensor 206k, an adhesive 210, and a distal side 207k. The cover 318k can comprise bellows (e.g., a pleated expandable portion 322) configured to at least partially unfold to enable the cover 318k to move from the retracted state to the extended state. The pleated expandable portion 322 can be configured to collapse to expose a distal end of the sensor 206k. The expandable portion 322 can comprise a pleated collapsible portion.

FIGS. 33 and 34 illustrate perspective views of the system 202k. In FIG. 33, the cover 318k is in an extended state to cover the sensor 206k. In FIG. 34, the cover 318k is in a retracted state (e.g., when the base 204k is coupled to skin of a host). In the retracted state of the cover 318k, a distal end of the sensor 206k is located distally relative to a distal end of the cover 318k.

The pleated expandable portion 322 can comprise a channel 319k in which a first portion of the sensor 206k is located. The cover 318k can comprise a distal hole 323 through which a second portion of the sensor 206k passes in the retracted state.

The retracted state can have a higher stored mechanical energy than the extended state such that the pleated expandable portion 322 is configured to expand from the retracted state in response to the sensor system 202k being removed from the host. The formed channel 319k may constrain the sensor 206k within a coaxial column.

A cap such as a tube or a silicone stopper can be placed over a distal end of the sensor and can be coupled to the base. The cap can shield the sensor from piercing skin.

The cap can be shaped like a thimble that covers a small area immediately around the portion of the sensor configured to be placed in tissue. In some embodiments, the cap is much larger and can couple to a perimeter of the base. In some cases, larger caps are easier for people to handle.

Figure 35:
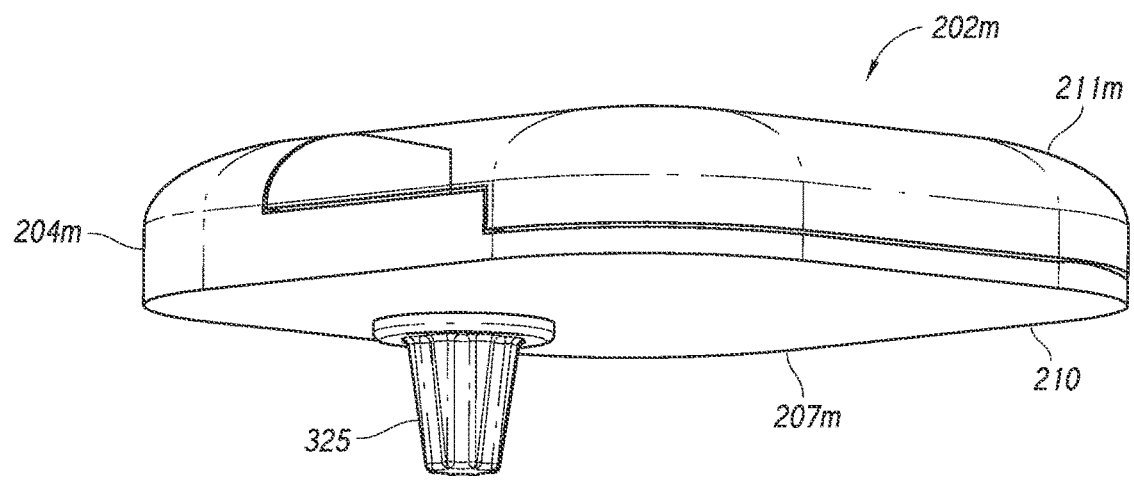
FIG. 35 illustrates a perspective view of a system, according to some embodiments.

FIG. 35 illustrates a perspective view of a system 202m. The system 202m can comprise a cap 325 that covers a distal end of the sensor 206m such that the cap 325 is configured to prevent the distal end from penetrating a person after the sensor system 202m is removed from the host and the cap 325 is coupled to the distal side 207m of the base 204m. A transmitter 211m can be coupled to the base 204m.

Figure 36:
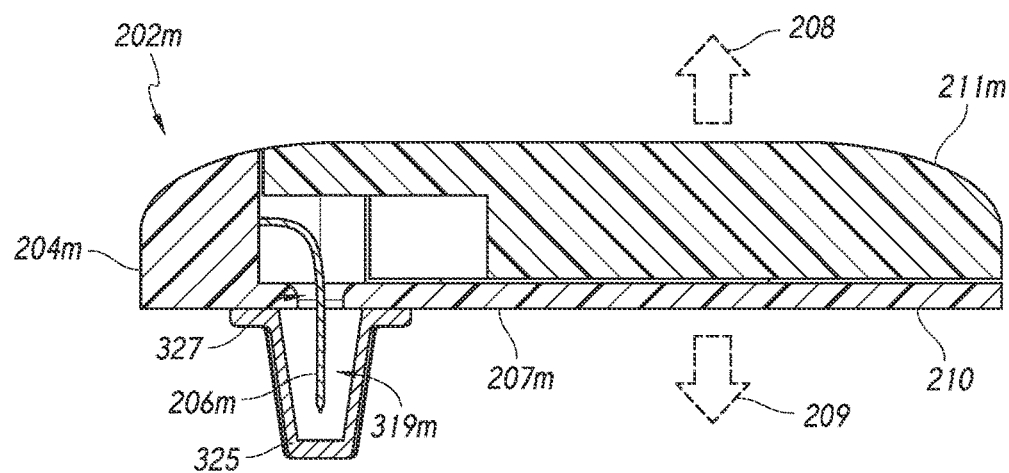
FIG. 36 illustrates a side, cross-sectional view of the system shown in FIG. 35, according to some embodiments.
Figure 37:
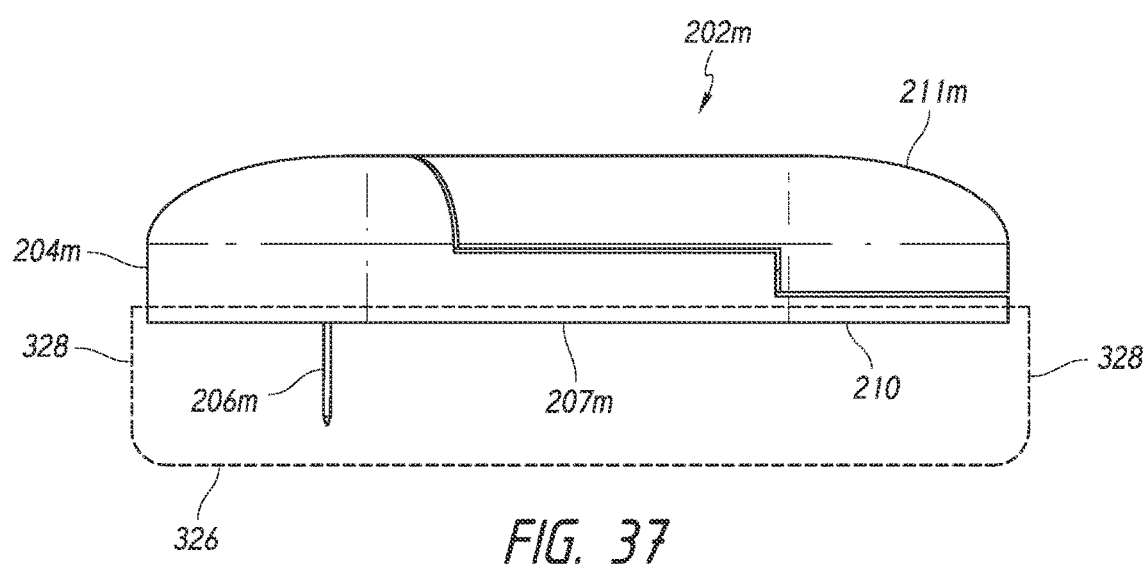
FIG. 37 illustrates a side view of the system, according to some embodiments.

FIG. 36 illustrates a side, cross-sectional view of the system 202m shown in FIG. 35. FIG. 37 illustrates a side view of the system 202m. In FIG. 37, the cap 325 has been removed.

Referring now to FIGS. 35-37, the cap 325 can comprise a channel 319m and/or a cavity having a first central axis. The base 204m can comprise a hole 327 having a second central axis. A portion of the sensor 206m can pass through the hole 327 and into a channel 319m. The first central axis can be within twenty degrees of parallel to the second central axis. The first central axis of the channel 319m can pass through the hole 327 of the base 204m (e.g., as the first central axis extends beyond a proximal end of the channel 319m).

FIGS. 35 and 36 illustrate a relatively small cap 325. FIG. 37 illustrates a much larger cap 37. Referring now to FIG. 37, the system 202m can comprise a cap 326 coupled to the base 204m. The cap 326 can cover at least a majority of the first adhesive 210. The cap 326 can cover a distal end of the sensor 206m such that the cap 326 is configured to prevent the distal end from penetrating a person after the sensor system 202m is removed from the host and the cap 326 is coupled to the base 204m.

The cap 326 can comprise sidewalls 328 that protrude proximally past at least a portion of an outer perimeter of the sensor system 202m (and/or past at least a portion of an outer perimeter of the base 204m). The cap 326 can be empty or can be filled with an easily pierceable (e.g., penetrable) material (e.g., foam). The material can help retain the cap 326 in place via friction.

Sensor Cover—Unlocking Device

A transmitter can be coupled to the base. A tool can be configured to facilitate uncoupling the transmitter from the base. The tool can also cover a distal end of the sensor to prevent the sensor from inadvertently piercing a person. Thus, the tool can serve two purposes: uncoupling the transmitter and covering the "used" sensor.

The tool can be a portion of the insertion device and/or packaging of a replacement sensor. In some embodiments, the tool is packaged with the replacement sensor.

Users often want to reuse their transmitter. The tool that allows users to detach their transmitter for reuse with another base also covers the sensor. Thus, the system obligates users to cover their sensor in order to reuse their transmitter. The dual purposes of the tool promotes more consistent use of the tool than would be the case if the tool only covered the sensor (but did not unlock the transmitter).

A flex arm can couple the transmitter to the base. The tool can include a protrusion that enters a hole in the base to unlatch the flex arm (to uncouple the transmitter from the base). The sensor can be shielded in an interior area of the tool.

FIGS. 38-41 illustrate a tool configured to facilitate uncoupling a transmitter from a base. The tool can also cover a distal end of the sensor to prevent the sensor from inadvertently piercing a person.

Figure 38:
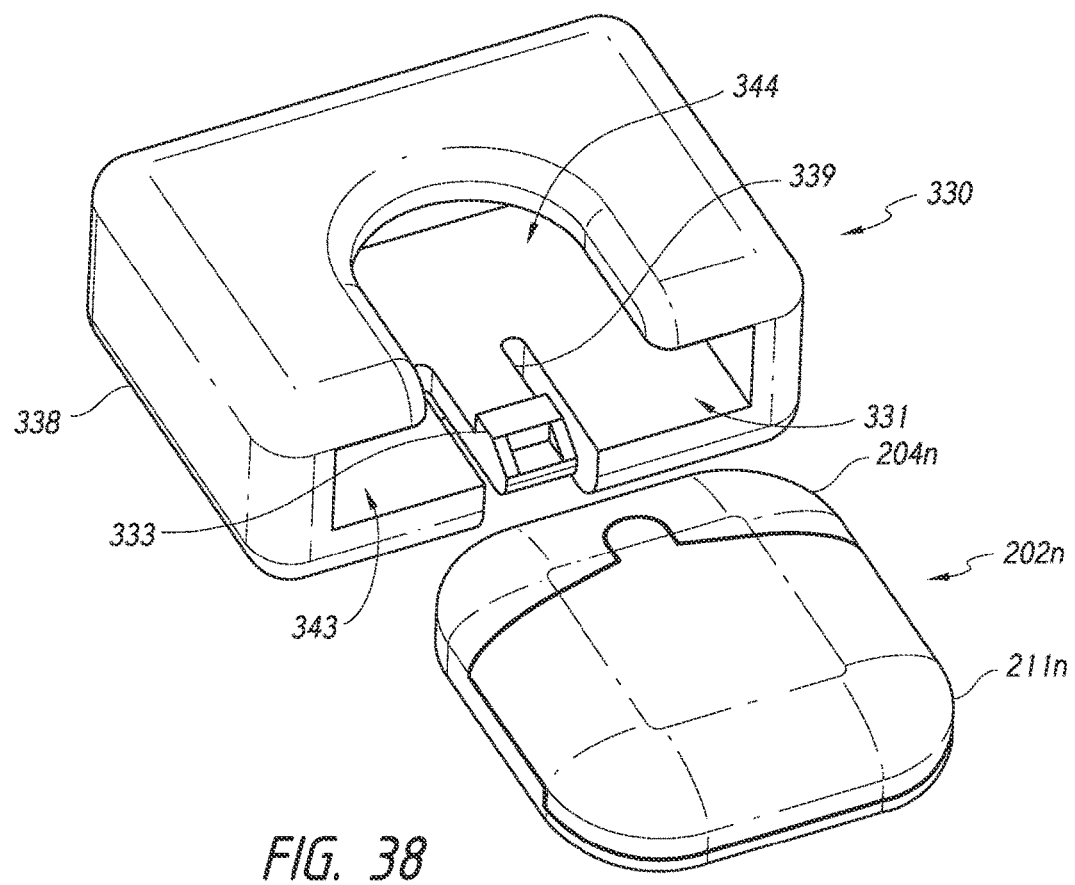
FIG. 38 illustrates a perspective view of a sensor system moving towards a tool, according to some embodiments.
Figure 39:
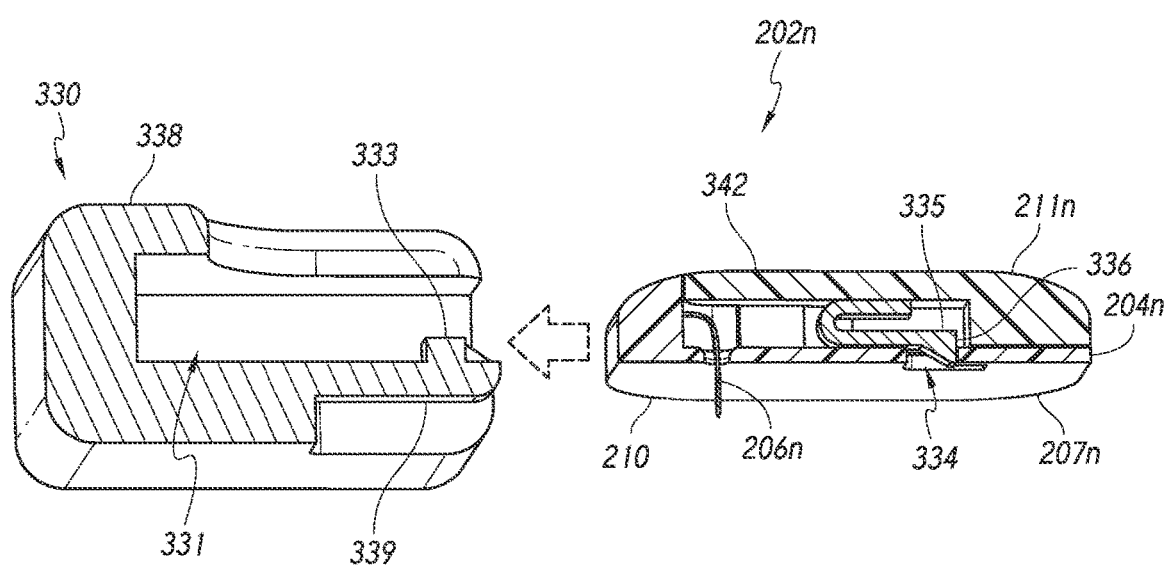
FIG. 39 illustrates a perspective, cross-sectional view of the sensory system moving towards the tool, according to some embodiments.

FIG. 38 illustrates a perspective view as the sensor system 202n is moving towards the tool, but prior to the sensor system 202n being inserted at least partially into the tool. FIG. 39 illustrates a perspective, cross-sectional view of the sensory system 202n moving towards the tool.

Figure 40:
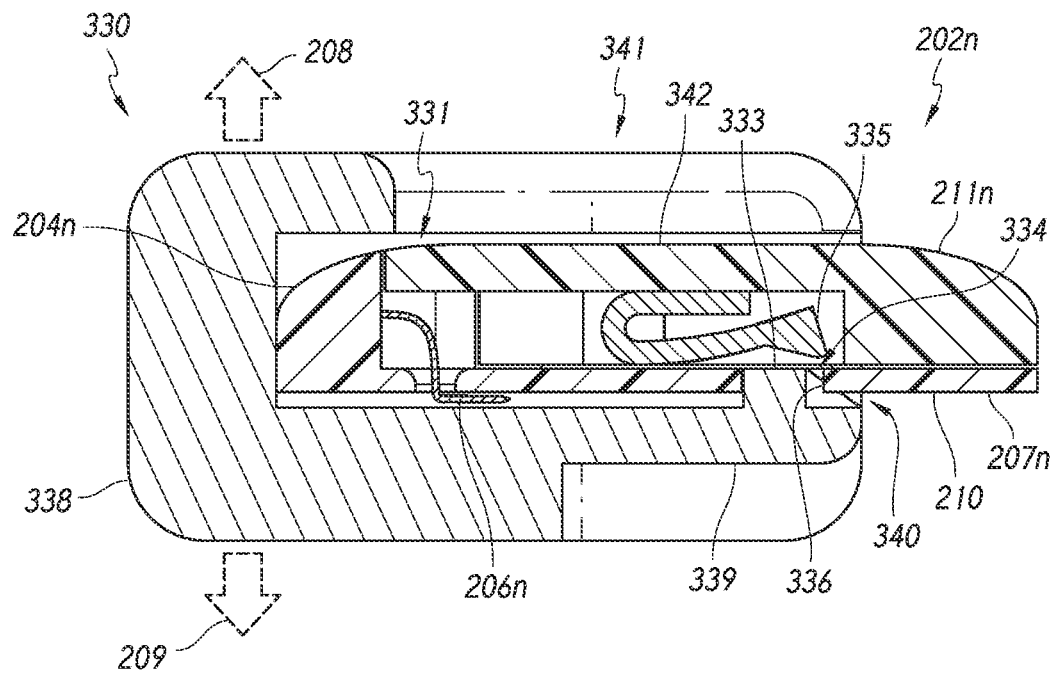
FIG. 40 illustrates a side, cross-sectional view of the system, according to some embodiments.
Figure 41:
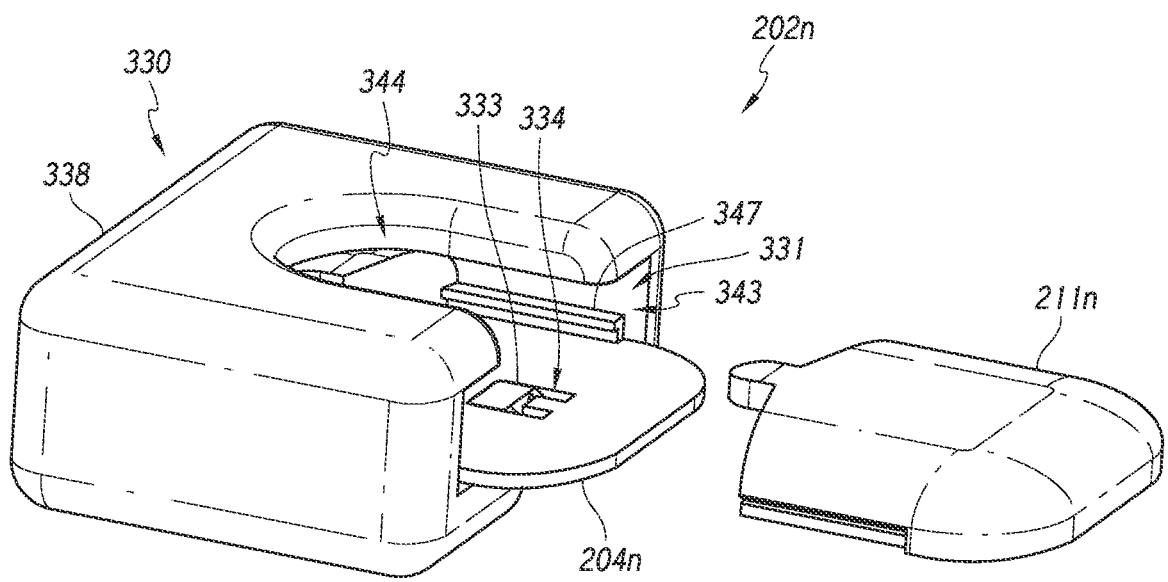
FIG. 41 illustrates a perspective view of the system, according to some embodiments.

FIG. 40 illustrates a side, cross-sectional view of the sensor system 202n "docked" with the tool to unlatch the transmitter 211n from the base 204n and to cover the sensor 206n. Once the transmitter 211n is unlatched from the base 204n, the transmitter 211n can move away from the base 204n and out of the tool (e.g., as shown in the perspective view of FIG. 41).

Once the transmitter 211n is unlatched from the base 204n, the user can apply a force to manually separate the transmitter 211n from the base 204n. In some embodiments, once the transmitter 211n is unlatched from the base 204n, the transmitter 211n automatically separates from the base 204n, moves away from the base 204n, and/or moves relative to the base 204n in response to inserting the sensor system 202n into the tool. The tool may contain a spring or deflecting member that assists the automatic separation by biasing the transmitter away from the tool.

Some embodiments comprise a sensor cover 330 having an interior area 331 and a protrusion 333. At least a portion of the base 204n can be located in the interior area 331 of the sensor cover 330 such that a distal end of the sensor 206n is located between the base 204n and the sensor cover 330. The protrusion 333 can be located in a channel 334 (e.g., a hole) of the base 204n such that the protrusion 333 unlatches the transmitter 211n from the base 204n.

The system 202n can comprise a sensor cover 330 configured to unlock the transmitter 211n from the base 204n in response to coupling the base 204n to the sensor cover 330. The transmitter 211n can be configured to be uncoupled from the base 204n once the transmitter 211n is unlocked from the base 204n.

The system 202n can comprise a first flex arm 335 and a wall 336. The first flex arm 335 and the wall 336 can form a latch assembly. The first flex arm 335 can comprise a first state in which the first flex arm 335 interferes with the wall 336 to lock the transmitter 211n to the base 204n.

The sensor cover 330 can comprise a protrusion 333 configured such that coupling the base 204n to the sensor cover 330 causes the protrusion 333 to move the first flex arm 335 to a second state in which the first flex arm 335 does not interfere with the wall 336 such that the first flex arm 335 does not lock the transmitter 211n to the base 204n.

The base 204n can comprise a channel 334 (e.g., a hole) in a distal side 207n of the base 204n. At least a portion of the protrusion 333 can pass through the hole to deflect the first flex arm 335 to the second state. The distal side 207n can comprise adhesive 210 to couple the base 204n to the skin of the host.

The sensor cover 330 can comprise a housing 338 and a second flex arm 339. The housing 338 can comprise an interior area 331. At least a portion of the base 204n can be located inside the interior area 331 of the housing 338. The second flex arm 339 can couple the protrusion 333 to the housing 338 such that the second flex arm 339 is configured to bend to move the protrusion 333 to facilitate inserting the portion of the base 204n into the interior area 331 of the housing 338.

The second flex arm 339 can be configured to move in a distal direction in response to coupling the base 204n to the sensor cover 330. The first flex arm 335 can be configured to move in a proximal direction in response to coupling the base 204n to the sensor cover 330. A portion of the sensor 206n can be bent in response to coupling the base 204n to the sensor cover 330 such that a distal end of the sensor 206n is located between the base 204n and the sensor cover 330.

The sensor cover 330 can comprise a first side 340 and a second side 341 (labeled in FIG. 40). The first side can be oriented within plus or minus thirty degrees of perpendicular to the second side. The first side can comprise a first channel 343 (e.g., a first hole) through which the portion of the base 204n is inserted. The second side can comprise a second channel 344 (e.g., a second hole) configured to provide access to a proximal surface 342 of the transmitter 211n to facilitate removing the transmitter 211n from the base 204n. (The first channel 343 and the second channel 344 are labeled in FIG. 41).

The system 202n can comprise a rail 347. The rail 347 can slidably couple the base 204n to the transmitter 211n.

The system 202n can comprise a sensor cover 330 configured to unlatch the transmitter 211n from the base 204n in response to coupling the base 204n to the sensor cover 330. The system 202n can comprise a first flex arm 335 configured to latch the base 204n to the transmitter 211n. The sensor cover 330 can comprise a second flex arm 339 configured to deflect the first flex arm 335 to unlatch the transmitter 211n from the base 204n.

The sensor cover 330 can comprise a distally facing wall 336. At least a portion coupled to the base 204n (e.g., a proximal side of the base 204n) can be pressed against the distally facing wall 336 such that a protrusion 333 of the second flex arm 339 is pressed into a channel 334 (e.g., a hole) of the base 204n to deflect the first flex arm 335.

Telescoping Assembly

FIGS. 42-47 illustrate a system 202p that comprises a spring 350 that is configured to retract a distal end of the sensor 206p into the base 204p (e.g., after the sensor 206p has been deployed). Once the sensor 206p is retracted, the sensor 206p cannot pierce the skin of another person.

The spring 350 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

Figure 46:
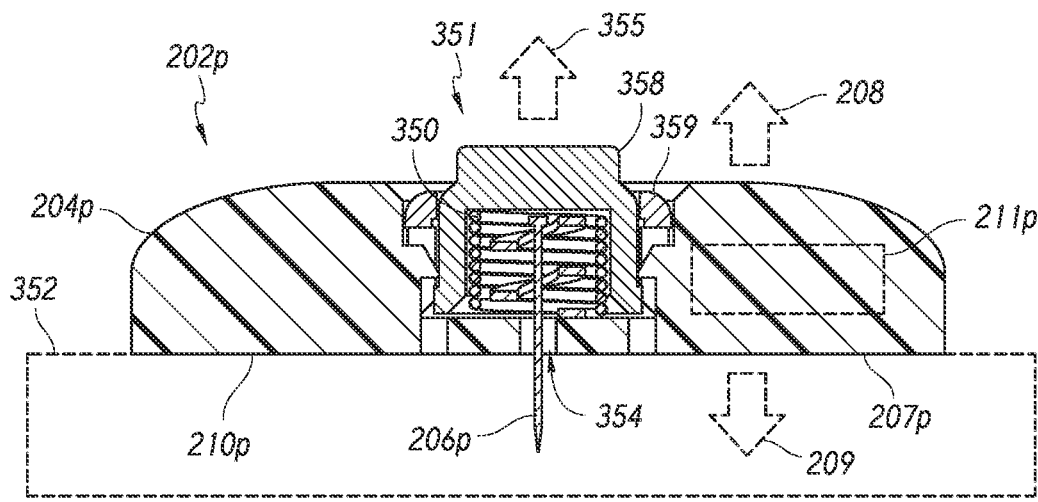
FIG. 46 illustrates a side, cross-sectional view taken along line 46-46 from FIG. 43, according to some embodiments.

The system 202p can comprise an assembly 351 configured to move distally to insert the sensor 206p and proximally to retract the sensor 206p. The assembly 351 can lock in a distal position configured to hold the sensor 206p in the tissue 352 of the host (e.g., as shown in FIG. 46). The assembly 351 can unlock to enable the spring 350 to move the sensor 206p proximally into an interior area 353 of the base 204p. In some embodiments, rotating the assembly 351 relative to the base 204p causes the assembly 351 to unlock and move proximally. The assembly 351 can be a telescoping assembly.

Figure 45:
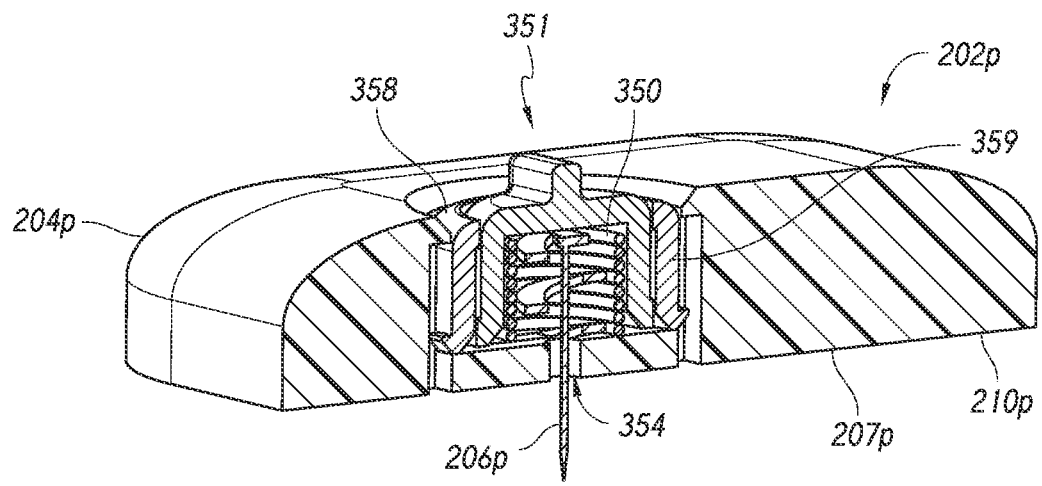
FIG. 45 illustrates a perspective, cross-sectional view, according to some embodiments.
Figure 47:
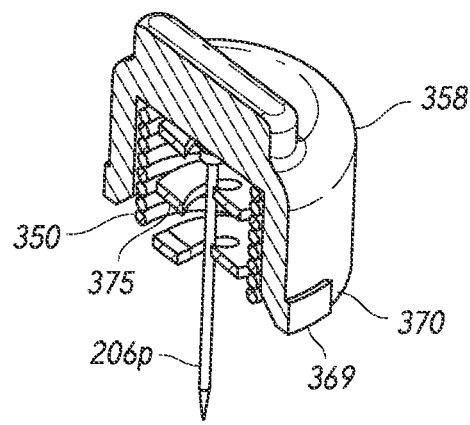
FIG. 47 illustrates a perspective view of the cross section shown in FIG. 46, according to some embodiments.

FIG. 42 illustrates a perspective view of the system 202p. FIG. 43 illustrates a top view of the system 202p. FIG. 44 illustrates a perspective, cross-sectional view along line 44-44 from FIG. 43. In FIG. 44, the assembly 351 is located in a proximal position. FIG. 45 illustrates the same perspective, cross-sectional view as FIG. 44 except that the assembly 351 is located in a distal position with the sensor 206p in a deployed state. FIG. 46 illustrates a side, cross-sectional view taken along line 46-46 from FIG. 43. In FIG. 46, the assembly 351 is located in the distal position. FIG. 47 illustrates a perspective view of the cross section shown in FIG. 46. Many components are hidden in FIG. 47 to permit clear viewing of particular features.

Referring now to FIGS. 42-47, the transmitter 211p can be integrated into the base 204p. The transmitter 211p can comprise a battery (e.g., such that a battery is integrated into the base 204p). The transmitter 211p can comprise a communication system configured to communicate with a remote computing device.

The transmitter 211p can be removable from the base 204p or permanently coupled to the base 204p. The base 204p can comprise a distal side 20'7p. Adhesive 210p can couple the distal side 207p to the skin 352 of a host.

The spring 350 can retract the sensor 206p through a channel 354 (e.g., a hole) in the base 204p in a direction 355 within plus or minus thirty degrees of a proximal direction 208 and/or within plus or minus thirty degrees of a central axis of the distal end of a sensor 206p.

The system 202p can include a locking mechanism configured to secure the spring 350 and the sensor 206p in a distal position (e.g., in which the sensor 206p is configured to be located in the tissue). Pressing distally on the locking mechanism (relative to the base 204p) can move the sensor 206p distally, insert the sensor 206p into the tissue, and secure the locking mechanism in a distal state.

Pressing the locking mechanism distally a second time, moving a removable pull tab, manually activating a radially deflecting arm, and/or rotating the locking mechanism (relative to the base 204p) can release the locking mechanism to enable the spring 350 to move proximally to retract the sensor 206p proximally out of the tissue and into a protective cavity 353 of the system 202p.

The system 202p can comprise a telescoping assembly 351 coupled to the base 204p. At least a first portion of the sensor 206p can be located between a portion of the telescoping assembly 351 and a distal side 20'7p of the base 204p such that the telescoping assembly 351 is configured to move from a distal position to a proximal position to retract a second portion of the sensor 206p into a protective cavity 353 of the system 202p.

The base 204p can comprise an interior channel 357 having a proximally facing opening. The telescoping assembly 351 can be located at least partially in the interior channel 357 such that the telescoping assembly 351 is configured to move proximally at least partially in the interior channel 357 from the distal position to the proximal position.

When the telescoping assembly 351 is in the distal position, the first portion of the sensor 206p can be located in the interior channel 357 of the base 204p, and the second portion of the sensor 206p can be located distally relative to the base 204p. When the telescoping assembly 351 is in the proximal position, the first and second portions of the sensor 206p can be located in the interior channel 357 of the base 204p.

The telescoping assembly 351 can comprise a first section 358 and a second section 359. The first section 358 can be slidably coupled to the second section 359. The second section 359 can be slidably coupled to an interior channel 357 of the base 204p such that the telescoping assembly 351 is configured to telescope relative to the base 204p to retract the sensor 206p.

The interior channel 357 can comprise a first overhang 360 (which can be oriented radially inward, radially outward, and/or in any suitable direction). The first overhang 360 can be configured to interfere with a second overhang 361 (which can be oriented radially outward, radially inward, and/or in any suitable direction) of the second section 359 to retain at least a portion of the second section 359 within the interior channel 357. The first overhang 360 and the second overhang 361 can form an interlock configured to couple the assembly 351 to the base 204p. (The first overhang 360 and the second overhang 361 are labeled in FIG. 44.)

The second section 359 can comprise a third overhang 363 (which can be oriented radially inward). The third overhang 363 can be configured to interfere with a fourth overhang 364 (which can be oriented radially outward) of the first section 358 to limit a distance the first section 358 can move proximally relative to the second section 359. (The third overhang 363 and the fourth overhang 364 are labeled in FIG. 44.) The third overhang 363 and the fourth overhang 364 can form an interlock configured to couple the first section 358 to the second section 359.

The system 202p can comprise a spring 350 and a locking mechanism. The locking mechanism can be configured to lock the telescoping assembly 351 in the distal position. The locking mechanism can comprise a first overhang 368 of the base 204p (labeled in FIG. 44) and a second overhang 369 of the first section 358. The first and second overhangs can be configured such that in a first angular position of the first section 358 relative to the base 204p, the first overhang 368 interferes with the second overhang 369 to limit proximal travel of the first section 358 relative to the base 204p. In some embodiments, in a second angular position of the first section 358 relative to the base 204p, the first overhang 368 does not limit the proximal travel of the first section 358 relative to the base 204p such that the spring 350 pushes the telescoping assembly 351 to the proximal position. Rotating the first section 358 relative to the base 204p can place the first overhang 368 in an open area 370 (labeled in FIG. 47) of the first section 358, which can permit the first section 358 to move proximally relative to the base 204p.

The base 204p can comprise a first overhang 360 configured to limit a first proximal travel of the second section 359 relative to the base 204p. The base 204p can comprise a second overhang 368 configured to impede proximal movement of the first section 358 such that the telescoping assembly 351 is held in the distal position.

The base 204p can comprise a first channel 372. The second section 359 can comprise a radially outward protrusion 373 located in the first channel 372 such that the first channel 372 limits a first angular movement of the second section 359 relative to the base 204p while the second section 359 permits a second angular movement of the first section 358 relative to the second section 359 and relative to the base 204p.

The sensor 206p can comprise a deformable connection 375 that communicatively couples (and/or electrically couples) a subcutaneous portion of the sensor 206p to a connection portion of the sensor 206p. (The deformable connection 375 is labeled in FIG. 47.) The connection portion of the sensor 206p can be located inside the base 204p and can communicatively couple the subcutaneous portion of the sensor 206p to a communication module of the sensor system 202p.

In the proximal position, the subcutaneous portion of the sensor 206p can be located within a center region of a coil (e.g., a deformable connection) of the sensor 206p. In many embodiments, the deformable connection 375 is configured such that the subcutaneous portion of the sensor 206p is not located in a center region of the deformable connection.

In some embodiments, the deformable connection 375 of the sensor 206p does not apply a biasing force. In several embodiments, the coil of the sensor 206p can apply a biasing force to push the telescoping assembly 351 to the proximal position. In many embodiments, a spring 350 applies a biasing force.

The system 202p can comprise a housing (e.g., the assembly 351) slidably coupled to the base 204p. The housing can move proximally relative to the base 204p to retract the sensor 206p.

At least a first portion of the sensor 206p can be located between a portion of the housing and a distal side 20'7p of the base 204p such that the housing is configured to move from a distal position to a proximal position to retract a second portion of the sensor 206p.

The base 204p can comprise an interior channel 357 having a proximally facing opening. The housing can be located at least partially in the interior channel 357 such that the housing is configured to move proximally at least partially in the interior channel 357 from the distal position to the proximal position to retract the second portion of the sensor 206p into the interior channel 357.

Top Cap

Figure 48:
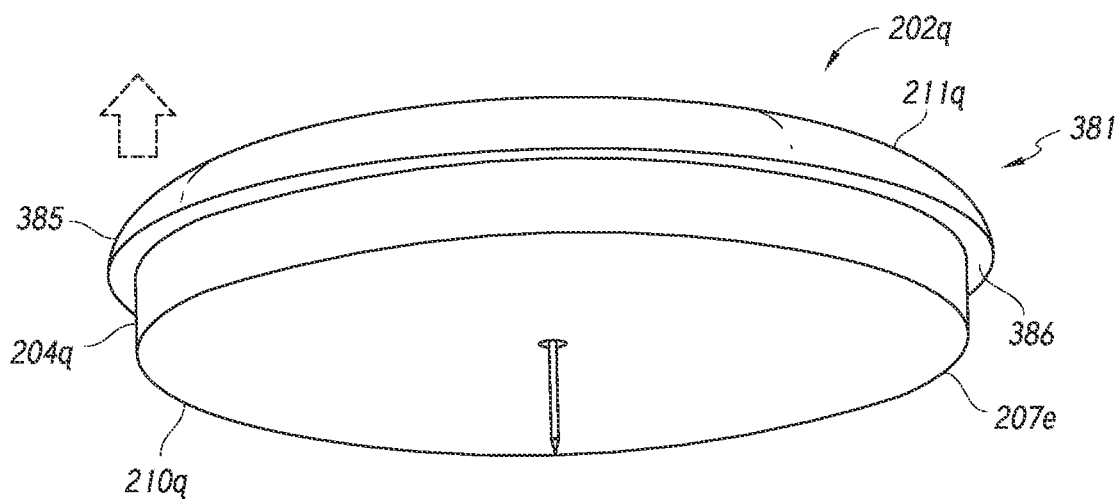
FIG. 48 illustrates a perspective view of a system, according to some embodiments.
Figure 49:
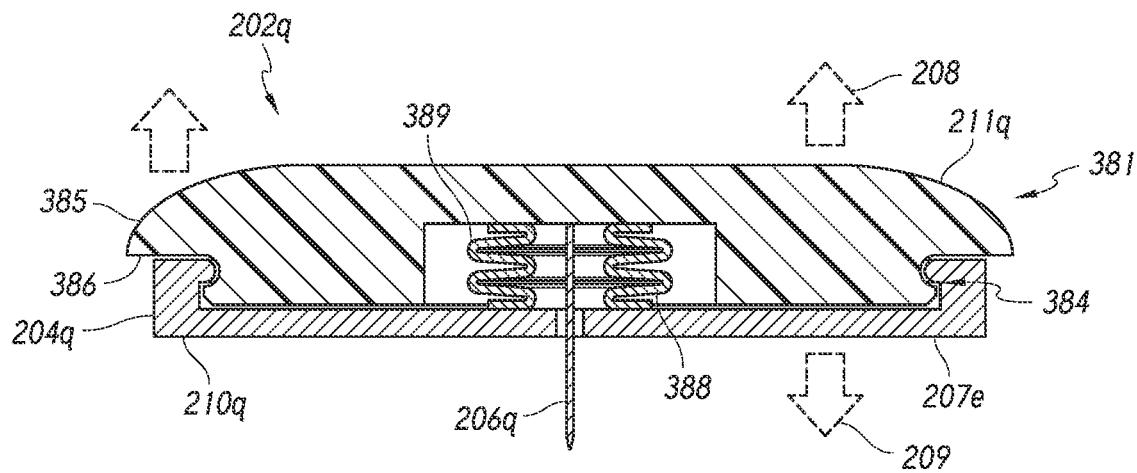
FIGS. 49 and 50 illustrate side, cross-sectional views of the system, according to some embodiments.
Figure 50:
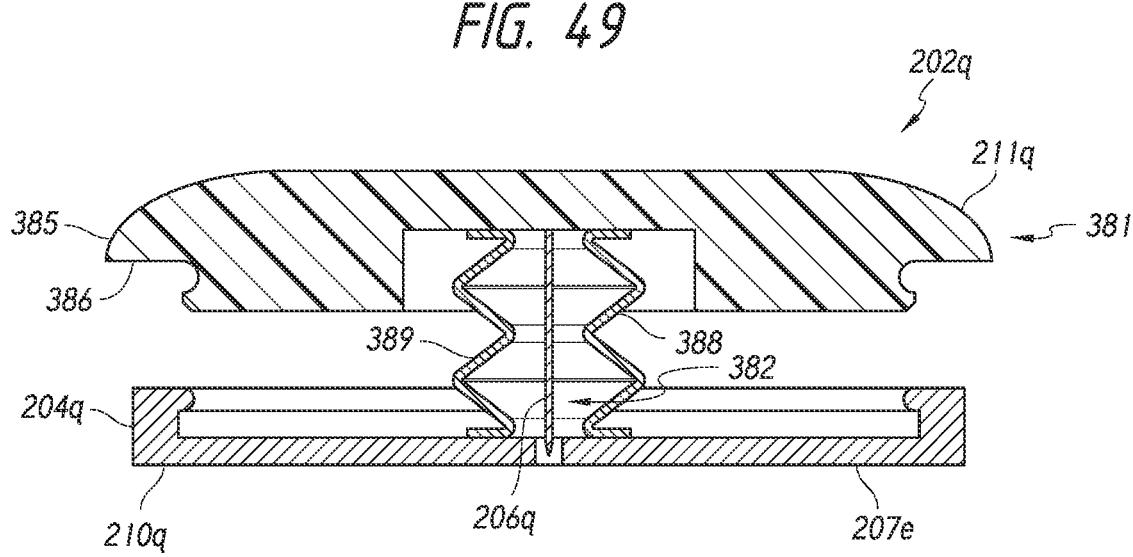

FIGS. 48-50 illustrate a system 202q that comprises a top cap 381. The top cap 381 can comprise a radially outward overhang that allows a user to "grip" the top cap 381 to pull the top cap 381 proximally (e.g., as indicated by the proximal direction arrow 208). Moving the top cap 381 proximally relative to the base 204q can retract the sensor 206q into an area between the top cap 381 and the base 204q. Once the sensor 206q is retracted, the system 202q prevents the sensor 206q from piercing a person.

FIG. 48 illustrates a perspective view of the system 202q. FIG. 49 illustrates a side, cross-sectional view of the system 202q in a compressed (e.g., collapsed) state. Moving the top cap 381 proximally relative to the base 204q can retract the sensor 206q into an expandable housing (e.g., bellows) as shown in FIG. 50, which is a side, cross-sectional view of the system 202q in an expanded state.

Referring now to FIGS. 48-50, a proximal portion of the sensor 206q can be coupled to the cap 381 such that pulling the cap 381 away from the base 204q pulls a distal portion of the sensor 206q into an area between the base 204q and the cap 381 (e.g., as shown in FIG. 50). Once the distal portion is located within a cavity 382 of the system 202q, the sensor 206q cannot pierce the skin of another person. Bellows can couple the proximal cap 381 to the base 204q.

The cap 381 can be a proximal portion of the base 204q. The base 204q can also include a distal portion that couples the proximal portion of the base 204q to the adhesive 210q and/or to the skin of the host. The adhesive 210q can be coupled to the distal side 207e of the base 204q.

The system 202q can comprise a cap 381 coupled to the base 204q and located proximally relative to the base 204q. A first portion of the sensor 206q can be coupled to the cap 381. The system 202q can be configured such that moving the cap 381 proximally relative to the base 204q retracts the sensor 206q.

The cap 381 can be movable between a distal position (e.g., as shown in FIG. 49) and a proximal position (e.g., as shown in FIG. 50). In the distal position, a second portion of the sensor 206q can be located distally relative to the base 204q. In the proximal position, the second portion of the sensor 206q can be located proximally relative to the base 204q. An interlock 384 can removably secure the cap 381 in the distal position.

At least a portion of an outer perimeter 385 of the cap 381 can protrude farther radially outward (relative to a central axis of the second portion) than the base 204q such that the outer portion of the outer perimeter 385 provides a distally facing wall 386 to enable a user to grip the cap 381 as the user moves the cap 381 from the distal position to the proximal position.

The system 202q can comprise a linkage 388 between the cap 381 and the base 204q. The linkage 388 can be configured to limit a distance that the cap 381 can move proximally relative to the base 204q.

The linkage 388 can comprise a pleated, collapsible and expandable portion 389 (e.g., bellows) configured to at least partially unfold to enable the cap 381 to move from the distal position to the proximal position to retract the second portion of the sensor 206q into the pleated, collapsible and expandable portion 389. The cap 381 can be rigidly coupled (and/or removably coupled) to the transmitter 211q such that moving the transmitter 211q retracts the sensor 206q proximally.

Biased Sensor

A sensor can be biased such that the relaxed state of the distal portion of the sensor is approximately perpendicular to a distal direction. As a result, when the sensor is removed from the tissue, the sensor automatically bends towards its lowest energy state (e.g., such that the sensor points to the side rather than points distally). In this orientation, the sensor is very unlikely to pierce the skin of another person.

The sensor, needle, and/or an anchoring structure coupled to a sensor and/or a needle can be elastically deformed for insertion by an applicator. The applicator can hold the distal portion of the sensor in an orientation in which the sensor is pointed distally. As a result, a biased sensor can be held in an insertion orientation by an applicator. Once the applicator and any other impediments (e.g., tissue) are removed, the biased sensor and/or the needle can automatically move towards its relaxed state.

Figure 51:
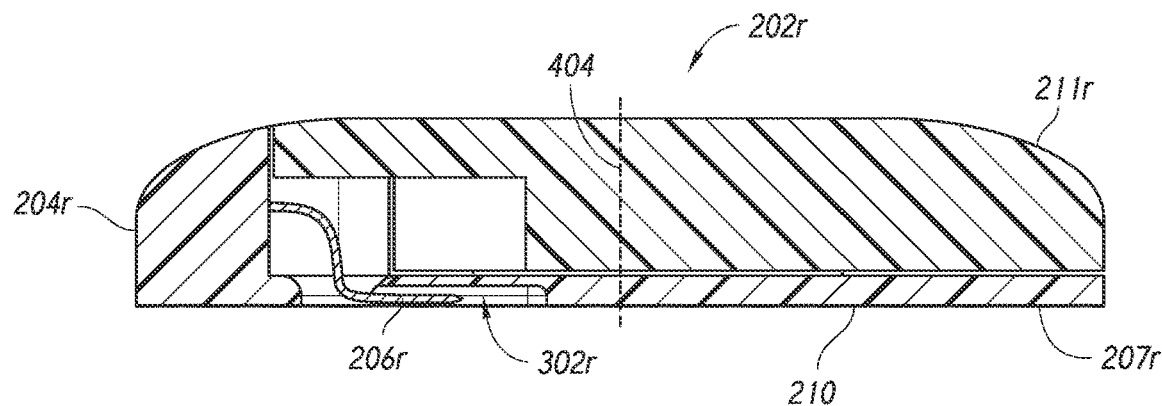
FIG. 51 illustrates a side, cross-sectional view of a system with a biased sensor, according to some embodiments.

FIG. 51 illustrates a side, cross-sectional view of a system 202r with a biased sensor 206r. In FIG. 51, the sensor 206r is in a relaxed state (or at least a lower energy state than when the sensor 206r is held in a distally pointing direction).

Figure 52:
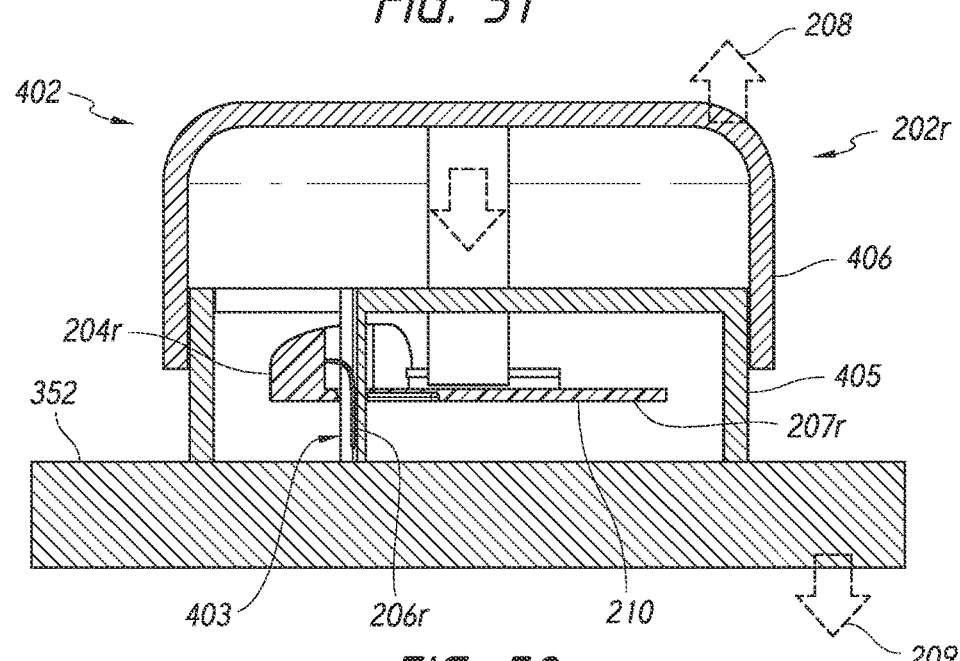
FIGS. 52 and 53 illustrate side, cross-sectional views of a telescoping applicator, according to some embodiments.

FIG. 52 illustrates a side, cross-sectional view of a telescoping applicator 402 configured to hold the sensor 206r in a distally oriented state (e.g., a constrained state). The applicator 402 comprises a channel 403 configured to prevent the sensor 206r from returning to the state of the sensor 206r shown in FIG. 51.

Figure 53:
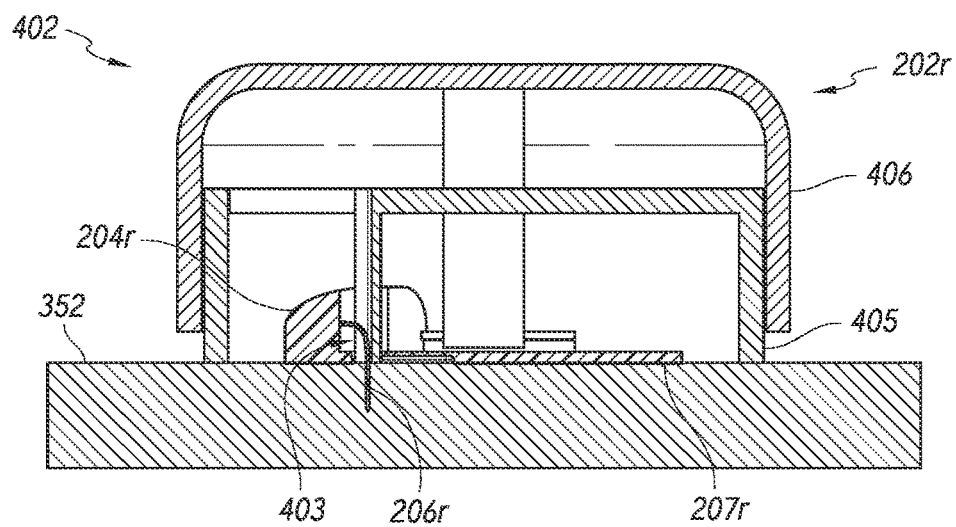

Moving the proximal portion of the applicator 402 distally (e.g., in the distal direction 209) moves the sensor 206r into the tissue 352 of the host. Once the applicator 402 reaches a distal ending position (e.g., as shown in FIG. 53), the applicator 402 can be removed because the tissue 352 resists the sensor 206r moving to the sensor 206r orientation shown in FIG. 51. FIG. 53 illustrates a side, cross-sectional view of the sensor 206r in a deployed state prior to the applicator 402 being removed from the sensor 206r.

The applicator 402 can be uncoupled from the base 204r. Removing the base 204r from the tissue 352 allows the sensor 206r to return to the state shown in FIG. 51. As illustrated in FIG. 51, a portion of the sensor 206r is located in a protective slot 302r of the base 204r. (A protective slot 302 is also shown in FIG. 24.) A transmitter 211r can be coupled to the base 204r. Adhesive 210 can couple the base 204r to the tissue 352 of the host.

In some embodiments, the system 202r comprises a central axis 404 oriented from a proximal end of the system 202r to the distal side 207r of the base 204r. A distal portion of the sensor 206r can comprise a relaxed state in which the distal portion is oriented within plus or minus 45 degrees of perpendicular to the central axis 404 of the system 202r such that the relaxed state is configured to reduce a likelihood of the distal portion penetrating a person (e.g., as illustrated in FIG. 51).

The distal portion of the sensor 206r can comprise a constrained state oriented within plus or minus 20 degrees of parallel to the central axis 404 (labeled in FIG. 51) such that the distal portion is oriented distally (e.g., as illustrated in FIG. 52). The constrained state has higher stored mechanical energy than the relaxed state.

The system 202r can comprise a channel 403 oriented within plus or minus 20 degrees of parallel to the central axis 404 (labeled in FIG. 51). A section of the sensor 206r can be located in the channel 403 such that the channel 403 orients the distal portion of the sensor 206r in the constrained state (e.g., as illustrated in FIG. 52).

As illustrated in FIG. 52, the channel 403 can comprise a slot 302r. The distal portion of the sensor 206r can be biased away from the slot 302r such that a bias of the distal portion of the sensor 206r is configured to facilitate maintaining the distal portion of the sensor 206r in the channel 403. The sensor 206r can be biased directly away and/or in a direction at least partially away from the slot 302r. As used herein, "away" does not necessarily mean "directly away."

The system 202r can comprise a telescoping applicator 402 having the channel 403. The applicator 402 can be removably coupled (and/or permanently coupled) to the base 204r such that the applicator 402 is configured to orient the distal portion of the sensor 206r in the constrained state. The applicator 402 can be configured to be uncoupled from the base 204r such that the distal portion of the sensor 206r is capable of entering the relaxed state.

The system 202r can comprise a telescoping applicator 402 having a distal portion 405 and a proximal portion 406. The proximal portion 406 of the applicator 402 can be configured to move distally relative to the distal portion 405 of the applicator 402 to insert the distal portion of the sensor 206r into the skin.

The distal portion 405 of the applicator 402 can comprise a C-shaped channel 403 (e.g., as illustrated in FIG. 52). A section of the sensor 206r can be located in the C-shaped channel 403 such that the C-shaped channel 403 orients the distal portion of the sensor 206r in the constrained state. The applicator 402 can be configured such that the proximal portion 406 of the applicator 402 moves distally relative to the C-shaped channel 403 to insert the distal portion of the sensor 206r into the skin.

The base 204r can be coupled to the proximal portion 406 of the applicator 402 such that the base 204r is configured to move distally relative to the C-shaped channel 403 and relative to the distal portion 405 of the applicator 402 as the sensor 206r is inserted into the skin.

Any of the features described in the context of FIGS. 2-53 can be applicable to all aspects and embodiments identified herein. For example, the embodiments described in the context of FIGS. 2-53 can be combined with the embodiments described in the context of FIGS. 1 and 54-126. Moreover, any of the features of an embodiment is independently combinable, partly or wholly with other embodiments described herein in any way (e.g., one, two, three, or more embodiments may be combinable in whole or in part). Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Buckling Support

Measuring analyte data often involves inserting an analyte sensor into subcutaneous tissue. Some embodiments use a needle to facilitate inserting the sensor into subcutaneous tissue. Some embodiments have a sensor configured to be inserted into subcutaneous tissue without the aid of a needle. (Embodiments can be used with or without a needle.)

Inserting a sensor into a person can cause the sensor to buckle due to the resistance of the skin and subcutaneous tissue to sensor insertion. For example, the sensor can buckle as a distal tip of the sensor attempts to pierce the skin and/or after the distal tip has pierced the skin as the sensor is moved deeper into the person. Many systems solve this problem by using a needle to help insert the sensor into the person. Needles, however, can cause long-term patient discomfort, and thus, are typically removed (while leaving the sensor at least partially inside in the person).

In some embodiments, using a needle may have several disadvantages. For example, retracting the needle can require extra steps, time, and/or hardware. In addition, the presence of a needle may create a larger wound than necessary for inserting a sensor. For example, a wound created by a needle to insert a sensor may be larger than a wound created to insert a sensor without a needle. Thus, in some cases, systems and methods that eliminate the need for using a needle to insert a sensor into a person are advantageous.

In some embodiments, one key to enabling systems and methods that do not use a needle is to eliminate sensor buckling. A system that eliminates sensor buckling typically does not need a needle. Thus, in some cases there is a need for systems and methods that eliminate sensor buckling such that a needle is not necessary to insert the sensor into the person.

The entire contents of the following applications are incorporated by reference herein: U.S. patent application Ser. No. 12/893,850; filed Sep. 29, 2010; and titled Transcutaneous Analyte Sensor; U.S. patent application Ser. No. 14/250,320; filed Apr. 10, 2014; and titled Sensors for Continuous Analyte Monitoring, and Related Methods; U.S. patent application Ser. No. 13/780,808; filed Feb. 28, 2013; and titled Sensors for Continuous Analyte Monitoring, and Related Methods; and U.S. Patent Application 62/244,520; filed Oct. 21, 2015; and titled Transcutaneous Analyte Sensors, Applicators Therefor, and Associated Methods.

Material Type and Dimensions

Some embodiments enable needle-free sensor insertion by using a sensor made from a material that has sufficient resistance to buckling. For example, the sensor materials can have a high modulus of elasticity and/or a high bending stiffness. While these embodiments can reduce the likelihood of sensor buckling, they also can cause in vivo patient discomfort (because a sensor that is stiff may be less prone to buckling, but can be so stiff that it is uncomfortable for the patient during chronic use).

Some embodiments enable needle-free sensor insertion by using a sensor with dimensions that make the sensor not prone to buckling. Several embodiments have sensors that are not prone to buckling due to the short length and/or large width (e.g., diameter) of the sensors.

When a force is applied to insert a sensor (e.g., a self-inserting sensor), buckling can occur before, during, and/or after skin penetration. The resistance of the sensor to buckling is typically dependent on several variables such as material properties and geometry (e.g., overall shape, cross-section geometry, thickness of the beam, length of the beam). Subtle elements such as straightness of the beam as well as induced moments from the load can have large effects on the buckling performance of the sensor.

A maximum buckling load of a sensor can be predicted using the Euler model (shown in FIG. 54). The variables of the Euler model can be used to represent a wide variety of column shapes and support scenarios:

F=maximum or critical force (vertical load on column)
E=modulus of elasticity
I=area moment of inertia of the cross section of the rod
L=unsupported length of column
K=column effective length factor, whose value depends on the conditions of end support of the column.

For one end fixed and the other end free to move laterally: K=2.0. KL is the effective length of the column.

Sensors sometimes have circular cross sections, in which case, the area moment of inertia of the cross section of the rod can be approximated by the formulas shown in FIGS. 55 and 56.

As can be seen by the Euler model, the maximum buckling load of a beam with a circular cross-section increases with radius to the fourth power (for a given material). The maximum buckling load of the beam is divided by the length squared. As a result, doubling the length results in a maximum buckling load that is just 25% as much as the buckling load before doubling the length (for a given support condition).

The ability of the sensor to resist buckling is typically not the only consideration. The sensor sometimes must retain sufficient flexibility to avoid causing patient discomfort when the sensor is located at least partially inside the patient. The sensor also must reach deeply enough below the skin surface to reliably measure analyte indications (e.g., to measure glucose in the interstitial fluid). A sensor that buckles during insertion can fail to penetrate the skin. A sensor that buckles after insertion can cause unreliable analyte measurements.

In some embodiments, the sensor comprises a diameter of greater than 0.004 inches and/or less than 0.015 inches. In several embodiments, the sensor comprises a non-circular cross section, but has a width that is greater than 0.004 inches and/or less than 0.015 inches. The sensor can comprise an insertion depth of greater than 2 mm and/or less than 8 mm (under the skin surface).

Collapsible Supports

Long, slender sensors can minimize patient discomfort, but can be highly susceptible to buckling. Several embodiments comprise support structures configured to resist lateral movements of the sensor as the sensor is inserted into the patient. One challenge, however, is creating a support structure that resists buckling forces of the sensor while not blocking distal movement of the sensor. In other words, a support structure that holds the sensor such that the sensor does not buckle during insertion can get in the way of the sensor as the sensor moves distally. Thus, in some cases there is a need for support structures that resist buckling while not impeding distal movement of the sensor.

Several embodiments include a collapsible support member configured to resist non-axial forces of the sensor. Collapsible support members can resist buckling forces and can also compress, deflect, and/or release to allow the sensor to move distally.

In some embodiments, the system comprises a collapsible support member configured to resist non-axial forces of the sensor. The collapsible support member can comprise a proximal end, a distal end, and a length measured from the proximal end to the distal end. The system can be configured to reduce the length in response to moving the sensor from a proximal position to a distal position.

As used herein, axial forces place a central axis of a sensor in compression or tension. Non-axial forces act in directions other than along the central axis.

In several embodiments, a collapsible support member comprises a channel. At least a portion of the sensor can pass through the channel. The channel can be configured to resist a buckling force of the sensor as the sensor moves from the proximal position to the distal position.

Collapsible Foam

FIG. 57 illustrates a perspective view of a system 202s with a collapsible support that resists buckling of the sensor 206s. The collapsible support can be a collapsible block 412 that has a channel 413. The sensor 206s can pass through the channel 413 such that the channel 413 resists buckling forces while the collapsible block 412 compresses to enable the sensor 206s to move distally.

FIG. 58 illustrates a side view of the system 202s in a state prior to compressing the collapsible block 412. FIG. 59 illustrates a side view of the system 202s in a state after compressing the collapsible block 412 to deploy the sensor 206s.

The channel 413 starts at a proximal portion 411 of the base and ends at a distal portion 204s of the base such that the channel 413 passes through the block 412. The block 412 can be a cube, a cylinder, a cone, and/or any suitable shape.

FIG. 58 illustrates a distal side 207s of the system 202s. Adhesive 210s can couple the distal side 207s to the skin of a host. FIG. 58 also illustrates a distal direction 209 and a proximal direction 208.

A proximal portion 411 of the base can move towards a distal portion 204s of the base (e.g., in the direction shown by arrow 209) while the block 412 prevents the sensor 206s from buckling. The block 412 can compress to enable the system 202s to deploy the sensor 206s. A transmitter 211s can be coupled to the proximal portion 411 of the base.

One advantage of a collapsible block 412 is that the structure provides robust lateral support such that the block 412 prevents the sensor 206s from buckling. For example, FIG. 58 illustrates a lateral direction 414. When the sensor 206s starts to move in this lateral direction 414, further lateral movement of the sensor 206s is blocked by a wall of the channel 413. (The channel 413 can appear like the inside of a tube.)

Another advantage is that the structure of the block 412 is also highly compressible such that a height of the block 412 can decrease dramatically to enable the system 202s to move the sensor 206s distally.

Referring now to FIGS. 57-59, the block 412 can be made from foam and/or any other suitable material. The foam can be open or closed cell foam. Open cell foam can be highly compressible. High compressibility can reduce the minimum height of the system 202s in a compressed state. Each foam enables a compression ratio (i.e., the ratio between the uncompressed height of the foam and the compressed height of the foam). In several embodiments, the compressed height of the foam is at least 1 percent, at least 10 percent, at least 20 percent, less than 25 percent, less than 35 percent, and/or less than 50 percent of the uncompressed height of the foam.

The foam can be anisotropic or isotropic. Foams can use a wide variety of materials including polyurethane, polystyrene, polymer, silicone, and/or any suitable material.

The system 202s can comprise a foam coupled to the base 204s and a channel 413 mechanically supported by the foam. At least a portion of the sensor 206s can be located in the channel 413. The portion of the sensor 206s can comprise a central axis. The channel 413 can be configured to resist lateral displacement of the portion of the sensor 206s relative to the central axis. The foam can be configured to compress in response to the system 202s moving the sensor 206s from a proximal position (e.g., as illustrated in FIG. 58) to a distal position (e.g., as illustrated in FIG. 59).

In some embodiments, the base comprises a distal portion 204s and a proximal portion 411. The system 202s can comprise a channel 413 having walls configured to compress in response to the system 202s moving the sensor 206s from a proximal position to a distal position. The channel 413 can be located at least partially between the distal portion 204s and the proximal portion 411 of the base such that a portion of the sensor 206s is located in the channel 413. The walls of the channel 413 can be configured to resist lateral displacement of the portion of the sensor 206s. This lateral displacement is defined relative to a distal direction 209 along a central axis of a portion of the sensor 206s located in the channel 413.

In several embodiments, the walls comprise foam configured to compress in response to moving the proximal portion 411 distally towards the distal portion 204s of the base. The walls can be made from collapsible structures and/or compressible materials other than foam.

The foam block 412 can have one or more intermediate layers made out of a more rigid and/or less compressible material. The layers of the foam block 412 can be adhered together. The intermediate layer 416 can be a more rigid foam. The intermediate layer 416 can be plastic, silicone, thermoplastic elastomer ("TPE"), and/or an elastomer such that the foam compresses at least 50 percent while the intermediate layer 416 compresses less than 25 percent.

The intermediate layer 416 can be located between a proximal layer 417 and a distal layer 418. The intermediate layer 416 can have a different material than the distal layer 418 and the proximal layer 417. The intermediate layer 416 can have a higher density, can be less compressible, can be harder (e.g., as measured on the Shore A scale), can have a higher modulus of elasticity, can be stiffer, and/or can be more rigid than the distal layer 418 and/or the proximal layer 417. The intermediate layer 416 can have a closed-cell structure while the distal layer 418 and/or the proximal layer 417 have an open-cell structure.

In some embodiments, the walls comprise a proximal section (e.g., a portion of the proximal layer 417) having a first material, an intermediate section (e.g., a portion of the intermediate layer 416) having a second material, and a distal section (e.g., a portion of the distal layer 418) having a third material. The second material can be more rigid than the first and third materials such that the intermediate section is configured to resist the lateral displacement. The second material can be stiffer than the first and third materials such that the intermediate section is configured to resist the lateral displacement. The second material can be less compressible than the first and third materials.

In several embodiments, the system 202s comprises an interlock 420 (e.g., a mechanical interlock) configured to secure the proximal portion 411 of the base to the distal portion 204s of the base in response to the system 202s moving the sensor 206s from the proximal position to the distal position.

A mechanical interlock 420 can secure the system 202s in the compressed state (as shown in FIG. 59). The mechanical interlock 420 can include arms and a snap fit that couples with an undercut or channel 413. The channel 413 can be formed by a hole, a pass through, or a slot.

Collapsible Bellows

FIGS. 60-63 illustrate a system 202t with a collapsible support that resists buckling of the sensor 206t. The collapsible support can be formed by bellows 421 that have a channel 422. A portion of the sensor 206t can be located in the channel 422 of the bellows 421. The sensor 206t can pass through the channel 422 such that the channel 422 resists buckling forces while the bellows 421 compress to enable the sensor 206t to move distally. Adhesive 210t can couple the system 202t to a person.

Figure 60:
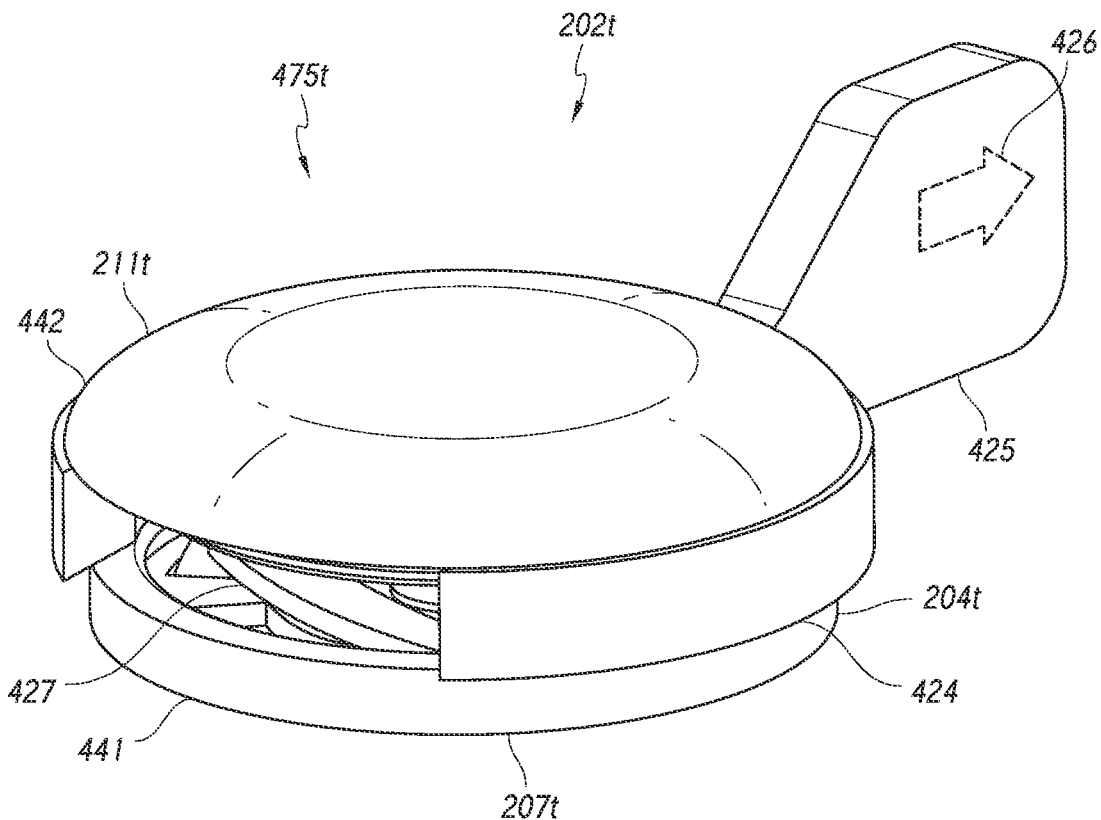
FIG. 60 illustrates a perspective view of a system, according to some embodiments.
Figure 61:
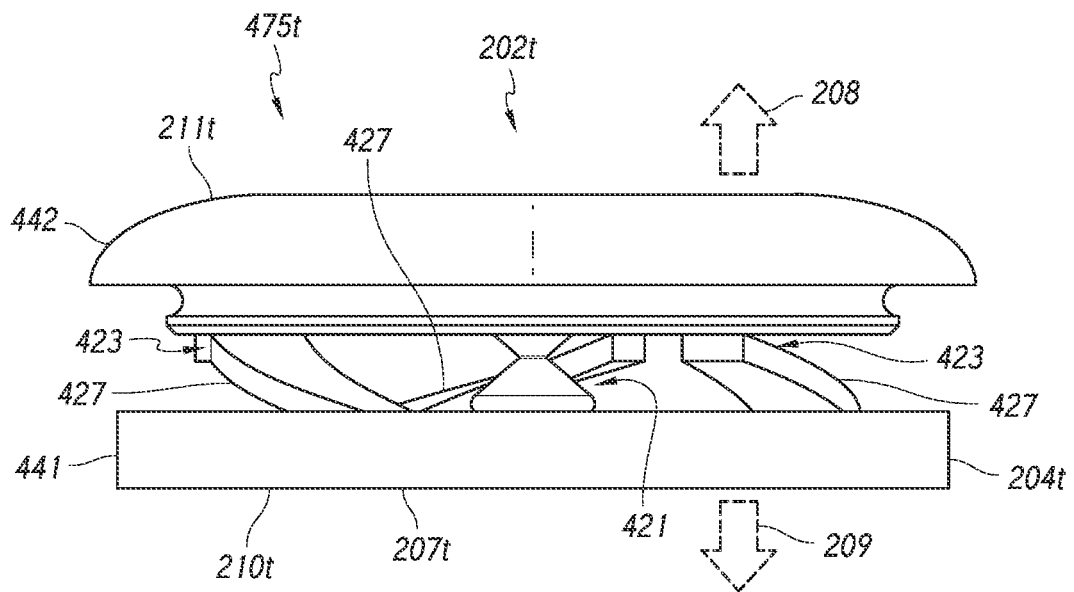
FIG. 61 illustrates a side view of the system prior to collapsing bellows, according to some embodiments.
Figure 62:
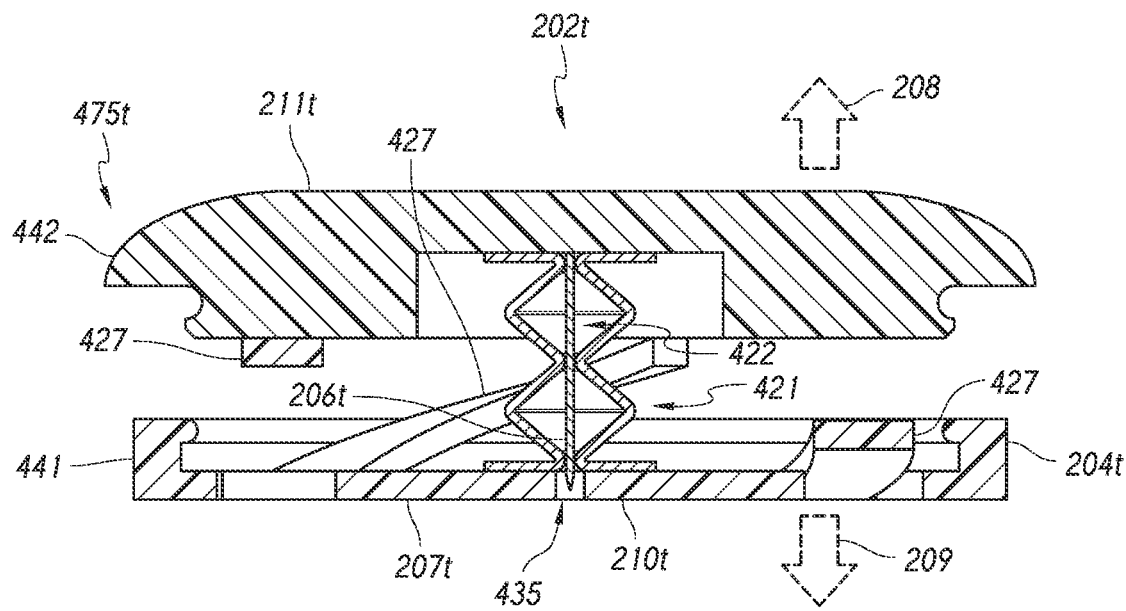
FIGS. 62 and 63 illustrate side, cross-sectional views, according to some embodiments.
Figure 63:
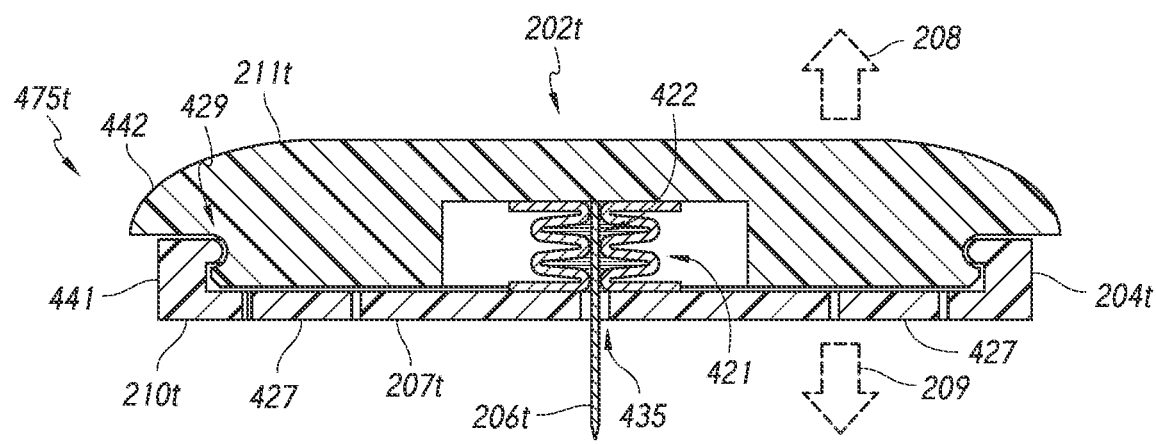

FIG. 60 illustrates a perspective view of the system 202t in a state prior to collapsing the bellows 421 (shown in FIG. 61). FIG. 61 illustrates a side view of the system 202t in the state prior to collapsing the bellows 421. FIG. 62 illustrates a side, cross-sectional view of the state shown in FIGS. 60 and 61. The sensor 206t can move in a distal direction 209 relative to the base 204t to compress the bellows 421 while the bellows 421 resist buckling of the sensor 206t. FIG. 63 illustrates a side, cross-sectional view of a state after collapsing the bellows 421 to deploy the sensor 206t.

Referring now to FIGS. 60-63, the bellows 421 can comprise pleated expansible parts made from an elastomeric material, a rigid plastic, a flexible plastic, a silicone, and/or a flexible polymer. The bellows 421 can include foldable sections configured to fold to enable the bellows 421 to compress from an initial height to a compressed height that is less than 50 percent and/or less than 35 percent of the initial height (measured in the proximal direction 208).

The system 202t can include arms 427 configured to guide a top portion (e.g., the transmitter 211t) towards the base 204t to control the collapse of the bellows 421. The arms 427 can support and position the top portion as the bellows 421 collapse such that the movement of the arms 427 translates into movement of the top portion relative to the base 204t and the at least partial collapse of the bellows 421. The arms 427 can be configured to guide the top portion in a linear manner towards the base 204t or can be configured to rotate the top portion relative to the base 204t as the bellows 421 are compressed.

The bellows 421 can be configured to laterally support at least a portion of the sensor 206t as the portion passes through an interior area (e.g., a channel 422) of the bellows 421. The system 202t can be configured such that moving the system 202t from an initial state (in which the sensor 206t is not at least partially located in the person) to a final state (in which the sensor 206t is located at least partially in the person) can cause the bellows 421 to collapse.

Several embodiments do not include a needle. Some embodiments include a needle (e.g., as shown in embodiments incorporated by reference) that is retracted into the bellows 421. The system 202t can include a spring that has a relaxed state such that the bellows 421 are expanded (e.g., the needle is retracted and/or the sensor 206t is not deployed). The arms 427 can act as a spring system.

The system 202t can include a mechanical interlock 429 configured to releasably hold the bellows 421 and/or a spring in a compressed state. Releasing the mechanical interlock 429 can retract the sensor 206t from the skin such that the portion of the sensor 206t that was located distally relative to the distal side 207t of the base 204t is moved proximally into an interior area of the system 202t. The interlock 429 can be a snap fit formed by an undercut (e.g., as shown in FIG. 63).

In some embodiments, the system 202t comprises bellows 421 coupled to the base 204t. At least a portion of the sensor 206t can be located in an interior area of the bellows 421. The portion of the sensor 206t can comprise a central axis. The bellows 421 can be configured to resist lateral displacement of the portion relative to the central axis. The bellows 421 can be configured to compress in response to the system 202t moving the sensor 206t from a proximal position to a distal position.

The system 202t can include a removable safety feature 424 configured to prevent premature and/or inadvertent sensor deployment. A tab 425 can be coupled to the safety feature such that moving the tab 425 (e.g., in a direction shown by arrow 426) moves the safety feature 424 relative to the base 204t to uncouple the safety feature 424 from the base 204t. The safety feature 424 can be C-shaped. For example, the safety feature 424 can be shaped like a hoop with an open section configured to enable the bellows 421 to pass through the open section as the safety feature 424 is removed.

Some embodiments comprise a distal portion of the base 204t and a proximal portion (which can include the transmitter 211t). The bellows 421 can couple the distal portion to the proximal portion. The system 202t can comprise a removable interference member 424 (e.g., a safety member) located between the distal portion and the proximal portion such that the removable interference member 424 is configured to block the system 202t from moving the sensor 206t from the proximal position (e.g., a proximal starting position) to the distal position (e.g., a distal ending position).

In some embodiments, the system comprises a tab coupled to the collapsible support member. The system can be configured such that actuating (e.g., pulling, pushing, moving, pressing, touching) the tab causes the collapsible support member to collapse and causes at least a portion of the sensor to move distally relative to the base.

Folded Flex Tab

FIGS. 64-67 illustrate a system 202u with a collapsible support that resists buckling of the sensor 206u. The collapsible support can be formed by a compliant sheet 438 located in a slot 439 (e.g., a passageway, a hole, a channel) of a housing 440. Moving the sheet 438 distally can cause the sensor 206u to move distally (e.g., into tissue of the host). The housing 440 can comprise a slot 439 configured to resist buckling forces of the sensor 206u as the sensor 206u moves distally (e.g., as indicated by the distal arrow 209 shown in FIG. 66).

FIG. 64 illustrates a perspective view of the system 202u, which can include a battery 430u and a transmitter 211u that can be electrically coupled to a flex circuit 431 located at least partially in the slot 439. FIG. 65 illustrates a different perspective view of the system 202u. Moving the sheet 438 in a direction that is within plus or minus 45 degrees of perpendicular to the distal direction 209 (shown in FIG. 66) can move a portion of the sheet 438 located in the slot 439 distally to move the sensor 206u distally. For example, the sheet 438 can be moved in direction 432 and/or in direction 433, which can cause the sheet 438 to move the sensor 206u in direction 434 (e.g., a distal direction).

The system 202u can include a distal side 207u having adhesive 210u configured to couple the system 202u to the skin of a host. The sheet 438 can couple the adhesive 210u to the base 204u and/or to the housing 440.

FIG. 66 illustrates a side view of the housing 440 that includes a slot 439. The slot 439 can go all the way through the housing 440 (e.g., from a left side to a right side of the housing 440) as illustrated in FIG. 66. In some embodiments, the slot 439 does not go all the way through the housing 440.

FIG. 67 illustrates a perspective view of the system 202u without the housing 440. The proximally protruding portion 436 of the sheet 438 is configured to fit within the slot 439 of the housing 440 (shown in FIG. 66). Moving this portion 436 distally causes the system 202u to move the sensor 206u distally.

Referring now to FIGS. 64-67, several embodiments include at least one tab 446, 447 coupled to a flexible member (e.g., the sheet 438). The flexible member and a portion of the sensor 206u can be located in a slot 439 such that moving the tab 446, 447 causes the flexible member to move, push, and/or pull the portion of the sensor 206u out of the slot 439 and into tissue of a person.

The slot 439 can support the sensor 206u by resisting buckling forces of the sensor 206u. The slot 439 can have an opening 448 that faces distally (labeled in FIG. 66). The slot 439 can support at least 80% of the ex vivo portion of the sensor 206u (e.g., when the sensor 206u is in a proximal starting position prior to sensor deployment). The slot 439 can be located in a housing 440, which can be a removable applicator.

The system 202u can comprise a pull tab 446, 447 and a slot 439 configured such that at least a portion of the sensor 206u is located in the slot 439. The system 202u can be configured such that pulling the pull tab 446, 447 causes the system 202u to move the sensor 206u from a proximal position to a distal position.

The system 202u can comprise a compliant sheet 438 located in the slot 439 and coupled to the pull tab 446, 447 such that the compliant sheet 438 is configured to move (e.g., push, pull) the portion of the sensor 206u distally in response to actuating (e.g., pulling) the pull tab 446, 447. As used herein, the sheet 438 is "compliant" if the sheet 438 can conform and/or bend to fit in the slot 439.

The system 202u can comprise a housing 440 coupled to the base 204u. The housing 440 can comprise the slot 439 and can be configured to cause the compliant sheet 438 to push the portion of the sensor 206u distally in response to pulling the pull tab 446, 447. The slot 439 can comprise a distally facing opening 448 (labeled in FIG. 66) configured to allow the portion of the sensor 206u to exit the slot 439 distally and enter subcutaneous tissue of the host.

High-Level Claims—Guide Members and Splitting Channels

As described above, long, slender sensors can be highly susceptible to buckling. Several embodiments comprise support structures configured to resist lateral movements of the sensor as the sensor is inserted into the patient. One challenge, however, is creating a support structure that resists buckling forces of the sensor while not blocking distal movement of the sensor. Some embodiments avoid blocking distal movement of the sensor by moving out of the way of the sensor as the sensor moves distally.

In some embodiments (e.g., as described in the context of FIGS. 74-84), systems can comprise a guide member configured to resist non-axial forces of the sensor. Thus, a guide member can brace the sensor against buckling.

The guide member can comprise an engagement feature releasably coupled to the sensor. The engagement feature can be configured to uncouple from the sensor in response to moving the sensor from a proximal position to a distal position.

In several embodiments, a guide member comprises a first portion and a second portion. At least a portion of the sensor can be located between the first and second portions of the guide member such that the first and second portions of the guide member are configured to resist a buckling force of the sensor.

In some embodiments, the first portion can be configured to move relative to the second portion of the guide member in response to the system moving the sensor from a proximal position to a distal position. The guide member can be configured such that displacement of the first portion relative to the second portion permits moving the sensor from the proximal position to the distal position.

In several embodiments, the portion of the sensor (that is located between the first and second portions of the guide member) comprises a central axis. The first and second portions of the guide member can form a channel. The portion of the sensor can be located in the channel. The channel can be configured to resist displacement of the portion of the sensor in a direction perpendicular to the central axis.

Splitting Channel

In some embodiments (e.g., as described in the context of FIGS. 74-84), systems can comprise a channel having a first side and a second side configured to at least partially separate in response to the system moving the sensor from a proximal position to a distal position. A portion of the sensor can be located in the channel such that the channel is configured to at least partially separate to permit the sensor to move from the proximal position to the distal position. The portion of the sensor can comprise a central axis. The channel can be configured to resist displacement of the portion of the sensor in a direction perpendicular to the central axis.

Splinter Insertion

Figure 68:
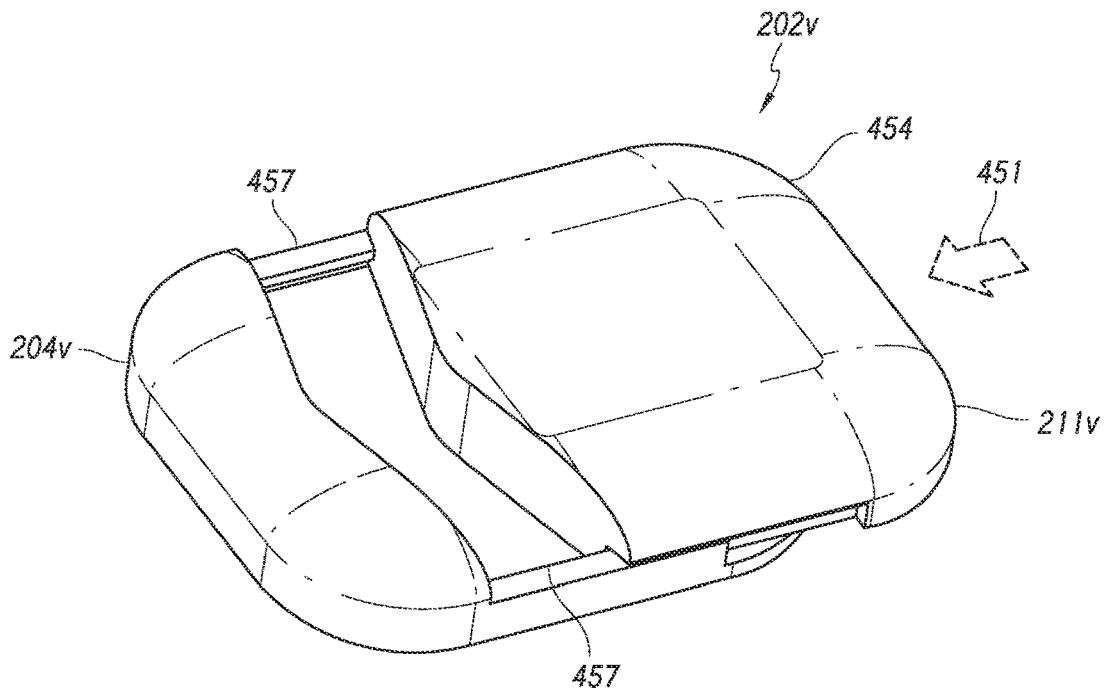
FIG. 68 illustrates a perspective view of a system, according to some embodiments.
Figure 69:
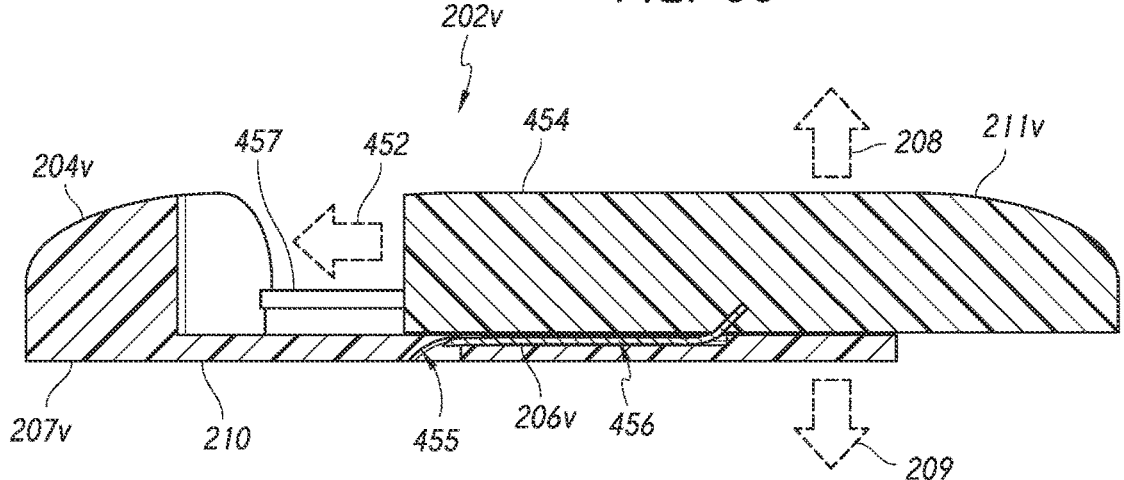
FIGS. 69 and 70 illustrate side, cross-sectional views of the system, according to some embodiments.
Figure 70:
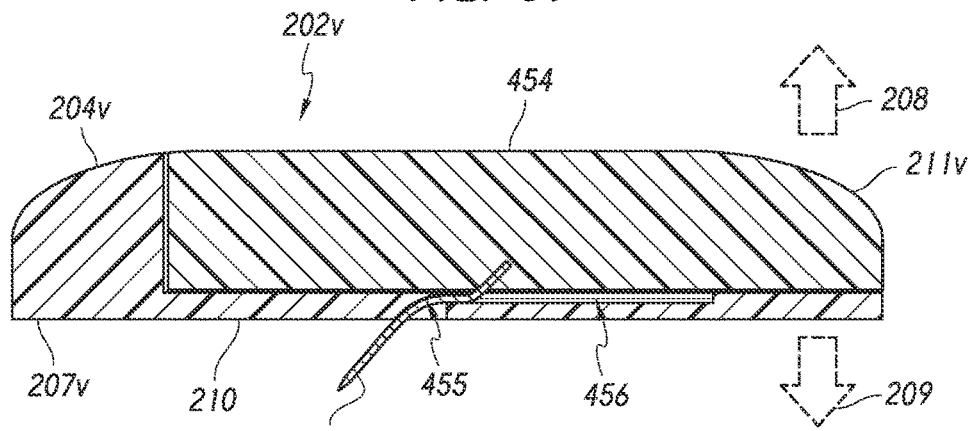

FIGS. 68-70 illustrate a system 202v that includes a guide member (e.g., a channel located at least partially between a first portion and a second portion of a base 204v). The guide member can support the sensor 206v to prevent harmful buckling. The guide member can include a curved and/or angled portion configured to deflect a distal portion of the sensor 206v into the skin of the host. As a result, moving the second portion of the base 204v relative to the first portion of the base 204v can cause a distal portion of the sensor 206v to change directions.

FIG. 68 illustrates a perspective view of the system 202v. Moving the second portion of the base 204v (e.g., as indicated by arrow 451) relative to the first portion of the base 204v can cause the sensor 206v to be deflected by the system 202v and exit a distal side 207v of the base 204v. Adhesive 210 can couple the distal side 207v to skin of the host.

FIG. 69 illustrates the same pre-deployment state as shown in FIG. 68. FIG. 69 illustrates a side, cross-sectional view. Sliding the second portion of the base 204v in the direction indicated by arrow 452 pushes the sensor 206v along an interior area between the first portion and the second portion of the base 204v. Continuing to slide the second portion of the base 204v in the direction indicated by arrow 452 causes a distal portion of the sensor 206v to protrude from the distal side 207v of the base 204v (e.g., as shown in FIG. 70). FIG. 70 illustrates a side, cross-sectional view of the system 202v in a state in which the sensor 206v is deployed.

Referring now to FIGS. 68-70, a first portion of the system 202v can be moved approximately horizontally to push the sensor 206v out of a distal side 207v of the base 204v. In some embodiments, the first portion of the system 202v can be configured to move in a direction that is within plus or minus 45 degrees and/or within plus or minus 25 degrees of perpendicular to a distal direction 209. The first portion can be coupled to the base 204v by a rail 457 such that the first portion is slidably coupled to the base 204v.

A curved channel 455 (which can be a slot) can deflect the sensor 206v such that movement of the top portion causes the sensor 206v to exit the distal side 207v of the base 204v. The movement can be in a direction that is within plus or minus 45 degrees and/or within plus or minus 25 degrees of perpendicular to a distal direction 209.

The sensor 206v is prevented from inadvertently buckling by being constrained between the first portion and the second portion of the base 204v. The system 202v can comprise a channel 456 configured to resist buckling forces of the sensor 206v as the sensor 206v is deployed. The channel 456 can be approximately straight and can be coupled with a curved and/or angled channel 455.

In several embodiments, a sensor 206v is coupled to a housing 454 that is slidably coupled to the base 204v. The system 202v can be configured to move a portion of the sensor 206v away from the distal side 207v of the base 204v (and into the skin) in response to moving the housing 454 in a first direction (e.g., as indicated by arrow 452) within plus or minus 10 degrees, within plus or minus 20 degrees, within plus or minus 45 degrees, and/or within plus or minus 60 degrees of perpendicular to a distal direction 209.

The system 202v can comprise a housing 454 slidably coupled to the base 204v. The base 204v can comprise a channel 455 (e.g., a curved channel and/or a channel oriented at an angle within plus or minus 45 degrees of parallel to a distal direction 209). A portion of the sensor 206v can be located in the channel 455. The sensor 206v can move through the curved and/or angled channel 455 as the sensor 206v is deployed into the skin. The channel 455 can be configured to deflect the portion of the sensor 206v to redirect the portion distally in response to moving the housing 454 relative to the base 204v.

A sensor path can have a first section 456 and a second section 455. At least a portion of the sensor 206v can move along the first section 456 and the second section 455 of the sensor path. The first section 456 can be oriented within plus or minus 20 degrees of perpendicular to a distal direction 209 and/or within plus or minus 45 degrees of perpendicular to a distal direction 209. The second section 455 can be oriented within plus or minus 45 degrees of parallel to the distal direction 209. The system 202v can be configured to deflect the sensor 206v to cause the sensor 206v to follow the sensor path such that the channel 455 redirects the sensor 206v towards the skin of the host.

The base 204v can comprise a first portion (e.g., the portion that comprises the distal side 207v) and a second portion (e.g., the portion that comprises the transmitter 211v). The first portion can be configured to couple the second portion to the skin. The second portion can be slidably coupled to the first portion. The base 204v can be configured such that moving the second portion (relative to the first portion) in a first direction (e.g., as shown by arrow 452) within plus or minus 20 degrees of perpendicular to a distal direction 209 (and/or within plus or minus 45 degrees of perpendicular to a distal direction 209) causes a distal tip of the sensor 206v to move in a second direction within plus or minus 45 degrees of parallel to the distal direction 209.

The sensor 206v can comprise a distal section and a proximal section. The proximal section can be rigidly coupled to the second portion of the base 204v. The distal section can pass through a channel 455, 456 of the first portion of the base 204v. The channel 455, 456 can comprise a radius configured to deflect at least a portion of the sensor 206v such that the portion of the sensor 206v is redirected distally towards the skin of the host.

The sensor 206v can be a glucose sensor and/or any type of sensor described herein and/or incorporated by reference. The transmitter 211v can be coupled to the second portion of the base 204v such that the second portion slidably couples the transmitter 211v to the first portion of the base 204v. The system 202v can comprise at least one rail 457 that slidably couples the second portion to the first portion of the base 204v. In some embodiments, the first and second portions may be coupled to a spring. In several embodiments, the sliding member may be shrouded internally to protect the mechanism from external influences.

Curved Support Channel

Figure 71:
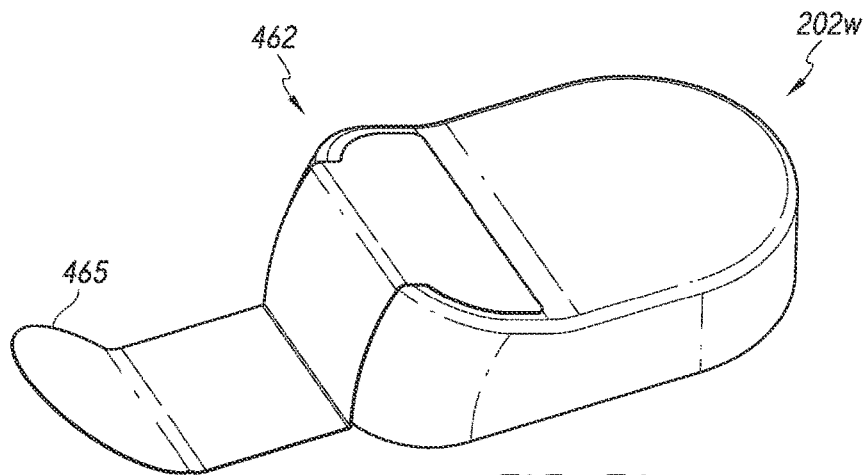
FIG. 71 illustrates a perspective view of a system, according to some embodiments.
Figure 72:
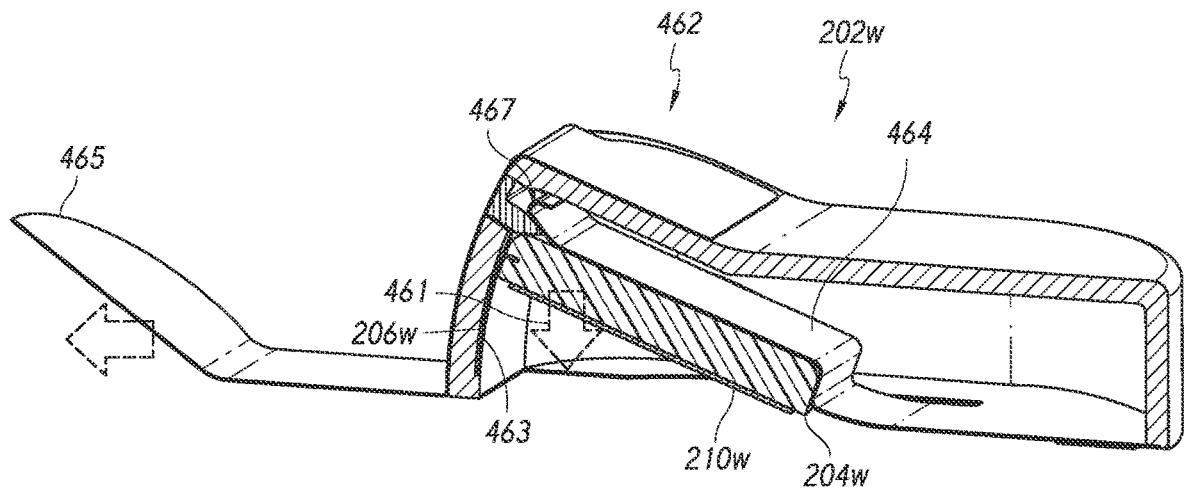
FIG. 72 illustrates a perspective, cross-sectional view of the system, according to some embodiments.
Figure 73:
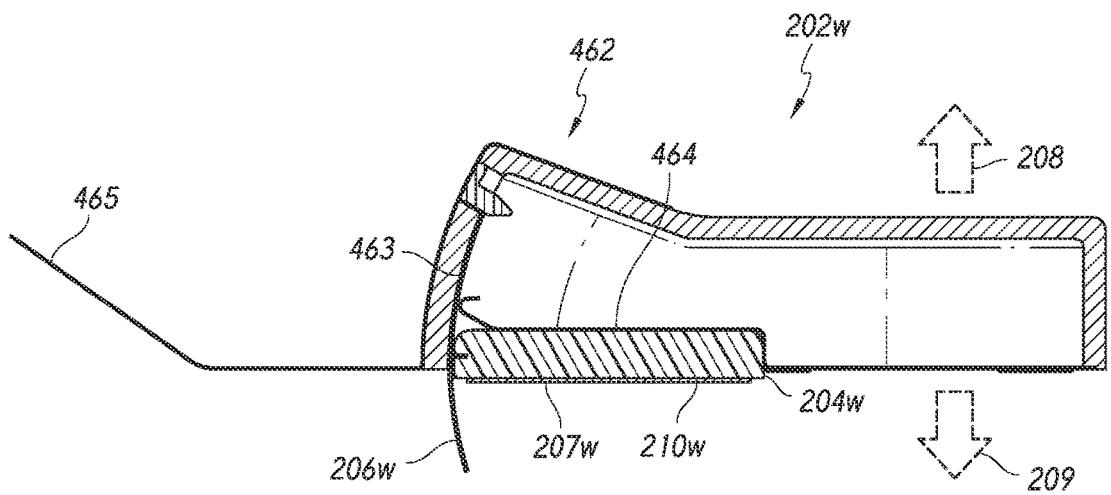
FIG. 73 illustrates a side, cross-sectional view of the system, according to some embodiments.

FIGS. 71-73 illustrate a system 202w that includes a guide member (e.g., a channel 463). Some embodiments maintain the sensor 206w in an approximately straight orientation to minimize buckling. However, other embodiments (e.g., as shown in FIGS. 71-73) deliberately bend the sensor 206w along a curved path to enable buckling forces that actually facilitate successful sensor 206w insertion. Thus, the system 202w can direct the buckling forces in a known, repeatable, predictable direction. A wall of a channel 463 can support the sensor 206w in this direction to preclude harmful buckling.

FIG. 71 illustrates a perspective view of the system 202w. FIG. 72 illustrates a perspective, cross-sectional view of the system 202w in a state prior to the sensor 206w being deployed (e.g., when the sensor 206w is in a proximal starting position). FIG. 73 illustrates a side, cross-sectional view of the system 202w in a state after the sensor 206w is deployed (e.g., when the sensor 206w is in a distal ending position).

The base 204w can rotate distally (e.g., as indicated by arrow 461 in FIG. 72) relative to the applicator 462 to move the sensor 206w into the tissue (e.g., as illustrated in FIG. 73). Adhesive 210w can couple the distal side 207w of the base 204w to the skin of the host.

The system 202w can include a curved channel 463 configured to support the sensor 206w as the sensor 206w is deployed into the skin of the person. The curved channel 463 can be part of an applicator 462 that is removably coupled to the base 204w.

The system 202w can include a spring 464 (e.g., a leaf spring 464) in a flexed state when the sensor 206w is in a proximal starting position (e.g., as shown in FIG. 72). A mechanical interlock 467 (e.g., an inward protrusion) can hold the spring 464 in the flexed state. Releasing the mechanical interlock 467 enables the spring 464 to push the sensor 206w to a distal position as a portion of the sensor 206w follows a curved path through the curved channel 463. Deflecting the protrusion (e.g., by pulling a pull tab 465 or by any other suitable means) can release the mechanical interlock 467.

The spring 464 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

The curved nature of the channel 463 determines the predominant direction of buckling forces. As a result, the buckling forces press the sensor 206w towards the bottom of the channel 463 (rather than out of the channel 463). The support provided by the curved channel 463 on predominantly one hemisphere of a cross section of the sensor 206w allows more force to transfer to the distal tip of the sensor 206w. The result is highly reliable sensor 206w insertion.

The system 202w can comprise a removable applicator 462 coupled to the base 204w. The base 204w can include a transmitter (e.g., as shown in other embodiments). The applicator 462 can be any type of applicator 462 described herein and/or incorporated by reference.

The applicator 462 can comprise a curved channel 463 configured to guide a portion of the sensor 206w along a curved path as the portion of the sensor 206w moves from a proximal position (e.g., as shown in FIG. 72) to a distal position (e.g., as shown in FIG. 73). (In some embodiments, the channel 463 is straight rather than curved.) The applicator 462 can comprise a leaf spring 464 configured to drive the portion of the sensor 206w along the curved path through the curved channel 463.

A curved channel 463 can be coupled to the base 204w. A curved portion of the sensor 206w can be located in the curved channel 463. The curved channel 463 can be configured to resist buckling forces of the curved portion as the system 202w moves the curved portion from a proximal position (e.g., as shown in FIG. 72) to a distal position (e.g., as shown in FIG. 73). The applicator 462 can be configured to facilitate moving the curved portion of the sensor 206w from the proximal position to the distal position.

The system 202w can comprise a spring 464 configured to move the curved portion of the sensor 206w from the proximal position to the distal position. The spring 464 can be any type of spring 464 described herein and/or incorporated by reference. The spring 464 can be a leaf spring in a flexed state.

The system 202w can comprise an interlock 467 (e.g., a mechanical interlock) configured to releasably hold the spring 464 (e.g., a leaf spring) in a flexed state. FIG. 72 illustrates an interlock 467 that comprises an inward protrusion of the applicator 462 that interferes with distal movement of a portion of the system 202w (e.g., a portion of the spring 464, a portion of the base 204w).

The system 202w can be configured to move the curved portion of the sensor 206w from the proximal position to the distal position in response to releasing the interlock 467. The system 202w can comprise a tab 465 (e.g., a pull tab) coupled to the interlock 467 such the system 202w is configured to disengage the interlock 467 to enable the spring 464 to move the curved portion of the sensor 206w from the proximal position to the distal position in response to actuating (e.g., pulling, pushing, moving) the tab 465.

Sensor Grip—Zipper Embodiment

Some embodiments use movable arms to support the sensor against buckling forces. The movable arms can move out of the way as the sensor moves from a proximal starting position to a distal ending position.

The movable arms can have many different shapes. In some embodiments, the movable arms can be shaped like a clothespin, opposing fingers, and/or a set of tongs. The movable arms can have a relaxed state in which the moveable arms form a channel through which at least a portion of the sensor passes as the sensor is deployed.

In several embodiments, the movable arms have a relaxed state in which the arms are spread apart from each other. The applicator can hold the arms together to support the sensor against buckling.

FIGS. 74-77 illustrate a system 202x that includes a guide member (e.g., a channel 473). The system 202x can comprise a channel 473 having a first side and a second side configured to at least partially separate in response to the system 202x moving the sensor 206x from a proximal position to a distal position.

Figure 74:
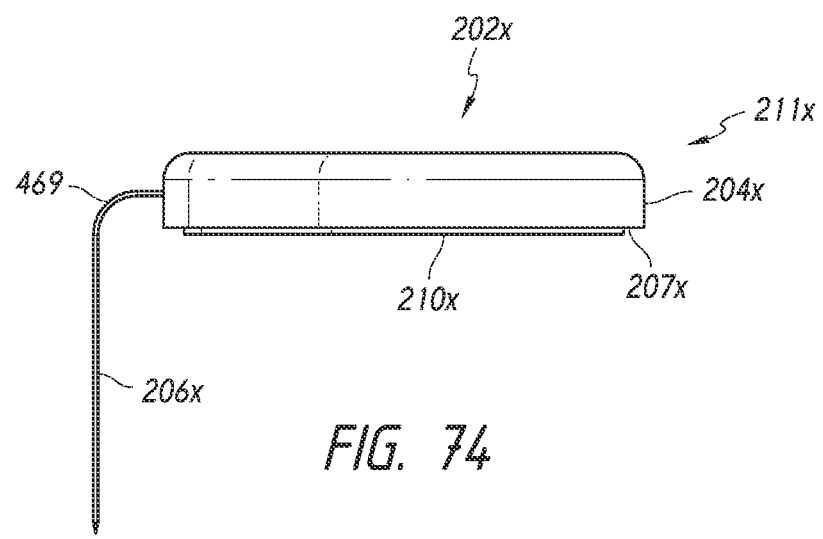
FIG. 74 illustrates a side view of a base, according to some embodiments.

FIG. 74 illustrates a side view of a base 204x. A transmitter 211x is located inside the base 204x. A sensor 206x is coupled to the base 204x. Adhesive 210x is coupled to a distal side 207x of the base 204x such that the adhesive 210x is configured to couple the base 204x to skin of the host.

Figure 75:
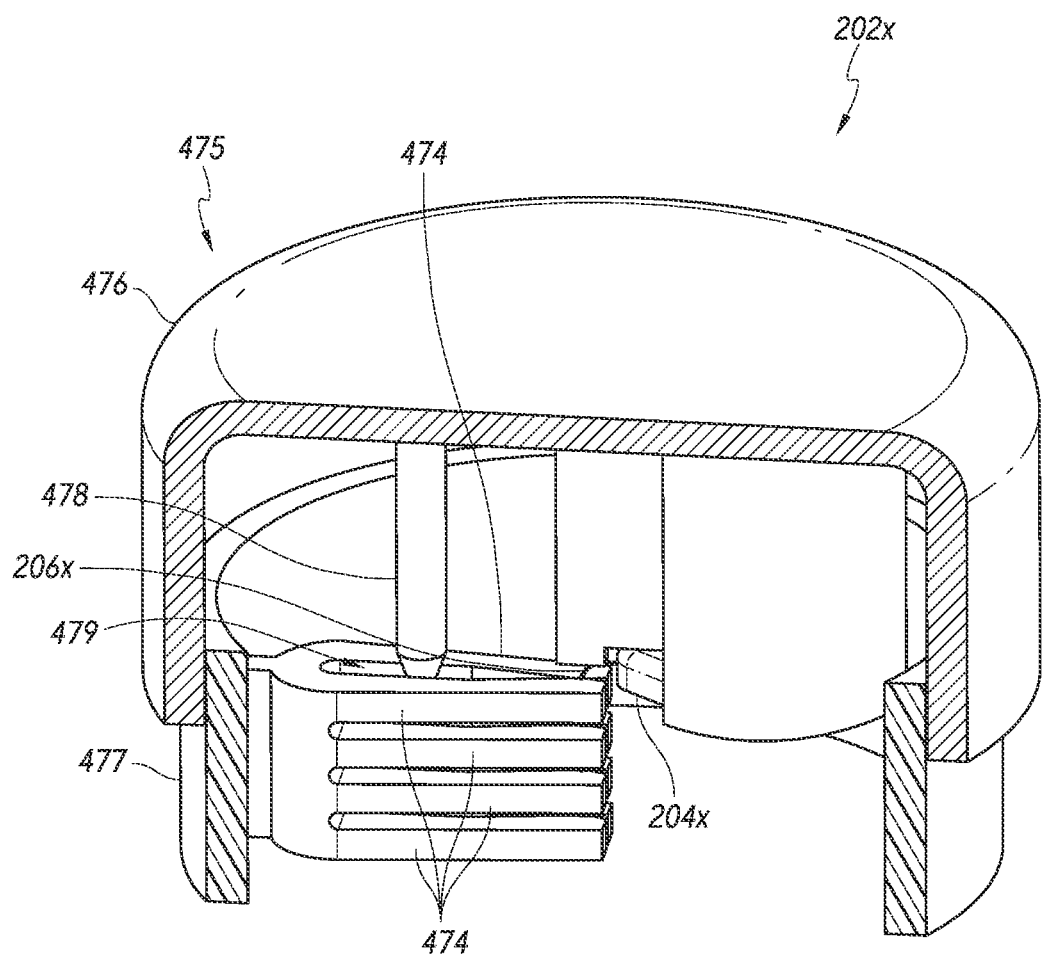
FIG. 75 illustrates a perspective, cross-sectional view of a telescoping applicator, according to some embodiments.

FIG. 75 illustrates a perspective, cross-sectional view of a telescoping applicator 475 that is removably coupled to the base 204x. The applicator 475 includes four sets of arms 474. Each set of arms 474 includes a first arm 474 and a second arm 474. The first arm 474 and the second arm 474 of each set can press towards each other (such that the relaxed state of the first arm 474 and the second arm 474 is when the end portions of the first arm 474 and the second arm 474 touch each other). In the area where the first arm 474 and the second arm 474 touch each other, the arms 474 can form a channel 473. At least a portion of the sensor 206x can be configured to pass through the channel 473. The channel 473 can resist buckling forces of the sensor 206x to help maintain the portion of the sensor 206x in an approximately straight configuration as the sensor 206x is deployed.

A proximal portion 476 of the applicator 475 can include a distal protrusion 478 configured to enter an area 479 between each set of arms 474 as the proximal portion 476 of the applicator 475 moves towards the distal portion 477 of the applicator 475. As the distal protrusion 478 enters the area 479 between each set of arms 474, the distal protrusion 478 can move the first arm 474 away from the second arm 474 to open the channel 473 to allow an angled portion 469 of the sensor 206x to pass between each set of arms 474.

Figure 76:
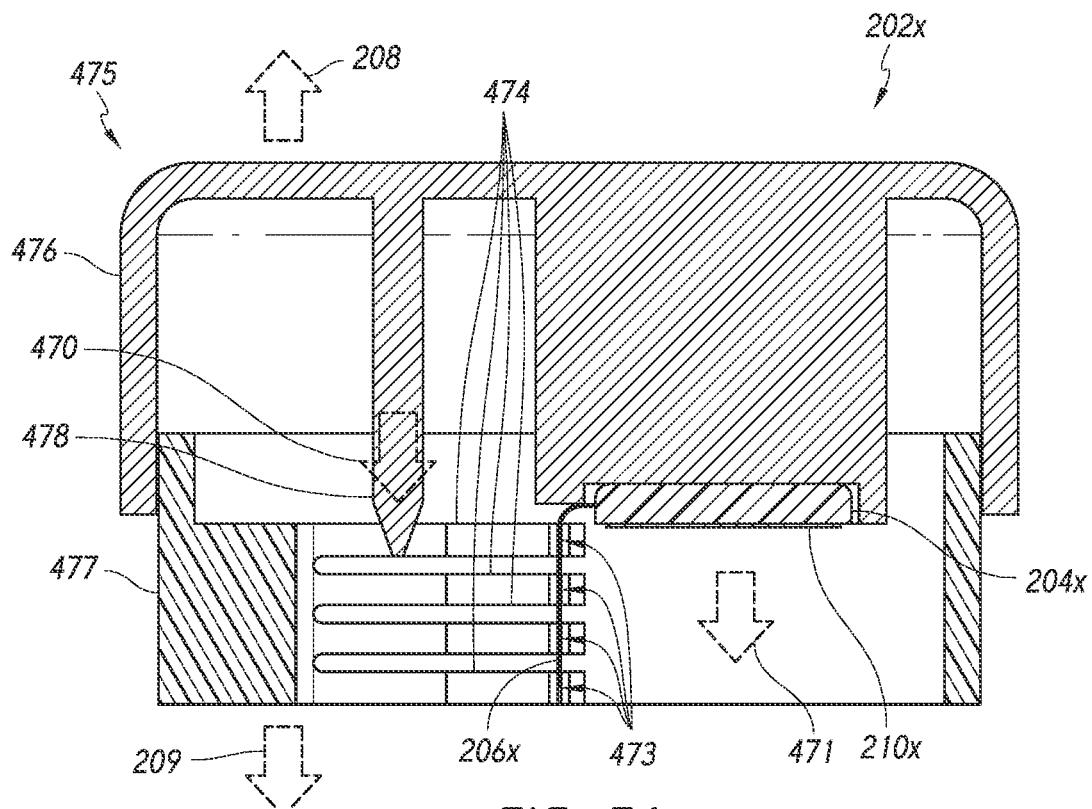
FIGS. 76 and 77 illustrate side, cross-sectional views of the system, according to some embodiments.

FIG. 76 illustrates a side, cross-sectional view of the system 202x when the system 202x is in a proximal starting position. The distal protrusion 478 can move in the direction indicated by arrow 470 as the system 202x moves the base 204x in a distal direction 209 (e.g., as indicated by arrow 471).

Figure 77:
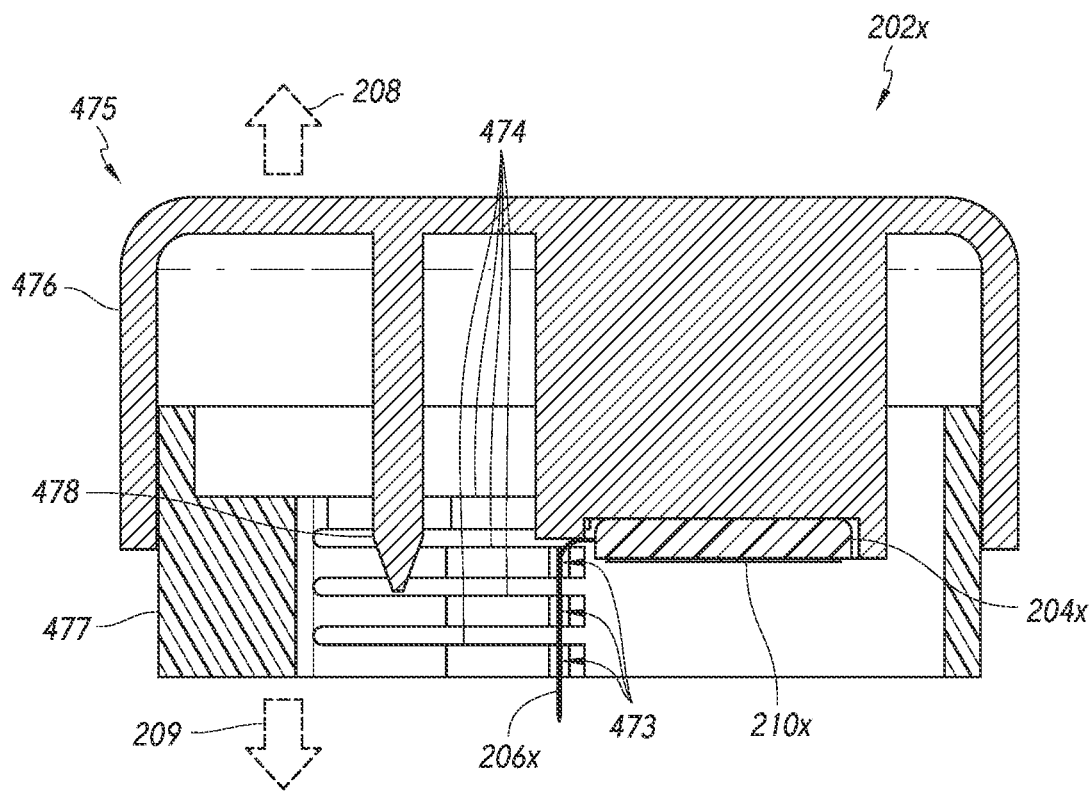

FIG. 77 illustrates a side, cross-sectional view of the system 202x as the system 202x is moving the sensor 206x distally. An end portion of each arm 474 can include an indentation that faces an indentation of an opposing arm 474. When the end portions of arms 474 touch each other (and/or are close to each other), the indentations can form channels 473 configured to support the sensor 206x against buckling forces. The sensor 206x can be at least partially located in each channel 473 formed by each set of arms 474. Thus, the system can include multiple, concentric channels 473.

A first channel can have a central axis that passes through a second channel located distally relative to the first channel (e.g., as shown in FIG. 77). The first channel can be formed by a first set of arms. The second channel can be formed by a second set of arms.

Referring now to FIGS. 74-77, a system 202x can include multiple sets of paired, movable, flexible arms 474. As the system 202x moves the sensor 206x from the proximal starting position to the distal ending position, the system 202x can push each set of arms 474 apart to enable the bent section (e.g., the angled portion 469) of the sensor 206x to pass through each set of arms 474. Each set of moveable arms 474 can open before the bent section of the sensor 206x reaches each set of moveable arms 474.

A distal protrusion 478 (e.g., a part of the applicator 475 and/or a part of a sensor module support) can enter an area 479 between each set of movable arms 474 to flex the arms 474 to an expanded state. A telescoping assembly 475 can move the protrusion distally relative to the movable arms 474 to expand each set of arms 474.

The system 202x can comprise a first arm 474 and a wall coupled to the base 204x. (The wall can be a surface of a second arm 474.) A portion of the sensor 206x can be secured between the first arm 474 and the wall such that the first arm 474 is configured to resist buckling forces of the sensor 206x as the system 202x moves the portion of the sensor 206x from a proximal position to a distal position.

The first arm 474 can be movably coupled to the base 204x such that at least a portion of the first arm 474 is configured to move (e.g., relative to the base 204x, relative to a housing of an applicator 475) to enable the system 202x to move the portion of the sensor 206x from the proximal position to the distal position.

At least one of the first arm 474 and the wall can form a channel 473. The portion of the sensor 206x can be at least partially located in the channel 473 such that the channel 473 is configured to resist the buckling forces. The system 202x can comprise a distal protrusion 478 configured to move the first arm 474 away from the wall to enable the system 202x to move the portion of the sensor 206x from the proximal position to the distal position. The portion of the sensor 206x can comprise a central axis. The first arm 474 can protrude in a direction within plus or minus 45 degrees of perpendicular to the central axis.

The system 202x can comprise a removable applicator 475 having a telescoping assembly that is removably coupled to the base 204x. The telescoping assembly can comprise a first set of tongs configured to resist a first buckling force of a first section of the sensor 206x.

Each set of arms 474 can form a set of tongs. As used herein, "tongs" is used broadly. Tongs can mean a tool used for holding objects, wherein the tool is made of two pieces connected at one end, in approximately the middle, and/or at any suitable location. The tongs can hold the sensor. In some embodiments, the tongs form a channel, but might not touch the sensor unless the sensor starts to buckle slightly such that the buckling causes the sensor to touch the tongs.

The telescoping assembly can comprise a second set of tongs (e.g., a second set of arms 474) configured to resist a second buckling force of a second section of the sensor 206x. The telescoping assembly can comprise a distal protrusion 478 configured to move distally into a first area between the first set of tongs and into a second area between the second set of tongs to expand the first and second sets of tongs.

Sensor Grip—Clamp Embodiment

In some embodiments, the arms are oriented at an angle within plus or minus 60 degrees of perpendicular to a distal direction 209 (e.g., as shown in FIGS. 75-77). In several embodiments, arms 474y are oriented at an angle of plus or minus 45 degrees of parallel to a distal direction 209 (e.g., as shown in FIGS. 78-81).

FIGS. 78-81 illustrate a clamp 480 configured to support the sensor 206y as the sensor 206y moves distally. This support can prevent the sensor 206y from buckling as the sensor 206y is inserted at least partially into a host.

The clamp 480 can be configured to open after a distal end of the sensor 206y pierces the skin. Thus, the clamp 480 can support the sensor 206y against buckling forces until the system 202y has overcome the peak buckling forces of sensor insertion. The clamp 480 constrains and/or supports at least a portion of the sensor 206y. As a result, the clamp 480 reduces the effective column length of the sensor 206y. As described herein, reducing the column length can dramatically increase the buckling resistance of the sensor 206y.

In some embodiments, the clamp 480 does not compress the sensor 206y, but instead allows the sensor 206y to move distally between a first arm 474y of the clamp 480 and a second arm 474y of the clamp 480. The first and second arms 474y can form a first channel 484 through which the sensor 206y can pass as the sensor 206y moves distally. Other embodiments prevent sensor movement (relative to the arms 474y) by clamping the sensor 206y until the clamp 480 releases the sensor 206y. In other words, the clamp 480 can apply a compressive force on the sensor 206y to help secure the sensor 206y.

The system 202y can comprise a second channel 483 configured to hold the first and second arms 474y of the clamp 480 in a compressed state until the first and second arms 474y reach a distal point at which the second channel 483 widens or ends. At this point, the first and second arms 474y can move away from each other towards a relaxed state of the first and second arms 474y. (The second channel 483 can be a lumen.)

In some embodiments, the clamp 480 is biased such that the lowest energy state of the clamp 480 is when the first arm 474y touches the second arm 474y. The system 202y can include features (e.g., a protrusion of the applicator 475y) configured to defect the arms 474y away from each other to open the clamp 480 (and move the clamp 480 into a higher energy state). Thus, the arms 474y can be flexed outward due to an input force applied by a user.

Moving the first and second arms 474y away from each other can enable a structure that supports a bent section of the sensor 206y to move between the first and second arms 474y to continue pushing the sensor 206y deeper into the person. (FIG. 74 illustrates a bent section 469.)

Figure 78:
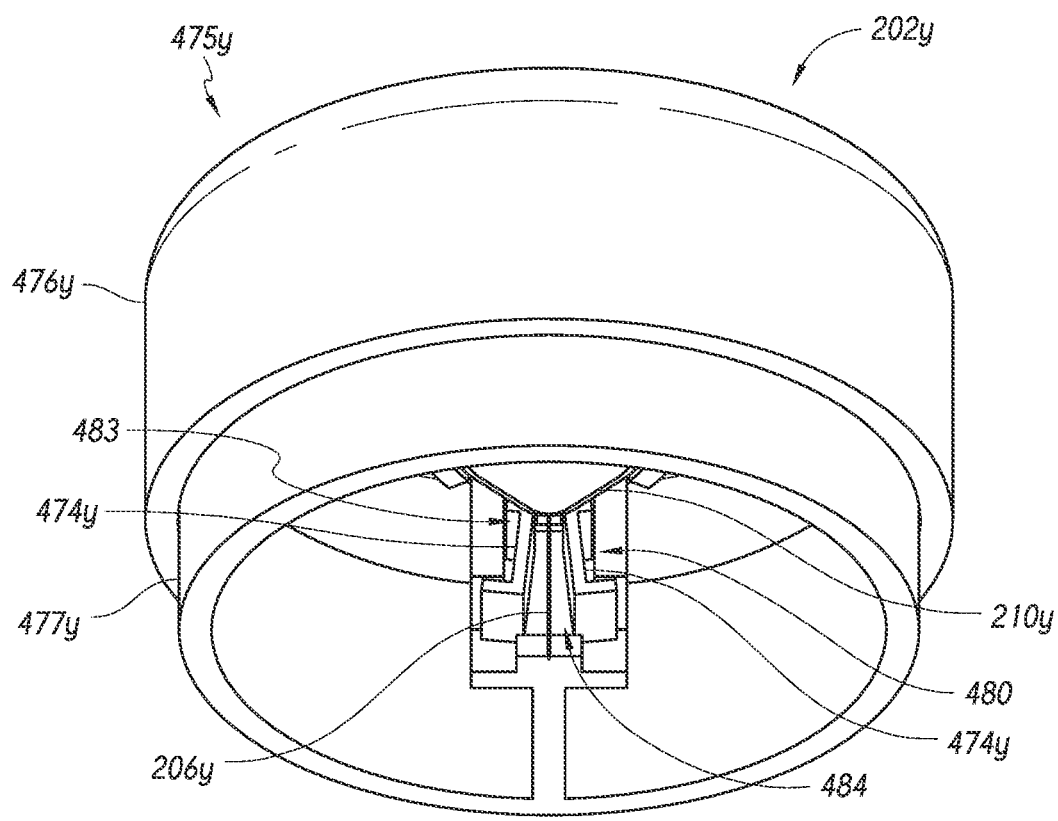
FIG. 78 illustrates a perspective view of a system, according to some embodiments.
Figure 79:
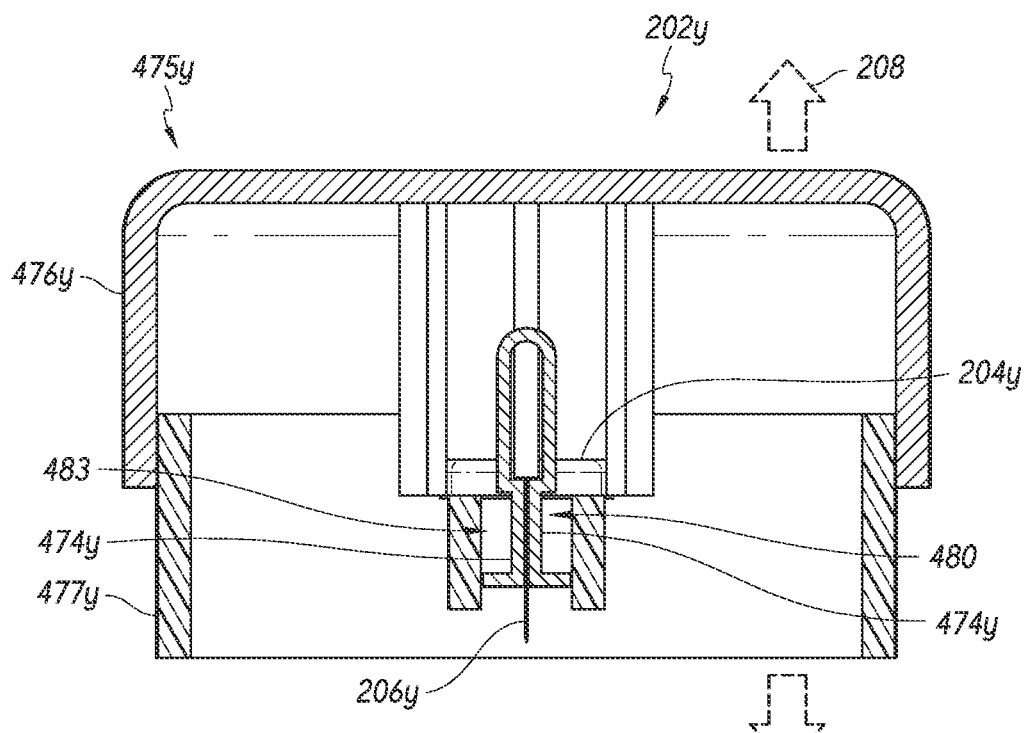
FIGS. 79-81 illustrate side, cross-sectional views of the system, according to some embodiments.

FIG. 78 illustrates a perspective view of the system 202y in a proximal starting position. FIG. 79 illustrates a side, cross-sectional view of the system 202y in the proximal starting position. The clamp 480 supports the sensor 206y against buckling forces to help maintain at least a portion of the sensor 206y in an approximately straight configuration.

Figure 80:
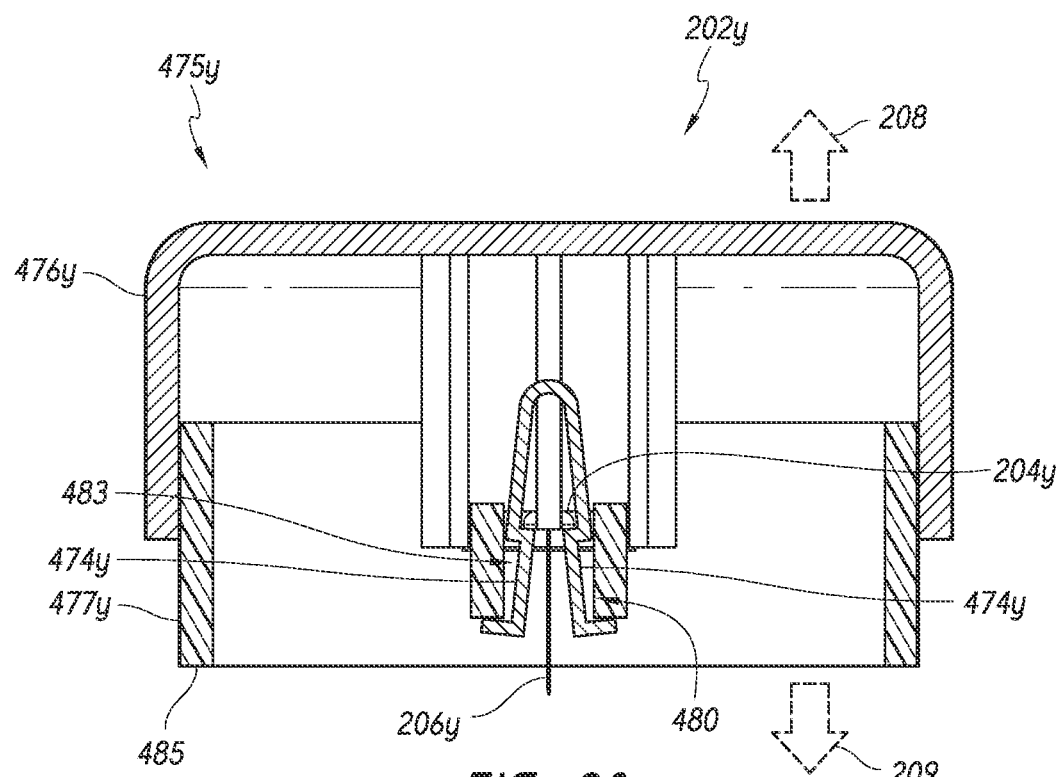

FIG. 80 illustrates a side, cross-sectional view of the system 202y in a position between the proximal starting position and a distal ending position. As illustrated in FIG. 80, the clamp 480 has opened to enable the system 202y to continue moving the base 204y distally relative to a distal portion 477y of the applicator 475y. The sensor 206y has already pierced the skin. As a result, the sensor 206y has typically already passed the peak buckling forces of the sensor insertion cycle. Thus, in some embodiments, supporting the sensor 206y with the clamp 480 is no longer necessary after the sensor 206v has pierced the skin 352.

The applicator 475y can comprise a proximal portion 476y and a distal portion 477y. The proximal portion 476y can be configured to move (e.g., telescope) relative to the distal portion 477y to move the sensor 206y and/or the base 204y distally towards the skin of the host.

Figure 81:
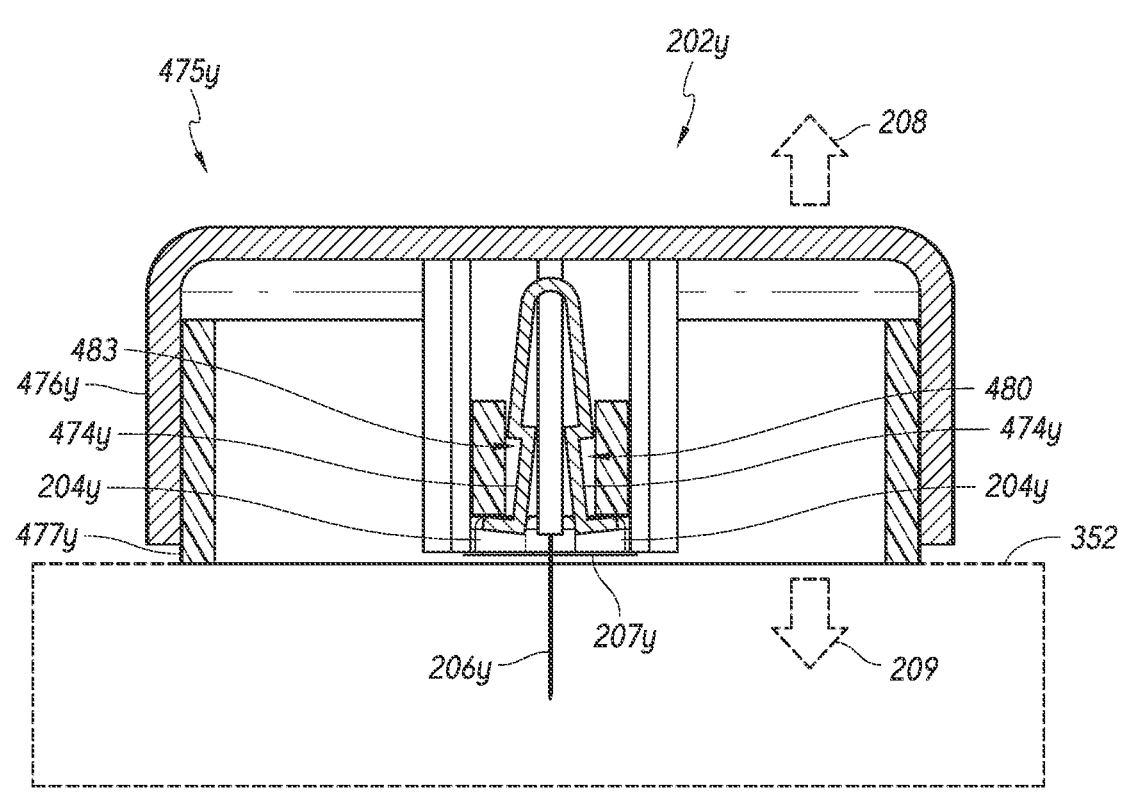

FIG. 81 illustrates a side, cross-sectional view of the system 202y as the system 202y approaches a distal ending position. In some embodiments, the adhesive 210y (labeled in FIG. 78) is configured to adhere to the skin 352 (shown in FIG. 81) in the distal ending position.

Referring now to FIGS. 78-81, the system 202y can comprise a removable applicator 475y coupled to the base 204y. The base 204y can include a transmitter. The applicator 475y can have a pair of biasing members (e.g., a set of tongs). The pair of biasing members can be a pair of arms 474y configured to move relative to each other and configured to resist buckling of at least a portion of the sensor 202y.

The pair of biasing members can comprise a first arm 474y coupled to a second arm 474y such that the arms 474y are configured to flex relative to each other. A portion of the sensor 206y can be located in an area between the pair of biasing members such that the pair of biasing members is configured to resist buckling forces of the sensor 206y (e.g., as shown in FIG. 79).

The pair of biasing members can be held in a compressed state by a channel 483 configured to enable the pair of biasing members to expand in response to moving the pair of biasing members far enough distally that a distal end of the sensor 206y is located distally relative to a distal side 485 (labeled in FIG. 80) of the applicator 475y. The pair of biasing members can be a set of tongs.

The system 202y can comprise a first arm 474y and a second arm 474y that extend distally. A portion of the sensor 206y can be located between the first and second arms 474y such that the first and second arms 474y are configured to resist buckling forces of the sensor 206y. The first and second arms 474y can be located in a channel 483 of the system 202y. The channel 483 can hold the first and second arms 474y in a compressed state. The channel 483 can be configured such that moving the first and second arms 474y distally causes the first and second arms 474y to spread apart from each other to facilitate the system 202y moving the portion of the sensor 206y from a proximal position to a distal position.

The system 202y can comprise a first arm 474y and a second arm 474y that extend distally. The first and second arms 474y can be configured to have a closed state in which the first and second arms 474y resist buckling forces of a portion of the sensor 206y located between the first and second arms 474y. The first and second arms 474y can be configured to have an open state to enable the system 202y to move the portion of the sensor 206y from a proximal starting position to a distal ending position.

Splitting Tube

Figure 82:
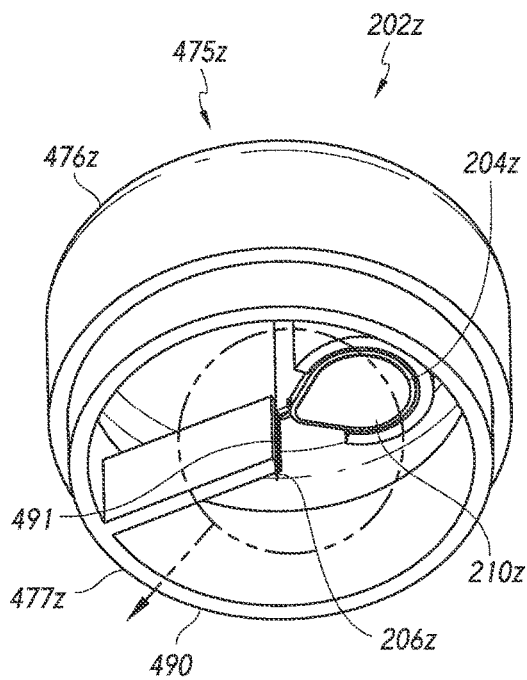
FIG. 82 illustrates a perspective view of a system, according to some embodiments.
Figure 83:
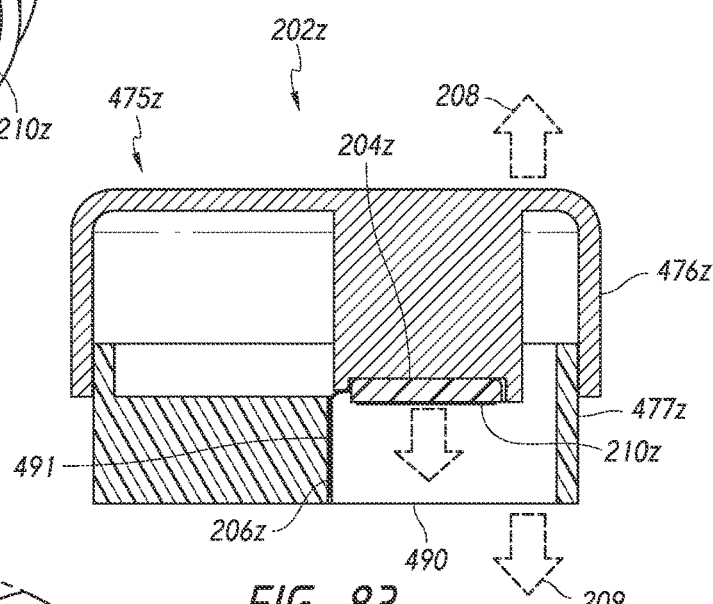
FIG. 83 illustrates a side, cross-sectional view of the system, according to some embodiments.
Figure 84:
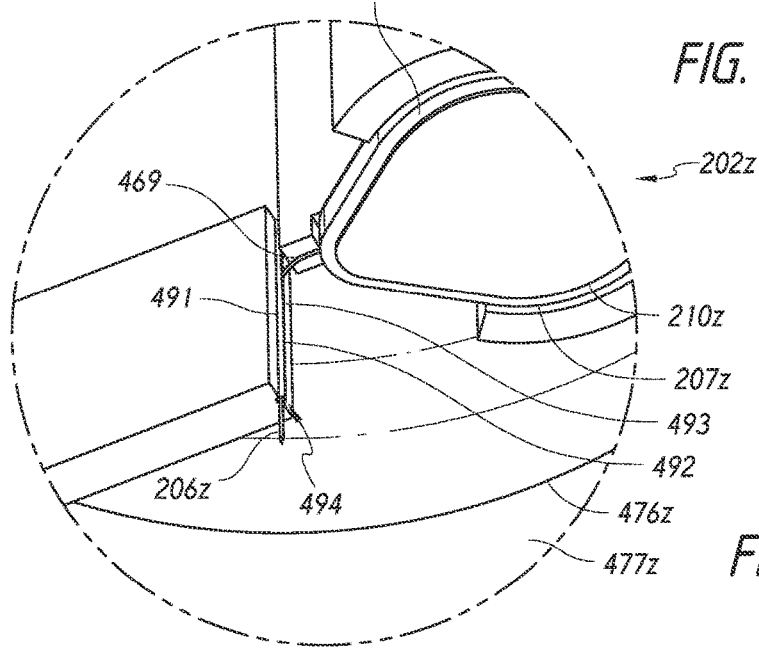
FIG. 84 illustrates a partial, perspective view from the perspective shown in FIG. 82, according to some embodiments.

FIGS. 82-84 illustrate a system 202z that includes a guide member (e.g., a tube 491). The tube 491 can support the sensor 206z as the sensor 206z is inserted into tissue to prevent the sensor 206z from buckling.

The system 202z comprises a channel (e.g., of the tube 491) having a first side and a second side (formed by the slot 492) configured to at least partially separate in response to the system 202z moving the sensor 206z from a proximal position (e.g., as shown in FIG. 83) to a distal position (e.g., as shown in FIGS. 82 and 84).

FIG. 82 illustrates a perspective view of a system 202z in a distal position (e.g., where a distal end of the sensor 206z) is located farther distally than the applicator 475z. FIG. 83 illustrates a side, cross-sectional view of the system 202z in a proximal starting position (e.g., prior to sensor deployment). FIG. 84 illustrates a partial view from the perspective shown in FIG. 82.

Referring now to FIGS. 82-84, the system 202z comprises a tube 491 through which at least a portion of the sensor 206z can move as the sensor 206z is driven from a proximal starting position (e.g., as shown in FIG. 83) to a distal ending position (e.g., as shown in FIGS. 82 and 84). The tube 491 can resist buckling forces of the sensor 206z to help maintain the portion of the sensor 206z in an approximately straight configuration. Adhesive 210z can couple a distal side 207z of the base 204z to skin of a host.

The tube 491 can be a feature of the distal portion 477z of the telescoping assembly. For example, a single piece can be molded. This piece can include the tube 491 and the other features of the distal portion 477z.

The tube 491 can be a separate component that is coupled to the distal portion 477z or to any other portion of the telescoping assembly. In some embodiments, the distal portion 477z comprises arms that couple the tube 491 to the distal portion 477z.

The tube 491 can support at least a majority of a length of the sensor 206z between (A) the sensor 206z module and/or the base 204z and (B) the distal side 490 of the applicator 475z. The base 204z can include a transmitter (e.g., as shown in other embodiments).

The applicator 475z can comprise a telescoping assembly (e.g., the applicator 475z). The tube 491 can be coupled to a distal portion 477z of the telescoping assembly. The sensor 206z can be coupled to a proximal portion 476z of the telescoping assembly such that moving the proximal portion 476z distally relative to the distal portion 477z moves a portion of the sensor 206z through a channel of the tube 491.

The tube 491 can include a slot 492 oriented approximately parallel to a central axis of the tube 491. The slot 294 can extend from a distal end of the tube 491 to a proximal end of the tube 491. In some embodiments, the slot 492 does not necessarily extend from a distal end to a proximal end of the tube 491, but at least extends from a distal portion to a proximal portion of the tube 491.

The slot 492 can enable a bent portion 469 of the sensor 206z to move distally (through the slot 492) as a portion of the sensor 206z moves distally within a channel of the tube 491. In some embodiments, the slot 492 is at least partially held closed until moving the bent portion 469 through the slot 492 causes the slot 492 to open (e.g., by partially unrolling the tube 491, by breaking linkages between each side of the slot 492).

The tube 491 can be manufactured using any suitable process. The tube 491 can be formed by an extrusion process (with a hoop-shaped cross section to form the channel). A side of the tube 491 can be cut (e.g., by a laser and/or by a mechanical cutting blade) to form the slot 492. The cut can extend from a distal end of the tube 491 to a proximal end of the tube 491. In some embodiments, only a portion of a length of the tube 491 is cut.

A side of the tube 491 can be perforated to enable the system 202z to move the bent portion 469 of the sensor 206z distally (by breaking through the area of the tube 491 that was weakened by the perforations). The tube 491 can be formed by creating a flat sheet and then rolling the sheet into a tubular shape. In this configuration, the ends of the tubular shape may be overlapping or may create a gap. The tube 491 can be made from a polymer (e.g., polyimide), metallic foil, silicone, and/or any suitable material.

The system 202z can include a cutting edge (e.g., a blade made of metal or plastic) configured to cut the tube 491 as the system 202z moves the sensor 206z distally to enable the bent portion 469 of the sensor 206z to move distally through a cutting path of the cutting edge.

The system 202z can comprise a tube 491 coupled to the base 204z. The tube 491 can comprise a slot 492 from a proximal portion of the tube 491 to a distal portion of the tube 491. The tube 491 can be configured to resist buckling forces of the sensor 206z. The slot 492 can be configured to enable moving a first portion (e.g., 469) of the sensor 206z distally outside of the tube 491 while moving a second portion of the sensor 206z distally inside the tube 491.

The system 202z can comprise a removable applicator 475z coupled to the base 204z. The applicator 475z can couple the tube 491 to the base 204z such that the system 202z is configured to move the base 204z distally relative to the tube 491 to pierce the skin with a distal end of the sensor 206z. The tube 491 can comprise a first side of the slot 492 and a second side of the slot 492. The first and second sides of the slot 492 can be coupled together by a linkage 493 configured to break open in response to moving the first portion of the sensor 206z distally. The tube 491 can be at least 4 millimeters long as measured along a central axis of the tube 491.

The system 202z can comprise an applicator 475z having a channel 494 configured to resist buckling forces of the sensor 206z. A distal portion of the sensor 206z can be located inside the channel 494. A proximal portion of the sensor 206z can be located outside the channel 494. An intermediate portion of the sensor 206z can couple the distal and proximal portions of the sensor 206z. The intermediate portion of the sensor 206z can be located in a slot 492 of the channel 494.

The slot 492 can be configured to enable the intermediate portion of the sensor 206z to move distally through the slot 492 as the sensor 206z moves from a proximal position to a distal position. The channel 494 can comprise a central axis oriented distally such that the channel 494 is configured to guide the distal portion of the sensor 206z towards the skin. The slot 492 can be oriented radially outward from the central axis.

The slot 492 can comprise at least one linkage 493 that couples a first side of the slot 492 to a second side of the slot 492. The at least one linkage can be configured to break in response to moving the intermediate portion of the sensor 206z distally through the slot 492. In some embodiments, the slot 492 is configured to expand (e.g., widen) in response to moving the intermediate portion of the sensor 206z distally through the slot 492.

Any of the features described in the context of FIGS. 54-84 can be applicable to all aspects and embodiments identified herein. For example, the embodiments described in the context of FIGS. 54-84 can be combined with the embodiments described in the context of FIGS. 1-53 and 85-126. Moreover, any of the features of an embodiment is independently combinable, partly or wholly with other embodiments described herein in any way (e.g., one, two, three, or more embodiments may be combinable in whole or in part). Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Additional Applicators

Measuring analyte data often involves inserting an analyte sensor into subcutaneous tissue. The user can actuate an applicator to insert the analyte sensor into its functional location (e.g., inside tissue of the host). This transcutaneous insertion can lead to incomplete sensor insertion, improper sensor insertion, and unnecessary pain.

Inserting a sensor into a person can cause the sensor to buckle due to the resistance of the skin and subcutaneous tissue to sensor insertion. For example, the sensor can buckle as a distal tip of the sensor attempts to pierce the skin and/or after the distal tip has pierced the skin as the sensor is moved deeper into the person. Many systems solve this problem by using a needle to help insert the sensor into the person. Needles, however, can cause long-term patient discomfort, and thus, are typically removed (while leaving the sensor at least partially inside in the person).

Using a needle has several disadvantages. For example, retracting the needle can require extra steps, time, and/or hardware. Placing a sensor inside or alongside a needle creates a larger wound and therefore a larger wound response in vivo. Thus, in some cases there is a need for systems and methods that eliminate the need for using a needle to insert a sensor into a person. Many embodiments described herein and/or incorporated by reference enable a user to insert a sensor into tissue without using a needle.

Many embodiments do not include a needle. However, all of the embodiments described herein can optionally use a needle to facilitate inserting a sensor into tissue. In some embodiments, sensors comprise a needle and additional features as described herein.

Several embodiments rely on a distal movement of an applicator in a direction approximately parallel to a central axis of a sensor to insert the sensor into the tissue of the person. All of the applicators described herein and/or incorporated by reference can be used with all of the systems and features described herein and/or incorporated by reference.

Preloaded Spring

FIGS. 85-88 illustrate an applicator 475aa that includes a distal portion 477aa and a proximal portion 476aa. The proximal portion 476aa can hold the base 204aa in a proximal starting position. Moving the proximal portion 476aa distally can unlatch the base 204aa such that a compressed spring 513 can push the base 204aa and the sensor 206aa distally. A transmitter can be coupled to the base 204aa.

The spring 513 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

Figure 85:
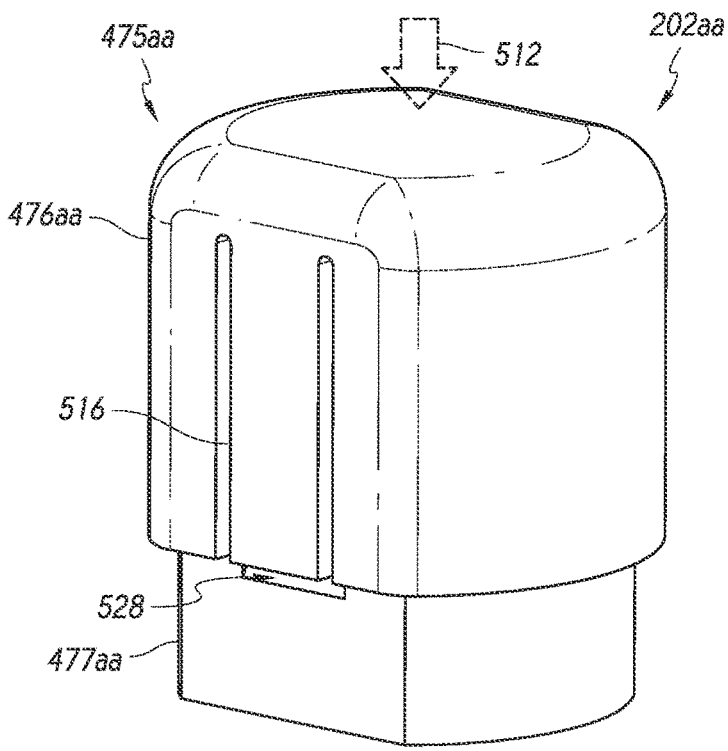
FIG. 85 illustrates a perspective view of an applicator, according to some embodiments.

FIG. 85 illustrates a perspective view of the applicator 475aa in a proximal starting position. The applicator 475aa is configured such that moving the proximal portion 476aa distally (e.g., as indicated by arrow 512) relative to the distal portion 477aa unlatches the base 204aa from the proximal portion 476aa to enable a compressed spring 513 to move the base 204aa and the sensor 206aa distally (e.g., into skin 352 of the host).

Figure 86:
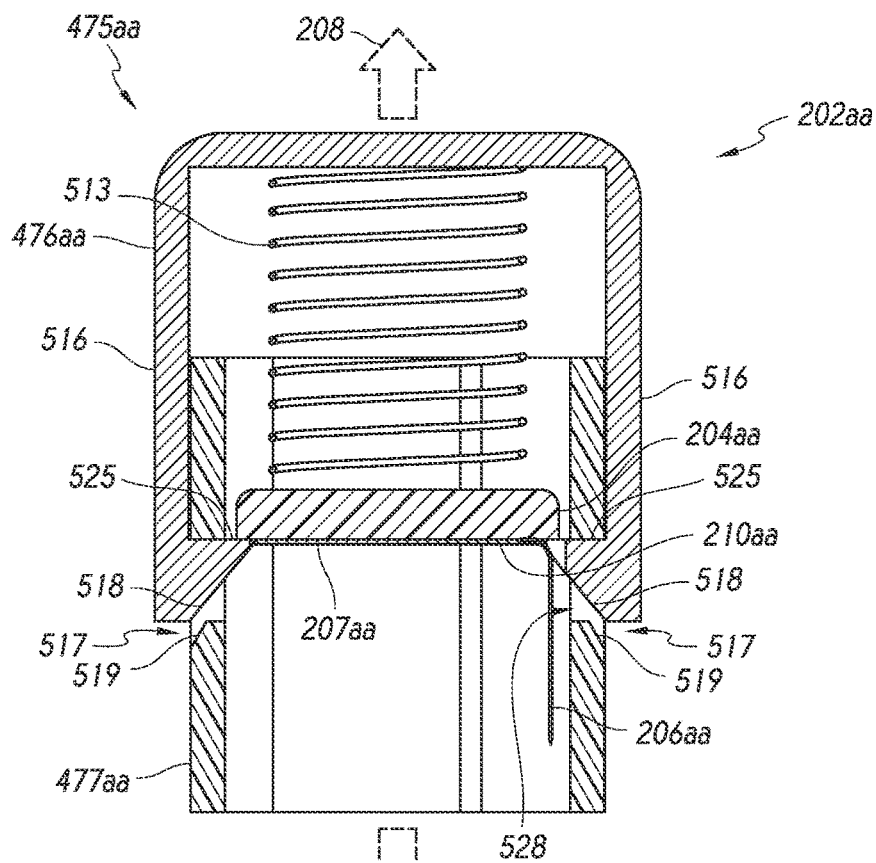
FIGS. 86-88 illustrate side, cross-sectional views of a system, according to some embodiments.

FIG. 86 illustrates a side, cross-sectional view of the system 202aa in a proximal starting position. In some embodiments, the spring 513 is in a compressed state when the system 202aa is in a proximal starting position. In several embodiments, moving the proximal portion 476aa of the applicator 475aa distally relative to the distal portion 477a a compresses the spring 513 to provide the force that moves the base 204aa and the sensor 206a distally. Arrow 208 illustrates a proximal direction. Arrow 209 illustrates a distal direction.

Figure 87:
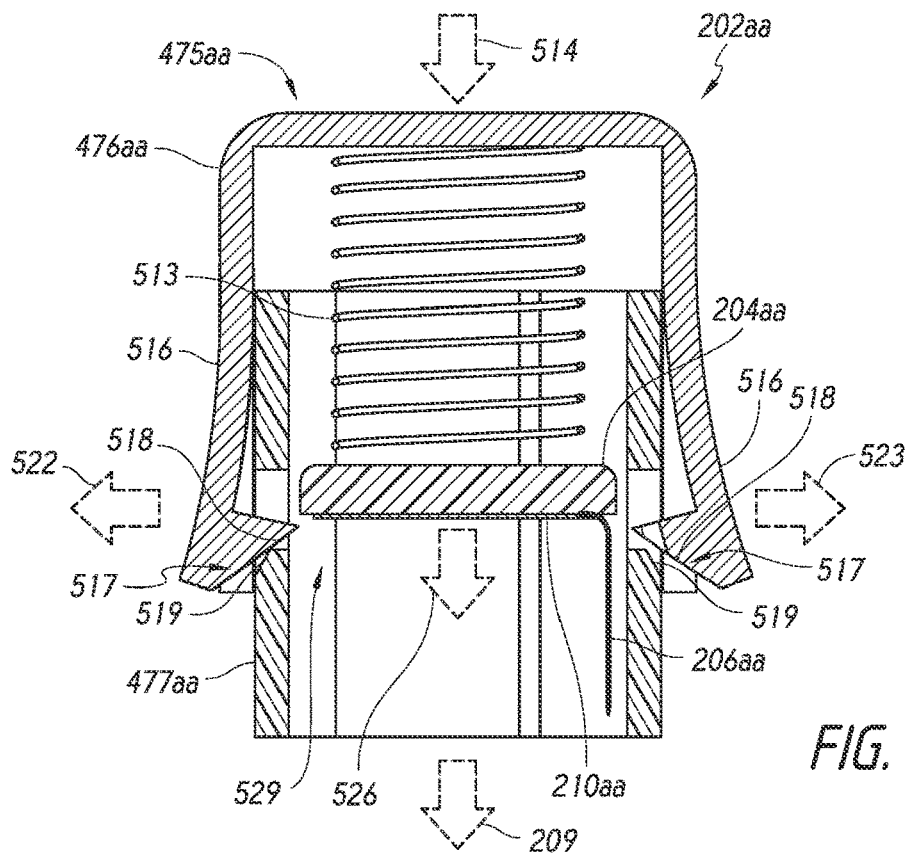

FIG. 87 illustrates a side, cross-sectional view of the system 202aa as the proximal portion 476aa releases the base 204aa in response to the proximal portion 476a a moving distally relative to the distal portion 477aa. The proximal portion 476aa can move distally (e.g., as indicated by arrow 514) relative to the distal portion 477aa, which can cause flex arms 516 to be pressed radially outward due to interfering with actuation features 517 of the distal portion 477aa. The flex arms 516 and/or the actuation features 517 can include ramps 518, 519 configured to force the flex arms 516 radially outward (or radially inward) in response to the proximal portion 476aa moving distally relative to the distal portion 477aa. Arrows 522, 523 indicate the arms 516 moving radially outward.

Figure 88:
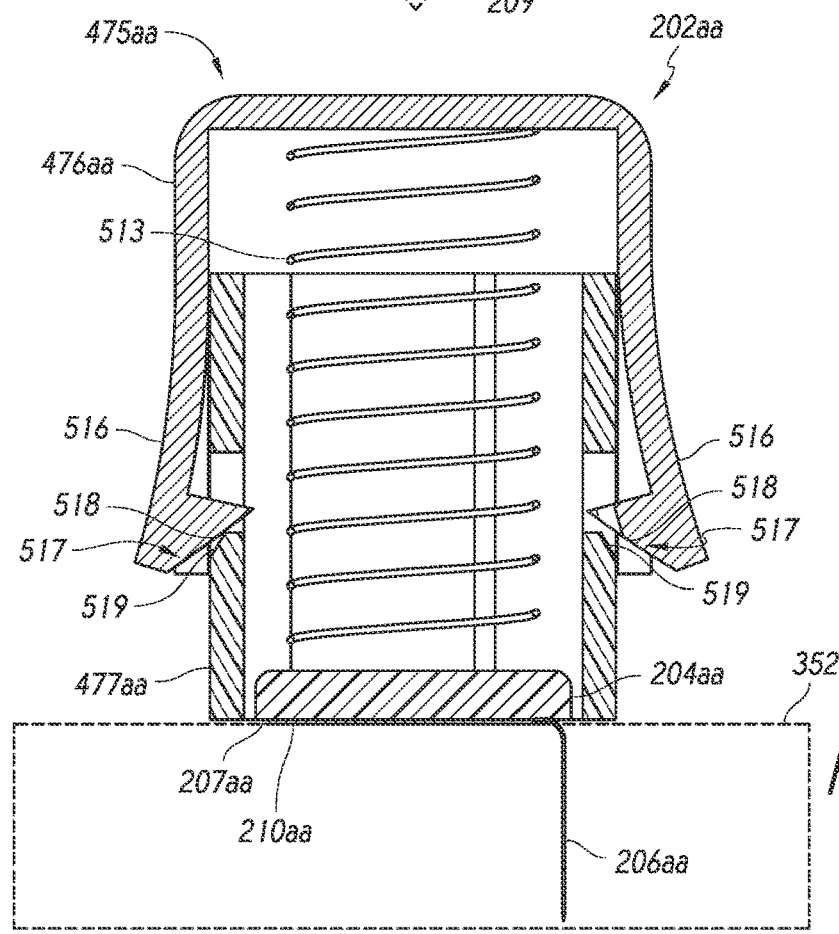

The arms 516 and/or others surfaces (e.g., proximally facing surfaces 525 labeled in FIG. 86) of the proximal portion 476aa can resist a distal force of the spring 513. In other words, the arms 516 can hold the base 204aa in the proximal starting position and/or can block the base 204aa from moving to a distal ending position (e.g., as shown in FIG. 88) until the arms 516 and/or other surfaces of the proximal portion 476aa release (e.g., uncouple from) the base 204aa. In FIG. 86, the arms 516 block the base 204aa from moving distally. FIG. 87 illustrates the arms 516 flexing radially outward to uncouple from the base 204aa to enable the base 204aa to move distally relative to the proximal portion 476aa and the distal portion 477aa of the applicator 475aa (e.g., as indicated by arrow 526).

FIG. 88 illustrates a side, cross-sectional view of the base 204aa after the base 204aa has moved distally. In FIG. 88, the base 204aa is in a distal ending position (e.g., such that the sensor 206aa is located at least partially in the tissue 352 of the host). As shown by the progression from FIG. 86 to FIG. 87 to FIG. 88, the base 204aa moves a first distance in response to the proximal portion 476aa moving a much smaller distance. The magnification of the movement of the proximal portion 476aa can enable a favorable insertion experience because the user perceives the sensor's insertion depth as being smaller than is actually the case (due to a perception of the distance of the movement of the proximal portion 476aa being equal to the depth of the sensor insertion).

Adhesive 210aa can couple a distal side 207aa of the base 204aa to the skin 352 of the host. The adhesive 210aa can have any suitable shape.

Referring now to FIGS. 85-88, a telescoping assembly (e.g., the applicator 475a a) can be coupled to the base 204aa. The telescoping assembly can comprise a distal portion 477aa, a proximal portion 476aa slidably coupled to the distal portion 477aa, and a spring 513 compressed between the proximal portion 476aa and the base 204aa. The proximal portion 476aa can releasably secure the sensor 206aa in a first proximal starting position such that the spring 513 is configured to push the base 204aa and the sensor 206aa distally in response to the system 202aa unlatching the base 204aa from the proximal portion 476aa.

The proximal portion 476aa can comprise a latch configured to releasably secure the base 204aa in a second proximal starting position. The latch can comprise an arm 516, a first ramp 518, a second ramp 519, actuation features 517, a proximal facing surface 525, and/or any suitable feature configured to releasably secure the base 204aa in a position that is proximal to a distal ending position of the base 204aa. The latch can be configured to release the base 204aa in response to moving the proximal portion 476aa distally relative to the distal portion 477aa to enable the spring 513 to push the base 204aa and the sensor 206aa distally.

As described above, a relatively small movement of the applicator 475aa can result in a larger movement of the base 204aa and/or the sensor 206aa movement. The sensor 206aa can be configured to move along a first path from the first proximal starting position to a first distal ending position (e.g., as shown by the progression from FIG. 86 to FIG. 88). The proximal portion 476aa can be configured to move along a second path from a third proximal starting position to a third distal ending position (e.g., as shown by the progression from FIG. 86 to FIG. 88). The first path of the sensor 206aa can be at least 20 percent longer and/or at least 40 percent longer than the second path of the proximal portion 476aa. The system 202a a can be configured to cause the sensor 206aa to move a first distance in response to the proximal portion 476aa moving a second distance that is at least 50 percent shorter than the first distance.

The system 202aa can comprise arms 516 configured to release the base 204aa and/or the sensor 206aa to enable the base 204aa and/or the sensor 206aa to move distally relative to the proximal portion 476aa and/or the distal portion 477aa of the telescoping applicator 475aa. The proximal portion 476aa can comprise a distally protruding arm 516 having an inward protrusion (e.g., a portion of the ramp 518) that passes through a hole 528 (labeled in FIG. 86) of the distal portion 477aa. The hole 528 can be a through hole or can be a partial hole (e.g., an indentation). The inward protrusion can be coupled to the base 204aa to secure the sensor 206aa in the first proximal starting position.

The system 202aa can be configured such that moving the proximal portion 476aa distally relative to the distal portion 477aa causes the distally protruding arm 516 to flex outward to release the inward protrusion from the base 204aa to enable the spring 513 to push at least a portion of the sensor 206aa into the skin 352.

The system 202aa can be configured to move the sensor 206aa a first distance in response to moving the proximal portion 476aa a second distance to unlatch the base 204a a. The first distance can be at least twice as long as the second distance such that the system 202a a is configured to magnify a first movement of the proximal portion 476aa into a larger second movement of the sensor 206aa and/or the base 204aa. The distal portion 477aa can comprise a channel 529 (labeled in FIG. 87) configured to orient the base 204aa as the spring 513 pushes the base 204aa distally.

Twist Tack

Some applicators move a sensor distally in response to distal movement of a portion of an applicator. Other applicators, however, can move a sensor into tissue in response to non-distal movements. For example, applicators can move a sensor distally in response to a rotation of a portion of the applicator. The rotation can be about a central axis of the applicator. Some applicators move the sensor distally in response to a rotation of a dial. The dial can be a part of the applicator's external body or can rotate independently of the external body.

FIGS. 89-93 illustrate an embodiment in which rotating an outer housing 532 relative to a base 204ab can release a compressed spring 538 to drive the sensor 206ab into the skin of a host. The outer housing 532 can be a dial that is removably coupled to the base 204ab. The spring 538 can be a conical spring 538 to enable a shorter compressed height.

The spring 538 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

A first housing 532 can be rotatably coupled to the base 204ab. A second housing 533 can be coupled to the sensor 206ab. A spring 538 can be compressed between a proximal end of the first housing 532 and the sensor 206ab. The spring 538 can be configured to push the second housing 533 and the sensor 206ab distally relative to the base 204ab and the first housing 532 in response to rotating the first housing 532 relative to the base 204ab.

Figure 89:
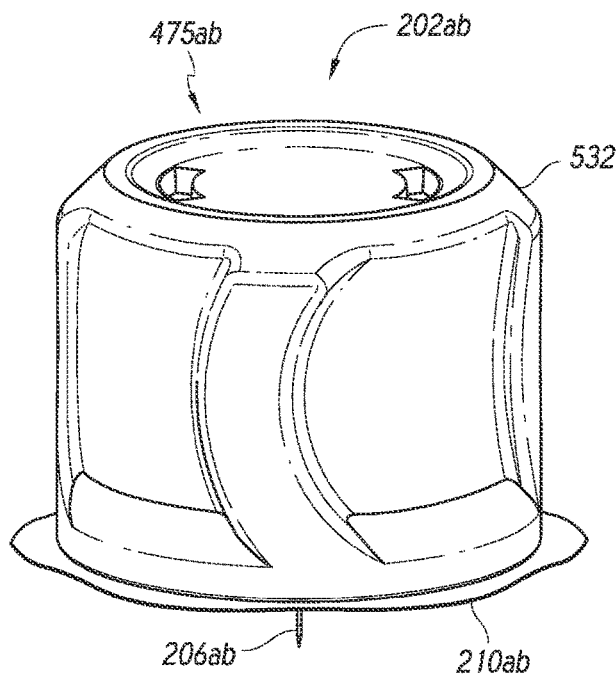
FIG. 89 illustrates a perspective view of a system, according to some embodiments.

FIG. 89 illustrates a perspective view of the system 202ab. The system 202ab can move the sensor 206ab distally into the skin in response to a user rotating the first housing 532 of the applicator 475ab relative to the adhesive 210ab (e.g., when the adhesive 210ab is coupled to the skin).

The system 202ab inherently guards against inadvertent sensor 206a b deployment because rotating the first housing 532 relative to the adhesive 210ab and/or the base 204ab is unlikely unless the base 204ab is coupled to the skin by the adhesive 210ab. For example, if the system 202ab is not coupled to the skin by the adhesive 210ab, rotating the first housing 532 will also rotate the adhesive 210ab, the sensor 206ab, and the base 204ab. In some embodiments, this rotation will not deploy the sensor 206ab because sensor 206ab deployment typically requires rotating the first housing 532 relative to the adhesive 210ab and/or the base 204ab.

Figure 90:
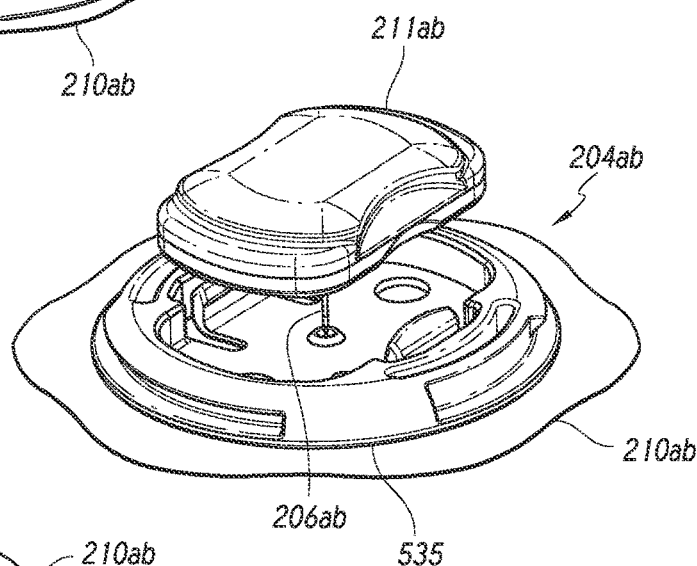
FIG. 90 illustrates a perspective view of a portion of the system, according to some embodiments.

FIG. 90 illustrates a perspective view of at least a portion of a base 204ab. A transmitter 211ab can be coupled to the base 204ab. The transmitter 211ab can comprise a battery and a wireless communication system configured to communicate with a remote device. Adhesive 210ab can couple the base 204ab to skin of the host.

Figure 91:
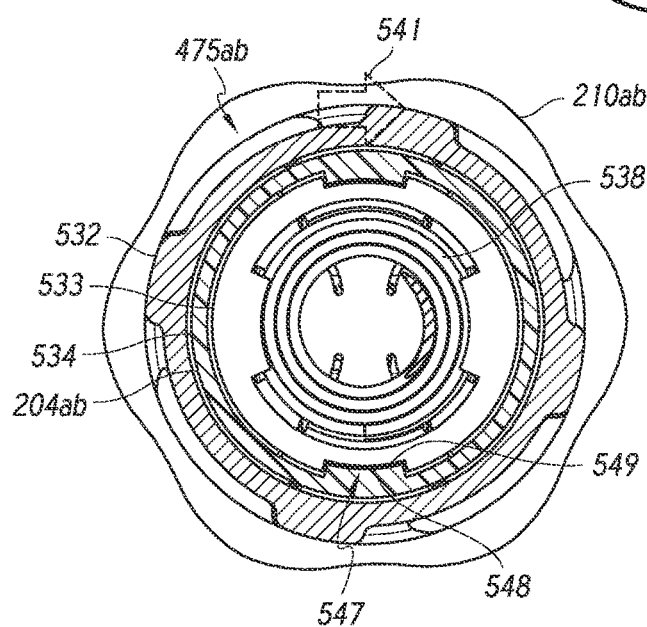
FIG. 91 illustrates a top, cross-sectional view of the system, according to some embodiments.

FIG. 91 illustrates a top, cross-sectional view of the system 202ab. The first housing 532 can be configured to rotate (e.g., as indicated by arrow 541) relative to the second housing 533 and the base 204ab.

Figure 92:
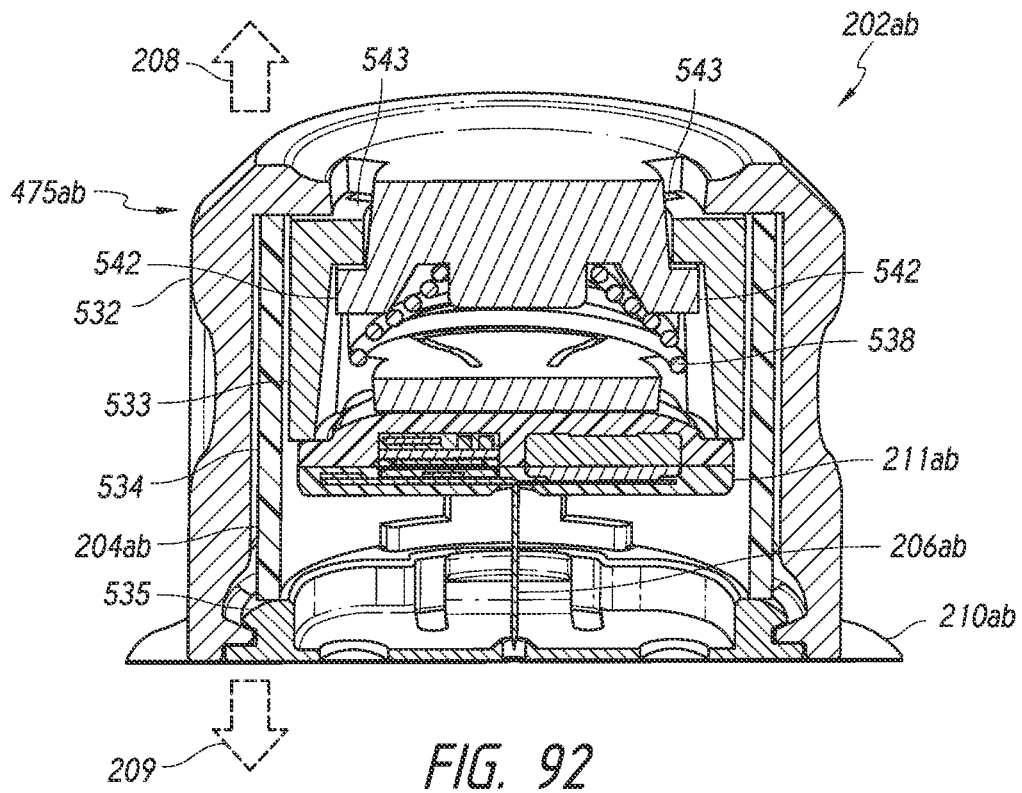
FIGS. 92 and 93 illustrate side, perspective, cross-sectional views of the system, according to some embodiments.

FIG. 92 illustrates a side, perspective, cross-sectional view of the system 202ab with the sensor 206ab in a proximal starting position. As illustrated in FIG. 92, the spring 538 can be in a compressed state (e.g., a high-energy state) when the sensor 206ab is in a proximal starting position. In some embodiments, the spring 538 is in an extended state (e.g., a high-energy state) when the sensor 206ab is in a proximal starting position.

Figure 93:
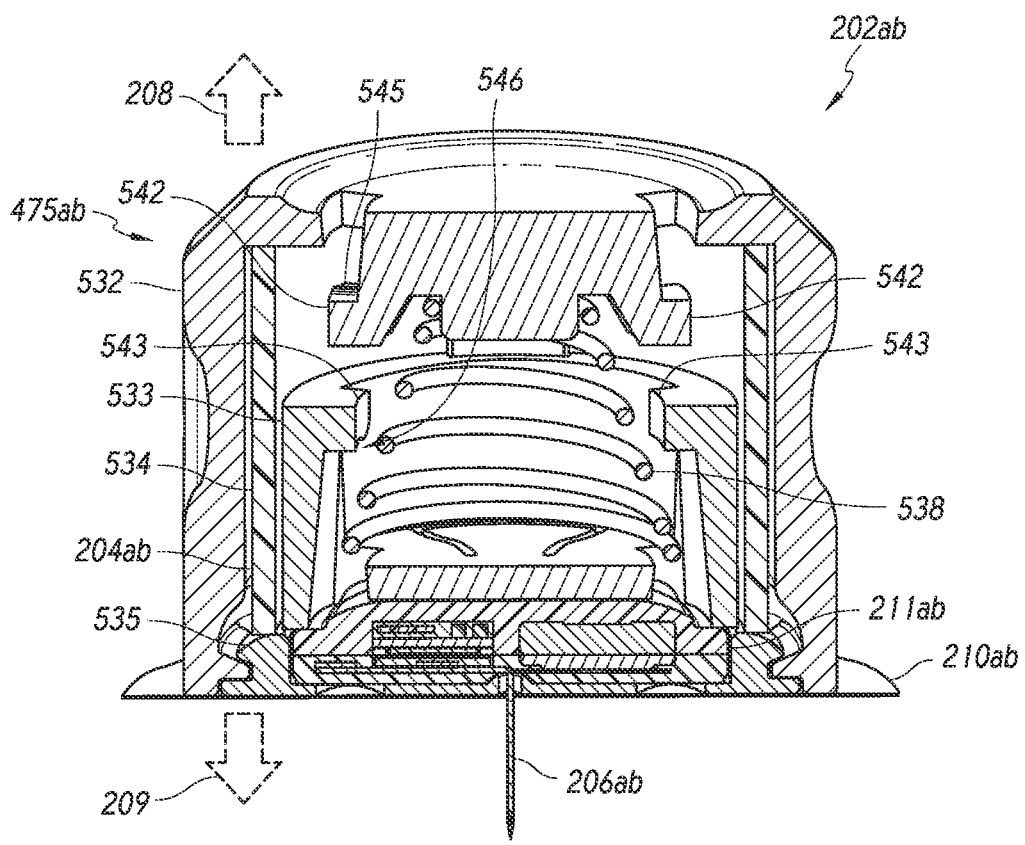

Rotating the first housing 532 relative to the base 204ab and/or the adhesive 210ab enables the spring 538 to move the second housing 533 and/or the sensor 206ab distally to a distal ending position (e.g., as shown in FIG. 93). FIG. 93 illustrates a side, perspective, cross-sectional view of the system 202ab.

Referring now to FIGS. 89-93, a first housing 532 can be rotatably coupled to the base 204ab. A spring 538 can be compressed between a portion of the first housing 532 and the sensor 206ab. The system 202ab can be configured to unlatch the sensor 206ab from the first housing 532 to enable the spring 538 to move the sensor 206ab distally in response to rotating the first housing 532 relative to the base 204ab and/or the adhesive 210ab.

The first housing 532 can comprise a first central axis (e.g., a rotational axis of the first housing 532). The sensor 206ab can comprise a portion configured to pierce the skin. The portion can comprise a second central axis. The first central axis can be oriented within plus or minus twenty degrees of parallel to the second central axis.

The spring 538 can be a helical spring and/or a conical spring configured to expand distally to move the sensor 206ab distally. In some embodiments, the spring 538 is any of the types of springs described herein and/or incorporated by reference.

The base 204ab can comprise a first portion 534 and a second portion 535. The applicator 475ab can be configured to be removed from the second portion 535 of the base 204ab (e.g., while the second portion 535 is coupled to the skin by adhesive 210a b). The applicator 475ab can retain the first portion 534 of the base 204ab (e.g., such that the first portion 534 of the base 204ab remains in the applicator 475ab while the second portion 535 of the base 204ab remains coupled to the skin after the applicator 475ab is uncoupled from the second portion 535 of the base 204ab).

A transmitter 211ab can be removably coupled to at least a portion of the base 204ab. In some embodiments, the transmitter 211ab is integrated into the base 204ab. In some embodiments, the transmitter 211ab is a portion of the base 204ab.

A first housing 532 can be rotatably coupled to the base 204ab. A second housing 533 can be coupled to the sensor 206ab. A spring 538 can be compressed between a proximal end of the first housing 532 and the sensor 206ab such that the spring 538 is configured to push the second housing 533 and the sensor 206ab distally relative to the base 204ab and the first housing 532 in response to rotating the first housing 532 relative to the base 204a b.

The second housing 533 can be located in an interior area of the first housing 532. The first adhesive 210ab can be configured to secure the base 204ab to the skin to enable the first housing 532 to rotate relative to the base 204ab and relative to the second housing 533.

The first housing 532 can comprise a first central axis (e.g., a rotational axis). The sensor 206ab can comprise a portion configured to pierce the skin. The portion can comprise a second central axis. The first central axis can be oriented within plus or minus ten degrees and/or within plus or minus 45 degrees of parallel to the second central axis. The spring 538 can be a conical spring 538 configured to expand in response to rotating the first housing 532 relative to the base 204a b.

The system 202ab can comprise a mechanical interlock between the first housing 532 and the second housing 533. The mechanical interlock can be configured to releasably hold the spring 538 in a compressed state such that the sensor 206ab is in a proximal starting position (e.g., as illustrated in FIG. 92).

The mechanical interlock can comprise a first protrusion 542 of the first housing 532 that interferes with distal movement of a second protrusion 543 of the second housing 533. The mechanical interlock can be configured such that rotating the first protrusion 542 relative to the second protrusion 543 causes the second protrusion 543 to fall distally off the first protrusion 542 and thereby enables the second housing 533 to move distally relative to the first housing 532.

The first protrusion 542 can be oriented radially outward, and the second protrusion 543 can be oriented radially inward. (In several embodiments, the first protrusion 542 is oriented radially inward, and the second protrusion 543 is oriented radially outward.) The mechanical interlock can comprise a ridge 545 and a groove 546 configured such that rotating the first housing 532 relative to the base 204ab requires overcoming a torque threshold to move the ridge 545 out of the groove 546. The ridge 545 and the groove 546 are shown in FIG. 93. In FIG. 92, the ridge 545 engages the groove 546, but the ridge 545 and the groove 546 are not visible.

In some embodiments, the system 202ab comprises a safety feature configured to insert the sensor 206ab and/or retract the sensor 206ab in response to a distal force on the first housing 532 and a rotation of the first housing 532 relative to the adhesive 210ab. Thus, the system 202ab can be configured to insert the sensor 206*ab* and/or retract the sensor 206*ab* in response to a combination of a distal "push" and a rotational movement (e.g., applied during the "push").

As illustrated in FIG. 91, the system 202*ab* can comprise an anti-rotation interface 547 between the second housing 533 and the base 204*ab*. The interface 547 can comprise a ridge 548 located in a groove 549 configured to limit rotation of the second housing 533 relative to the base 204*ab* during rotation of the first housing 532 relative to the base 204*ab*. The interface 547 can be oriented from a proximal portion of the second housing 533 to a distal portion of the second housing 533.

Scotch Yoke

Some systems convert rotational motion into linear motion in order to insert a sensor. Systems can hold a sensor in a distal position (e.g., such that the sensor is fully inserted into the tissue) while other portions of the system move proximally (e.g., to uncouple the applicator from the sensor). Thus, the system can ensure full sensor insertion is not jeopardized by the removal of the applicator.

FIG. 74 illustrates a base 204*x* and a sensor 206*x*. In FIGS. 94-99, the base 204*x* and the sensor 206*x* are removably coupled to an applicator 475*ac*.

The applicator 475*ac* is configured to insert the sensor 206*x* into the skin of a host. The applicator 475*ac* can be configured to convert rotational motion (e.g., caused by a spring force) into a linear motion that inserts a sensor 206*x* into the skin. The applicator 475*ac* can block the sensor 206*x* from moving distally until a user presses a button 567 (e.g., an actuation member). The button 567 can release the spring force to cause a rotational motion that the applicator 475*ac* converts into an approximately linear motion that inserts the sensor 206*x*.

The applicator 475*ac* can include a button 567 configured to release a torsional spring 568. The torsional spring 568 causes a rotational motion that the system 202*ac* converts into linear motion to move the sensor 206*x* distally into the skin.

The spring 568 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

The system 202*ac* can include two bodies 557, 558, which can move distally together. The two bodies 557, 558 can be arms.

Once the sensor 206*x* has reached its distal ending position, the first body 557 moves proximally (to uncouple the first body 557 from the base 204*x* and/or the sensor 206*x*) while the second body 558 holds the sensor assembly distally (to prevent the base 204*x* and/or the sensor 206*x* from moving proximally with the first body 557).

In some embodiments, a first adhesive 210*x* couples the sensor assembly to the skin. A second adhesive 554 couples the first body 557 to the sensor assembly (e.g., the wearable analyte monitor). The second body 558 prevents the first adhesive 210*x* from having to resist the second adhesive 554 as the first body 557 moves proximally. In other words, without the second body 558 blocking proximal movement of the sensor assembly, moving the first body 557 proximally could apply a substantial proximal force on the first adhesive 210*x* (which could cause the first adhesive 210*x* to uncouple from the skin).

In some embodiments, retention features (e.g., movable arms, clamping arms, snap fits) couple the first body 557 to the sensor assembly. The second body 558 prevents the first adhesive 210*x* from having to resist the retention features as the first body 557 moves proximally. Unique channel shapes enable the first body 557 to move proximally while the second body 558 holds the sensor assembly down (in the distal position).

Figure 94:
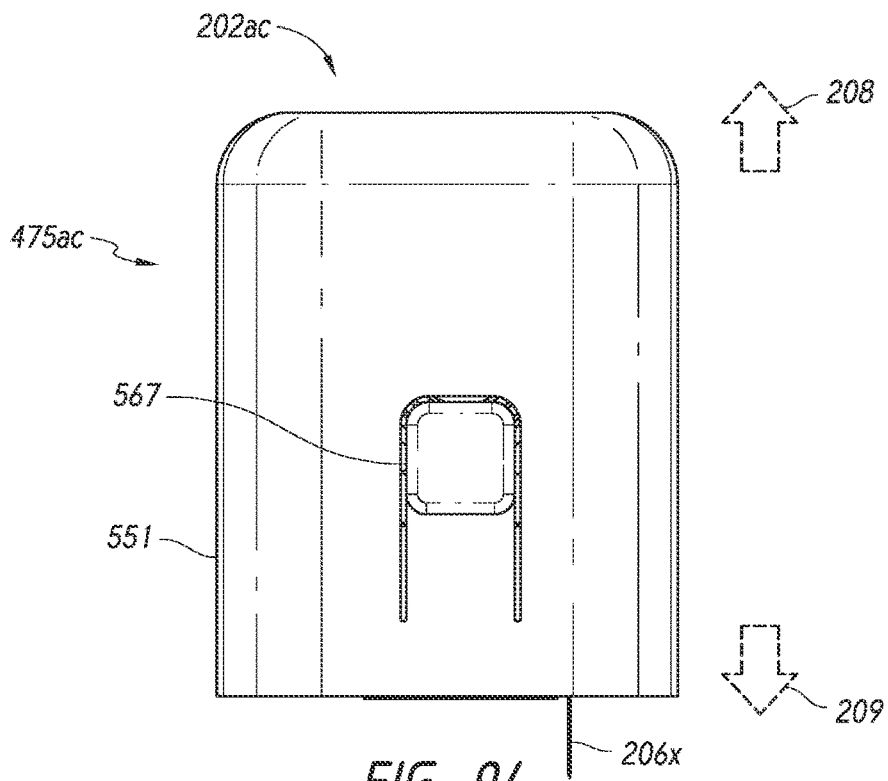
FIG. 94 illustrates a side view of an applicator, according to some embodiments.

FIG. 94 illustrates a side view of the applicator 475*ac* with the sensor 206*x* in a distal ending position (e.g., in tissue of the host). The applicator 475*ac* can move the sensor 206*x* distally in response to a user actuating (e.g., pressing) the button 567.

FIGS. 95-98 illustrate perspective, cross-sectional views of the system 202*ac* at various moments in an insertion cycle of the sensor 206*x*. Portions of the first housing 551 are hidden in FIGS. 95-98 to permit clear viewing of internal features.

Figures 95, 96:
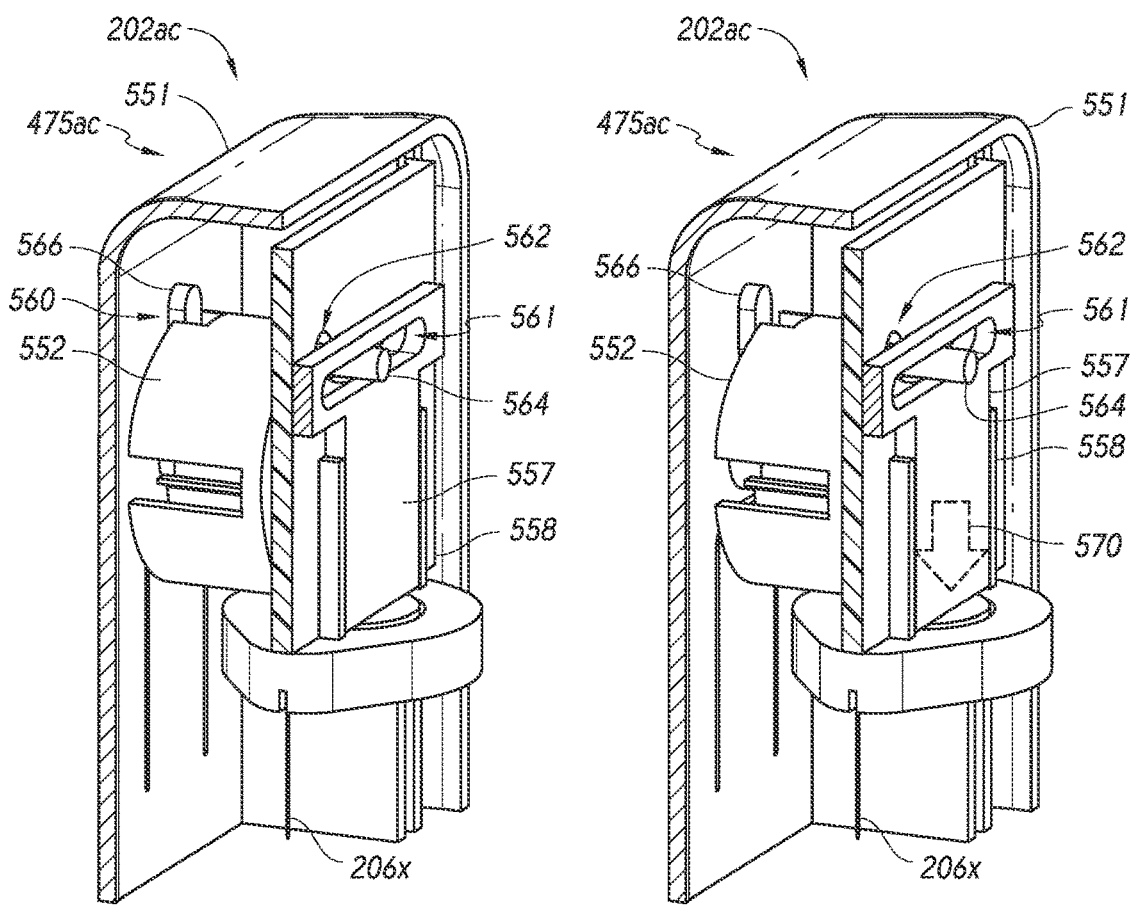

A spring 568 (shown in FIG. 99) located inside of a rotating housing 552 applies a torsional force between the rotating housing 552 and the first housing 551. A protrusion 566 blocks rotational movement of the rotating housing 552 relative to the first housing 551. FIG. 95 illustrates the protrusion 566 located in a channel of the rotating housing 552 to block rotational movement of the rotating housing 552.

In the state illustrated in FIG. 96, the user has already pressed the button 567 (shown in FIG. 94) to move the rotational housing 552 away from the protrusion 566. As a result, the protrusion 566 is no longer in the channel of the rotational housing, and thus, the protrusion 566 no longer impedes rotational movement of the rotational housing 552 relative to the first housing 551. As a result, the rotational housing 552 rotates relative to the first housing 551, which causes the first body 557 and the second body 558 to move distally (e.g., as indicated by arrow 570. The distal movement of the first body 557 and/or the second body 558 moves the sensor 206*x* distally (e.g., as shown in FIG. 97).

FIG. 97 illustrates the sensor 206*x* in a distal ending position. Continued rotation of the rotational housing 552 relative to the first housing 551 moves the first body 557 proximally (e.g., as indicated by arrow 571), but typically does not (at least immediately or initially) move the second body 558 proximally due to a divergent portion 563 (e.g., a proximally curved portion) of the second channel 562 (shown in FIG. 100). As a result, the second body 558 blocks proximal movement of the base 204*x* and/or the sensor 206*x* while the first body 557 detaches proximally from the base 204*x* and/or the sensor 206*x*. FIG. 98 illustrates the system 202*ac* after the first body 557 has moved proximally relative to the base 204*x* and the second body 558 to uncouple the first body 557 from the base 204*x* and/or the sensor 206*x*.

FIG. 99 illustrates a side view of portions of the system 202*ac*. The first housing 551 is hidden in FIG. 99. FIG. 99 illustrates the same state illustrated in FIG. 98.

FIG. 100 illustrates a side view of the second body 558. The divergent portion 563 of the second channel 562 is clearly visible in FIG. 100. In some embodiments, the second channel 562 includes a portion that curves more proximally than the related portion of the first channel 561 such that the first body 557 is configured to impede proximal movement of the base 204*x* and/or the sensor 206*x* as the first body 557 moves proximally relative to the base 204*x*, the sensor 206*x*, and/or the second body 558. The protrusion 564 of the rotational housing 552 identifies the related portion.

Referring now to FIGS. 94-100, a removable applicator 475*ac* can be coupled to the base 204*x*. The applicator 475*ac* can comprise a rotating housing 552 configured to push the first and second bodies 557, 558 distally. A second adhesive 554 can couple the base 204x to the first body 557. The second body 558 can be configured to hold the base 204x in a distal position while the first body 557 moves proximally to uncouple the first body 557 from the base 204x.

The applicator 475ac can comprise a locking mechanism configured to prevent the first body 557 and/or the second body 558 from moving distally until the locking mechanism is disengaged. The locking mechanism can comprise the button 567 and/or the protrusion 566 configured to impede rotational movement of the rotational housing 552.

The applicator 475ac can comprise a locking mechanism configured to block rotational movement of the rotating housing 552. The system 202ac can be configured to disengage the locking mechanism in response to linear movement of the rotational housing 552 (e.g., in response to actuation of the button 567).

The system 202ac can comprise a removable applicator 475ac coupled to the base 204x. The applicator 475ac can comprise a first housing 551, a second housing 552 rotatably coupled to the first housing 551, and a torsion spring 568. (Some embodiments use other types of springs.) The torsion spring 568 can have a first portion coupled to the first housing 551 and a second portion coupled to the second housing 552 (e.g., as indicated in FIG. 99) such that the torsion spring 568 is configured to rotate the second housing 552 relative to the first housing 551.

The applicator 475ac can have a first body 557 slidably coupled to the first housing 551 and coupled to the second housing 552 such that the first body 557 is configured to linearly push the sensor 206x from a proximal starting position (e.g., as illustrated in FIG. 95) to a distal ending position (e.g., as illustrated in FIG. 97) in response to the second housing 552 rotating relative to the first housing 551.

The applicator 475ac can have a second body 558 slidably coupled to the first housing 551 and coupled to the second housing 552 such that the second body 558 is configured to block proximal movement of the sensor 206x after the sensor 206x has reached the distal ending position as the system 202ac uncouples the first body 557 from the base 204x.

A second adhesive 554 can couple the first body 557 to the base 204x. The first and second arms 557,558 can be configured to move linearly and distally in response to rotating the second housing 552 relative to the first housing 551.

The second body 558 can be configured to block the proximal movement of the sensor 206x as rotation of the second housing 552 relative to the first housing 551 uncouples the second adhesive 554 from the base 204x to enable the first body 557 to move proximally relative to the base 204x and relative to the second body 558.

The first body 557 can be coupled to a first linear channel 561. A first protrusion 564 can couple the first linear channel 561 to the second housing 552. The first linear channel 561 can be configured such that a first rotational movement of the second housing 552 relative to the first housing 551 causes a first distal linear movement of the first body 557 relative to the first housing 551.

The second body 558 can be coupled to a second channel 562 having a divergent portion 563. The first protrusion 564 can couple the second channel 562 to the second housing 552. The second channel 562 can be configured such that the first rotational movement of the second housing 552 relative to the first housing 551 causes a second distal linear movement of the second body 558 relative to the first housing 551.

The divergent portion 563 of the second channel 562 can be configured such that continued rotational movement of the second housing 552 relative to the first housing 551 after the sensor 206x has reached the distal ending position does not cause proximal movement of the second body 558 as the continued rotational movement uncouples the second adhesive 554 from the base 204x by moving the first body 557 proximally.

The second housing 552 can be coupled to the first housing 551 by a second protrusion 565 (shown in FIG. 99) about which the second housing 552 is configured to rotate relative to the first housing 551. The second housing 552 can be slidably coupled to the second protrusion 565 such that the second housing 552 is configured to move from a first position (e.g., as shown in FIG. 95) to a second position (e.g., as shown in FIG. 96) along the second protrusion 565. In the first position, a third protrusion 566 can block rotational movement of the second housing 552 relative to the first housing 551 to impede distal movement of the sensor 206x.

The system 202ac can comprise a release mechanism (e.g., the button 567 and the components actuated by the button 567). The release mechanism can be configured to enable the second housing 552 to rotate relative to the first housing 551. The release mechanism can comprise a button 567 and/or any suitable trigger. The first housing 551 can comprise a button 567 configured to move the second housing 552 from the first position to the second position in which the second housing 552 is configured to rotate relative to the first housing 551 to move the sensor 206x distally.

Flex—Tornado

Applicators can be removable (e.g., can be uncoupled from a base). In some embodiments, applicators are a permanent part of the sensor system. For example, any of the applicators described herein can be permanently integrated into each system such that removing the applicators from the base is unnecessary. Some of the applicators are illustrated as being large to increase the clarity of certain features. The applicators, however, can be miniaturized such that they are not cumbersome even if the applicators are part of the system that the host wears for days, weeks, months, or even years.

FIGS. 60-63 illustrate an example of a system 202t that can include an integrated applicator. A separate, removable applicator is not necessary in the embodiment illustrated in FIGS. 60-63. In several embodiments, the applicator is removable to minimize the size of the wearable device.

Applicators can be configured to compress distally via flexing of the applicators. Certain portions of the applicators can be compliant to enable flexing. This flexing can enable the applicator to move a sensor distally into the skin.

FIGS. 8A-D of the following patent application illustrate applicator embodiments configured to flex to insert the sensor into the skin: U.S. patent application Ser. No. 12/893,850; filed Sep. 29, 2010; and titled Transcutaneous Analyte Sensor. The entire contents of the following application are incorporated by reference herein: U.S. patent application Ser. No. 12/893,850; filed Sep. 29, 2010; and titled Transcutaneous Analyte Sensor.

FIGS. 60-63 illustrate an embodiment of an applicator 475t that can compress distally via flexing. (Additional details regarding embodiments illustrated in FIGS. 60-63 are explained above.)

The system 202t can include arms 427 configured to guide a top portion (e.g., the transmitter 211t) towards the base 204t. The arms 427 can support and position the top portion as the arms 427 flex to enable the system 202t to compress to move the sensor 206t distally (e.g., into the skin of the host). The arms 427 can be configured to guide the top portion in a linear manner towards the base 204*t* or can be configured to rotate the top portion relative to the base 204*t* as the system 202*t* moves the sensor 206*t* distally. The system 202*t* illustrated in FIGS. 60-63 can be used with or without bellows 421.

Applicators (e.g., 745*t*) can comprise living hinges 423 (labeled in FIG. 61) configured to flex to enable the applicators to compress. This compressive movement can drive a sensor 206*t* (e.g., 206*t*) into the skin of a host.

Some embodiments comprise multiple living hinges 423 located radially outward from a distal portion of the sensor 206*t* (e.g., as shown in FIG. 62). The living hinges 423 can be spaced apart around a perimeter of a hole 435 in the base 204*t* such that the living hinges 423 are configured to help guide the distal portion of the sensor 206*t* through the hole 435 and into the skin. The living hinges 423 can facilitate linear and/or rotational movement of the proximal portion relative to the distal portion.

The living hinges 423 can be configured to cause a proximal portion (e.g., the transmitter 211*t*) of the base 204*t* to rotate relative to a distal portion of the base 204*t* as the proximal portion moves towards the distal portion.

The living hinges 423 can have a first position (e.g., a starting position as illustrated in FIGS. 61 and 62) in which the living hinges 423 hold the proximal portion in a proximal starting position such that the sensor 206*t* is in a predeployed state (prior to user activation). The living hinges 423 can have a second position (e.g., as illustrated in FIG. 63) in which the sensor 206*t* is in a deployed state and in which the living hinges 423 are in a flexed state.

A blocking structure (e.g., 424) can be located between the proximal portion and the distal portion to prevent the sensor 206*t* from being deployed before the blocking structure is removed.

A base 204*t* can comprise a proximal portion 442 coupled to a distal portion 441 by flex arms 427 configured to facilitate moving and guiding the proximal portion 442 towards the distal portion 441 in response to a distal force on the proximal portion 442. Thus, the flex arms 427 can facilitate inserting at least a portion of the sensor 206*t* into the skin. The proximal portion 442 can couple the transmitter to the distal portion 441.

A base 204*t* can comprise a proximal portion 442 coupled to a distal portion 441 by flex arms 427 configured to cause the proximal portion 442 to rotate relative to the distal portion 441 in response to moving the proximal portion 442 distally (relative to the distal portion 441) to insert at least a portion of the sensor 206*t* into the skin.

The flex arms 427 can comprise at least one living hinge 423 that couples the flex arm 427 to at least one of the proximal portion 442 and the distal portion 441 of the base 204*t*. In some embodiments, the living hinges 423 and/or the arms 427 are configured to rotate the proximal portion 442 relative to the distal portion 441 in response to moving the sensor 206*t* distally. The flex arms 427 can be spaced around a distal end of the sensor 206*t* such that the flex arms 427 are configured to rotate the distal end as the distal end moves from a proximal starting position (e.g., as illustrated in FIG. 62) to a distal ending position (e.g., as illustrated in FIG. 63).

A removable interference member (e.g., 242 in FIG. 60) can be located between the distal portion 441 and the proximal portion 442 such that the removable interference member is configured to block the system 202*t* from moving the sensor 206*t* from a proximal starting position to a distal ending position. Removing the interference member can enable the system 202*t* to move the sensor 206*t* to the distal ending position.

The base 204*t* can comprise a proximal portion 442 coupled to a distal portion 441 by a first arm 427 and a second arm 427. A distal end portion of the sensor 206*t* comprises a central axis. The first arm 427 can be oriented at a first angle of plus or minus 45 degrees of perpendicular to the central axis. The second arm 427 can be oriented at a second angle of plus or minus 45 degrees of perpendicular to the central axis.

The first and second arms 427 can be configured to guide the proximal portion 442 linearly relative to the distal portion 441 as the proximal portion 442 moves towards the distal portion 441. The first and second arms 427 can be configured to cause the proximal portion 442 to rotate relative to the distal portion 441 in response to moving the distal end portion of the sensor 206*t* from a proximal starting position to a distal ending position.

The second arm 427 can slant away from the first arm 427 (e.g., as illustrated in FIG. 61) such that the first and second arms 427 are configured to rotate the distal end portion of the sensor 206*t* as the system 202*t* moves the sensor 206*t* from the proximal starting position to the distal ending position.

The system 202*t* can include a mechanical interlock 429 configured to releasably hold the bellows 421, arms, and/or a spring in a compressed state. Releasing the mechanical interlock 429 can retract the sensor 206*t* from the skin such that the portion of the sensor 206*t* that was located distally relative to the distal side 207*t* of the base 204*t* is moved proximally into an interior area of the system 202*t*. The interlock 429 can be a snap fit formed by an undercut (e.g., as shown in FIG. 63).

Hinge Applicator—Broad Version

Several embodiments use rotational movement to insert a sensor. Some embodiments rely on a hinge pivoting to insert the sensor. Rotational movement can enable structurally-robust, low-profile applicators that are less intimidating to users (due to their small size).

As described above, the system 202*f* illustrated in FIGS. 17-19 can be used to retract a sensor 206*f*. The system 202*f*, however, can also be used to insert a sensor 206*f* into tissue of a host (e.g., by reducing rather than increasing a pivot angle 271 between a first portion 272 and a second portion 273). Thus, the system 202*f* can insert the sensor 206*f* and retract the sensor 206*f*. When the system 202*f* is used to insert the sensor 206*f*, FIG. 19 can illustrate a proximal starting position, and FIG. 18 can illustrate a distal ending position.

The sensor system 202*f* can comprise a base 204*f*, a transmitter 211*f*, and a distal side 207*f*. A spring 275 (e.g., a helical spring, a compression spring, a tension spring, a leaf spring, a torsional spring) can be configured to decrease the pivot angle 271 (e.g., once released by a triggering mechanism and/or any suitable mechanism) to insert the sensor 206*f*. Some embodiments do not include a spring 275, but rely on a user applying a distal force on the second portion 273 to push the second portion 273 towards the first portion 272.

The spring 275 can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

The hinge 270 can comprise a pin 276 rotatably coupled to a sleeve 277 configured to retain the pin 276 as the second portion 273 rotates relative to the first portion 272. The base 204*f* can comprise the first portion 272 and the second portion 273. The first portion 272 can couple the first adhesive 210 to the second portion 273. The second portion 273 can comprise the transmitter 211*f*.

Pivoting the second portion 273 towards the first portion 272 can push the sensor 206*f* out of a hole 278 in the base 204*f*. Some embodiments use a spring 275 to pivot the hinge 270.

A detent can releasably secure the hinge 270 in a starting position such that pivoting the hinge 270 requires overcoming a torque threshold or a force threshold. The detent can be built into the hinge 270. The detent can be positioned between a first surface of the first portion 272 and a second surface of the second portion 273.

A base 204*f* can comprise a first portion 272 and a second portion 273 coupled by a hinge 270 configured such that pivoting the second portion 273 towards the first portion 272 causes the sensor 206*f* to move from a proximal starting position (e.g., as illustrated in FIG. 19) to a distal ending position (e.g., as illustrated in FIG. 18). The second portion 273 can couple the transmitter 211*f* to the first portion 272. The first portion 272 can couple the adhesive 210 to the second portion 273.

The base 204*f* can be configured such that decreasing a pivot angle 271 between the first portion 272 and the second portion 273 moves a distal end of the sensor 206*f* out of a hole 278 of the distal side 207*f* of the base 204*f* to facilitate the distal end of the sensor 206*f* piercing the skin. A proximal segment of the sensor 206*f* can be coupled to the second portion 273 such that the system 202*f* can be configured to move a portion of the sensor 206*f* out of an area 283 between the first portion 272 and the second portion 273, and then distally through the hole 278 of the base 204*f* in response to decreasing the pivot angle 271.

The base 204*f* can comprise a left half 279 and a right half 280. The left half 279 can comprise the hole 278 of the base 204*f*. The right half 280 can comprise the hinge 270 (such that the hole 278 and the hinge 270 are located on different halves of the base 204*f*). The hinge 270 can comprise a pin 276 rotatably coupled to a sleeve 277 configured to retain the pin 276 as the second portion 273 rotates relative to the first portion 272.

Hinge Applicator—Mouse-Trap Version

Embodiments that use rotational motion to insert and/or retract a sensor can include one, two, three, or more rotating supports (e.g., arms, bodies). FIGS. 101-106 illustrate an applicator 475*ad* that comprises two rotating supports.

Some hinge 584 embodiments include a first body 581 (e.g., a first arm, a first support) configured to rotate in order to move the sensor 206*ad* and/or the base 204*ad* distally (e.g., into the skin of the host). Several embodiments include a second body 582 (e.g., a second arm, a second support) configured to rotate in order to uncouple the applicator 475*ad* from the base 204*ad* and/or the sensor 206*ad*.

Figure 101:
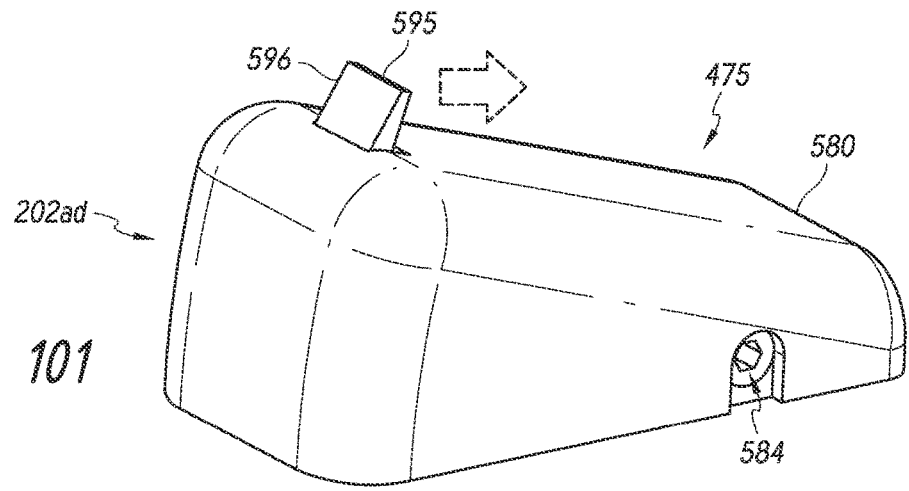
FIG. 101 illustrates a perspective view of a system, according to some embodiments.

FIG. 101 illustrates a perspective view of a system 202*ad* with a removable applicator 475*ad* in a proximal starting position. Actuating the tab 596 (e.g., by pressing and/or moving the tab 596) can cause the system 202*ad* to move the sensor 206*ad* distally by rotating bodies 581, 582 about a hinge 584.

Figure 102:
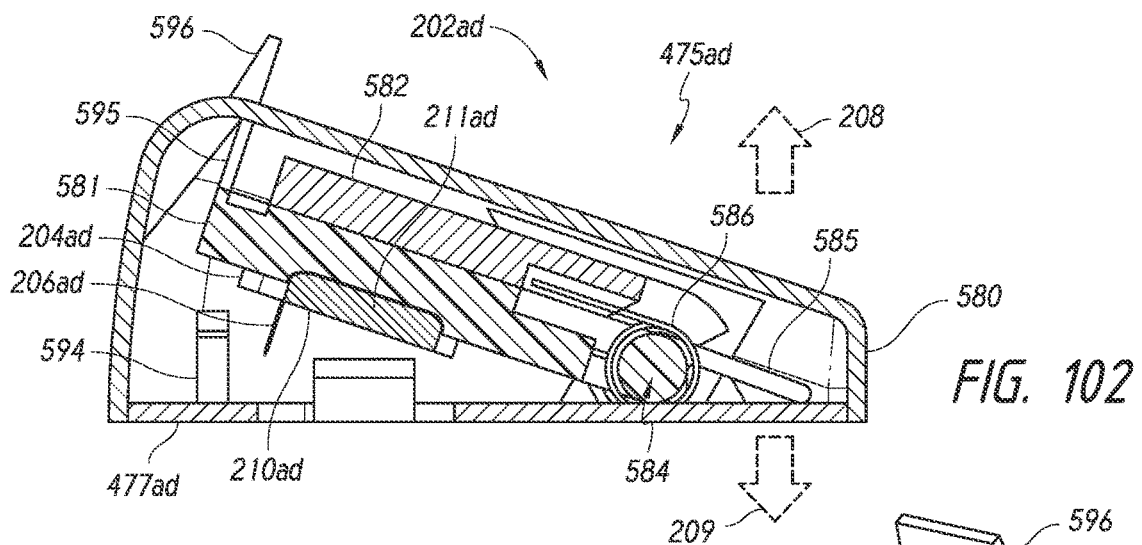
FIG. 102 illustrates a side, cross-sectional view of the system, according to some embodiments.

FIG. 102 illustrates a side, cross-sectional view of the system 202*ad* in the proximal starting position. A first spring 585 (e.g., a leaf spring) is in a flexed state (e.g., a high-energy state). The fifth arm 595 and the tab 596 are coupled to the housing 580 to resist the rotational force (i.e., a torque) of the first spring 585. Disengaging the tab 596 enables the first spring 585 to rotate the first body 581 and the second body 582 in a counter-clockwise direction about the hinge 584.

A second spring 586 is in a flexed state (e.g., a high-energy state) that applies a clockwise rotational force (i.e., a torque). The second body 582 is secured to the first body 581 by a third arm 590 (shown in FIG. 103) that resists the clockwise rotational force of the second spring 586 (until the third arm 590 and/or another arm that is a mirror image of the third arm 590 flex to disengage the second body 582 from the first body 581 to enable the second body 582 to rotate away from the first body 581).

The each spring (e.g., 585, 586) can be a torsion spring, a leaf spring, a helical spring, a conical spring, a compression spring, a tension spring, an integrally molded deforming body, a flex arm, any type of spring described herein, any type of spring incorporated by reference, and/or any suitable type of spring.

The applicator 475*ad* can comprise a distal portion 477*ad*. The hinge 584 can couple the first body 581 and the second body 582 to the distal portion 477*ad* of the applicator 475*ad*. The base 204*ad* can comprise a transmitter 211*ad*.

Figure 103:
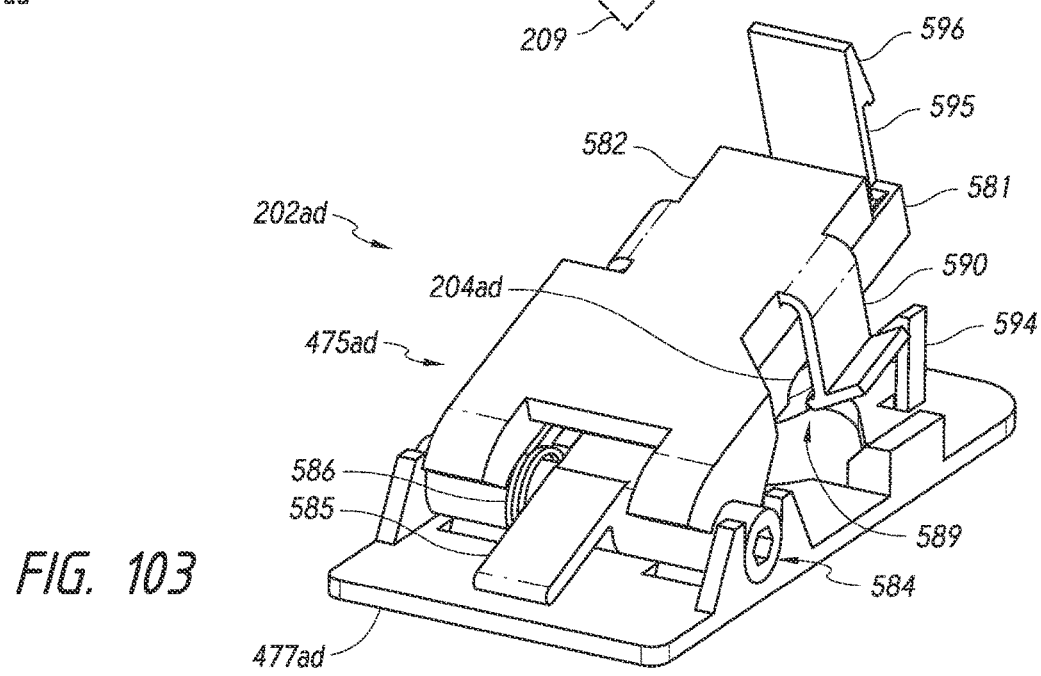
FIGS. 103-106 illustrate perspective views of the system, according to some embodiments.

FIG. 103 illustrates a perspective view of the system 202*ad* in the proximal starting position. (The housing 580 is hidden in FIGS. 103-106 to enable clear viewing of internal features.) The first body 581 and the second body 582 can rotate about the same rotational axis (e.g., of the hinge 584).

Figure 104:
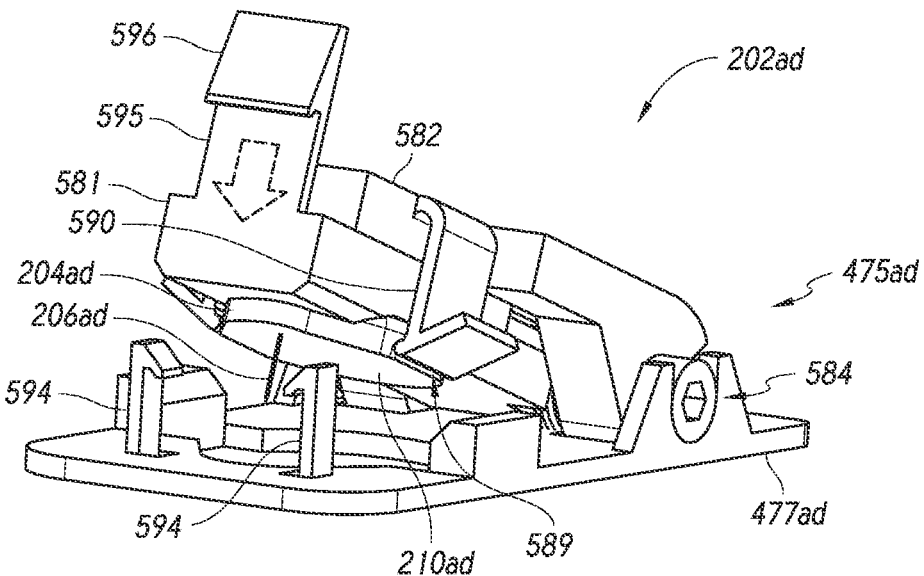

FIG. 104 illustrates another perspective view of the system 202*ad* in the proximal starting position. The third arm and its opposite 590 can reach around the first body 581 such that the first body 581 is located at least partially between the second body 582 and the base 204*ad*, which can secure the second body 582 to the first body 581.

In the state illustrated in FIG. 104, the first spring 585 (shown in FIG. 102) applies a rotational force oriented to move the base 204*ad* and/or the sensor 206*ad* distally. The rotational force of the first spring 585 is counter balanced due to the fifth arm 595 being coupled to the housing 580 (e.g., as shown in FIGS. 101 and 102).

In the state illustrated in FIG. 104, the second spring 586 (shown in FIG. 102) applies a rotational force oriented to rotate the second body 582 away from the first body 581. The rotational force of the second spring 586 is counter balanced by the third arm 590 (which couples the second body 582 to the base 204*ad* to block the second body 582 from rotating away from the first body 581).

Figure 105:
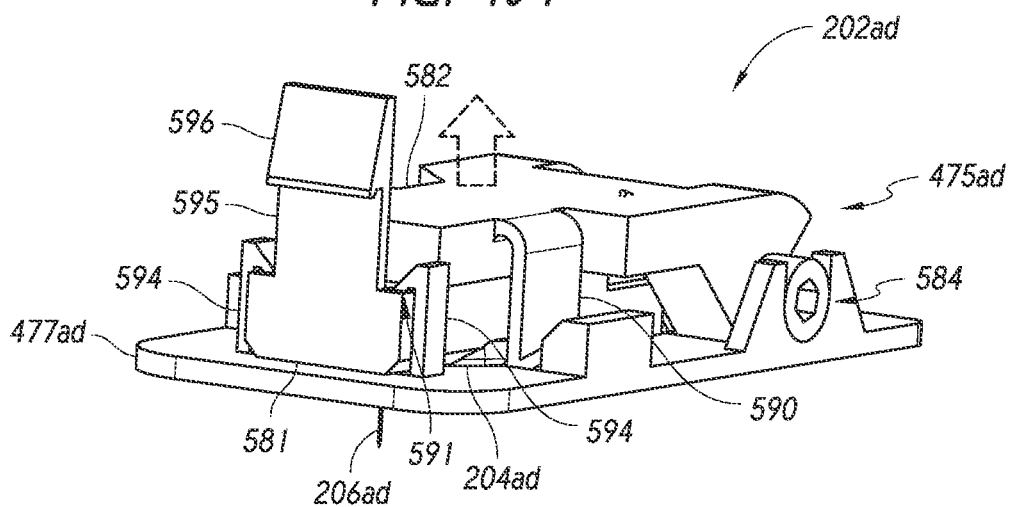

Uncoupling the fifth arm 595 from the housing 580 (e.g., by actuating the tab 596) enables the first spring 585 to rotate the first body 581, the second body 582, the base 204*ad*, and the sensor 206*ad* to the state illustrated in FIG. 105. Arriving at the state illustrated in FIG. 105 causes a portion of the third arm and its opposite 590 to contact disengagement features (e.g., of the base 204*a* d). The disengagement features of the base 204*ad* cause the third arm and its opposite 590 to uncouple from the base 204*ad* to uncouple the second body 582 from the first body 581, which enables the adhesive 210*ad* to couple the base 204*ad* to the skin as the second body 582 rotates away from the first body 581.

Figure 106:
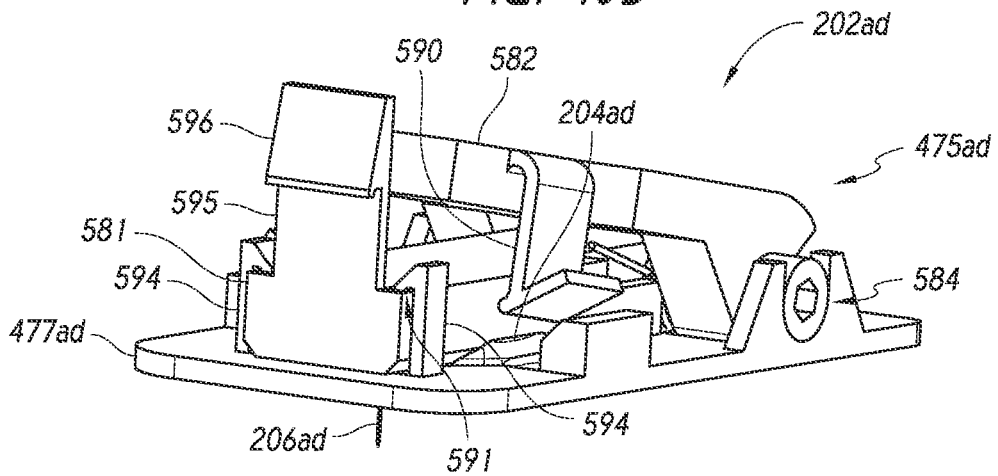

FIG. 106 illustrates a perspective view of the system 202*ad* after the second body 582 has rotated away from the first body 581 and the adhesive 210*ad* has coupled the base 204*ad* to the skin of the host. In the state illustrated in FIG. 106, the applicator 475*ad* is no longer coupled to the base 204*ad* and the sensor 206*ad*. As a result, the applicator 475*ad* can be moved proximally while leaving the base 204*ad* and the sensor 206*ad* coupled to the skin of the host.

Referring now to FIGS. 101-106, some hinge embodiments use two arms configured to rotate about at least one pivot axis. The first body 581 can be configured to push the sensor 206*ad* from a proximal starting position (e.g., as illustrated in FIG. 104) to a distal ending position (e.g., as illustrated in FIG. 106). The second body 582 can be configured to secure the base 204ad and/or the sensor 206ad to the first body 581 while the first body 581 inserts the sensor 206ad into the skin. The second body 582 can also release the base 204ad and/or the sensor 206ad (e.g., while the first body 581 holds the sensor 206ad in the distal ending position).

Each of the bodies 581, 582 can have a spring 585, 586 (e.g., a torsional spring, a leaf spring, an integrally molded flex tab). A first spring 585 of the first body 581 can provide energy to rotate the first body 581 in a first rotational direction that inserts the sensor 206ad. A second spring 586 can provide energy that rotates the second body 582 in a second rotational direction (that is opposite relative to the first rotational direction) to release the base 204ad from the applicator 475ad.

Thus, springs 585, 586 can be configured to facilitate pivoting a second portion relative to a first portion. Either spring 585, 586 can be a torsional spring, integrally molded flex tab, and/or a leaf spring configured to apply a torque about the hinge 584.

The system 202ad can comprise a removable applicator 475ad. The applicator 475ad can comprise a housing 580; a first body 581 rotatably coupled to the housing 580 by a hinge 584 having a hinge axis; a second body 582 rotatably coupled to the housing 580 about the hinge axis; a first spring 585 configured to rotate the first body 581 in a first rotational direction to move the sensor 206ad from a proximal starting position to a distal ending position; and a second spring 586 configured to rotate the second body 582 in a second rotational direction that is opposite to the first rotational direction.

The second body 582 can be configured to couple the base 204ad to the housing 580 as the first body 581 rotates in the first rotational direction. The first body 581 can be configured to hold the sensor 206ad in the distal ending position while the second body 582 uncouples the base by detaching a retaining feature (e.g., an undercut, an adhesive) 204ad from the applicator 475ad by rotating in the second rotational direction.

The applicator 475ad can comprise a first interlock (e.g., a first mechanical interlock 589) that releasably couples the second body 582 to the base 204ad such that the first body 581 is configured to move the second body 582 and the base 204ad in the first rotational direction.

The first body 581 can be located at least partially between the base 204ad and the second body 582. The first mechanical interlock 589 can comprise a third flex arm 590 that secures the first body 581 at least partially between the base 204ad and the second body 582. The first mechanical interlock 589 can be configured to uncouple from the base 204ad to enable the second body 582 to rotate in the second rotational direction in response to the first body 581 moving the second body 582 in the first rotational direction.

The housing 580 (or another portion of the applicator 475ad) can comprise a second interlock (e.g., a second mechanical interlock 591) configured to hold the first body 581 in a distal position while the second body 582 rotates in the second rotational direction. The second mechanical interlock 591 can comprise a left fourth flex arm 594 and a right fourth flex arm 594 configured to couple to least a portion of the first body 581.

The applicator 475ad can comprise a fifth flex arm 595 that couples the first body 581 (and/or the second body 582) to the housing 580 such that the sensor 206ad is in the proximal starting position. The fifth flex arm 595 can be configured to resist a rotational force of the first spring 585. A portion of the fifth flex arm 595 can protrude through a channel of the housing 580. The channel can couple (e.g., connect and be oriented between) an interior of the housing 580 and an exterior of the housing 580.

A portion of the fifth flex arm 595 can protrude from an exterior of the housing 580 such that the portion comprises an actuation tab 596 and/or an actuation lever. The fifth flex arm 595 can be configured to uncouple from the housing 580 to enable the first body 581 to rotate in response to moving the actuation tab 596 and/or the actuation lever. The fifth flex arm 595 may be actuated and/or triggered by an electronic, moving, translating, and/or sliding user activation button.

Any of the features described in the context of FIGS. 85-106 can be applicable to all aspects and embodiments identified herein. For example, the embodiments described in the context of FIGS. 85-106 can be combined with the embodiments described in the context of FIGS. 1-84 and 107-126. Moreover, any of the features of an embodiment is independently combinable, partly or wholly with other embodiments described herein in any way (e.g., one, two, three, or more embodiments may be combinable in whole or in part). Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Sensors

Many embodiments described herein comprise a sensor (e.g., a transcutaneous analyte measurement sensor). Many sensor features are described below. Each of the sensor embodiments can be used with and/or in the place of each of the sensors described in the context of FIGS. 1-106, other locations herein, and/or as incorporated by reference. To avoid unnecessary redundancy to and facilitate focusing on sensor details, many sensor features are not described for each embodiment, but instead are described below to enable the reader to understand the many sensor features that can be used with and/or in the place of each of the sensors described in the context of FIGS. 1-106, in other locations herein, and/or as incorporated by reference.

Patients sometimes feel pain when a distal portion of the sensor is inserted into the skin. Thus, in some cases there is a need for systems and methods that minimize or even eliminate this pain. A distal tip of the sensor should be sharp enough to easily pierce the skin (e.g., have a low insertion force), which minimizes the discomfort patients feel.

The sensor can include a membrane coating. The membrane can cover a sharp distal tip. The sharp distal tip can cause the sensor membrane to delaminate (e.g., shear off) during insertion of the distal tip into the skin or during in vivo use of the sensor. Preventing membrane breeching and maintaining the adhesion between the membrane and the distal tip can be very difficult. Decreasing the sharpness of the distal tip allows for more robust membrane adhesion but introduces other disadvantages such as pain, higher insertion forces, sensor deployment failure, and inaccurate sensor data (due to the tissue trauma).

Thus, in some cases there is a need for systems and methods that minimize patient pain (e.g., by being sharp) while also minimizing tissue trauma and preventing membrane delamination. Many unique sensor tip shapes described herein can accomplish all of these seemingly incompatible and conflicting goals.

Sensors can be at least partially coated by a membrane. The following patent application includes membrane details:

U.S. patent application Ser. No. 14/250,320; filed Apr. 10, 2014; and entitled Sensors for Continuous Analyte Monitoring and Related Methods. The entire contents of U.S. patent application Ser. No. 14/250,320 are incorporated by reference herein.

Some embodiments include novel geometries that enable low insertion forces and minimal tissue trauma while guarding against membrane delamination. Reducing the sharpness of the distal tip of the sensor can reduce the likelihood of piercing cellular walls. Reducing the sharpness of the distal tip can reduce the immune response by pushing cells out of the way of the sensor insertion path rather than cutting cells and/or piercing cells.

Figure 107:
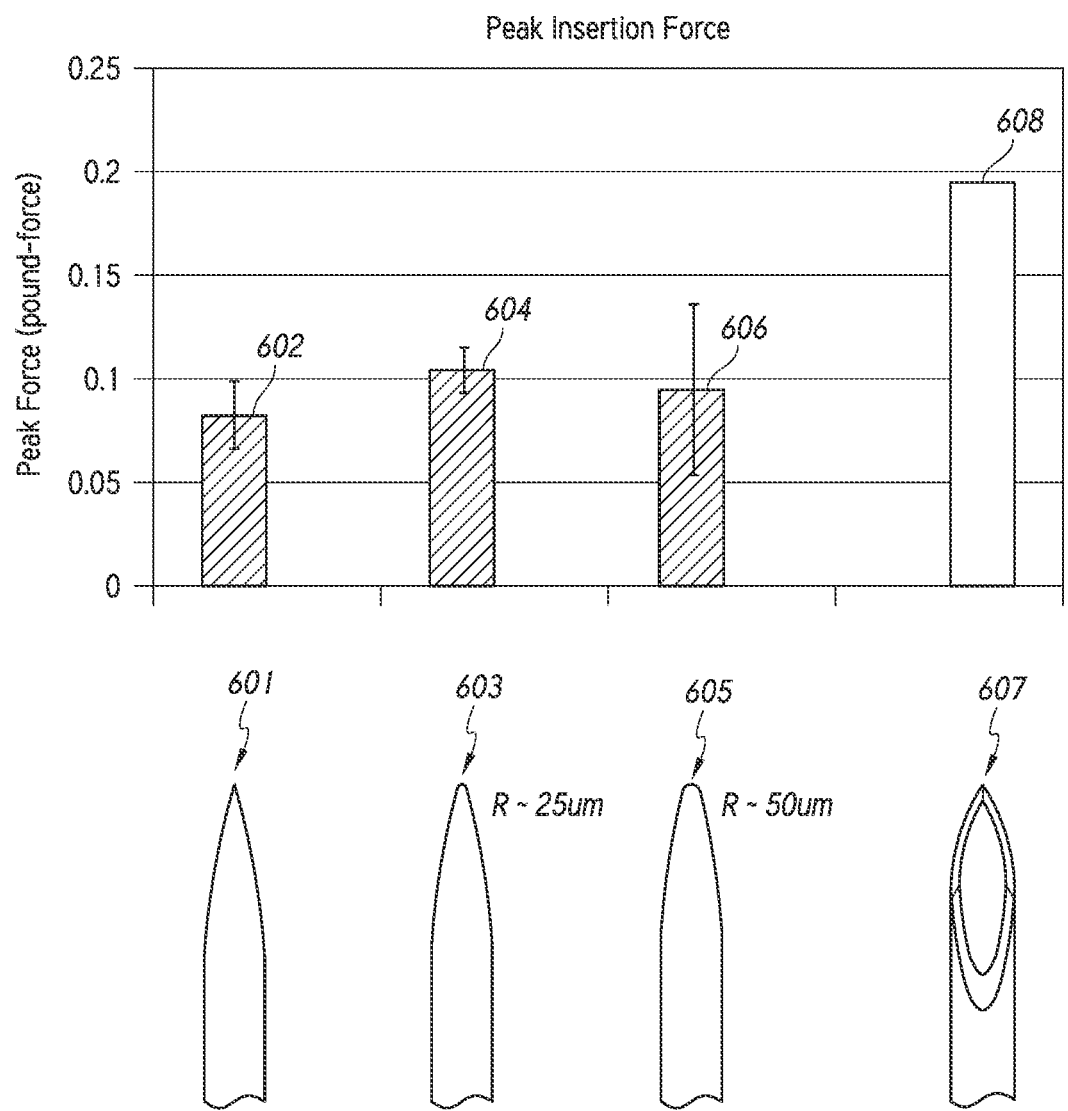
FIG. 107 illustrates a sensor insertion chart and distal portions of sensors, according to some embodiments.

When a sensor is inserted into tissue, the force necessary to insert the sensor into the tissue can be measured. An insertion force peak can be identified each time a sensor is inserted into tissue (e.g., synthetic tissue, human tissue). FIG. 107 illustrates peak insertion forces of four sensors. The shape of each of the sensors is illustrated in FIG. 107. A first sensor tip 601 has a first peak insertion force indicated by a first bar 602. A second sensor tip 603 has a second peak insertion force indicated by a second bar 604. A third sensor tip 605 has a third peak insertion force indicated by a third bar 606. A fourth sensor tip 607 has a fourth peak insertion force indicated by a fourth bar 608.

The fourth sensor tip 607 was made by forming a tube and then removing an end portion of the tube at an angle to create a bevel needle (with a hollow interior and a hole in a distal portion). The other sensor tips 601, 603, 605 do not include a hollow interior and a hole in a distal portion.

The first three sensors 601, 603, 605 enable dramatically lower insertion forces than the fourth sensor 607. The first sensor 601, however, has a sharp distal tip that often results in delamination of a membrane that coats the first sensor 601. This delamination can jeopardize the ability of the sensor system to accurately analyze analyte indications.

Figure 108:
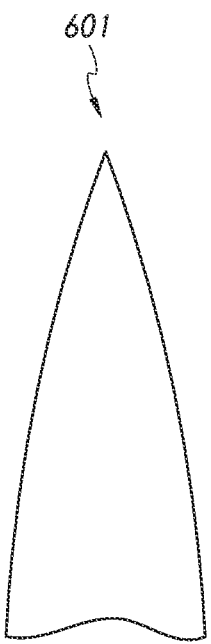
FIG. 108 illustrates a side view of a distal portion of a sensor, according to some embodiments.
Figure 109:
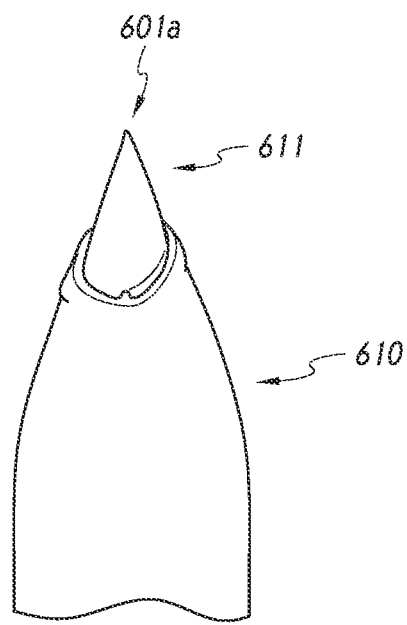
FIG. 109 illustrates a perspective view of a distal portion of a sensor, according to some embodiments.

FIG. 108 illustrates the first sensor 601 in a first state prior to being coated by a membrane. FIG. 109 illustrates the first sensor 601a after being coated by a membrane and then being cycled one hundred times within tissue. A first portion 610 of the sensor 601a is coated by the membrane. The membrane has delaminated from a second portion 611 of the sensor 601a.

Figure 110:
FIG. 110 illustrates a side view of a distal portion of a sensor, according to some embodiments.
Figure 111:
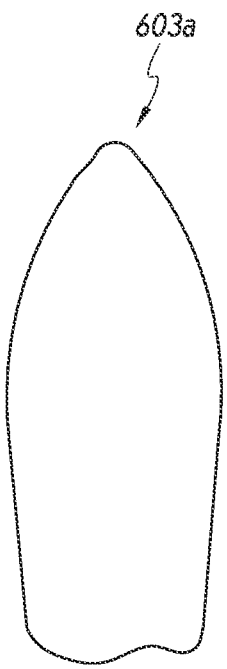
FIG. 111 illustrates a perspective view of a distal portion of a sensor, according to some embodiments.

FIG. 110 illustrates the second sensor 603 in a first state prior to being coated by a membrane. FIG. 111 illustrates the second sensor 603a after being coated by a membrane and then being cycled 100 times within tissue. As shown in FIG. 111, the membrane has not delaminated due to the unique shape of the distal tip of the sensor 603a. The third sensor 605 also effectively resists delamination of the membrane. Thus, the second sensor 603a and the third sensor 605 provide far superior membrane delamination resistance than the first sensor 601a while still achieving far lower insertion forces than the fourth sensor 607. Additional details are described below regarding specific geometries that enable these benefits.

Parabolic Tip

Figure 112:
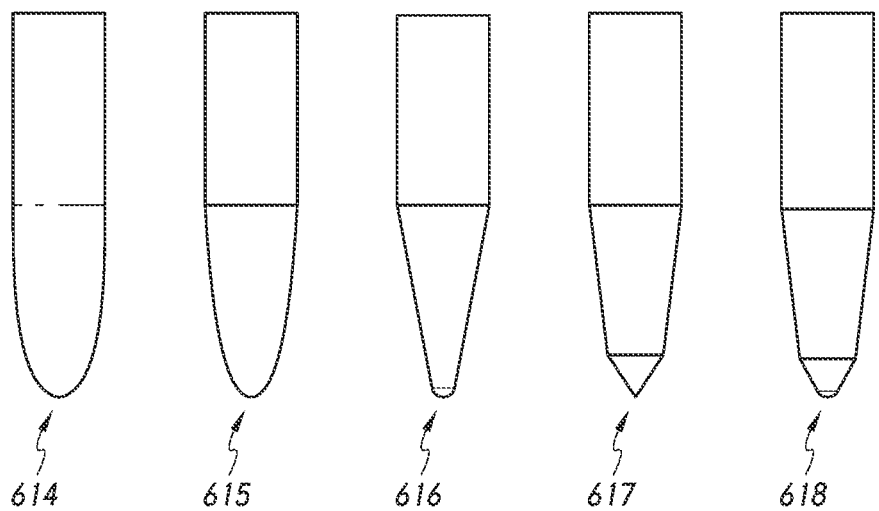
FIG. 112 illustrates a side view of distal portions of sensors, according to some embodiments.
Figure 113:
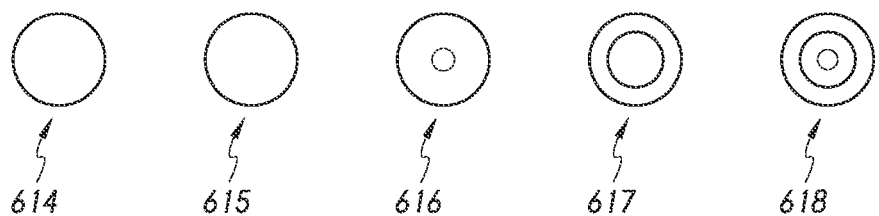
FIG. 113 illustrates a bottom view of distal portions of sensors, according to some embodiments.
Figure 114:
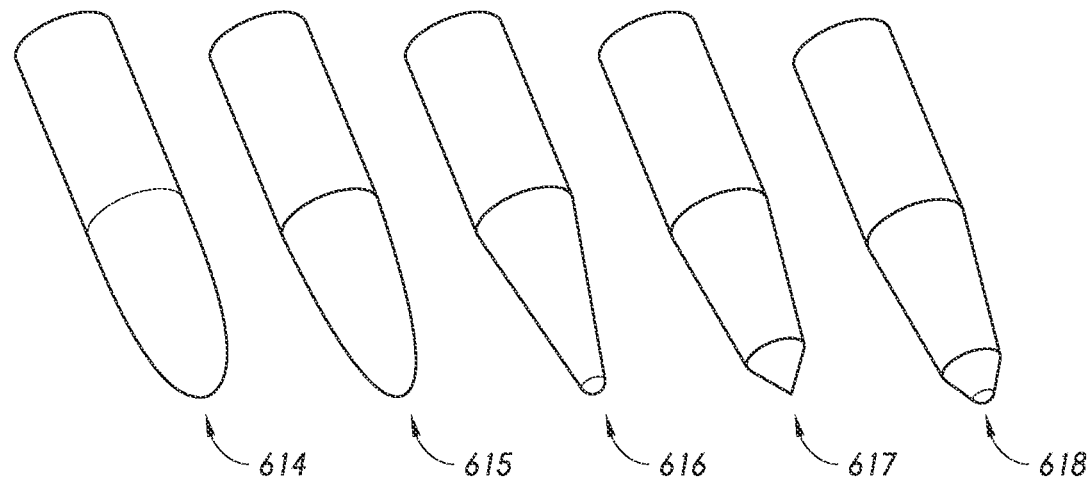
FIG. 114 illustrates a perspective view of distal portions of sensors, according to some embodiments.

FIG. 112 illustrates a side view of sensors 614-618. FIG. 113 illustrates a bottom view of the sensors 614-618. FIG. 114 illustrates a perspective view of the sensors 614-618. The proximal portions of the sensors 614-618 are hidden in FIGS. 112-114.

The first sensor 614 and the second sensor 615 have a distal end portion with a parabolic shape. A slope of the parabolic distal end portion can comprise a linear derivative. Parabolic shapes can be well-suited to resisting membrane delamination while facilitating low insertion forces.

The maximum width of the parabolic shape can be at least 50 percent of the maximum width of a distal portion of the sensor configured to be inserted into the skin. In some embodiments, the maximum width of the parabolic shape can be at least 60 percent, at least 80 percent, 100 percent, less than 90 percent, and/or less than 100 percent of the maximum width of the distal portion of the sensor configured to be inserted into the skin.

A parabolic shape allows for approximately uniform membrane coating of the distal end portion of the sensor. A parabolic shape, however, can be expensive and difficult to manufacture in a repeatable fashion. The parabolic distal end portion can be formed by grinding, electrical discharge machining ("EDM"), laser cutting, and/or laser ablation of the distal end portion, but achieving a precise profile can be difficult.

Figure 115:
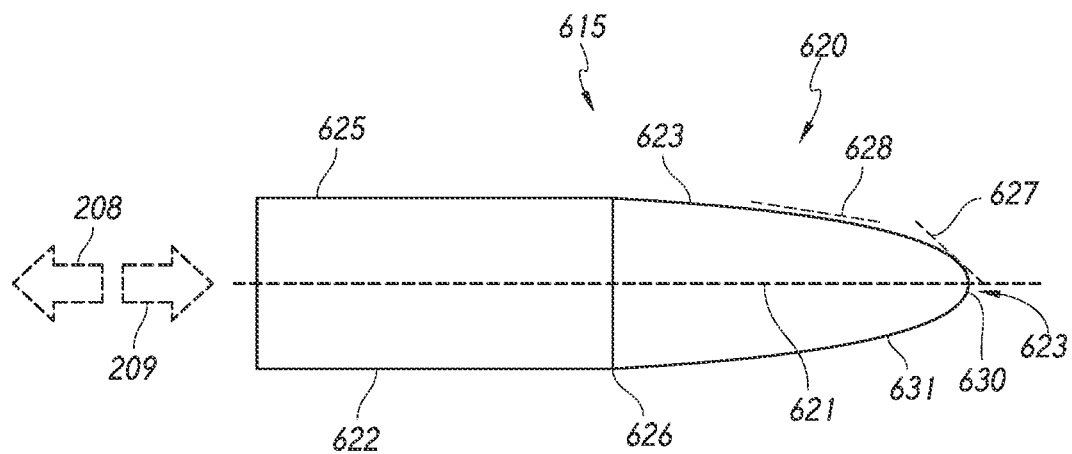
FIGS. 115-117 illustrate side views of distal portions of sensors, according to some embodiments.

FIG. 115 illustrates a side view of a distal portion of a sensor 615. The sensor 615 comprises a distal end portion 620 having a central axis 621 and a planar profile coincident with the central axis 621. The planar profile of the distal end portion 620 can be parabolic (e.g., as illustrated in FIG. 115).

In some embodiments, the distal end portion 620 of the sensor 615 is coated with a membrane 622. A distal tip 623 of the sensor 615 can be configured to pierce the skin and can be rounded to resist delamination of the membrane 622.

In several embodiments, the distal end portion 620 of the sensor 615 is coated with a membrane 622. The parabolic distal end portion 620 can be configured to provide a gradual diameter increase to reduce tissue trauma and to provide a curved distal tip 623 configured to resist delamination of the membrane 622.

In some embodiments, a segment of the sensor 615 is configured to be inserted into the skin. The segment can comprise a first maximum width 625. The parabolic distal end portion 620 can comprise a second maximum width 626 that is at least 50 percent of the first maximum width.

In several embodiments, the distal end portion 620 is coated by a membrane 622 configured to enable the sensor 615 system to measure a glucose indication. The membrane 622 can comprise a thickness that varies by less than plus or minus 30 percent relative to an average thickness of the membrane 622.

In some embodiments, the parabolic distal end portion 620 comprises a distal section and a proximal section. The distal section can comprise a first angle relative to the central axis 621. (The first angle can be measured between line 627 and the central axis 621.) The proximal section can comprise a second angle relative to the central axis 621. (The second angle can be measured between line 628 and the central axis 621.) The first angle can be at least twice as large as the second angle such that the first angle is configured to resist delamination of the membrane 622 and the second angle is configured to gradually increase a width of the profile.

In several embodiments, the sensor 615 comprises a distal end portion 620 having a central axis 621 and a planar profile coincident with the central axis 621. A distal tip 623 of the sensor 615 can be curved such that the planar profile comprises a curved distal end 630 that couples a first curved side 631 to a second curved side 632.

In some embodiments, the distal end portion 620 of the sensor 615 is coated with a membrane 622. The curved distal end can be configured to resist delamination of the membrane 622. The first curved side 631 and the second curved side 632 can be configured to provide a smooth transition from the distal tip 623 to resist delamination and to provide a gradual transition from a first diameter of the distal tip 623 to a maximum diameter 626 of the distal end portion 620.

Blunted Tip

FIGS. 112-114 illustrate a sensor 616 with a shape that is relatively easy to manufacture. The profile of the distal end portion 638 of the sensor 616 has straight sides coupled by a parabolic and/or rounded distal tip 637. The straight sides enable low insertion forces while the rounded distal tip 637 resists membrane 639 delamination.

The distal end portion 638 of the sensor 616 can be manufactured by forming a conical shape and then grinding (e.g., with abrasive disks) the distal tip 637 until the end of the distal tip 637 comprises a parabolic and/or rounded shape. This embodiment can be much easier and more repeatable to manufacture while (a) having a low insertion force and (b) resisting membrane 639 delamination.

Membrane 639 delamination typically starts at the distal tip 637 and propagates proximally along the sensor 616. The blunted tip provides a substantial surface oriented at a large angle relative to the insertion direction (e.g., as indicated by distal arrow 209). This surface geometry resists membrane 639 delamination at the distal tip 637 because inserting the distal tip 637 into the skin places the membrane 639 that covers the distal tip 637 in a compressed state (rather than in a shear state). The blunted tip also resists membrane 639 delamination by dramatically lowering the stress concentration on the distal tip 637 (compared to a more pointed tip). Stress can be approximated as force divided by area. As the area approaches zero, the local stress on the tip becomes infinite. Increasing the area reduces the stress. Resisting membrane 639 delamination at the tip also precludes delamination from spreading proximally along the sensor 616 by preventing the initiation of delamination.

FIG. 116 illustrates a side view of a distal portion of a sensor 616. The distal portion of the sensor 616 comprises a central axis 634 and a profile (defined by the central axis 634). The profile can comprise straight sides 635, 636 and a rounded distal tip 637. The straight sides 635, 636 (of the profile taken along a central axis 634 of the distal tip 637) result in a shape with very little insertion resistance and thus provide a low insertion force.

In some embodiments, the sides 635, 636 are rounded and the distal tip 637 is parabolic. The parabolic tip provides a very small angle between a direction of insertion (e.g., as indicated by distal arrow 209) and a surface to which the membrane 639 is adhered. As a result, the distal tip 637 provides robust delamination resistance.

The radius of the distal tip 637, the latus rectum of the parabola of the distal tip 637, and/or the maximum width of the parabola of the distal tip 637 can be 25 plus or minus 10 micrometers. The angle between the straight sides 635, 636 of the profile can be 20 degrees plus or minus 5 degrees.

The sensor 616 can comprise a distal end portion 638 that is conical with a rounded distal tip 637. The rounded distal tip 637 can be configured to resist delamination of a membrane 639 that coats the distal end portion 638. The distal end portion 638 can be conical to facilitate piercing the skin.

The sensor 616 can comprise a distal end portion 638 that is conical with a blunted distal tip 637. The blunted distal tip 637 can be configured to resist delamination of a membrane 639 that coats the distal end portion 638.

The sensor 616 can comprise a distal end portion 638 having a central axis 634 and a planar profile coincident with the central axis 634. A distal tip 637 of the sensor 616 can be curved such that the planar profile comprises a curved distal end that couples a first straight side 635 to a second straight side 636.

In some embodiments, the distal end portion 638 can be coated by a membrane 639. The distal tip 637 can be curved such that the distal tip 637 is configured to resist delamination of the membrane 639. The first and second sides 635, 636 can be straight such that the sides 635, 636 are configured to linearly increase a diameter of the distal end portion 638 to reduce tissue trauma caused by inserting the distal end portion 638 into the skin.

In several embodiments, the curved distal end comprises a radius that is greater than 10 micrometers and less than 35 micrometers such that the curved distal end is configured to be large enough to resist delamination of a membrane 639 that coats the curved distal end and small enough to reduce patient discomfort associated with piercing of the skin.

In some embodiments, the curved distal end comprises a maximum width that is greater than 10 micrometers and less than 35 micrometers such that the curved distal end is configured to be large enough to resist delamination of a membrane 639 that coats the curved distal end and small enough to reduce patient discomfort associated with piercing of the skin. An angle between the first and second straight sides 635, 636 can be greater than 15 degrees and less than 25 degrees such that the angle is configured to reduce patient discomfort associated with piercing of the skin.

Dual-Angle Tip

FIGS. 112-114 illustrate sensors 617, 618 that include dual-angle distal end portions. The sensors 617, 618 each have a profile that includes two angles. The second angle can be larger (relative to a central axis) than the first angle. A first sensor 617 comprises a sharp distal tip. A second sensor 618 comprises a rounded distal tip to resist membrane delamination.

Figure 117:
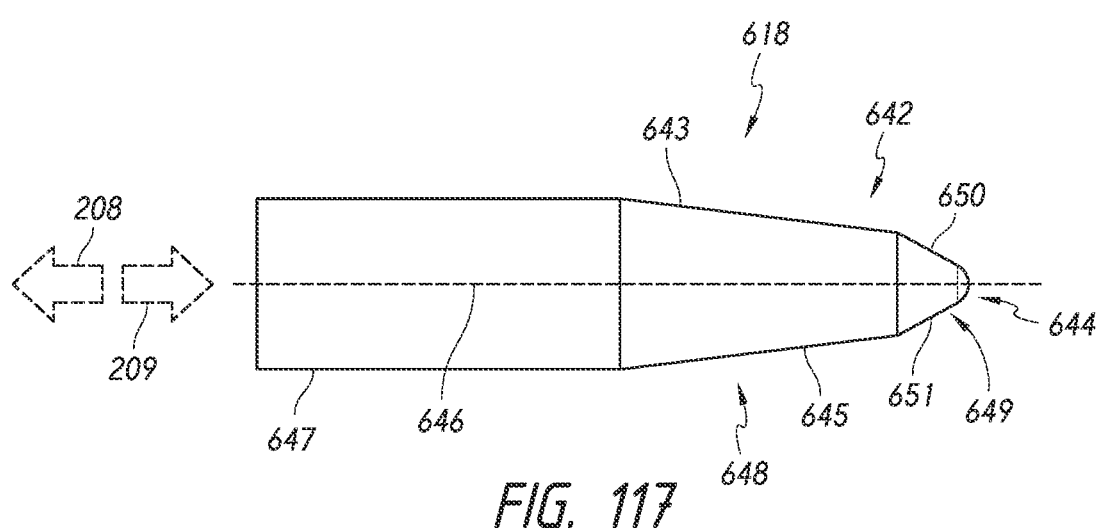

FIG. 117 illustrates a side view of a distal portion 642 of a sensor 618. The distal portion 642 of the sensor 618 comprises a central axis 646 and a profile (defined by the central axis 646). The sides 643, 650, 645, 651 of the profile comprise a first angle (relative to the central axis 646) and a second angle (relative to the central axis 646). The second angle can be larger than the first angle such that the second angle is configured to resist membrane 647 delamination and the first angle is configured to provide a gradual diameter increase.

The sensor 618 can comprise a distal end portion 642 having a central axis 646 and a planar profile coincident with the central axis 646. The planar profile can comprise a left portion having a first side 643 coupled to a second side 650. The planar profile can comprise a right portion having a third side 645 coupled to a fourth side 651. A first angle between the first side 643 and the third side 6445 can be smaller than a second angle between the second side 650 and the fourth side 651 such that a proximal section 648 of the end portion 642 provides a more gradual width increase than a distal section 649 of the end portion 642. The first, second, third, and fourth sides 643, 650, 645, 651 can be straight. The first, second, third, and fourth sides 643, 650, 645, 651 can be curved.

A curved distal end 644 can couple the second side 650 to the fourth side 651. The curved distal end 644 can be configured to resist delamination of a membrane 647 that coats the distal end portion 642 of the sensor 618.

The sensor 618 can be a glucose sensor 618 comprising a membrane 647 that coats the distal end portion 642 of the sensor 618. The distal end portion 642 can be configured to resist delamination of the membrane 647, reduce tissue trauma, and/or reduce patient discomfort caused by piercing the skin.

Faceted Tips

Any of the sensors described herein can be faceted (e.g., with one, two, three, four, five, or more facets). The distal tips of the faceted embodiments can be rounded to achieve the membrane delamination resistance described above.

Figure 118:
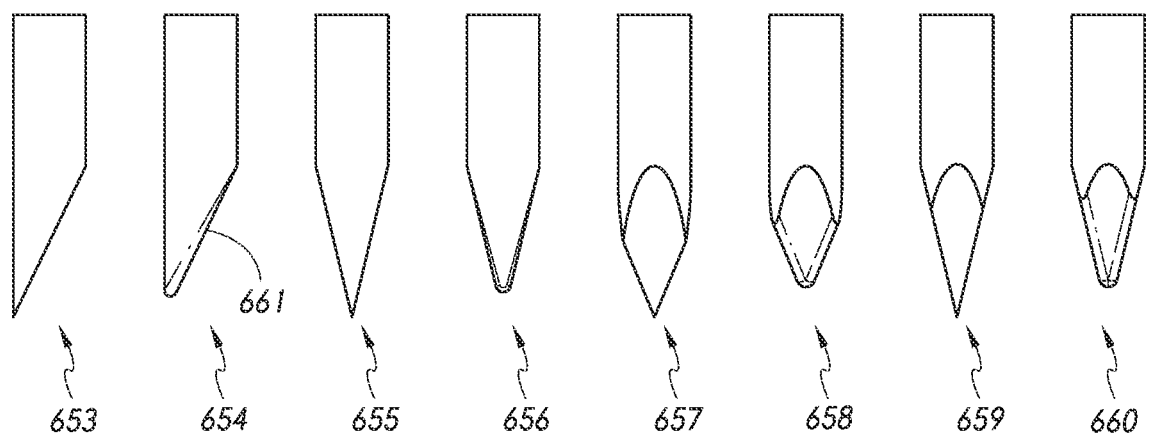
FIG. 118 illustrates a side view of distal portions of sensors, according to some embodiments.
Figure 119:
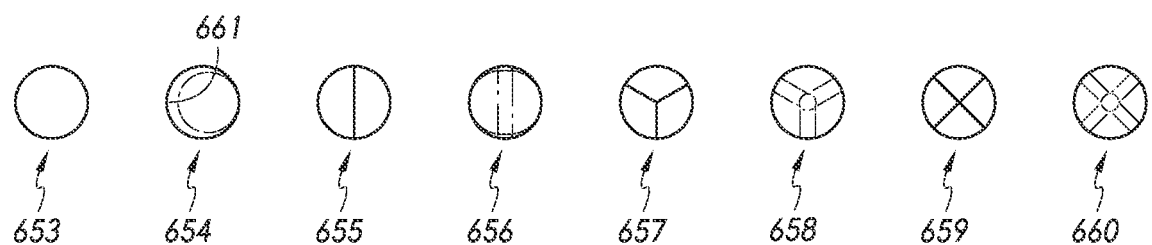
FIG. 119 illustrates a bottom view of distal portions of sensors, according to some embodiments.
Figure 120:
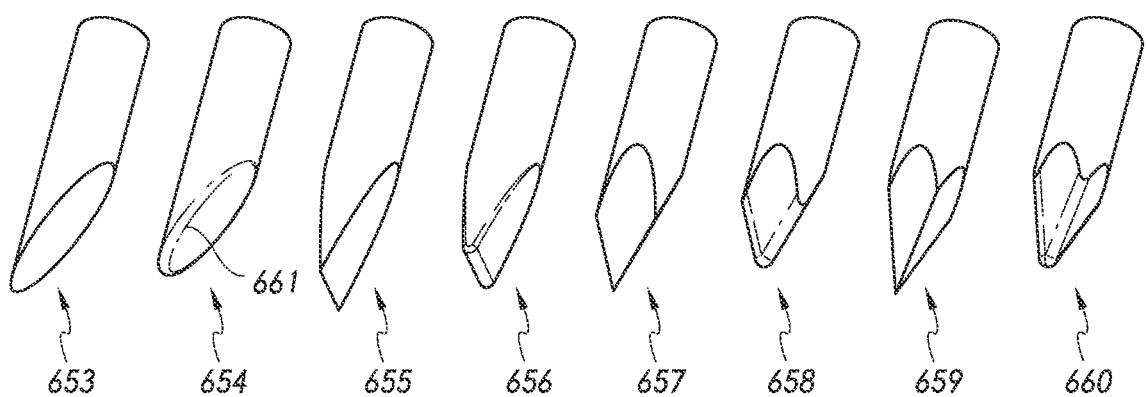
FIG. 120 illustrates a perspective view of distal portions of sensors, according to some embodiments.

Each of the sensors 653-660 illustrated in FIGS. 118-120 are faceted. Each facet can be formed by a planar grinding process. Faceted tips enable repeatable manufacturability, enable a relatively small (yet rounded) distal tip, and provide a gradual transition from the distal tip to a maximum diameter of the sensor.

The facets can be flat or curved surfaces that intersect with adjacent facets. The intersection between facets can form a ridge. The ridge can be rounded to reduce tissue trauma and to increase membrane delamination resistance.

FIG. 118 illustrates a side view of sensors 653-660. FIG. 119 illustrates a bottom view of the sensors 653-660. FIG. 120 illustrates a perspective view of the sensors 653-660. The proximal portions of the sensors 653-660 are hidden in FIGS. 118-120.

A first sensor 653 has one facet. A second sensor 654 also has one facet, but also includes a rounded ridge 661. A third sensor 655 and a fourth sensor 656 each have two facets, but the fourth sensor 656 also includes a rounded distal tip and rounded ridges. A fifth sensor 657 and a sixth sensor 658 each have three facets, but the sixth sensor 658 also includes a rounded distal tip and rounded ridges. A seventh sensor 659 and an eighth sensor 660 each have four facets, but the eighth sensor 660 also includes a rounded distal tip and rounded ridges.

Figure 121:
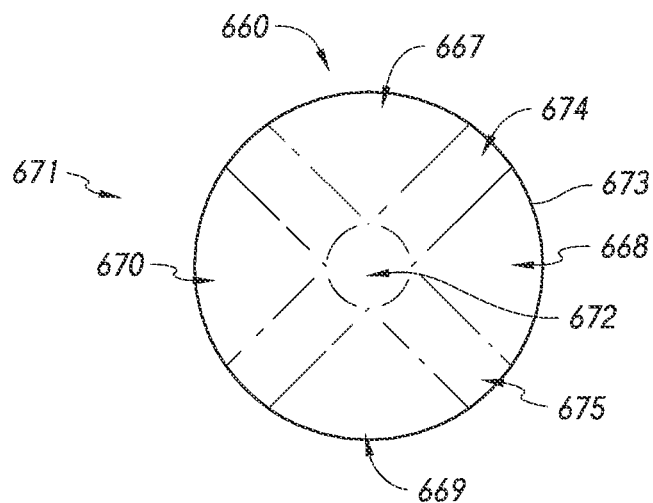
FIG. 121 illustrates a bottom view of a sensor, according to some embodiments.
Figure 122:
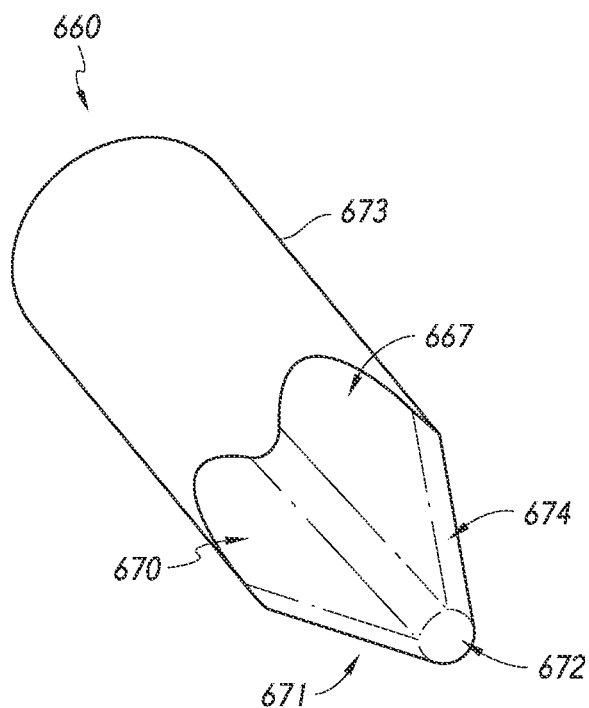
FIGS. 122 and 123 illustrate perspective views of a distal portion of the sensor, according to some embodiments.
Figure 123:
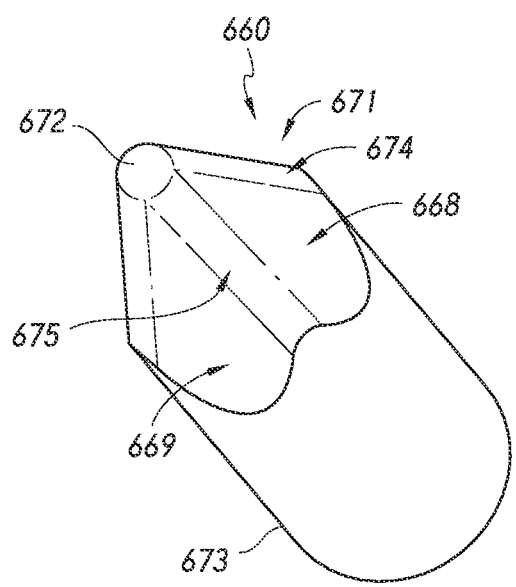

FIG. 121 illustrates a bottom view of a sensor 660 that comprises four facets 667, 668, 669, 670. FIG. 122 illustrates a first perspective view of the sensor 660. FIG. 123 illustrates a second perspective view of the sensor 660. A proximal portion of the sensor 660 is hidden in FIGS. 121-123.

In some embodiments, the sensor 660 comprises a distal end portion 671 having a central axis and a first facet 667 oriented at a first angle of less than 25 degrees relative to the central axis such that the first facet 667 is configured to facilitate piercing the skin. The distal end portion 671 of the sensor 660 can comprise a second facet 668 oriented at a second angle of less than 25 degrees relative to the central axis. The first facet 667 can be oriented at a third angle relative to the second facet 668. The third angle can be greater than 10 degrees and less than 25 degrees.

In several embodiments, the first facet 667 and a second facet (e.g., 669) form a wedge configured to facilitate piercing the skin. The distal end portion 671 of the sensor 660 can be coated by a membrane 673. A rounded ridge 674 can couple the first facet 667 to the second facet 668 such that the rounded ridge 674 is configured to resist delamination of the membrane 673.

In some embodiments, the distal end portion 671 of the sensor 660 comprises a third facet 669 oriented at a fourth angle of less than 25 degrees relative to the central axis. The first, second, and third facets can form a triangular pyramid configured to facilitate piercing the skin. The distal end portion 671 of the sensor 660 can be coated by a membrane 673. The triangular pyramid can comprise a rounded distal tip configured to resist delamination of the membrane 673.

In several embodiments, a first rounded ridge 674 couples the first facet 667 to the second facet 668. A second rounded ridge 675 can couple the second facet 668 to the third facet 669. The first rounded ridge 674 and the second rounded ridge 675 can be configured to reduce tissue trauma caused by inserting the distal end portion 671 of the sensor 660 into the host.

In some embodiments, the distal end portion 671 of the sensor 660 comprises a fourth facet 670 oriented at a fifth angle of less than 25 degrees relative to the central axis. The first, second, third, and fourth facets 667, 668, 669, 670 can form a rectangular pyramid configured to facilitate piercing the skin of the host.

Stepped Tips

The distal tip of a sensor can include one or more steps to provide a surface that is approximately perpendicular to a central axis of the distal tip. This perpendicular surface can provide robust membrane delamination protection. Even if membrane delamination occurs at the distal end, the perpendicular surface can stop the proximal spread of the delamination. The perpendicular surface can be formed by a distal end of the insulation and/or by creating a step in the conductive core (e.g., a wire) of the sensor.

In some embodiments, the step surface is within plus or minus 35 degrees of being perpendicular to the central axis of the sensor. The step surface can be located distally relative to a gap located between proximal insulation and distal insulation.

The distal end of the sensor can have any of the shapes described herein and/or incorporated by reference. The distal end of the sensor can be beveled, faceted, curved, and/or parabolic.

Figure 124:
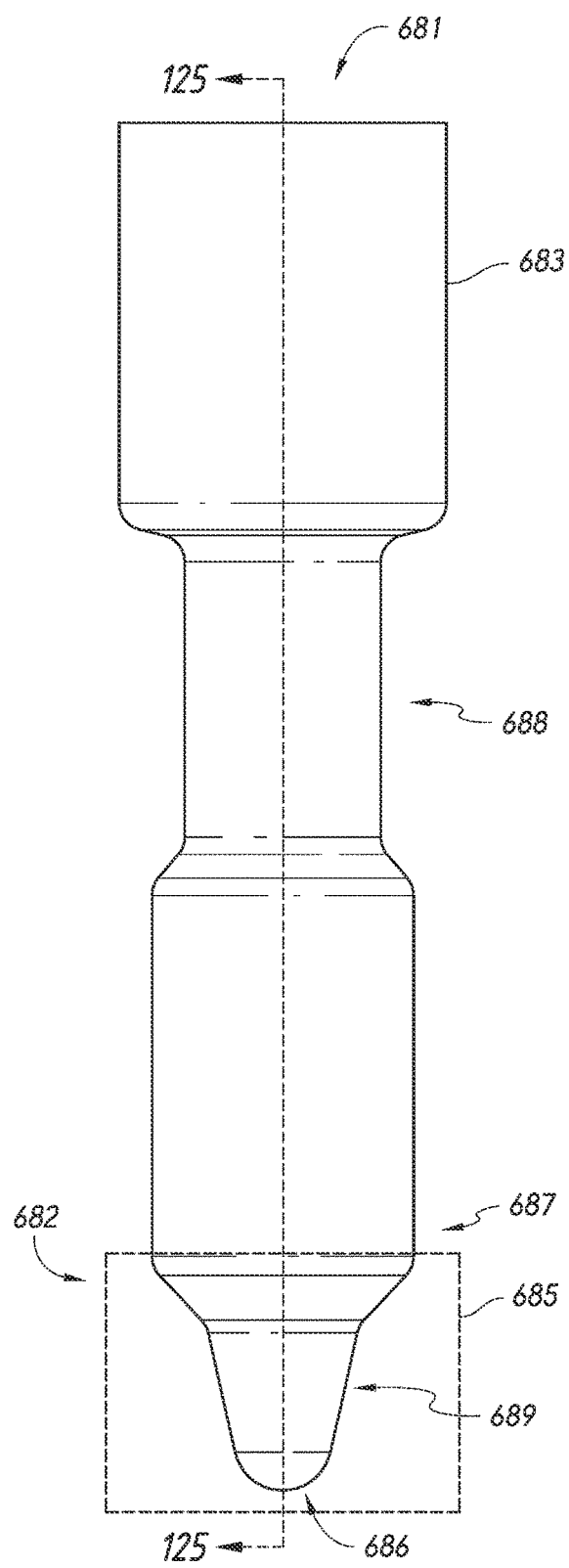
FIG. 124 illustrates a side view of a distal portion of a sensor, according to some embodiments.
Figure 125:
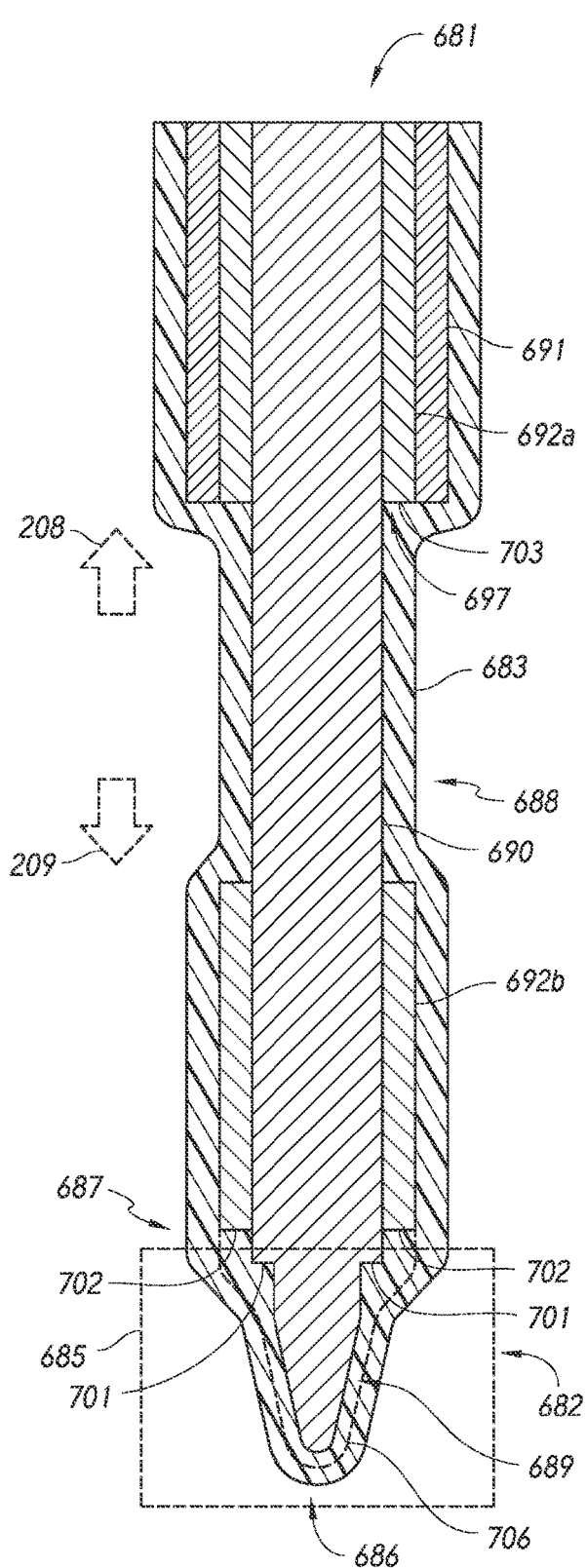
FIG. 125 illustrates a cross-sectional view along line 125-125 from FIG. 124, according to some embodiments.

FIG. 124 illustrates a side view of a sensor 681. FIG. 125 illustrates a cross-sectional view along line 125-125 from FIG. 124. The dimensions of some features have been exaggerated in FIGS. 124 and 125 to increase the clarity of certain features. A proximal portion of the sensor 681 is hidden in FIGS. 124 and 125.

Referring now to FIGS. 124 and 125, the sensor 681 can comprise a tapered end section 685 coated by a membrane 683. The tapered end section 685 comprises the distal tip 686 of the sensor 681. The tapered end section 685 can comprise a first step 701 configured to resist proximal movement of the membrane relative to the first step 701.

In the orientation illustrated in FIGS. 124 and 125, the tapered end section 685 faces downward such that the tapered end portion comprises surfaces that expand a hole in the tissue until the hole is large enough to permit the sensor 681 to enter the tissue.

Moving along the sensor 681 in a proximal direction 208, the tapered end section 685 increases in diameter from the distal tip 686 such that the tapered section transitions the sensor 681 from a relatively narrow distal tip 686 to a section 687 that has a larger diameter.

Moving along the sensor 681 in a distal direction 209, the tapered end section 685 makes a distal end portion 682 of the sensor 681 progressively narrowed towards the distal tip 686.

The sensor 681 can comprise a tapered end section 685 coated by a membrane. The tapered end section 685 comprises the distal tip 686. The sensor 681 can comprise a second step 702 located within plus or minus 1 millimeter and/or within plus or minus 2.1 millimeters of the tapered end section 685. The second step 702 can be configured to resist proximal movement of the membrane relative to the second step 702. The second step 702 can be formed by insulation 692b that at least partially surrounds a conductive core 690.

The sensor 681 can be coated by a membrane and can comprise a first step 701. The sensor 681 can comprise a groove 688 configured to be inserted into tissue of the host. As illustrated in FIGS. 124 and 125, the groove 688 is narrower (e.g., has a smaller diameter) than an adjacent proximal section and an adjacent distal section. The groove 688 can be located within 1 millimeter, 3 millimeters, 6 millimeters, and/or 8 millimeters of the distal tip 686 of the sensor 681. The groove 688 can be located distally relative to the base (e.g., when the base is coupled to the skin of the host). The first step 701 and/or the second step 702 can be located distally relative to the groove 688. The first step 701 and/or the second step 702 can be configured to resist proximal movement of the membrane relative to the first step 701 and/or the second step 702.

The sensor 681 can comprise a conductive distal end portion 689 coated by a membrane 683. The conductive distal end portion 689 can comprise a first step 701 configured to resist proximal movement of the membrane 683 relative to the first step 701. The conductive distal end portion 689 can be made of a conductive metal. The distal end portion 682 can include the conductive distal end portion 689 and other features (e.g., insulation, a membrane).

The sensor 681 can comprise a portion coated by a membrane 683. The portion of the sensor 681 can comprise a first conductive layer 690 electrically insulated from a second conductive layer 691 by an insulation layer 692*a*. The first conductive layer 690 can be configured to be electrically coupled to the second conductive layer 691 via tissue of the host. The first conductive layer 690 can extend farther distally than the second conductive layer 691. The first conductive layer 690 can comprise a first step 701 configured to resist proximal movement of the membrane 683 relative to the first step 701. The first step 701 can be located farther distally than the second conductive layer 691.

A distal portion of the sensor 681 can comprise a first step 701, a second step 702, and/or a third step 703. The third step 703 can be located proximally relative to the groove 688 and/or at a proximal end of the groove 688. The second step 702 and/or the third step 703 can be spaced proximally relative to the first step 701. The distal portion of the sensor 681 can be coated by a membrane 683. The first step 701, the second step 702, and the third step 703 can face distally. The steps 701, 702, 703 can be configured to resist proximal movement of the membrane 683.

The steps 701, 702, 703 can each comprise a surface oriented within plus or minus 25 degrees of perpendicular to a central axis of the portion of the sensor 681. The steps 701, 702, 703 can each comprise a surface oriented within plus or minus 15 degrees of perpendicular to a central axis of the portion of the sensor 681. The surface can form an interference feature configured to impede proximal movement of the membrane 683 relative to the surface by causing a compressive force within the membrane 683 in response to the proximal movement of the membrane 683.

The sensor 681 can comprise a first conductive layer 690 electrically insulated from a second conductive layer 691 by an insulation layer 692*a*. The first conductive layer 690 can be conductively coupled to the conductive distal end portion 689 such that the conductive distal end portion 689 is configured to be conductively coupled to the second conductive layer 691 via tissue of the host.

A sensor 681 can comprise a distal end portion 682 coated by a membrane 683. The distal end portion 682 can comprise a gap 697 between a conductive core 690 and a conductive layer 691 of the sensor 681. The gap 697 can be configured to enable a subcutaneous current between the conductive core 690 and the conductive layer 691. The distal end portion 682 can comprise a step (e.g., 701, 702) located distally relative to the gap 697 and configured to resist proximal movement of the membrane 683 relative to the step.

The step can comprise a surface oriented within plus or minus 25 degrees of perpendicular to a central axis of the distal end portion 682. The surface can form an interference feature configured to impede proximal movement of the membrane 683 relative to the surface by causing a compressive force within the membrane 683 in response to the proximal movement of the membrane 683 relative to the distal tip 686 and/or the step. The conductive core 690 can comprise the step (e.g., step 701). An insulation layer 692*b* located around the conductive core 690 can form the step (e.g., step 702).

The distal end portion 682 can comprise at least one of a rounded distal tip, a parabolic shape, a conical shape, a wedge shape, a triangular pyramid shape, a rectangular pyramid shape, and/or any of the shapes described in the context of FIGS. 112-123 such that the distal end portion 682 is configured to facilitate piercing the skin.

The sensor 681 can comprise a distal end portion 682 coated by a membrane 683. The distal end portion 682 of the sensor 681 can comprise a central axis, a distal tip 686, and a distally facing surface (e.g., step 701, step 702) spaced proximally apart from the distal tip 686. The distally facing surface can form a mechanical interlock with the membrane 683 such that the mechanical interlock is configured to impede proximal movement of the membrane 683 relative to the distally facing surface.

As used herein, the term "mechanical interlock" is used broadly. In some embodiments, a mechanical interlock can comprise two parts coupled such that the motion of a first part relative to a second part can cause the first part to compress (and/or experience a compressive force without compressive movement) due to the position of the second part. As a result, the motion of the first part is constrained by the second part. As used herein, in some embodiments, a mechanical interlock can comprise a releasable locking feature such as a snap fit formed by a flex arm coupled to an undercut, a hole, or another feature configured to at least temporarily impede movement.

The sensor 681 can comprise a conductive core 690, a conductive layer, and an insulation layer 692*a* configured to electrically insulate the conductive core 690 from the conductive layer. The conductive core 690 can extend farther distally than the insulation layer 692*a* to form a shortest conduction path between the conductive core 690 and the conductive layer. The distally facing surface can be located distally relative to the shortest conduction path (e.g., such that the third step 703 is not the distally facing surface, but another step 701, 702 comprises the distally facing surface).

As used herein, "extends" means to continue in a specified direction or over a specified distance, but unless stated otherwise, typically does not mean to become longer.

The sensor 681 can comprise a conductive core 690 and a conductive layer 691 configured to enable the system (e.g., any of the systems described herein and/or incorporated by reference) to apply a voltage between the conductive core 690 and the conductive layer 691 to measure an analyte indication. The sensor 681 can comprise a first electrical insulation layer 692*a* located around a first section of the conductive core 690 and a second electrical insulation layer 692*b* located around a second section of the conductive core 690.

The conductive layer 691 can be located radially outward from the first insulation layer 692*a*. The first insulation layer 692*a* can be spaced apart from the second insulation layer 692*b* to form a gap 697 configured to enable the system to apply the voltage between the conductive core 690 and the conductive layer 691. The distally facing surface (e.g., 701, 702) can be located distally relative to the gap 697. The distally facing surface can be oriented within a range of plus or minus 20 degrees relative to perpendicular to the central axis of the distal end portion 682 of the sensor 681.

Can Apply to All Sensor Embodiments

In several embodiments, the sensor is a glucose sensor having a conductive core and a conductive layer configured to enable the system to apply a voltage between the conductive core and the conductive layer to measure a glucose indication.

In some embodiments, the sensor comprises a first electrical insulation layer located around a first section of the conductive core. The sensor can comprise a second electrical insulation layer located around a second section of the conductive core. The conductive layer can be located radially outward from the first insulation layer. The first insulation layer can be spaced apart from the second insulation layer to form a gap configured to enable the system to apply the voltage between the conductive core and the conductive layer. The sensor can comprise an electrical insulation cap that covers a distal end of the conductive core.

Any of the sensors described herein can be coated by a membrane. The membrane can be a composite membrane that comprises two or more layers. The membrane can include an enzyme layer and a resistance layer. The membrane can also include an interferent layer and/or an under layer. In some embodiments, the membrane thickness can be approximately 12 to 20 micrometers.

The sensor can be coated by a membrane such that the membrane forms an approximately uniform outer layer. The membrane layer can have an average thickness. The membrane layer's thickness (e.g., of the tapered end section, of a section from a distal tip to an insulation layer, of a distal portion, of a section that is 3 millimeters long as measured along the central axis of the sensor from the distal tip) can vary by less than plus or minus 30 percent, less than plus or minus 40 percent, and/or less than plus or minus 50 percent relative to the average thickness of the membrane. As noted above, the following patent application includes membrane details: U.S. patent application Ser. No. 14/250,320. The entire contents of the following application are incorporated by reference herein: U.S. patent application Ser. No. 14/250,320; filed Apr. 10, 2014; and titled Sensors for Continuous Analyte Monitoring, and Related Methods.

Any of the sensors described herein can comprise one or more electrical insulation layers. A section of the sensor can comprise a conductive core within one or more insulation layers configured to electrically insulate the section from subcutaneous body fluid (e.g., blood) of the host. The insulation layer can be planar, tubular, and/or any suitable shape.

Any of the sensors described herein can comprise a distal end portion that has a conductive core that is electrically insulated by an electrical insulation cap 706. Referring now to FIG. 125, the insulation cap 706 can be at least partially covered by a membrane 683. The insulation cap 706 can have any suitable shape.

The insulation cap 706 can be coupled and/or attached to the insulation layer 692*b* such that an interface between the insulation cap 706 and the insulation layer 692*b* electrically insulates a distal end portion of the conductive core 690.

The insulation cap 706 can be a chemical cap 706 that electrically insulates the distal tip 686 of the sensor 681. The insulation cap 706 can be made of adhesive, cyanoacrylate, epoxy, thermoplastic, thermoset, polyurethane, silicone, thermoplastic silicone polycarbonate urethane, thermoplastic, polycarbonate-urethane, acrylonitrile butadiene styrene, polyvinyl chloride, and/or any suitable electrically insulating material.

Any of the systems described herein can apply a fixed voltage between the conductive core 690 (e.g., a wire, a conductive layer) and a conductive layer 691 located radially outward relative to the conductive core 690. Analyte measurements can include measuring the current between the conductive core 690 and the conductive layer 691. Analyte measurements can also include other procedures and types of measurements.

In some embodiments, the sensor is a glucose sensor having a conductive portion 690 at least partially covered by a first electrical insulation layer 692*a*. The first electrical insulation layer 692*a* can be at least partially covered by a conductive layer 691. The conductive portion 690 can have a distal tip located farther distally than a distal end of the conductive layer 691. Tissue and/or fluid of the host can electrically couple the distal tip of the conductive portion 690 to the conductive layer 691 to enable the system to apply a voltage between the conductive portion 690 and the conductive layer 691 such that the system can measure a current indicative of glucose between the conductive portion 690 and the conductive layer 691. The system can use electrochemical reactions to facilitate analyte measurements.

In some embodiments, the sensor is a glucose sensor having a conductive core 690 at least partially covered by a first electrical insulation layer 692*a* and a second electrical insulation layer 692*b*. (In several embodiments, the distal end of the conductive core 690 is covered by insulation 706.) The first electrical insulation layer 692*a* can be at least partially covered by a conductive layer 691. A gap (e.g., in the region of the groove 688) between the first electrical insulation layer 692*a* and the second electrical insulation layer 692*b* can enable the system to apply a voltage between the conductive core 690 and the conductive layer 691 such that the system can measure a current indicative of glucose between the conductive core 690 and the conductive layer 691. An assembly (comprising the conductive core 690, the first electrical insulation layer 692*a* and the second electrical insulation layer 692*b*, and/or the conductive layer 691) can be coated by a membrane 683 such that the membrane 683 covers the gap.

Any of the features described in the context of FIGS. 107-126 can be applicable to all aspects and embodiments identified herein. For example, the embodiments described in the context of FIGS. 107-126 can be combined with the embodiments described in the context of FIGS. 1-106. Moreover, any of the features of an embodiment is independently combinable, partly or wholly with other embodiments described herein in any way (e.g., one, two, three, or more embodiments may be combinable in whole or in part). Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

Interpretation

None of the steps described herein is essential or indispensable. Any of the steps can be adjusted or modified. Other or additional steps can be used. Any portion of any of the steps, processes, structures, and/or devices disclosed or illustrated in one embodiment, flowchart, or example in this specification can be combined or used with or instead of any other portion of any of the steps, processes, structures, and/or devices disclosed or illustrated in a different embodiment, flowchart, or example. The embodiments and examples provided herein are not intended to be discrete and separate from each other.

The section headings and subheadings provided herein are nonlimiting. The section headings and subheadings do not represent or limit the full scope of the embodiments described in the sections to which the headings and subheadings pertain. For example, a section titled "Topic 1" may include embodiments that do not pertain to Topic 1 and embodiments described in other sections may apply to and be combined with embodiments described within the "Topic 1" section.

Some of the devices, systems, embodiments, and processes use computers. Each of the routines, processes, methods, and algorithms described in the preceding sections may be embodied in, and fully or partially automated by, code modules executed by one or more computers, computer processors, or machines configured to execute computer instructions. The code modules may be stored on any type of non-transitory computer-readable storage medium or tangible computer storage device, such as hard drives, solid state memory, flash memory, optical disc, and/or the like. The processes and algorithms may be implemented partially or wholly in application-specific circuitry. The results of the disclosed processes and process steps may be stored, persistently or otherwise, in any type of non-transitory computer storage such as, for example, volatile or non-volatile storage.

Any of the features of each embodiment is applicable to all aspects and embodiments identified herein. Moreover, any of the features of an embodiment is independently combinable, partly or wholly with other embodiments described herein in any way (e.g., one, two, three, or more embodiments may be combinable in whole or in part). Further, any of the features of an embodiment may be made optional to other aspects or embodiments. Any aspect or embodiment of a method can be performed by a system or apparatus of another aspect or embodiment, and any aspect or embodiment of a system can be configured to perform a method of another aspect or embodiment.

The various features and processes described above may be used independently of one another, or may be combined in various ways. All possible combinations and subcombinations are intended to fall within the scope of this disclosure. In addition, certain method, event, state, or process blocks may be omitted in some implementations. The methods, steps, and processes described herein are also not limited to any particular sequence, and the blocks, steps, or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to be present.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments can include A, B, and C. The term "and/or" is used to avoid unnecessary redundancy.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein.

For ease of explanation and illustration, in some instances the detailed description describes exemplary systems and methods in terms of a continuous glucose monitoring environment; however it should be understood that the scope of the invention is not limited to that particular environment, and that one skilled in the art will appreciate that the systems and methods described herein can be embodied in various forms. Accordingly any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g. smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e. transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

What is claimed is:

1. A sensor system for measuring an analyte concentration, the sensor system comprising:
   a base having a distal side configured to face towards a skin of a host;
   a first adhesive coupled to the base and configured to couple the base to the skin;
   a transmitter coupled to the base and configured to transmit analyte measurement data;
   a transcutaneous analyte measurement sensor coupled to the base and configured to be bent against the first adhesive or the base after removal of the base from the skin; and
   a surface configured to bend at least a portion of the sensor towards the base after removal of the sensor from the host, wherein a distal tip of the sensor is located between the base and the surface.

2. The system of claim 1, wherein the base further comprises a first portion and a second portion, wherein the second portion of the base includes the surface, and the second portion of the base is coupled to the first portion of the base by a hinge configured such that decreasing a pivot angle between the first and second portions of the base places a portion of the sensor between the first portion of the base and the surface.

3. The system of claim 2, wherein the first adhesive comprises a first section and a second section, the first section is coupled to the first portion of the base such that the first section is configured to adhere the first portion of the base to the skin, and the second section is coupled to the second portion of the base such that the second section is configured to adhere the second portion of the base to the skin.

4. The system of claim 3, wherein the hinge is configured to enable the first section of the first adhesive to face towards the second section of the first adhesive while the portion of the sensor is at least partially confined between the first portion of the base and the surface.

5. The system of claim 2, wherein the system is configured to bend the portion of the sensor in response to rotating the hinge, wherein the portion of the sensor is bent between the first portion of the base and the surface to guard against the distal tip of the sensor penetrating tissue after the sensor system is removed from the skin.

6. The system of claim 2, wherein the first portion of the base is rotationally spring-loaded relative to the second portion of the base such that the system is configured to decrease the pivot angle in response to a rotational spring bias.

7. The system of claim 2, further comprising a torsion spring coupled to the hinge such that the torsion spring is configured to decrease the pivot angle to place the portion of the sensor between the first portion of the base and the surface.

8. The system of claim 1, wherein the surface comprises a compliant sheet.

9. The system of claim 8, wherein the first adhesive couples the compliant sheet to the base.

10. The system of claim 8, wherein the compliant sheet comprises a first state in which the compliant sheet is folded, is located proximally relative to the distal tip, does not cover the distal tip, and forms a tab configured to enable a user to unfold the compliant sheet.

11. The system of claim 10, wherein the compliant sheet comprises a second state in which the compliant sheet is at least partially unfolded relative to the first state, is at least partially located distally relative to the distal tip, and the distal tip of the sensor is at least partially confined between the compliant sheet and the first adhesive.

12. The system of claim 8, wherein the system further comprises a second sheet having a second puncture resistance that is greater than a first puncture resistance of the compliant sheet, wherein the second sheet is located between the distal tip and the compliant sheet to protect the compliant sheet from being punctured by the distal tip.

13. The system of claim 12, wherein the first and second puncture resistances are measured using a distal tip of the sensor.

14. The system of claim 12, wherein the second sheet is coupled to the compliant sheet such that the second sheet is configured to deform the distal tip as the compliant sheet is folded over the distal tip.

15. The system of claim 1, wherein the surface comprises a pliable sheet, and the distal tip of the sensor is at least partially confined between the pliable sheet and the base such that the pliable sheet holds at least a portion of the sensor in a bent position and the pliable sheet is adhered to the first adhesive.

* * * * *